(12) United States Patent
Hansen et al.

(10) Patent No.: US 7,459,022 B2
(45) Date of Patent: Dec. 2, 2008

(54) MICROFLUIDIC PROTEIN CRYSTALLOGRAPHY

(75) Inventors: Carl L. Hansen, Pasadena, CA (US); Morten Sommer, Copenhagen NV (DK); Stephen R. Quake, Stanford, CA (US)

(73) Assignee: California Institute of Technology, Pasadena, CA (US)

( * ) Notice: Subject to any disclaimer, the term of this patent is extended or adjusted under 35 U.S.C. 154(b) by 330 days.

(21) Appl. No.: 11/006,522

(22) Filed: Dec. 6, 2004

(65) Prior Publication Data

US 2005/0205005 A1   Sep. 22, 2005

Related U.S. Application Data

(63) Continuation-in-part of application No. 10/637,847, filed on Aug. 7, 2003, now Pat. No. 7,244,402, which is a continuation-in-part of application No. 10/117,978, filed on Apr. 5, 2002, now Pat. No. 7,195,670, and a continuation-in-part of application No. 09/887,997, filed on Jun. 22, 2001, now Pat. No. 7,052,545, which is a continuation-in-part of application No. 09/826,583, filed on Apr. 6, 2001, now Pat. No. 6,899,137, said application No. 10/637,847 and a continuation-in-part of application No. 10/265,473, filed on Oct. 4, 2002, now Pat. No. 7,306,672.

(60) Provisional application No. 60/572,060, filed on May 18, 2004, provisional application No. 60/447,157, filed on Feb. 12, 2003, provisional application No. 60/433,160, filed on Dec. 13, 2002, provisional application No. 60/323,524, filed on Sep. 17, 2001.

(51) Int. Cl.
*C30B 7/14* (2006.01)
(52) U.S. Cl. .............................. 117/68; 117/69; 117/70
(58) Field of Classification Search ................... 117/68, 117/69, 70
See application file for complete search history.

(56) References Cited

U.S. PATENT DOCUMENTS 3,570,515 A    3/1971   Kinner (Continued)

FOREIGN PATENT DOCUMENTS

EP           0 592 094 A2      4/1994

(Continued)

OTHER PUBLICATIONS

"The Liver Chip," Technology Review, pp. 64-67, Mar. 2003.

(Continued)

*Primary Examiner*—Robert M Kunemund
(74) *Attorney, Agent, or Firm*—Townsend and Townsend and Crew LLP

(57) ABSTRACT

The use of microfluidic structures enables high throughput screening of protein crystallization. In one embodiment, an integrated combinatoric mixing chip allows for precise metering of reagents to rapidly create a large number of potential crystallization conditions, with possible crystal formations observed on chip. In an alternative embodiment, the microfluidic structures may be utilized to explore phase space conditions of a particular protein crystallizing agent combination, thereby identifying promising conditions and allowing for subsequent focused attempts to obtain crystal growth.

30 Claims, 74 Drawing Sheets

U.S. PATENT DOCUMENTS

| | | | |
|---|---|---|---|
| 3,747,628 | A | 7/1973 | Holster et al. |
| 4,046,159 | A | 9/1977 | Pegourie |
| 4,119,368 | A | 10/1978 | Yamazaki |
| 4,153,855 | A | 5/1979 | Feingold |
| 4,245,673 | A | 1/1981 | Bouteille et al. |
| 4,434,704 | A | 3/1984 | Surjaatmadja |
| 4,898,582 | A | 2/1990 | Faste |
| 4,948,564 | A | 8/1990 | Root et al. |
| 4,992,312 | A | 2/1991 | Frisch |
| 5,085,562 | A | 2/1992 | Van Lintel |
| 5,088,515 | A | 2/1992 | Kamen |
| 5,096,388 | A | 3/1992 | Weinberg |
| 5,126,115 | A | 6/1992 | Fujita et al. |
| 5,164,558 | A | 11/1992 | Huff et al. |
| 5,171,132 | A | 12/1992 | Miyazaki |
| 5,224,843 | A | 7/1993 | Van Lintel |
| 5,259,737 | A | 11/1993 | Kamisuki et al. |
| 5,265,327 | A | 11/1993 | Faris et al. |
| 5,290,240 | A | 3/1994 | Horres, Jr. |
| 5,336,062 | A | 8/1994 | Richter |
| 5,346,372 | A | 9/1994 | Naruse et al. |
| 5,375,979 | A | 12/1994 | Trah |
| 5,376,252 | A | 12/1994 | Ekstrom |
| 5,400,741 | A | 3/1995 | DeTitta et al. |
| 5,423,287 | A | 6/1995 | Usami et al. |
| 5,529,465 | A | 6/1996 | Zengerle et al. |
| 5,593,130 | A | 1/1997 | Hansson et al. |
| 5,637,469 | A | 6/1997 | Wilding et al. |
| 5,642,015 | A | 6/1997 | Whitehead et al. |
| 5,659,171 | A | 8/1997 | Young et al. |
| 5,660,370 | A | 8/1997 | Webster |
| 5,681,024 | A | 10/1997 | Lisec et al. |
| 5,705,018 | A | 1/1998 | Hartley |
| 5,759,014 | A | 6/1998 | Van Lintel |
| 5,775,371 | A | 7/1998 | Pan et al. |
| 5,788,468 | A | 8/1998 | Dewa et al. |
| 5,836,750 | A | 11/1998 | Cabuz |
| 5,842,787 | A | 12/1998 | Kopf-Sill et al. |
| 5,875,817 | A | 3/1999 | Carter |
| 5,876,187 | A | 3/1999 | Afromowitz |
| 5,876,675 | A | 3/1999 | Kennedy |
| 5,885,470 | A | 3/1999 | Parce et al. |
| 5,932,100 | A | 8/1999 | Yager et al. |
| 5,932,799 | A | 8/1999 | Moles |
| 5,942,443 | A | 8/1999 | Parce et al. |
| 6,007,309 | A | 12/1999 | Hartley |
| 6,043,080 | A | 3/2000 | Lipshutz et al. |
| 6,123,769 | A | 9/2000 | Sanjoh |
| 6,155,282 | A | 12/2000 | Zachary et al. |
| 6,165,694 | A | 12/2000 | Liu |
| 6,174,365 | B1 | 1/2001 | Sanjoh |
| 6,174,675 | B1 | 1/2001 | Chow et al. |
| 6,296,673 | B1 | 10/2001 | Santarsiero et al. |
| 6,345,502 | B1 | 2/2002 | Tai et al. |
| 6,409,832 | B2 | 6/2002 | Weigl et al. |
| 6,767,706 | B2 | 7/2004 | Quake et al. |
| 2001/0027745 | A1 | 10/2001 | Weigl et al. |
| 2002/0029814 | A1 | 3/2002 | Nassef et al. |
| 2002/0037499 | A1 | 3/2002 | Quake et al. |
| 2002/0145231 | A1 | 10/2002 | Hansen et al. |
| 2002/0191048 | A1* | 12/2002 | Mutz et al. .................... 347/46 |
| 2003/0061687 | A1 | 4/2003 | Hansen et al. |
| 2003/0096310 | A1 | 5/2003 | Hansen |
| 2004/0115731 | A1 | 6/2004 | Hansen et al. |
| 2005/0019794 | A1 | 1/2005 | Hansen et al. |
| 2005/0062196 | A1 | 3/2005 | Hansen et al. |
| 2005/0229839 | A1 | 10/2005 | Quake et al. |

FOREIGN PATENT DOCUMENTS

| | | |
|---|---|---|
| EP | 0 703 364 A1 | 3/1996 |
| EP | 0 706 004 A2 | 4/1996 |
| EP | 0 779 436 A2 | 6/1997 |
| EP | 0 829 360 A2 | 3/1998 |
| EP | 0 845 603 A1 | 6/1998 |
| EP | 0 999 055 A2 | 5/2000 |
| GB | 2 155 152 A | 9/1985 |
| GB | 2 308 460 A | 6/1997 |
| WO | WO 99/00655 | 1/1988 |
| WO | WO 98/07069 A1 | 2/1998 |
| WO | WO 99/04361 A1 | 1/1999 |
| WO | WO 99/17093 A1 | 4/1999 |
| WO | WO 99/52633 | 10/1999 |
| WO | WO 00/00678 A1 | 1/2000 |
| WO | WO 00/43748 | 7/2000 |
| WO | WO 00/60345 A1 | 10/2000 |
| WO | WO 01/09595 A2 | 2/2001 |
| WO | WO 01/09595 A3 | 2/2001 |

OTHER PUBLICATIONS

Black, Harvey, "Tiny Technology Promises Tremendous Profits," The Scientist, vol. 15, No. 21, 4 pages, Oct. 29, 2001.

Chang, Jun Keun et al., "Functional Integration Of Serial Dilution And Capillary Electrophoresis On A PDMS Microchip," Biotechnology and Bioprocess Engineering, vol. 8, No. 4, pp. 233-239, 2003.

Chayen, Naomi E., "Protein Crystallization For Genomics: Throughput Versus Output," Journal of Structural and Functional Genomics, vol. 4, pp. 115-120, 2003.

Chen, Chihchen et al., "Gray-Scale Photolithography Using Microfluidic Photomasks," PNAS, vol. 100, No. 4, pp. 1499-1504, Feb. 18, 2003.

D'Arcy, Allan et al., "The Advantages Of Using A Modified Microbatch Method For Rapid Screening Of Protein Crystallization Conditions," Acta Crystallographica, vol. D59, pp. 1-3, 2003.

Eyal, Shulamit et al., "Velocity-Independent Microfluidic Flow Cytometry," Electrophoresis, vol. 23, pp. 2653-2657, 2002.

Fitzgerald, Deborah A., "Making Every Nanoliter Count," The Scientist, vol. 15, No. 21, 8 pages, Oct. 29, 2001.

Gao, Jun et al:, "Integrated Microfluidic System Enabling Protein Digestion, Peptide Separation, And Protein Identification," Analytical Chemistry, vol. 73, No. 11, pp. 2648-2655, Jun. 1, 2001.

Garno, Jayne C. et al., "Production Of Periodic Arrays Of Protein Nanostructures Using Particle Lithography," Langmuir, vol. 18, No. 21, pp. 8186-8192, 2002.

Grover, William H. et al., "Monolithic Membrane Valves And Diaphragm Pumps For Practical Large-Scale Integration Into Glass Microfluidic Devices," Sensors and Actuators B, vol. 89, pp. 315-323, 2003.

Hansen, Carl L. et al., "Systematic Investigation Of Protein-Phase Behavior With A Microfluidic Formulator," PNAS Early Edition, 6 pages, 2004.

Hofmann, Oliver et al., "Modular Approach To Fabrication Of Three-Dimensional Microchannel Systems In PDMS—Application To Sheath Flow Microchips," Lab on a Chip, vol. 1, pp. 108-114, 2001.

Hong, Jong Wook et al., "A Nanoliter-Scale Nucleic Acid Processor With Parallel Architecture," Nature Biotechnology, vol. 22, No. 4, pp. 1-5, Apr. 2004.

Hosokawa, Kazuo et al., "A Microfluidic Device For Mixing Of Capillary-Drive Liquids," IEEJ Trans. SM, vol. 123, No. 1, pp. 23-24, 2003.

Juárez-Martinez, G. et al., "High-Throughput Screens For Postgenomics: Studies Of Protein Crystallization Using Microsystems Technology," Analytical Chemistry, vol. 74, No. 14, pp. 3505-3510, Jul. 15, 2002.

Kuhn, Peter et al., "The Genesis Of High-Throughput Structure-Based Drug Discovery Using Protein Crystallography," Current Opinion in Chemical Biology, vol. 6, pp. 704-710, 2002.

Lagally, Eric T. et al., "Fully Integrated PCR-Capillary Electrophoresis Microsystem For DNA Analysis," Lab On A Chip, vol. 1, pp. 102-107, 2001.

Liu, Jian et al., "A Nanoliter Rotary Device For Polymerase Chain Reaction," Electrophoresis, vol. 23, pp. 1531-1536, 2002.

McDonald, J. Cooper et al., "Poly(dimethylsiloxane) As A Material For Fabricating Microfluidic Devices," Accounts of Chemical Research, vol. 35, No. 7, pp. 491-499, 2002.

Ng, Jessamine M. K. et al., "Components For Integrated Poly(Dimethylsiloxane) Microfluidic Systems," Electrophoresis, vol. 23, pp. 3461-3473, 2002.

Nollert, Peter et al., "Crystallization Of Membrane Proteins in Cubo," Methods in Enzymology, vol. 343, pp. 183-199, 2002.

Santarsiero, B. D. et al., "An Approach To Rapid Protein Crystallization Using Nanodroplets," Journal of Applied Crystallography, vol. 35, pp. 278-281, 2002.

Sasserath, J. et al., "Rapid Prototyping And Development Of Microfluidic And BioMEMS Devices," IVD Technology, 12 pages, Jun. 2002.

Stevens, Raymond C., "The Cost And Value Of Three-Dimensional Protein Structure," Drug Discovery World, pp. 35-48, Summer 2003.

Thorsen, Todd et al., "Dynamic Pattern Formation In A Vesicle-Generating Microfluidic Device," Physical Review Letters, vol. 86, No. 18, pp. 4163-4166, Apr. 30, 2001.

Thorsen, Todd et al., "Microfluidic Large-Scale Integration," Science, vol. 298, No. 5593, pp. 580-584, Oct. 18, 2002.

Van Der Woerd, Mark et al., "Lab-On-A-Chip Based Protein Crystallization," National Aeronautics and Space Administration and Caliper, pp. 1-27, Oct. 25, 2001.

Van Der Woerd, Mark et al., "The Promise Of Macromolecular Crystallization In Microfluidic Chips," Journal of Structural Biology, vol. 142, pp. 180-187, 2003.

Velev, Orlin D., "On-Chip Manipulation Of Free Droplets," Nature, vol. 426, pp. 515-516, Dec. 4, 2003.

Weber, Patricia C. et al., "Applications Of Calorimetric Methods To Drug Discovery And The Study of Protein Interactions," Current Opinion in Structural Biology, vol. 13, pp. 115-121, 2003.

Weselak, Mark et al., "Robotics For Automated Crystal Formation And Analysis," Methods in Enzymology, pp. 1-13, 2002.

Whitesides, George M. et al., "Flexible Methods For Microfluidics," Physics Today, pp. 42-48, Jun. 2001.

Wu, Hongkai et al., "Fabrication Of Complex Three-Dimensional Microchannel Systems In PDMS," J. Am. Chem. Soc., vol. 125, No. 2, pp. 554-559, 2003.

Yeh, Joanne I., "A Manual Nanoscale Method For Protein Crystallization," Acta Crystallographica, vol. D59, pp. 1408-1413, 2003.

Zhao, Zhan, et al., "An Integrated Biochip Design And Fabrication," Proceedings of SPIE, vol. 4936, pp. 321-326, 2002.

Zheng, Bo et al., "A Droplet-Based, Composite PDMS/Glass Capillary Microfluidic System For Evaluating Protein Crystallization Conditions By Microbatch And Vapor-Diffusion Methods With On-Chip X-Ray Diffraction," Angew. Chem., pp. 1-4, 2004.

Ahn et al:, "Fluid Micropumps Based on Rotary Magnetic Actuators," Proceedings of 1995 IEEE Micro Electro Mechanical Systems Workshop (MEMS '95), held in Amsterdam, Netherlands on Jan. 29-Feb. 2, 1995, pp. 408-412.

Andersson et al. "Consecutive Microcontact Printing—Ligands for Asymmetric Catalysis in Silicon Channel" Sensors&Actuators, B, 3997, 2001, pp. 1-7.

Benard et al., "A Titanium-Nickel Shape-Memory Alloy Actuated Micropump," Proceedings of Transducers '97, 1997 International Conference on Solid-State Sensors and Actuators, held in Chicago, IL, Jun. 16-19, 1997, 1:361-364 (1997).

Brechtel et al.; "Control of the electroosmotic flow by metal-salt-containing buffers", J Chromatography A, 1995, pp. 97-105, vol. 716.

Bryzek et al.; "Micromachines on the March", IEEE Spectrum, 1994, pp. 20-31, vol. 31, No. 5.

Buchaillot et al.; "Silicon nitride thin films Young's modulus determination by an optical non-destructive method", Jpn. J Appl Phys, 1995, pp. L794-L797, vol. 36, No. 2:6B.

Carter et al. "Protein Crystallization Using Incomplete Factorial Experiments", the Journal of Biological Chemistry, 1979, pp. 12219-12223, vol. 254, No. 23.

Carter et al., "Statistical Design of Experiments for Protein Crystal Growth and the Use of a Precrystallization Assay", Journal of Crystal Growth 90, 1998, pp. 60-73.

Chayen, N.E., "The Role of Oil in Macromolecular Crystallisation" Structure 5 (1997), 1269-1274.

Chiu et al.; "Patterned Deposition of Cells and Proteins onto Surfaces by Using Three-Dimensional Microfluidic Systems", Proc. Natl. Acad. Sci., 2000, pp. 2408-2413, vol. 97, No. 6.

Chou et al. "A microfabricated device for sizing and sorting DNA molecules", Applied Physical Sciences, Biophysics, Proc. Natl. Acad. Sci., 1999, pp. 11-13, vol. 96, U.S.A.

Delamarche et al.; "Patterned delivery of immunoglobulins to surfaces using microfluidic networks", Science, 1997, pp. 779-781, vol. 276.

Ducruix A, Giegé R. *Crystallization of nucleic acids and proteins.* 1992, pp. 73-98, Oxford; IRL Press.

Duffy et al. "Patterning Electroluminescence Materials with Feature Sizes as Small as 5μm Using Elastomeric Membranes as Masks for Dry Lift-Off", Advanced Materials, 1999, pp. 546-552, vol. 11, No. 7.

Duffy et al. "Rapid Prototyping of Microfluidic Switches in Poly(dimethylsiloxane) and Their Actuation by Electro-Osmotic Flow" Journal of Microeng, 1999, pp. 211-217, vol. 9.

Duffy et al. "Rapid Prototyping of Microfluidic Systems in Poly(dimethylsiloxane)", Analytical Chemistry, 1998, pp. 4974-4984, vol. 70, No. 23.

Effenhauser et al.; "Integrated capillary electrophoresis on flexible silicone microdevices: Analysis of DNA restriction fragments and detection of single DNA molecules on microchips", Anal. Chem, 1997, pp. 3451-3457, vol. 69.

Effenhauser et al.; "Integrated chip-based capillary electrophoresis", Electrohphoresis, 1997, pp. 2203-2213, vol. 18.

Fahrenberg et al. "A microvalve system fabricated by thermoplastic molding", J Micromech Microeng, 1995, pp. 169-171, vol. 5.

Fu et al.; "A microfabricated fluorescence-activated cell-sorter", Nature Biotechnology, 1999, pp. 1109-1111, vol. 17.

Gass et al.; "Integrated flow-regulated silicon micropump," Sensors and Actuators A Physical, 1994, p. 335-338, vol. 43.

Gerlach, T., "Pumping Gases by a Silicon Micro Pump with Dynamic Passive Valves," Proceedings of Transducers '97, 1997 International Conference on Solid-State Sensors and Actuators, held in Chicago, Il., Jun. 16-19, 1997, pp. 357-360, vol. 1.

Goll et al., "Microvalves with bistable buckled polymer diaphragms," J. Micromech. Microeng., 1996, pp. 77-79, vol. 6.

Gravesen et al.; "Microfluids- A Review", Journal Micromech Microeng, 1993, pp. 168-192, vol. 3.

Hansen et al., "A Robust and Scalable Microfluidic Metering Method that Allows Protein Crystal Growth by Free Interface Diffusion", *Proc. Nat'l Acad. Sci.* 99:16531-6 (2002).

Harrison et al., "Micromachining a Miniaturized Capillary Electrophoresis-Based Chemical Analysis System on a Chip," Science, 1993, pp. 895-897, vol. 261.

Hornbeck et al., "Bistable Deformable Mirror Device," Spatial Light Modulators and Applications 1988 Technical Digest Series, vol. 8, Postconference Edition, Summaries of papers presented at the Spatial Light Modulators and Applications Topical Meeting, Jun. 15-17, 1988, Optical Society of America, pp. 107-110.

Hosokawa et al., "Handling of Picoliter Liquid Samples in a Poly(dimethylsiloxane)-Based Microfluidic Device," Anal. Chem., 1999, 71(20):4781-4785.

Ikuta et al., "Three dimensional micro integrated fluid systems (MIFS) fabricated by stereo lithography," IEEE Kyushu Institute of Technology, 1994, pp. 1-6.

Jacobson et al., "High-speed separations on a microchip," Anal. Chem., 1994, 66(7):1114-1118.

Jacobson et al., "Microfluidic Devices for Electrokinetically Driven Parallel and Serial Mixing," Anal. Chem., 1999, 71(20):4455-4459.

Jaramillo et al., "Crystallization and Cryocrystallography inside X-ray capillaries", J. Appl. Cryst., (2001), 34, pp. 365-370.

Jerman, H., "Electrically-Activated, Normally-Closed Diaphragm Valves," Proceedings of Transducers '91, 1991 International Conference on Solid State Sensors and Actuators, pp. 1045-1048 (1991).

Jung et al., "Chemical and Physical Interactions at Metal/Self-Assembled Organic Monolayer Interfaces," Critical Reviews in Solid State and Material Sciences, 1994, pp. 2-10, vol. 19, No. 1.

Kamholz et al., Quantitative Analysis of Molecular Interaction in a Microfluidic Channel: The T-Sensor, Analytical Chemistry, vol. 17, No. 23, Dec. 1, 1999, pp. 5340-5347.

Kenis et al. "Microfabrication Inside Capillaries Using Multiphase Laminar Flow Patterning," Science, 1999, 285: 83-85.

Kim, Enoch et al., "Micromolding in Capillaries: Applications in Material Science," J. American Chemical Society, 118:5722-5731 (1996).

Kopp et al. "Chemical Amplification: Continuous-Flow PCR on a Chip", Science, 1998, 280:1046-1048.

Kuhn et al. "Silicon Charge Electrode Array for Ink Jet Printing", IEEE Transactions on Electron Devices, 1978, pp. 1257-1260, vol. ED-25, No. 10.

Lin et al. "Free-Space Micromachined Optical Switches for Optical Networking," IEEE J. Selected Topics in Quantum Electronics, 1999, pp. 4-9, vol. 5, No. 1.

Lin et al., Convective-diffusive transport in protein crystal growth, Journal of Crystal Growth, 151 (1995), pp. 153-162.

Lotters et al. "The mechanical properties of the rubber elastic polymer polydimethylsiloxane for sensor applications," J. Micromech. Microeng., 1997, 7:145-147.

Lucy et al., "Characterization of the Cationic Surfactant Induced Reversal of Electroosmotic Flow in Capillary Electrophoresis," Anal. Chem., 1996, pp. 300-305, vol. 68.

Luft et al., Kinetic Aspects of Macromolecular Crystallization, Methods in Enzymology, 1997, pp. 110-130, vol. 276.

Luft et al., Microbatch Macromolecular crystallization in micropipettes—Structure, Function and Genetics, Journal of Crystal Grown, North-Holland Publishing Co., Amsterdam, NL., vol. 196, No. 204, 1999, pp. 450-455.

Luft, J.R. et al. "Microbatch Macromolecular Crystallization In Micropipettes", J. Crystal Growth, 1999, pp. 450-455, vol. 196.

Maluf, N., *An Introduction to Microelectromechanical Systems Engineering*, Dec. 1999, pp. 42-45, Artech House Publishers, Boston London.

McPherson, et al. "Crystallization of Macromolecules: General Principles" Methods Enzymol. 1985; 114: 112-120.

McPherson, et al. "Crystallization of Proteins by Variation of pH or Temperature" Methods Enzymol. 1985; 114: 125-127.

McPherson, et al. "Use of Polyethylene Glycol in the Crystallization of Macromolecules" Methods Enzymol. 1985; 114: 120-125.

Miller et al., A Comparison between Protein Crystals Grown with Vapor Diffusion Methods in Microgravity and Protein Crystals using a Gel Liquid-liquid diffusion Ground-Based Method, Journal of Crystal Growth 132 (1992), pp. 306-309.

Muller et al., "Surface-Micromachined Microoptical Elements and Systems," Proceedings of IEEE, 1998, 86(8): 1705-1720.

Nerad et al., Ground-Based Experiments on the Minimization of Convention During the Growth of Crystals From Solution, Journal of Crystal Growth, 1986, pp. 591-608, vol. 75.

Olsson et al., "Simulation Studies of Diffuser and Nozzle Elements for Valve-less Micropumps," Proceedings of Transducers '97, 1997 International Conference on Solid-State Sensors and Actuators, held in Chicago, Il., Jun. 16-19, 1997, 2:1039-1042 (1997).

Pethig & Markx "Applications of dielectrophoresis in biotechnology," Tibtech, 15:426-432 (1997).

Phillips, W.C. and Rayment, I. "A systematic method for aligning double focusing mirrors." Methods in Enzymology, 1985, vol. 114 (Wyckoff, Hirs and Timasheff, eds.), 316-329, Academic Press.

Qin et al., "Photolithography with transparent reflective photomasks," J. Vac.Sci. Technology, 16(1):98-103 (1998).

Qin et al., "Elastomeric Light Valves", Adv. Mater., 1997, pp. 407-410, vol. 9, No. 5.

Quake S.R. and Scherer A.; "From Micro- to Nanofacrication with Soft Materials", Science, Nov. 24, 2000; pp. 1536-1540, vol. 290, No. 5496.

Rapp, R., "LIGA micropump for gases and liquids," Sensors and Actuators A, 1994, pp. 57-61, vol. 40.

Roylance et al., "A Batch-Fabricated Silicon Accelerometer", IEEE Transactions on Electron Devices, Dec. 1979, pp. 1911-1917, vol. ED-26, No. 12.

Ruiz et al., Agarose as Crystallization Media for Proteins I: Transport Processes, Journal of Crystal Growth, 2001, pp. 165-172, vol. 232.

Ruiz et al., Investigations on Protein Crystal Growth by the Gel Acupuncture Method, Acta Crystallographica, 1994, pp. 484-490, Section D.

Salemme, A Free Interface Diffusion Technique for the Crystallization of Proteins for X-Ray Crystallography, Archives of Biochemistry and Biophysics, 1972, pp. 533-539. vol. 151.

Schasfoort et al., "Field-Effect Flow Control for Microfabricated Fluidic Networks," Science, 1999, 286:942-945.

Schueller et al., "Fabrication of glassy carbon microstructures by soft lithography," Sensors and Actuators, 72(2):125-139 (1999).

Shoji et al.; "Smallest Dead Volume Microvalves for Integrated Chemical Analyzing Systems", Proceedings of Transducers '91, 1991, pp. 1052-1055, San Francisco.

Shoji, S., "Fluids for Sensor Systems", Topics in Current Chemistry, 1998, pp. 162-188, vol. 194, Springer Verlag Berlin Heidelberg.

Smits, J.G., "Piezoelectric Micropump with Three Valves Working Peristaltically", Sensors and Actuators, 1990, pp. 203-206, vol. A21-A23.

Sohn et al., "Capacitance cytometry: Measuring biological cells one by one," PNAS, 97(20):10687-10690 (2000).

Thomas et al., Distribution coefficients of Protein Impurities in Ferritin and Lysozyme Crystals Self-Purification in Microgravity, Journal of Crystal Growth 211 (2000), pp. 149-156.

Tufte et al., "Silicon Diffused-Element Piezoresistive Diaphragms," J. Appl. Phys., Nov. 1962, pp. 3322-3327, vol. 33, No. 11.

Ullmann's Encyclopedia of Industrial Chemistry, Sections 6 to 6.3, Topic: Carbon Black, Sixth Edition, 1999.

Unger, Marc A. et al. "Monolithic Microfabricated Valves and Pumps by Multilayer Soft Lithography" *Science*, Apr. 7, 2000, vol. 288, 113-116.

Van De Pol et al., "Micro Liquid Handling Devices—A Review", Micro Systems Technologies, 1990, pp. 799-805, vol. 90.

Van De Pol, F.C.M. et al. "A Thermo-Pneumatic Actuation Principle for a Microminiature Pump and Other Micromechanical Devices" Sensors and Actuators, May 3, 1989, pp. 139-143, vol. 17, Nos. 1-2.

Vieider et al.; "A Pneumatically Actuated Micro Valve with a Silicon Rubber Membrane for Integration with Fluid Handling Systems", Proceedings of Transducers '90, the 8th International Conference on Solid-State Sensors and Actuators and Eurosensors IX, held in Stockholm, Sweden on Jun. 25-29, 1995, pp. 284-286, Stockholm, Sweden.

Ward et al., Automatic Preparation of Protein Crystals Using Laboratory Robotics and Automated Visual Inspection, Journal of Crys. Growth 90 (1988), pp. 326-339.

Washizu et al., "Molecular Dielectrophoresis of Biopolymers," IEEE Transactions on Industry Applications, 1994, 30(4):835-843.

Wu, S. et al. "MEMS Flow Sensors for Nano-fluidic Applications", Sensors and Actuators A: Physical 2001, vol. 89, Nos. 1-2, pp. 152-158.

Xia et al., "Complex Optical Surfaces Formed by Replica Molding Against Elastomeric Masters," Science, 1996, 273:347-349.

Xia et al., "Soft Lithography," Angew. Chem. Int. Ed., 1998, 37:551-575.

Xia, Y. et al., "Micromolding of Polymers in Capillaries: Applications in Microfabrication," Chemistry of Materials, 1996, pp. 1558-1567, vol. 8, No. 7.

Yang et al., "A Mems Thermopneumatic Silicone Membrane Valve", Proceedings of IEEE 10th Annual International Workshop on MicroElectro Mechanical Systems, Sensors and Actuators, 1998, A64(1):101-108.

Yang et al., "A MEMS Thermopneumatic silicone Membrane Valve," Proceedings of the IEEE 10th Annual Workshop of Micro Electro Mechanical Systems Workshop (MEMS '97), held Jan. 26-30, 1997 in Nagoya, Japan, pp. 114-118.

Yazdi et al. "Micromachined Inertial Sensors," Proceedings of IEEE, 1998, 86(8):1640-1659.

Young et al. "Contoured elastic-membrane microvalves for microfluidic network integration," Biomechanical Engineering, 1999, 121:2-6.

Zengerle et al., "A Micro Membrane Pump with Electrostatic Actuation," 1992 IEEE Conf. on Micro Electro Mechanical Systems, held Feb. 4-7, 1992 in Travemunde Germany, pp. 19-24.

Zengerle et al., "Performance Simulation of Microminiaturized Membrane Pumps," from 7th International Conference on Solid-State Sensors and Actuators held Jun. 7-10, 1993 in Yokohama Japan, pp. 106-107.

"Biochips," Nature Biotechnology, vol. 18, Supplement 2000, pp. IT43-IT44, 2000.

"Chapter 9: Microfluidic Devices," Micromachined Transducers Sourcebook, pp. 779-882, 1998.

"Electro Microfluidic Dual In-Line Package (EMDIP)," Sandia National Laboratories, 2 pages, no date.

"Last Chance for Micromachines," The Economist Technology Quaterly, printed from website http://www.economist.com/science/displayStory.cfm?Story_ID=442930 on Jan. 25, 2001, 8 pages, Dec. 7, 2000.

Abola, Enrique et al., "Automation Of X-Ray Crystallography," Nature Structural Biology, Structural Genomics Supplement, pp. 973-977, Dec. 2000.

Andersen, Gregers Rom et al., "A Spreadsheet Approach Automated Protein Crystallization," Journal of Applied Crystallography, vol. 29, pp. 236-240, 1996.

Anderson, Rolfe C. et al., "Microfluidic Biochemical Analysis System," Transducers '97, 1997 International Conference on Solid-State Sensors and Actuators, Chicago, Illinois, pp. 477-480, Jun. 16-19, 1997.

Angell, James B. et al., "Silicon Micromechanical Devices," Scientific American, pp. cover, 44-55, Apr. 1983.

Armani, Deniz et al., "Re-Configurable Fluid Circuits By PDMS Elastomer Micromachining," IEEE Int. Conf. Micro Electro Mech. Syst. Tech. Digest, vol. 12, pp. 222-227, 1999.

Ballantyne, J.P. et al., "Selective Area Metallization By Electron-Beam Controlled Direct Metallic Deposition," J. Vac. Sci. Technol., vol. 10, No. 6, pp. 1094-1097, Nov. 1973.

Belgrader, Phillip et al., "Rapid Pathogen Detection Using A Microchip PCR Array Instrument," Clinical Chemistry, vol. 44, No. 10, pp. 2191-2194, 1998.

Berry, Michael B., "Protein Crystallization: Theory And Practice," Excerpts from Doctoral Thesis, 36 pages, Sep. 17, 1995.

Bloomstein, T. M. et al., "Laser-Chemical Three-Dimensional Writing For Microelectromechanics And Application To Standard-Cell Microfluidics," J. Vac. Sci. Technol. B, vol. 10, No. 6, pp. 2671-2674, Nov. 1992.

Bousse, Luc et al., "Electrokinetically Controlled Microfluidic Analysis Systems," Annu. Rev. Biophys. Biomol. Struct., vol. 29, pp. 155-181, 2000.

Brush, Michael, "Automated Laboratories," The Scientist, vol. 13, No. 4, 10 pages, Feb. 15, 1999.

Burbaum, Jonathan J. et al., "New Technologies For High-Throughput Screening," Current Opinion in Chemical Biology, vol. 1, pp. 72-78, 1997.

Calkins, Kathryn, "Mycometrix: Rubber Chips," BioCentury, 2 pages, Oct. 16, 2000.

Chayen, Naomi E., "A Novel Technique To Control The Rate Of Vapour Diffusion, Giving Larger Protein Crystals," Journal of Applied Crystallography, vol. 30, pp. 198-202, 1997.

Chayen, Naomi E. et al., "An Automated System For Micro-Batch Protein Crystallization And Screening, " J. Appl. Cryst., vol. 23, pp. 297-302, 1990.

Chayen, Naomi E., "Comparative Studies Of Protein Crystallization By Vapour-Diffusion And Microbatch Techniques," Acta Cryst., vol. D54, pp. 8-15, 1998.

Chayen, Naomi E. et al., "Microbatch Crystallization Under Oil—A New Technique Allowing Many Small-Volume Crystallization Trials," Journal of Crystal Growth, vol. 122, pp. 176-180, 1992.

Chayen, Naomi E. et al., "New Developments Of The IMPAX Small-Volume Automated Crystallization System," Acta Cryst., vol. D50, pp. 456-458, 1994.

Chou, Hou-Pu et al., "A Microfabricated Rotary Pump," Biomedical Microdevices, vol. 3, No. 4, pp. 323-330, 2001.

Chou, Hou-Pu et al., "Integrated Elastomer Fluidic Lab-On-A-Chip-Surface Patterning And DNA Diagnostics," Proceedings of the Solid State Actuator and Sensor Workshop, Hilton Head, South Carolina, 4 pages, 2000.

Chou, Hou-Pu et al., "Multiple Disease Diagnostics On A Single Chip," Biophysics Lab, Caltech, pp. 1-4, Mar. 1, 2000.

Cox, M. Jane et al., "Experiments With Automated Protein Crystallization," J. Appl. Cryst., vol. 20, pp. 386-373, 1987.

Eiselé, Jean-Luc "Preparation Of Protein Crystallization Buffers With A Computer-Controlled Motorized Pipette—PIPEX," J. Appl. Cryst., vol. 26, pp. 92-96, 1993.

Fenna, R. E., "Crystallization Of Human $\alpha$-Lactalbumin," J. Mol. Biol., vol. 161, pp. 211-215, 1982.

Fettinger, J. C. et al., "Stacked Modules For Micro Flow Systems In Chemical Analysis: Concept And Studies Using An Enlarged Model," Sensors and Actuators B, vol. 17, pp. 19-25, 1993.

Folch, A. et al., "Molding Of Deep Polydimethylsiloxane Microstructures For Microfluidics And Biological Applications," Journal of Biomechanical Engineering, vol. 121, pp. 28-34, Feb. 1999.

Fox, Kristin M. et al., "Crystallization Of Old Yellow Enzyme Illustrates An Effective Strategy For Increasing Protein Crystal Size," J. Mol. Biol., vol. 234, pp. 502-507, 1993.

Galambos, Paul et al., "Electrical And Fluidic Packaging Of Surface Micromachined Electro-Microfluidic Devices," 8 pages, no date.

Greene, Chana, "Characterizing The Properties OF PDMS," pp. 1-11, Summer 2000.

Guerin, L. J. et al., "Simple And Low Cost Fabrication Of Embedded Micro-Channels By Using A New Thick-Film Photoplastic," Transducers '97, 1997 International Conference on Solid-State Sensors and Actuators, Chicago, Illinois, pp. 1419-1422, Jun. 18-19, 1997.

Hicks, Jennifer, "Genetics And Drug Discovery Dominate Microarray Research," R&D Magazine, pp. 28-33, Feb. 1999.

Horn, Howard, "Lab Chips Sector: Microtechnologies Are Changing Healthcare And More," Life Sciences, pp. 19-21, Mar. 20, 2001.

Jo, Byung-Ho et al., "Fabrication Of Three-Dimensional Microfluidic Systems By Stacking Molded Polydimethylsiloxane (PDMS) Layers" SPIE, vol. 3877, pp. 222-229, Sep. 1999.

Jo, Byung-Ho et al., "Three-Dimensional Micro-Channel Fabrication In Polydimethylsiloxane (PDMS) Elastomer," Journal of Microelectromechanical Systems, vol. 9, No. 1, pp. 76-81, Mar. 2000.

Kagan, C. R., "Organic-Inorganic Hybrid Materials As Semiconducting Channels in Thin-Film Field-Effect Transistors," Science, vol. 286, pp. 945-947, Oct. 29, 1999.

Kapur, Ravi et al., "Fabrication And Selective Surface Modification Of 3-Dimensionally Textured Biomedical Polymers From Etched Silicon Substrates," Journal of Biomedical Materials Research, vol. 33, pp. 205-216, 1996.

Khoo, Melvin et al., "A Novel Micromachined Magnetic Membrane Microfluid Pump," pp. 1-4, no date.

Kim, Enoch et al., "Polymer Microstructures Formed By Moulding In Capillaries," Nature, vol. 376, pp. 581-584, Aug. 17, 1995.

Kirk-Othmer, "Concise Encyclopedia of Chemical Technology," John Wiley & Sons, 5 pages, no date.

Kumar, Amit et al., "Features of Gold Having Micrometer To Centimeter Dimensions Can Be Formed Through A Combination Of Stamping With An Elastomeric Stamp And An Alkanethiol 'Ink' Followed By Chemical Etching," Appl. Phys. Lett., vol. 63, No. 14, pp. 2002-2004, Oct. 4, 1993.

Kumar, Amit et al., "Patterning Self-Assembled Monolayers: Applications In Materials Science," Langmuir, vol. 10, pp. 1498-1511, 1994.

Kwong, Peter D. et al., "Probability Analysis Of Variational Crystallization And Its Application To gp120, the Exterior Envelope Glycoprotein Of Type 1 Human Immunodeficiency Virus (HIV-1)," Journal of Biological Chemistry, vol. 274, No. 7, pp. 4115-4123, Feb. 12, 1999.

Kwong, Peter D. et al., "Structure Of An HIV gp 120 Envelope Glycoprotein In Complex With The CD4 Receptor And A Neutralizing Human Antibody," Nature, vol. 393, pp. 648-659, Jun. 18, 1998.

Lagally, Eric T. et al., "Monolithic Integrated Microfluidic DNA Amplification And Capillary Electrophoresis Analysis System," Sensors and Actuators B, vol. 63, pp. 138-146, 2000.

Lagally, E. T. et al., "Single-Molecule DNA Amplification And Analysis In An Integrated Microfluidic Device," Analytical Chemistry, vol. 73, No. 3, pp. 565-570, Feb. 1, 2001.

Lammerink, T. S. J. et al., "Modular Concept For Fluid Handling Systems," IEEE, pp. 389-394, 1996.

Li, Paul C. H. et al., "Transport, Manipulation, And Reaction Of Biological Cells On-Chip Using Electrokinetic Effects," Analytical Chemistry, vol. 69, No. 8, pp. 1564-1568, Apr. 15, 1997.

Licklider, Larry et al., "A Micromachined Chip-Based Electrospray Source For Mass Spectrometry," Analytical Chemistry, vol. 72, No. 2, pp. 367-375, Jan. 15, 2000.

Luft, Joseph R. et al., "A Method To Produce Microseed Stock For Use in The Crystallization Of Biological Macromolecules," Acta Cryst., vol. D55, pp. 988-993, 1999.

Luft, Joseph R. et al., "Macromolecular Crystallization In A High Throughput Laboratory—The Search Phase," Journal of Crystal Growth, vol. 232, pp. 591-595, 2001.

Manz, A. et al., "Micromachining Of Monocrystalline Silicon And Glass For Chemical Analysis Systems," Trends in Analytical Chemistry, vol. 10, No. 5, pp. 144-149, 1991.

Marshall, SID, "Fundamental Changes Ahead For Lab Instrumentation," R&D Magazine, 5 pages, Feb. 1999.

Marsili, Ray, "Lab-On-A-Chip Poised To Revolutionize Sample Prep," R&D Magazine, 5 pages, Feb. 1999.

McDonald, J. Cooper et al., "Fabrication Of Microfluidic Systems In Poly(dimethylsiloxane)," Electrophoresis, vol. 21, pp. 27-40, 2000.

Morris, Daniel W. et al., "Automation Of Protein Crystallization Trials: Use Of A Robot To deliver Reagents To a Novel Multi-Chamber Vapor Diffusion Plate," BioTechniques, vol. 7, No. 5, pp. 522-527, 1989.

Oldfield, T. J. et al., "A Flexible Approach To Automated Protein Crystallization," J. Appl. Cryst., vol. 24, pp. 255-260, 1991.

Oleschuk, Richard D. et al., "Analytical Microdevices For Mass Spectrometry," Trends In Analytical Chemistry, vol. 19, No. 6., pp. 379-388, 2000.

Reshetnyak, I. I., "Characteristics Of The Influence Of Ultrasound On The Crystallization Kinetics In Small-Volume Solutions," Sov. Phys. Acoust., vol. 21, No. 1, pp. 61-63, Jul. 1975.

Rubin, Byron et al., "Minimal Intervention Robotic Protein Crystallization," Journal of Crystal Growth, vol. 110, pp. 156-163, 1991.

Rummel, Gabriele et al., "Lipidic Cubic Phases: New Matrices For The Three-Dimensional Crystallization Of Membrane Proteins," Journal of Structural Biology, vol. 121, pp. 82-91, 1998.

Sadaoui, Nouredine et al., "TAOS: An Automatic System For Protein Crystallization," Journal of Applied Crystallization, vol. 27, pp. 622-626, 1994.

Snook, Christopher F. et al., "Use Of A Crystallization Robot To Set Up Sitting-Drop Vapor-Diffusion Crystallization And in situ Crystallization Screens," Journal of Applied Crystallography, vol. 33, pp. 344-349, 2000.

Soriano, Thierry M. B. et al., "ASTEC: An Automated System For Sitting-Drop Protein Crystallization," Journal of Applied Crystallography, vol. 26, pp. 558-562, 1993.

Stevens, Raymond C., "High-Throughput Protein Crystallization," Current Opinion in Structural Biology, vol. 10, pp. 558-563, 2000.

Thompson, L.F. et al., "Introduction To Microlithography," 185th Meeting of the American Chemical Society, Seattle, WA, pp. 2 cover pages, 1-13, Mar. 20-25, 1983.

Todd, Paul et al., "Application Of Osmotic Dewatering To The Controlled Crystallization Of Biological Macromolecules And Organic Compounds," Journal of Crystal Growth, vol. 110, pp. 283-292, 1991.

Van Den Berg, A. et al., "Micro Total Analysis Systems," Proceedings of the µTAS '94 Workshop, University of Twente, The Netherlands, 17 pages, Nov. 21-22, 1994.

Verpoorte, Elisabeth M. J. et al., "Three-Dimensional Micro Flow Manifolds For Miniaturized Chemical Analysis Systems," J. Micromech. Microeng., vol. 7, pp. 246-256, 1994.

Vogelstein, Bert et al., "Digital PCR," Proc. Natl. Acad. Sci. USA, vol. 96, pp. 9236-9241, Aug. 1999.

Whelen, A. Christian et al., "The Role Of Nucleic Acid Amplification And Detection In The Clinical Microbiology Laboratory," Annu. Rev. Microbiol., vol. 50, pp. 349-373, 1996.

Whitesides, George M. et al., "Soft Lithography In Biology And Biochemistry," Annu. Rev. Biomed. Eng., vol. 3, pp. 335-373, 2001.

Wiencek, J. M., et al., "New Strategies For Protein Crystal Growth," Annu. Rev. Biomed. Eng., vol. 1, pp. 505-534, 1999.

Wilbur, James L. et al., "Lithographic Molding: A Convenient Route To Structures With Sub-Micrometer Dimensions," Adv. Mater., vol. 7, No. 7, pp. 649-652, 1995.

Xia, Younan et al., "Reduction In The Size Of Features Of Patterned SAMs Generated By Microcontact Printing With Mechanical Compression Of The Stamp," Adv. Mater., vol. 7, No. 5, pp. 471-473, 1995.

Xu, Bing et al., "Making Negative Poisson's Ratio Microstructures By Soft Lithography," Adv. Mater., vol. 11, No. 14, pp. 1186-1189, 1999.

Yang, Xing et al., "A Low Power MEMS Silicone/Parylene Valve," Solid-State Sensor and Actuator Workshop, Hilton Head Island, South Carolina, 4 pages, Jun. 7-11, 1998.

Zampighi, G. et al., "Structural Organization Of $(Na^+ + K^+)$-ATPase In Purified Membranes," Journal of Cell Biology, vol. 98, pp. 1851-1864, May 1984.

* cited by examiner

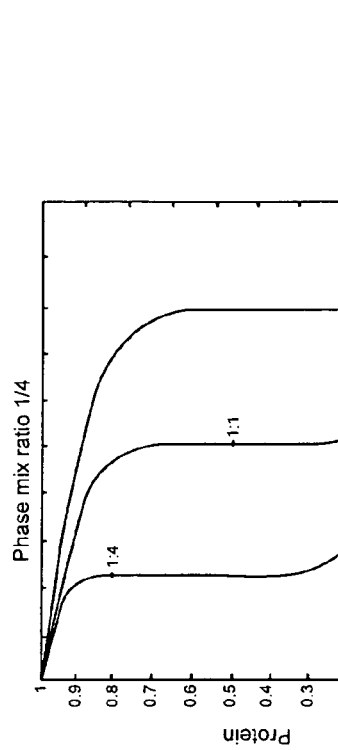
FIG. 42
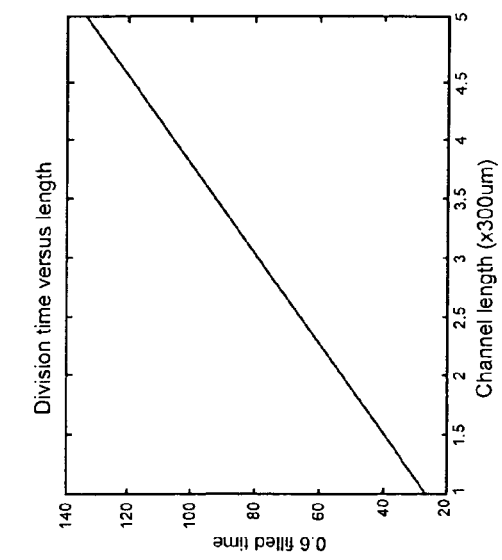
FIG. 43
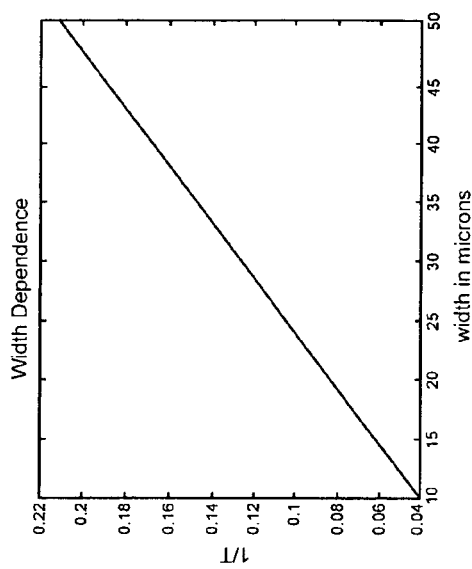
FIG. 40A
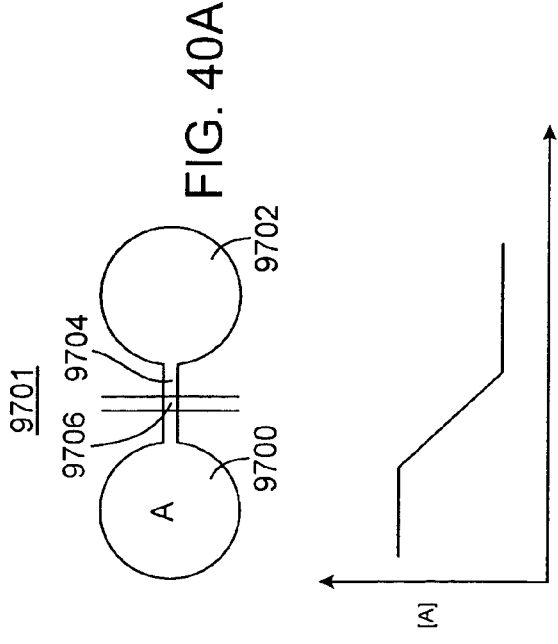
FIG. 40B
FIG. 41

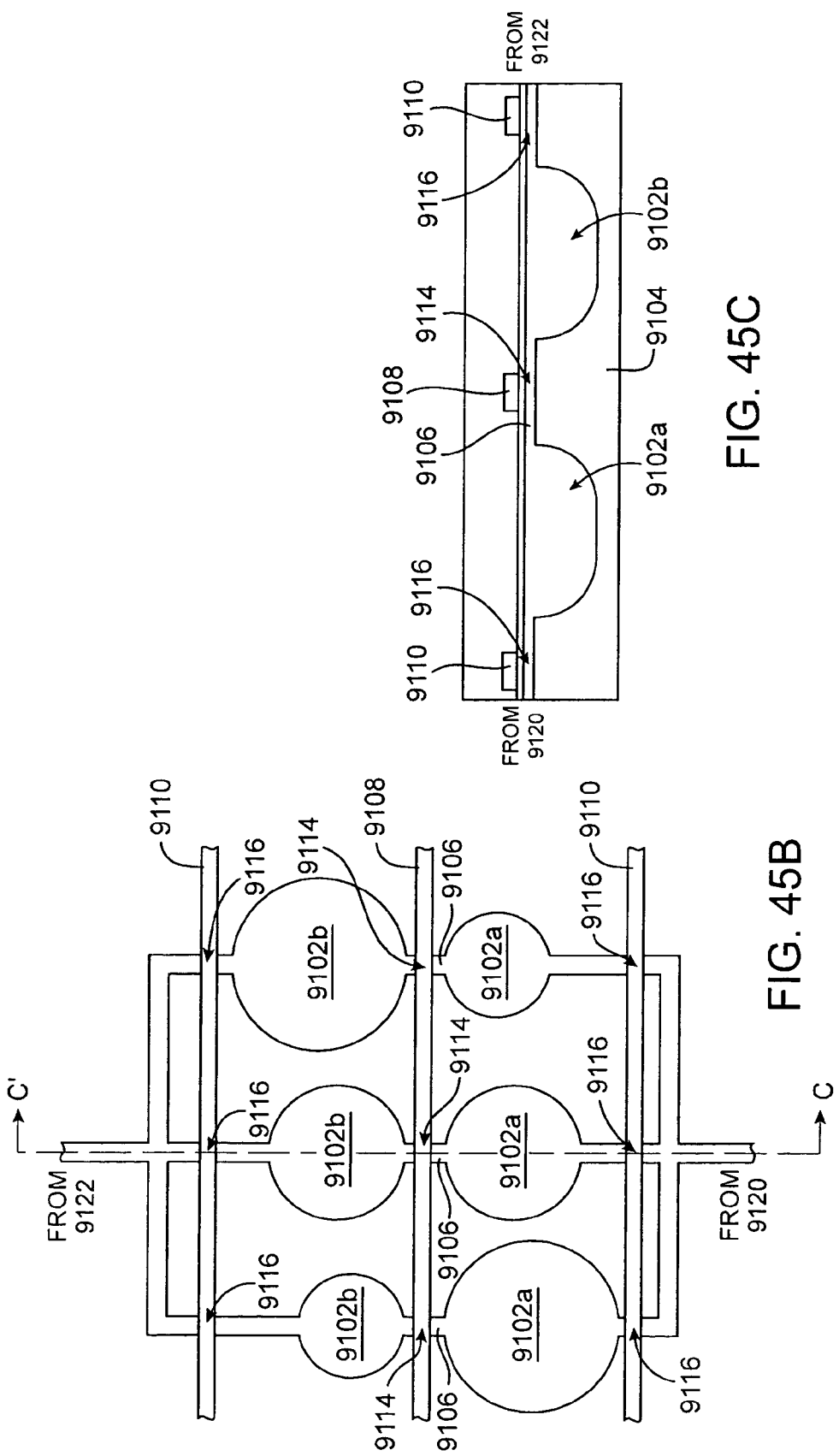

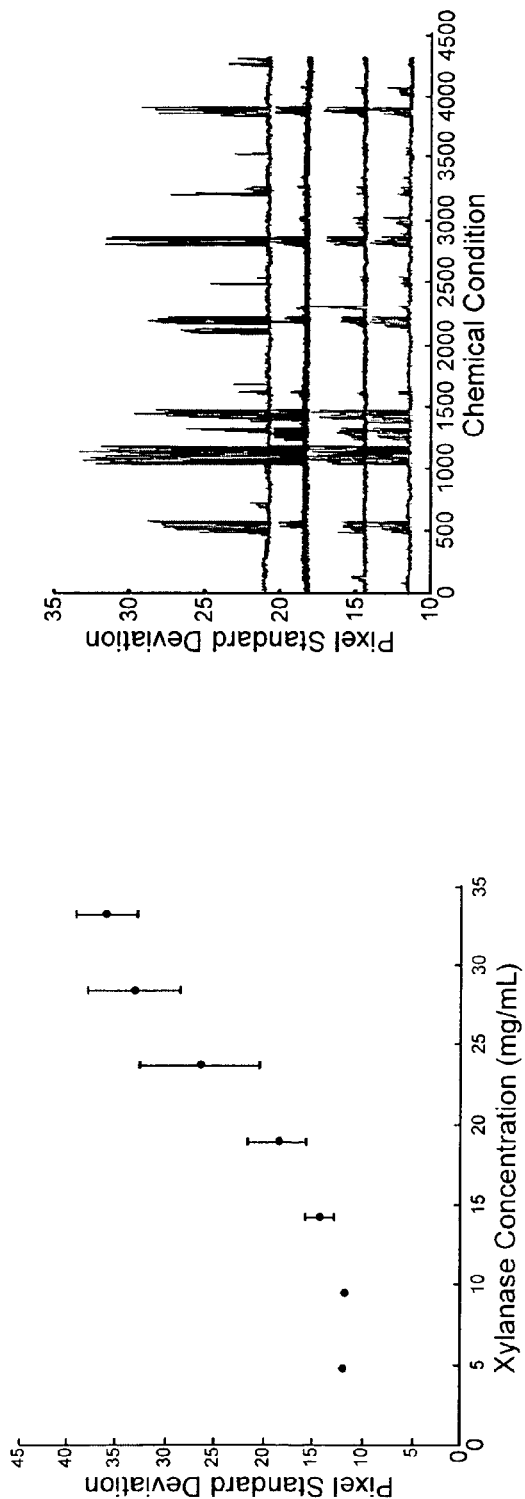
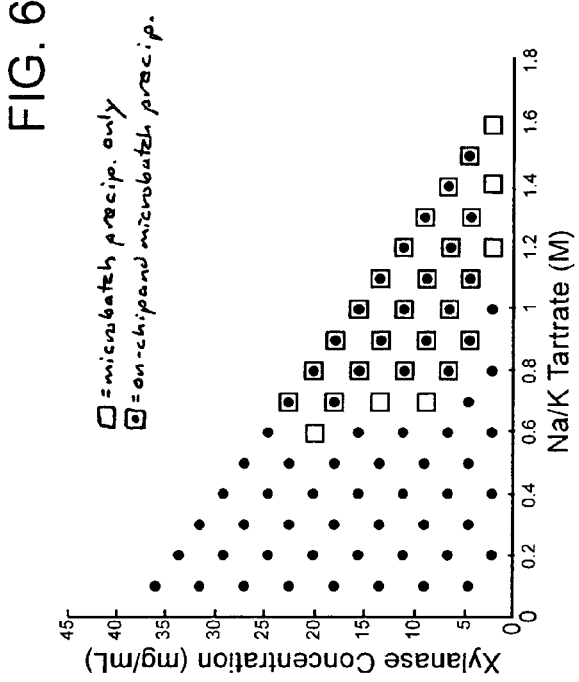
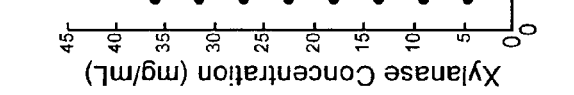
FIG. 65A
FIG. 65B
FIG. 65C

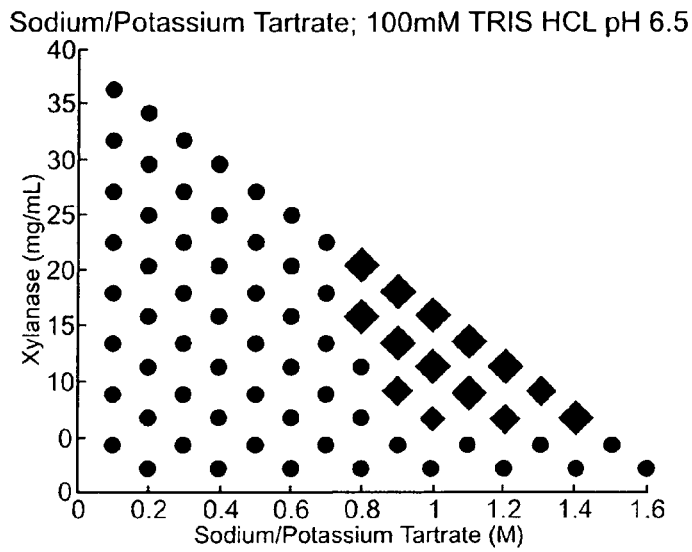
FIG. 65C1
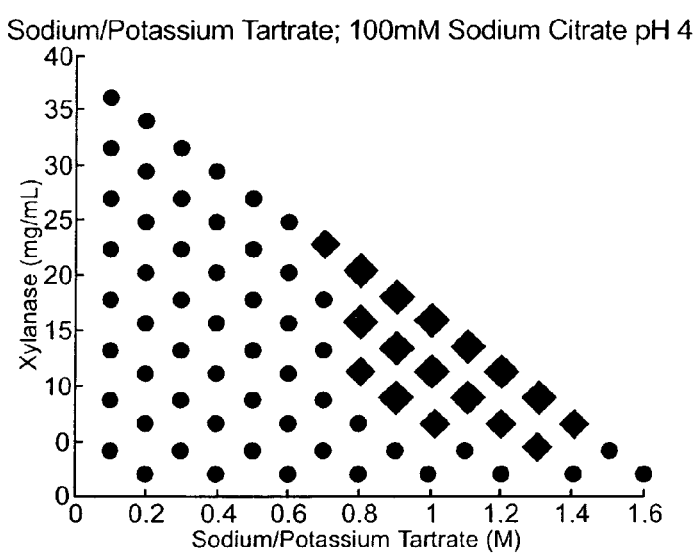
FIG. 65C2
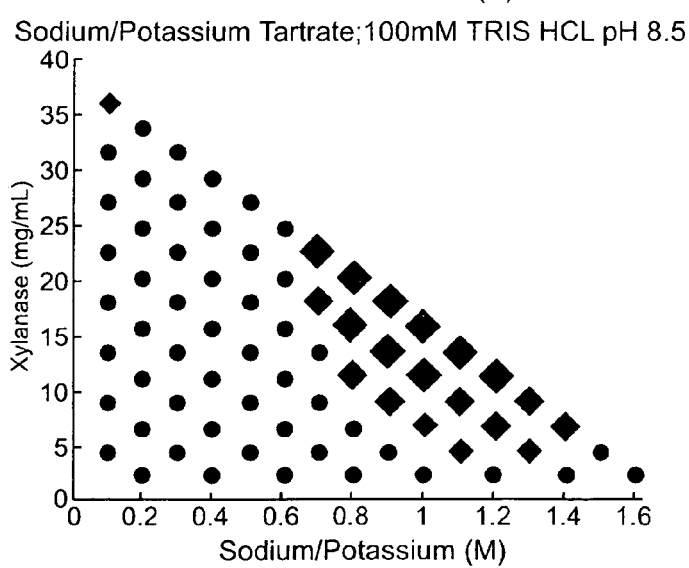
FIG. 65C3

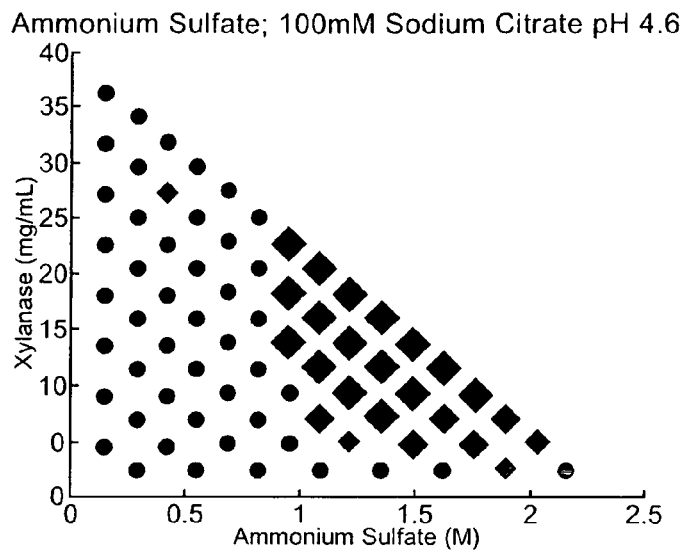
FIG. 65C4
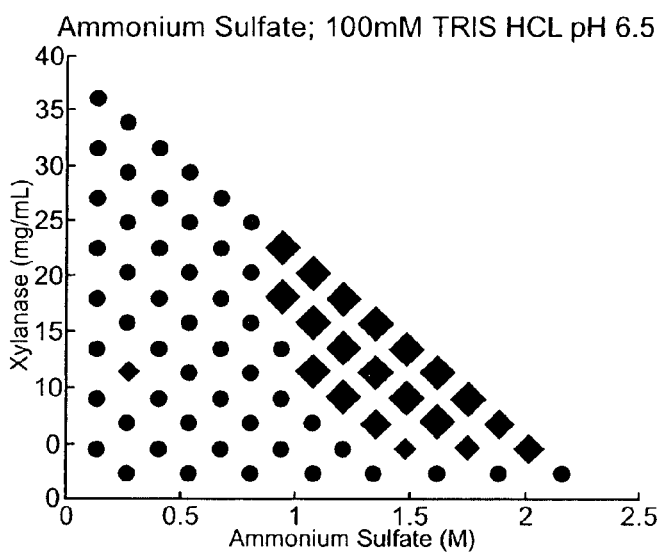
FIG. 65C5
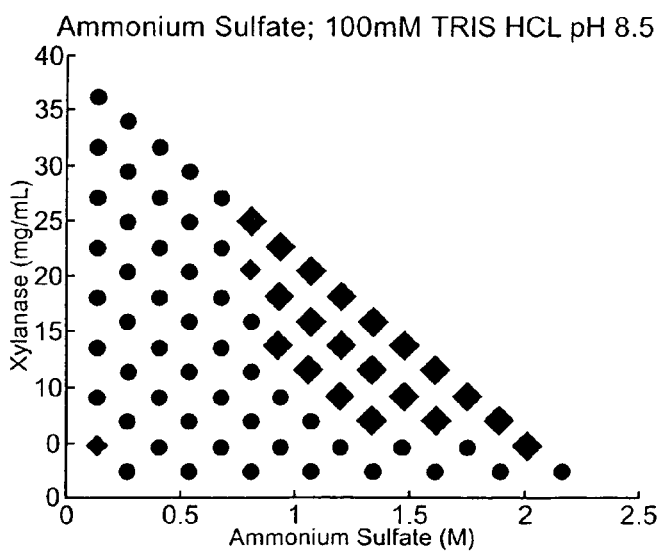
FIG. 65C6

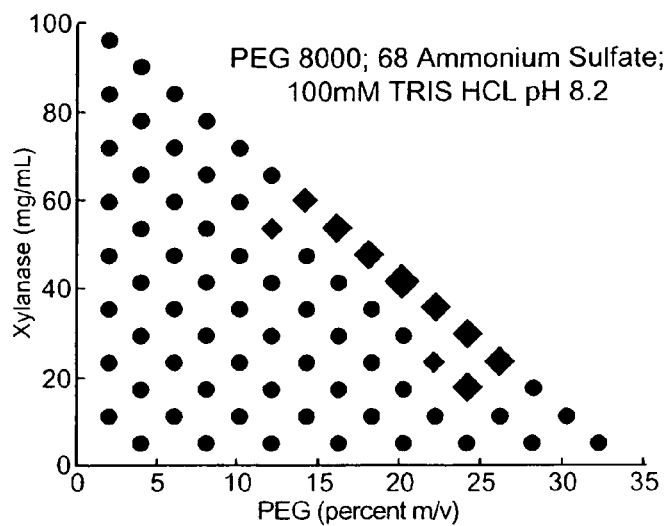
FIG. 65C7
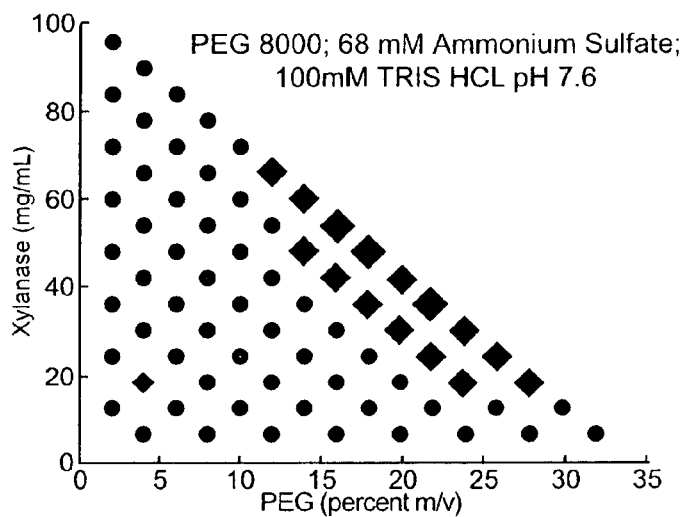
FIG. 65C8
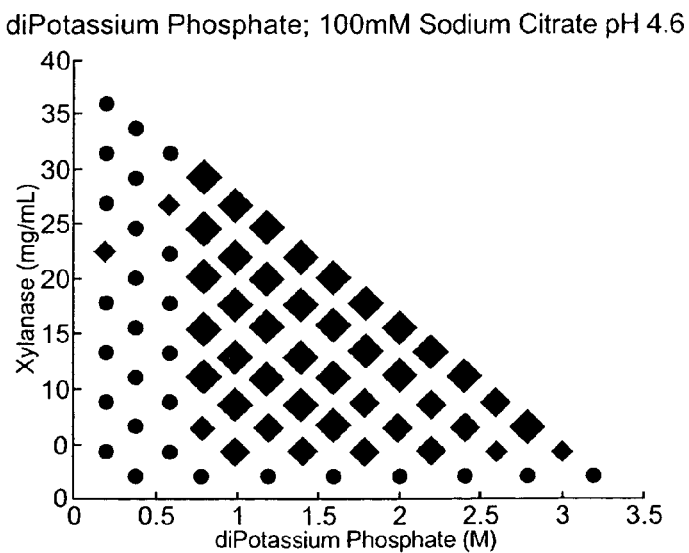
FIG. 65C9

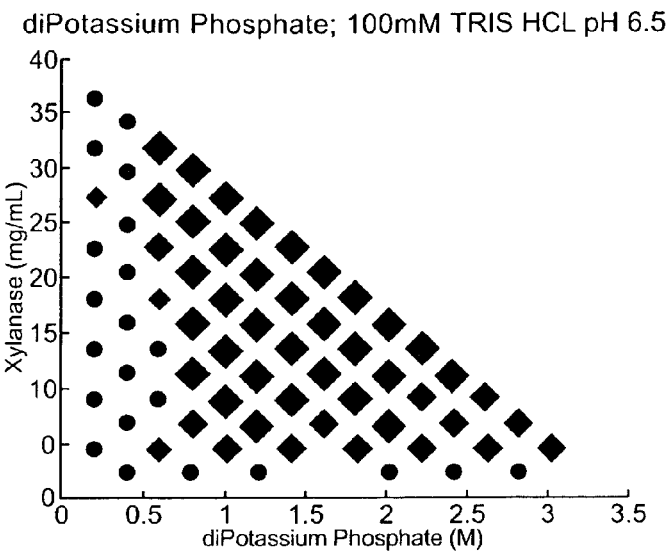
FIG. 65C10
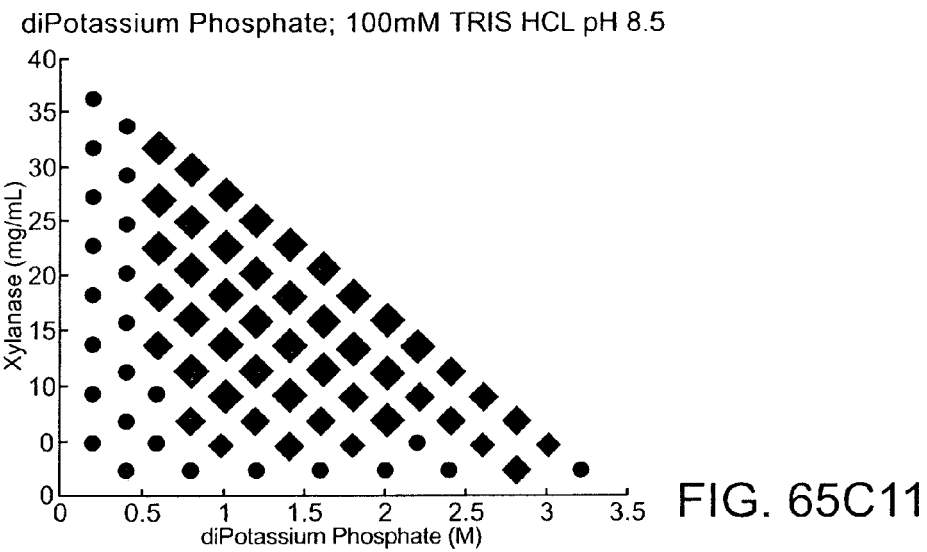
FIG. 65C11
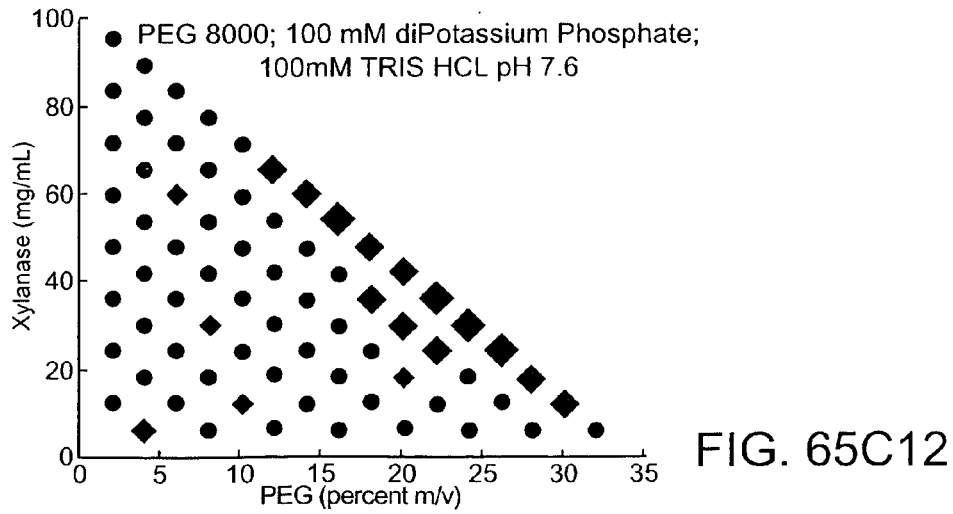
FIG. 65C12

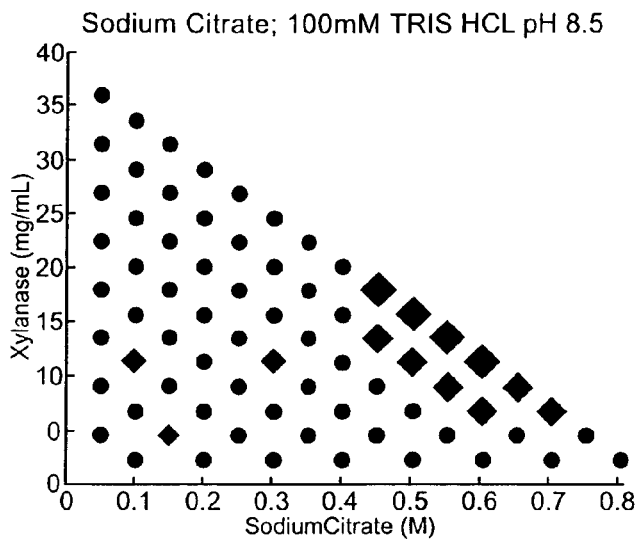
FIG. 65C13
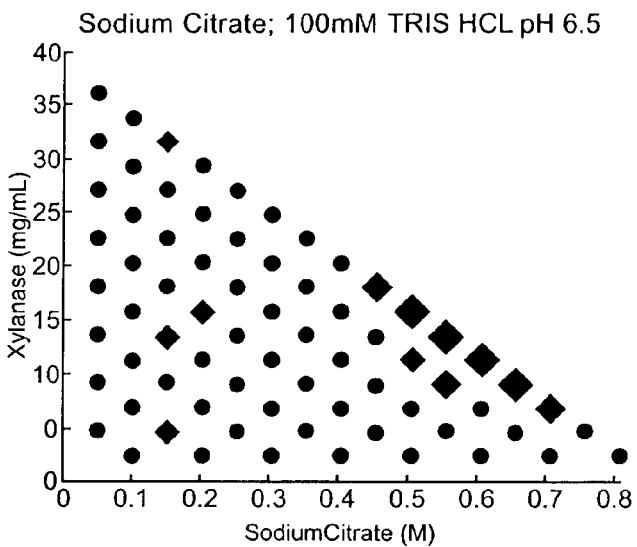
FIG. 65C14
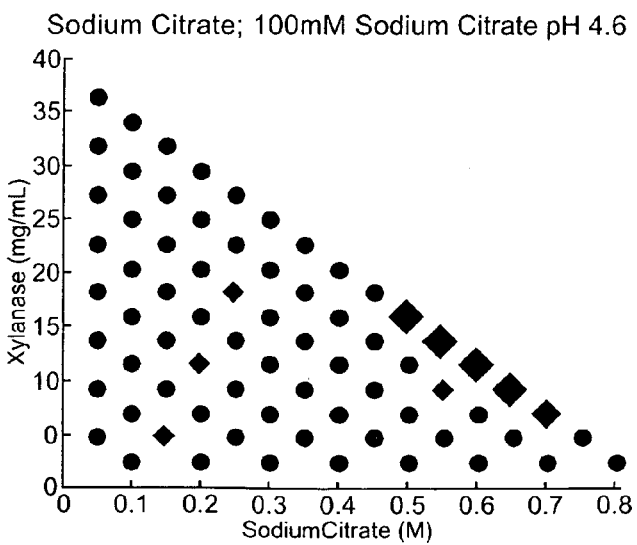
FIG. 65C15

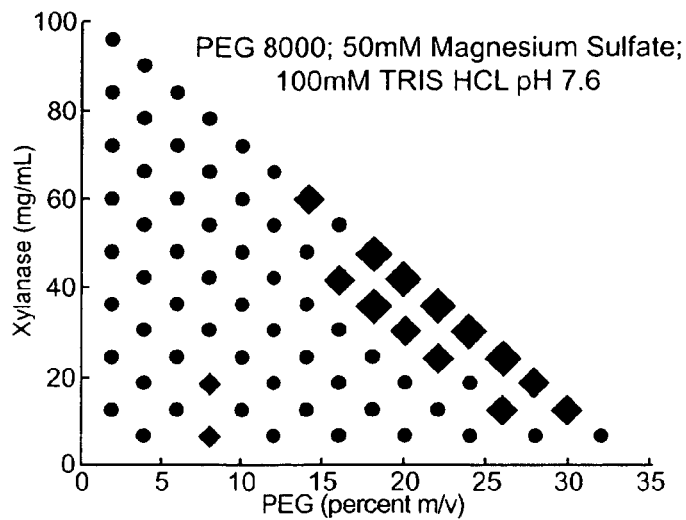
FIG. 65C16
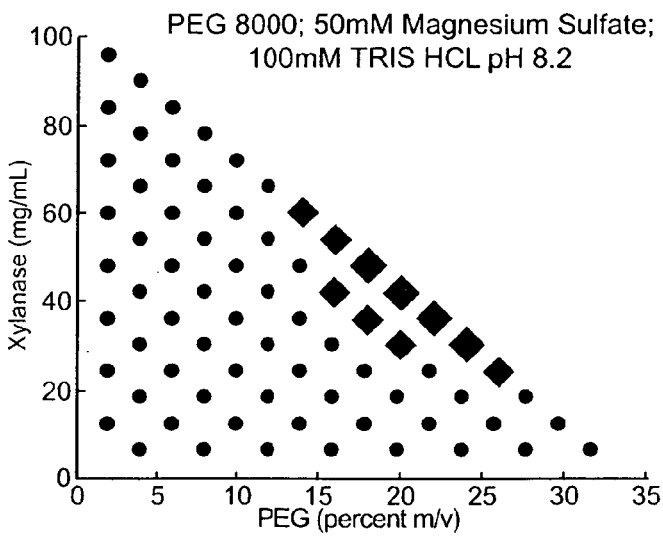
FIG. 65C17
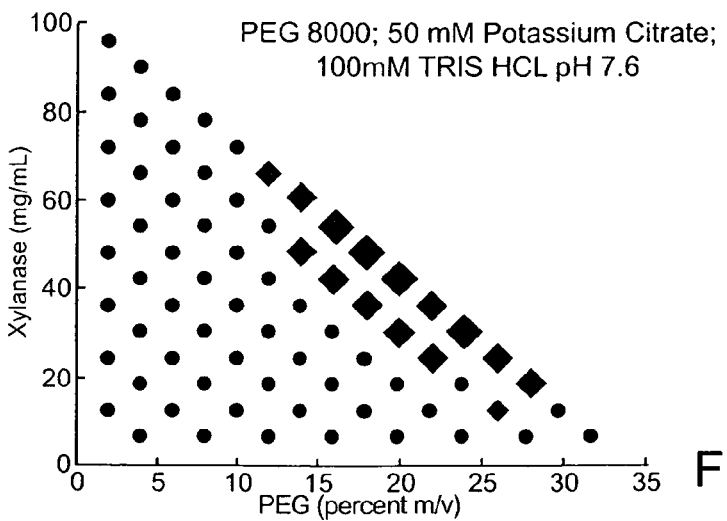
FIG. 65C18

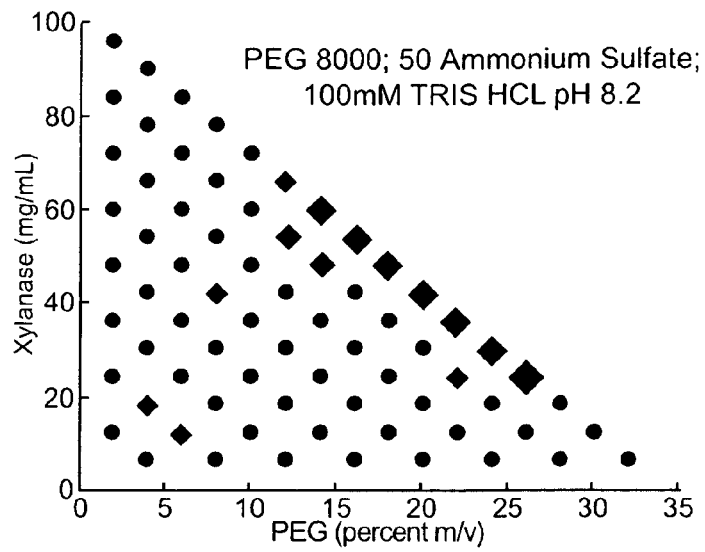
FIG. 65C19
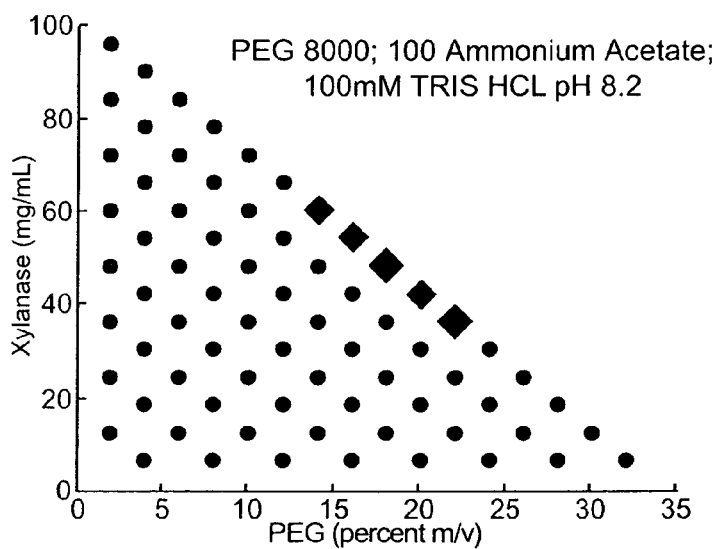
FIG. 65C20
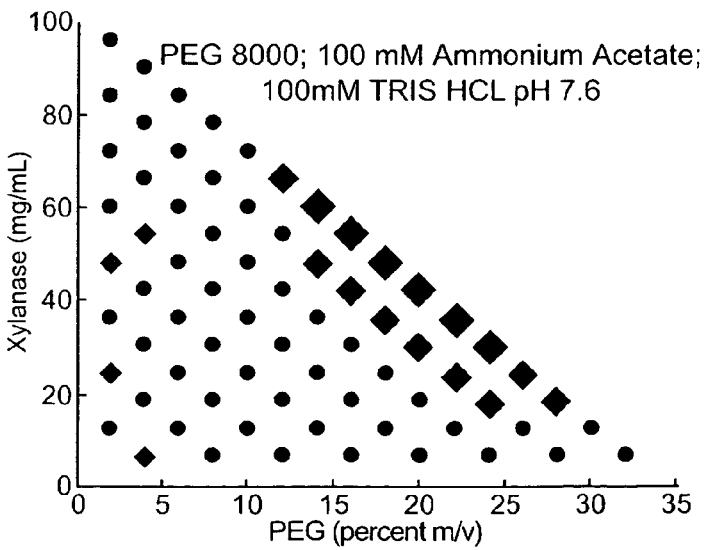
FIG. 65C21

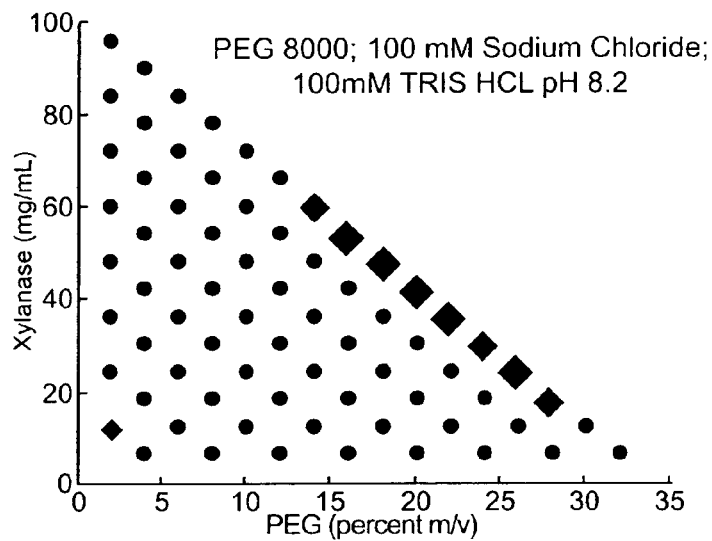
FIG. 65C22
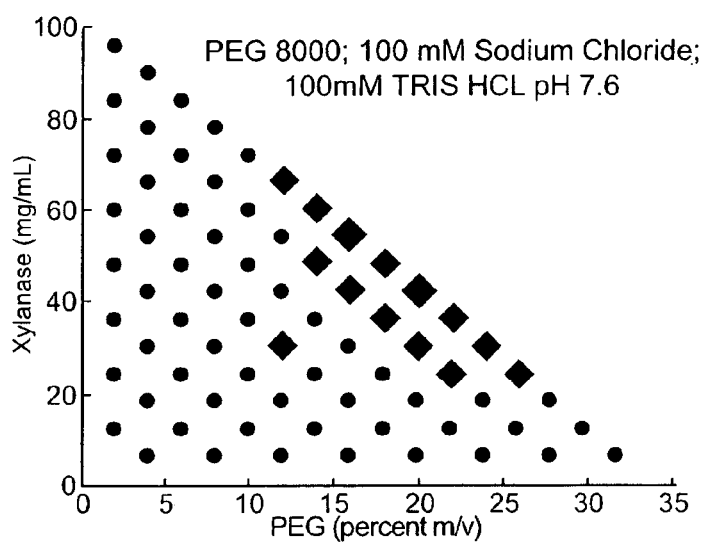
FIG. 65C23
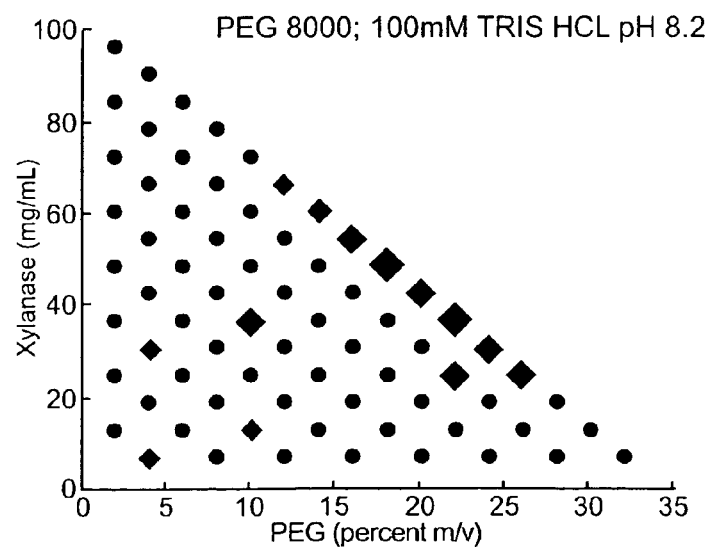
FIG. 65C24

FIG. 68
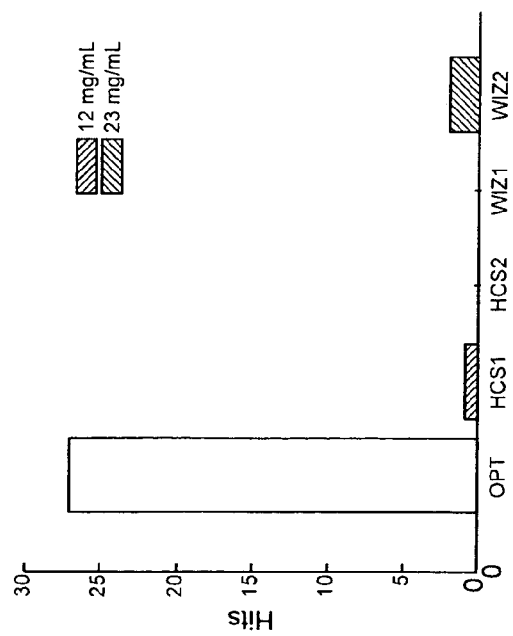
FIG. 67
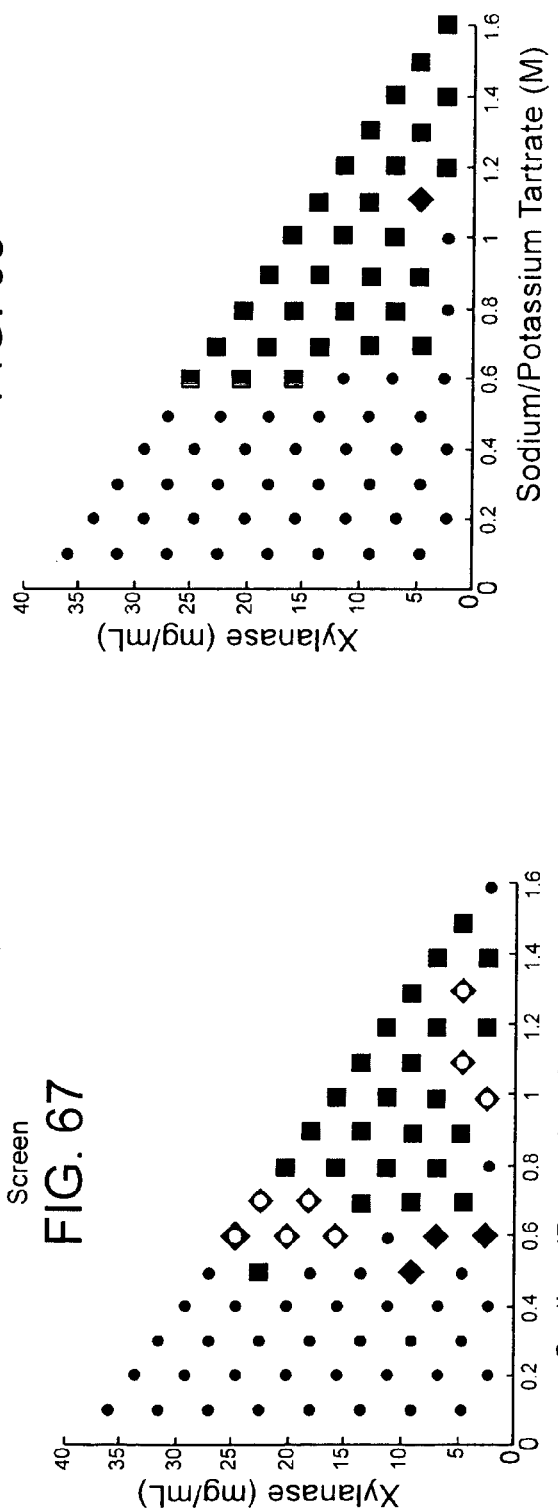
FIG. 69B
FIG. 69A

MICROFLUIDIC PROTEIN CRYSTALLOGRAPHY

CROSS-REFERENCE TO RELATED APPLICATIONS

The instant nonprovisional patent application claims priority to U.S. provisional patent application No. 60/572,060, filed May 18, 2004. The instant patent application is also a continuation-in-part of U.S. nonprovisional patent application Ser. No. 10/637,847, filed Aug. 7, 2003, which is a continuation-in-part of U.S. nonprovisional patent application Ser. No. 10/117,978, filed Apr. 5, 2002, which claims priority as a nonprovisional application from U.S. provisional patent application No. 60/323,524 filed Sep. 17, 2001, and which is also a continuation-in-part of U.S. nonprovisional application Ser. No. 09/887,997 filed Jun. 22, 2001, which is in turn a continuation-in-part of U.S. nonprovisional patent application Ser. No. 09/826,583 filed Apr. 6, 2001. The U.S. nonprovisional patent application Ser. No. 10/637,847 is also a continuation-in-part of U.S. nonprovisional patent application Ser. No. 10/265,473, filed Oct. 4, 2002, and further claims priority from U.S. provisional patent application No. 60/447,157 filed Feb. 12, 2003, and from U.S. provisional patent application No. 60/433,160 filed Dec. 13, 2002. Each of these prior patent applications are hereby incorporated by reference for all purposes.

STATEMENT AS TO RIGHTS TO INVENTIONS MADE UNDER FEDERALLY SPONSORED RESEARCH AND DEVELOPMENT

Work described herein has been supported, in part, by NSF (xyz in a chip program); National Institute of Health grant CA 77373; NSERC (Julie Payette Fellowship); David H. & Lucille M. Packard Foundation; and G. Harold and Leila Y. Mathers Charitable Foundation. Work described herein has also been supported in part by National Science Foundation Grant No. CTS 0088649, National Institutes of Health Grant Nos. CA 77373 and HG 1642-$O_2$, and Army Research Office Grant No. DAAD19-00-1-0392 awarded by DARPA. The United States Government may have certain rights in the invention.

BACKGROUND OF THE INVENTION

Crystallization is an important technique to the biological and chemical arts. Specifically, a high-quality crystal of a target compound can be analyzed by x-ray diffraction techniques to produce an accurate three-dimensional structure of the target. This three-dimensional structure information can then be utilized to predict functionality and behavior of the target.

In theory, the crystallization process is simple. A target compound in pure form is dissolved in solvent. The chemical environment of the dissolved target material is then altered such that the target is less soluble and reverts to the solid phase in crystalline form. This change in chemical environment typically accomplished by introducing a crystallizing agent that makes the target material is less soluble, although changes in temperature and pressure can also influence solubility of the target material.

In practice however, forming a high quality crystal is generally difficult and sometimes impossible, requiring much trial and error and patience on the part of the researcher. Specifically, the highly complex structure of even simple biological compounds means that they are not amenable to forming a highly ordered crystalline structure. Therefore, a researcher must be patient and methodical, experimenting with a large number of conditions for crystallization, altering parameters such as sample concentration, solvent type, countersolvent type, temperature, and duration in order to obtain a high quality crystal, if in fact a crystal can be obtained at all.

Accordingly, there is a need in the art for methods and structures for performing high throughput screening of crystallization of target materials.

SUMMARY OF THE INVENTION

The use of microfluidic structures enables high throughput screening of protein crystallization. In one embodiment, an integrated combinatoric mixing chip allows for precise metering of reagents to rapidly create a large number of potential crystallization conditions, with possible crystal formations observed on the chip. In an alternative embodiment, the microfluidic structures may be utilized to explore phase space conditions of a particular protein crystallizing agent combination, thereby identifying promising conditions and allowing for subsequent focused attempts to obtain crystal growth.

An embodiment of a method in accordance with the present invention of crystallization, comprises, utilizing a microfludic formulator device to generate a solubility fingerprint of a crystallization target over a range of conditions, and utilizing the microfluidic formulator to map phase space around those conditions of the solubility fingerprint resulting in precipitation of the crystallization target.

Another embodiment of a crystallization method in accordance with the present invention, comprises, empirically determining a solubility curve for a crystallization target mixed with a precipitant utilizing a microfluidic device, and mixing the crystallization target with the precipitant at a ratio that places a final concentration of the crystallization target and the precipitant on a boundary of the solubility curve.

An embodiment of an apparatus in accordance with the present invention for investigating crystallization, comprises, a microfluidic formulator comprising a microfluidic chamber configured to receive a crystallization target and a precipitant, a light source configured to illuminate the microfluidic chamber, and a light detector configured to receive light transmitted through the microfluidic chamber.

These and other embodiments of the present invention, as well as its advantages and features, are described in more detail in conjunction with the text below and attached figures.

BRIEF DESCRIPTION OF THE DRAWINGS

FIG. 40A shows a plan view of a simple embodiment of a microfluidic structure in accordance with the present invention.

FIG. 40B is a simplified plot of concentration versus distance for the structure of FIG. 40A.

FIG. 41 plots the time required for the concentration in one of the reservoirs of FIG. 40 to reach 0.6 of the final equilibration concentration, versus channel length.

FIG. 42 plots the inverse of the time required for the concentration in one of the reservoirs to reach 0.6 of the final equilibration concentration ($T_{0.6}$), versus the area of the fluidic interface of FIG. 40.

FIG. 43 presents a phase diagram depicting the phase space between fluids A and B, and the path in phase space traversed in the reservoirs as the fluids diffuse across the microfluidic free interface of FIG. 40

FIG. 45B shows as simplified enlarged plan view of a set of three compound wells of the chip shown in FIG. 45A.

FIG. 45C shows a simplified cross-sectional view of the compound wells of FIGS. 45A-B.

FIG. 65A plots pixel standard deviation versus xylanase concentration.

FIG. 65B plots pixel standard deviation versus a number of chemical conditions.

FIGS. 65C1-24 plot Xylanase phase for protein concentration versus concentration of a first precipitant stock, under a variety of different conditions.

FIG. 65D is a simplified schematic plot of xylanase phase space over different relative protein/salt concentrations for on-chip and microbatch.

FIG. 67 is a histogram showing number of successful crystallization conditions identified with sparse matrix screens (each at protein concentrations of 12 mg/mL and 23 mg/mL) and optimal screen.

FIG. 68 is a polarized micrograph of large single crystals grown directly from optimal screen.

FIGS. 69A and 69B plot phase space behavior for different samples of Xylanase under microbatch conditions.

DETAILED DESCRIPTION OF THE PRESENT INVENTION

I. Microfabrication Overview

The following discussion relates to formation of microfabricated fluidic devices utilizing elastomer materials, as described generally in U.S. patent application Ser. No. 09/826,585 filed Apr. 6, 2001, Ser. No. 09/724,784 filed Nov. 28, 2000, and Ser. No. 09/605,520, filed Jun. 27, 2000. These patent applications are hereby incorporated by reference.

1. Methods of Fabricating

Exemplary methods of fabricating the present invention are provided herein. It is to be understood that the present invention is not limited to fabrication by one or the other of these methods. Rather, other suitable methods of fabricating the present microstructures, including modifying the present methods, are also contemplated.

FIGS. 1 to 7B illustrate sequential steps of a first preferred method of fabricating the present microstructure, (which may be used as a pump or valve). FIGS. 8 to 18 illustrate sequential steps of a second preferred method of fabricating the present microstructure, (which also may be used as a pump or valve).

As will be explained, the preferred method of FIGS. 1 to 7B involves using pre-cured elastomer layers which are assembled and bonded. In an alternative method, each layer of elastomer may be cured "in place". In the following description "channel" refers to a recess in the elastomeric structure which can contain a flow of fluid or gas.

Figure 1:
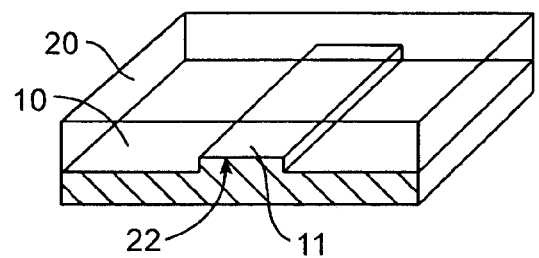
FIG. 1 is an illustration of a first elastomeric layer formed on top of a micromachined mold.

Referring to FIG. 1, a first micro-machined mold 10 is provided. Micro-machined mold 10 may be fabricated by a number of conventional silicon processing methods, including but not limited to photolithography, ion-milling, and electron beam lithography.

As can be seen, micro-machined mold 10 has a raised line or protrusion 11 extending therealong. A first elastomeric layer 20 is cast on top of mold 10 such that a first recess 21 will be formed in the bottom surface of elastomeric layer 20, (recess 21 corresponding in dimension to protrusion 11), as shown.

Figure 2:
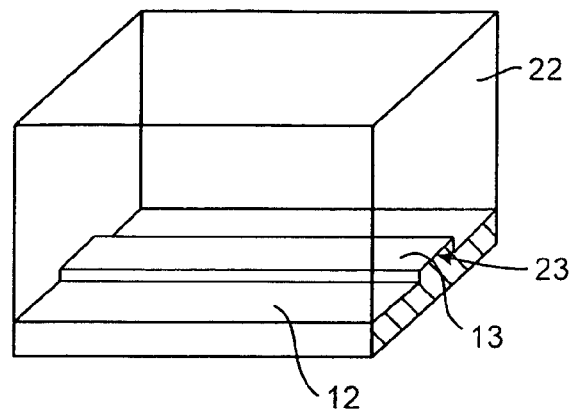
FIG. 2 is an illustration of a second elastomeric layer formed on top of a micromachined mold.

As can be seen in FIG. 2, a second micro-machined mold 12 having a raised protrusion 13 extending therealong is also provided. A second elastomeric layer 22 is cast on top of mold 12, as shown, such that a recess 23 will be formed in its bottom surface corresponding to the dimensions of protrusion 13.

Figure 3:
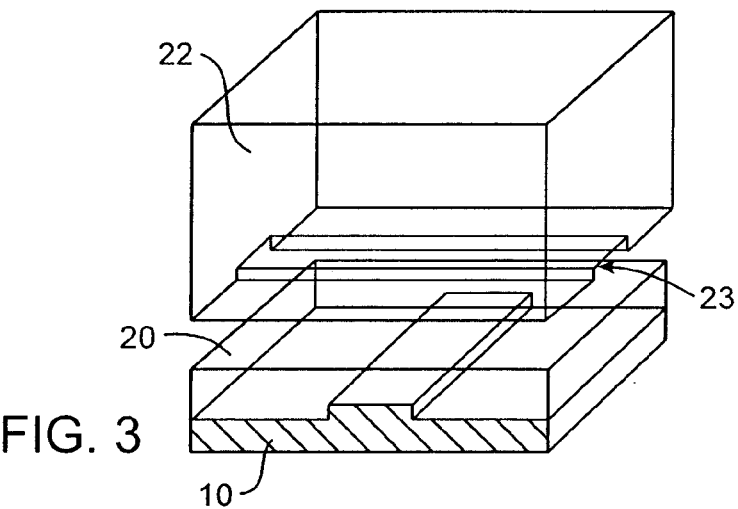
FIG. 3 is an illustration of the elastomeric layer of FIG. 2 removed from the micromachined mold and positioned over the top of the elastomeric layer of FIG. 1
Figure 4:
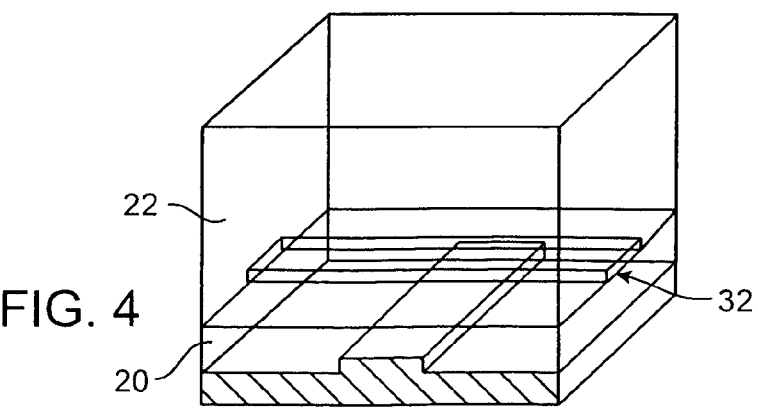
FIG. 4 is an illustration corresponding to FIG. 3, but showing the second elastomeric layer positioned on top of the first elastomeric layer.

As can be seen in the sequential steps illustrated in FIGS. 3 and 4, second elastomeric layer 22 is then removed from mold 12 and placed on top of first elastomeric layer 20. As can be seen, recess 23 extending along the bottom surface of second elastomeric layer 22 will form a flow channel 32.

Figure 5:
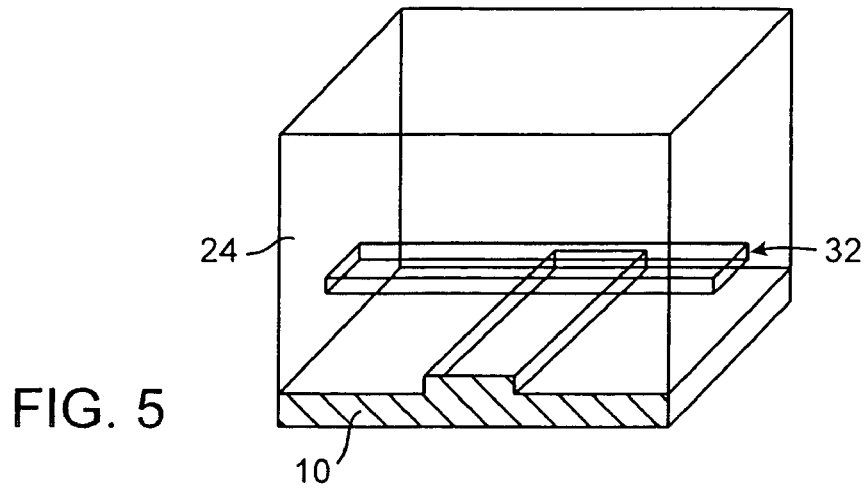
FIG. 5 is an illustration corresponding to FIG. 4, but showing the first and second elastomeric layers bonded together.

Referring to FIG. 5, the separate first and second elastomeric layers 20 and 22 (FIG. 4) are then bonded together to form an integrated (i.e.: monolithic) elastomeric structure 24.

Figure 6:
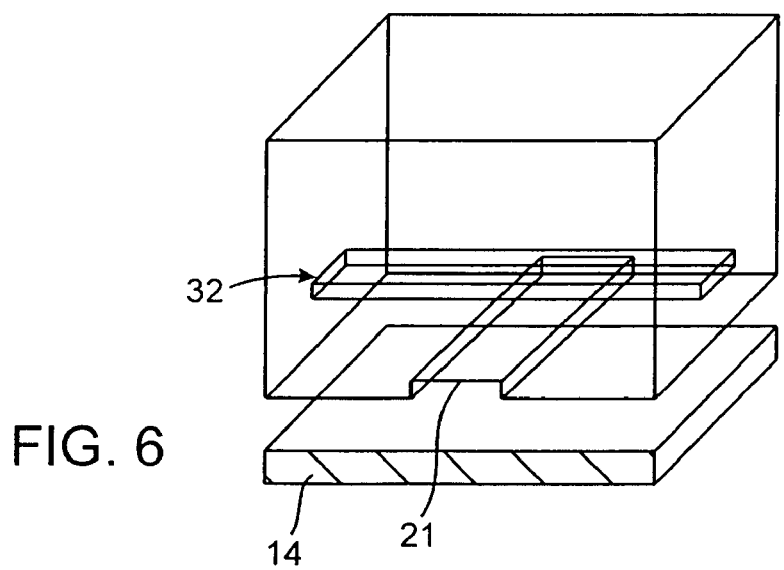
FIG. 6 is an illustration corresponding to FIG. 5, but showing the first micromachined mold removed and a planar substrate positioned in its place.
Figure 7A:
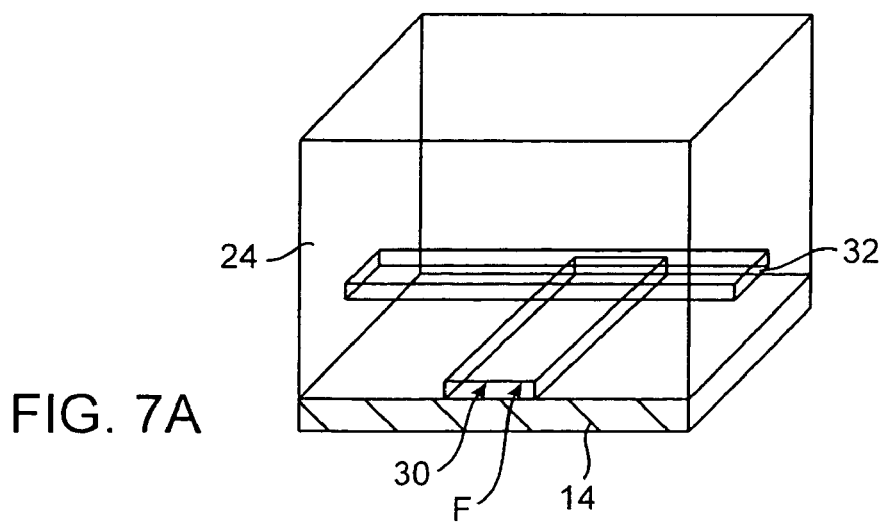
FIG. 7A is an illustration corresponding to FIG. 6, but showing the elastomeric structure sealed onto the planar substrate.
Figure 7B:
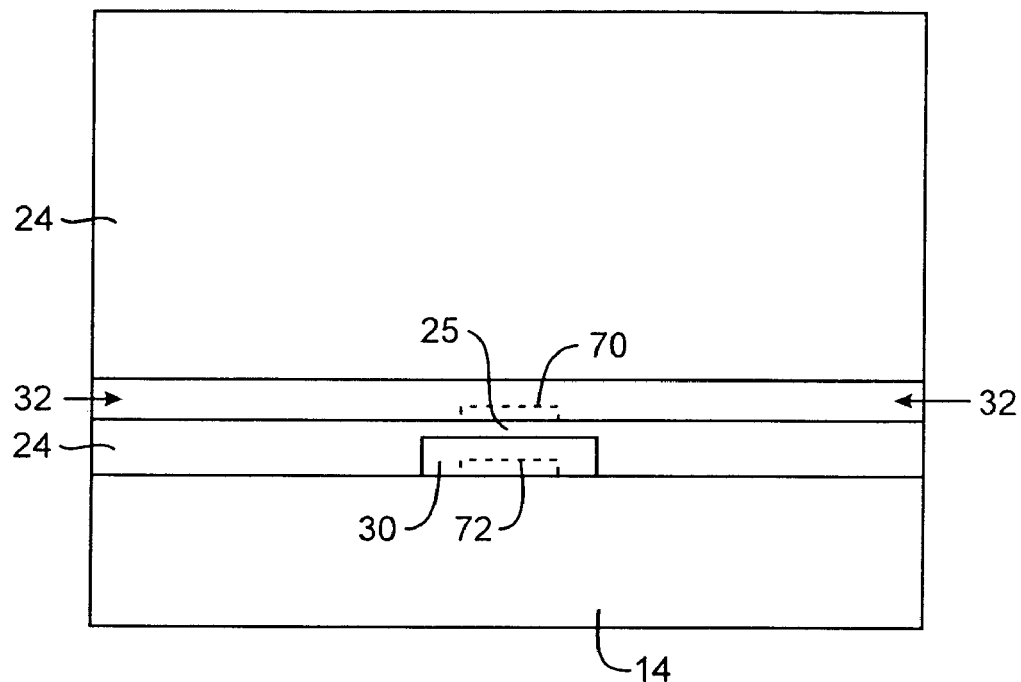
FIG. 7B is a front sectional view corresponding to FIG. 7A, showing an open flow channel.

As can been seen in the sequential step of FIGS. 6 and 7A, elastomeric structure 24 is then removed from mold 10 and positioned on top of a planar substrate 14. As can be seen in FIGS. 7A and 7B, when elastomeric structure 24 has been sealed at its bottom surface to planar substrate 14, recess 21 will form a flow channel 30.

The present elastomeric structures form a reversible hermetic seal with nearly any smooth planar substrate. An advantage to forming a seal this way is that the elastomeric structures may be peeled up, washed, and re-used. In preferred aspects, planar substrate 14 is glass. A further advantage of using glass is that glass is transparent, allowing optical interrogation of elastomer channels and reservoirs. Alternatively, the elastomeric structure may be bonded onto a flat elastomer layer by the same method as described above, forming a permanent and high-strength bond. This may prove advantageous when higher back pressures are used.

As can be seen in FIGS. 7A and 7B, flow channels 30 and 32 are preferably disposed at an angle to one another with a small membrane 25 of substrate 24 separating the top of flow channel 30 from the bottom of flow channel 32.

In preferred aspects, planar substrate 14 is glass. An advantage of using glass is that the present elastomeric structures may be peeled up, washed and reused. A further advantage of using glass is that optical sensing may be employed. Alternatively, planar substrate 14 may be an elastomer itself, which may prove advantageous when higher back pressures are used.

The method of fabrication just described may be varied to form a structure having a membrane composed of an elastomeric material different than that forming the walls of the channels of the device. This variant fabrication method is illustrated in FIGS. 7C-7G.

Figure 7H:
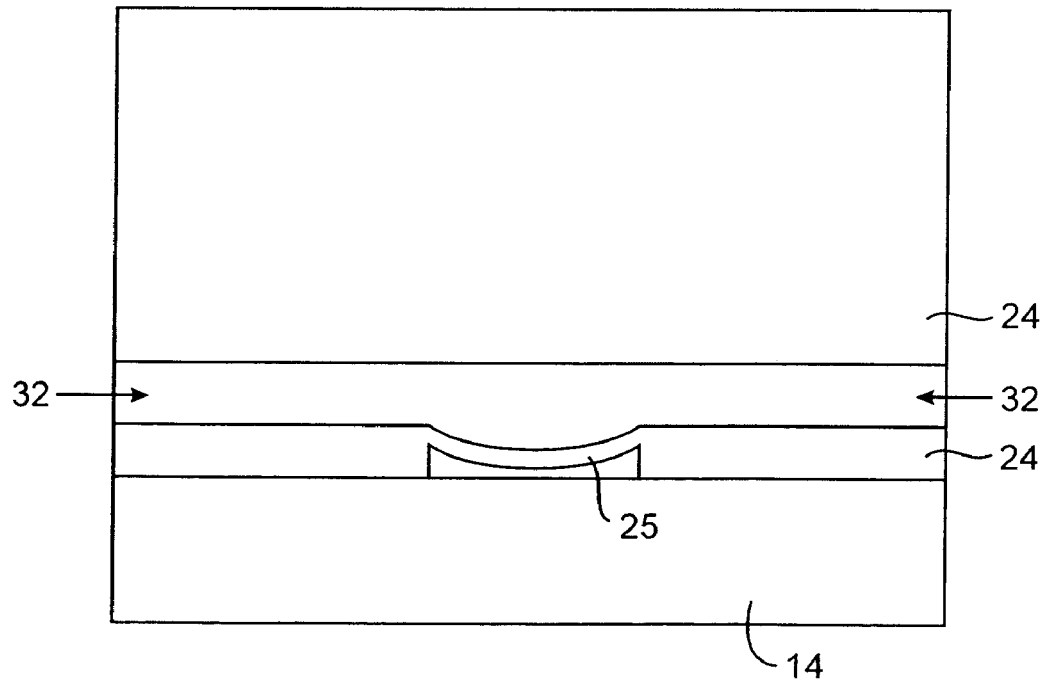
FIG. 7H is a front sectional view showing the valve of FIG. 7B in an actuated state.
Figure 7C:
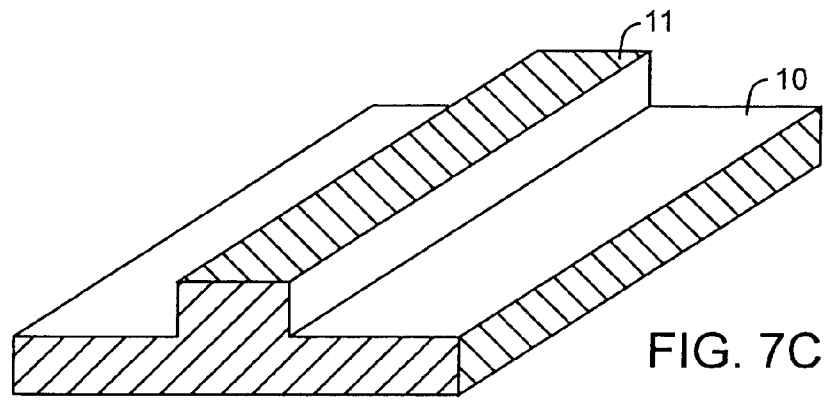
FIGS. 7C-7G are illustrations showing steps of a method for forming an elastomeric structure having a membrane formed from a separate elastomeric layer.
Figure 7D:
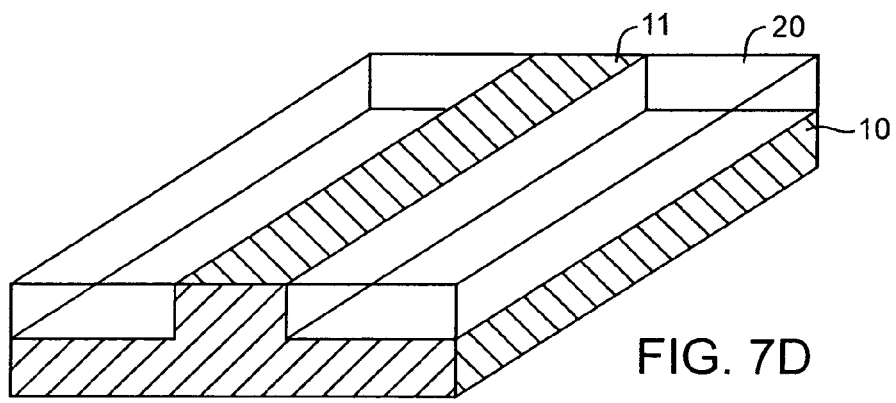

Referring to FIG. 7C, a first micro-machined mold 10 is provided. Micro-machined mold 10 has a raised line or protrusion 11 extending therealong. In FIG. 7D, first elastomeric layer 20 is cast on top of first micro-machined mold 10 such that the top of the first elastomeric layer 20 is flush with the top of raised line or protrusion 11. This may be accomplished by carefully controlling the volume of elastomeric material spun onto mold 10 relative to the known height of raised line 11. Alternatively, the desired shape could be formed by injection molding.

Figure 7E:
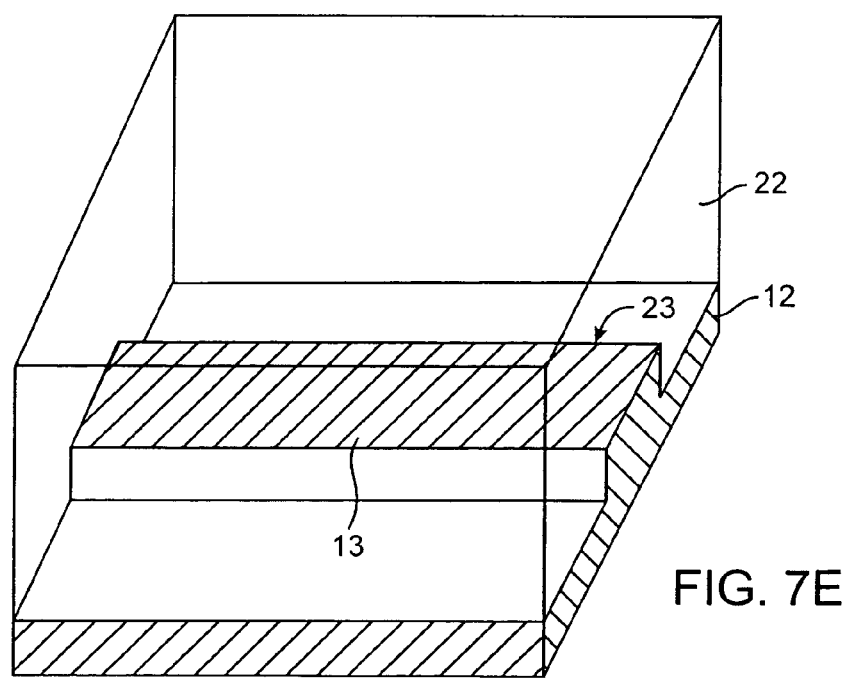

In FIG. 7E, second micro-machined mold 12 having a raised protrusion 13 extending therealong is also provided. Second elastomeric layer 22 is cast on top of second mold 12 as shown, such that recess 23 is formed in its bottom surface corresponding to the dimensions of protrusion 13.

Figure 7F:
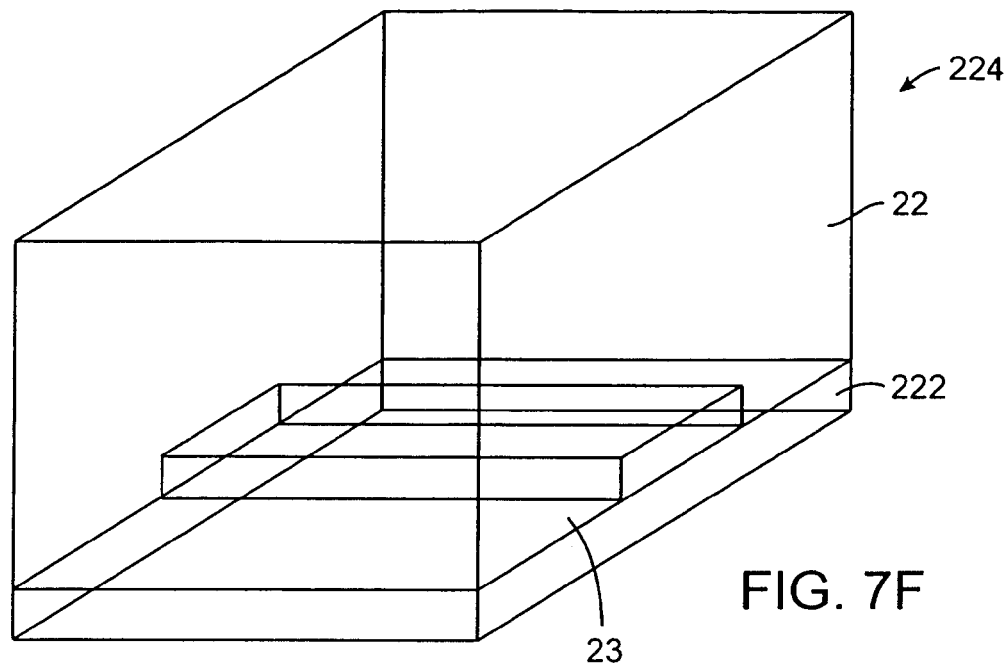

In FIG. 7F, second elastomeric layer 22 is removed from mold 12 and placed on top of third elastomeric layer 222. Second elastomeric layer 22 is bonded to third elastomeric layer 20 to form integral elastomeric block 224 using techniques described in detail below. At this point in the process, recess 23 formerly occupied by raised line 13 will form flow channel 23.

Figure 7G:
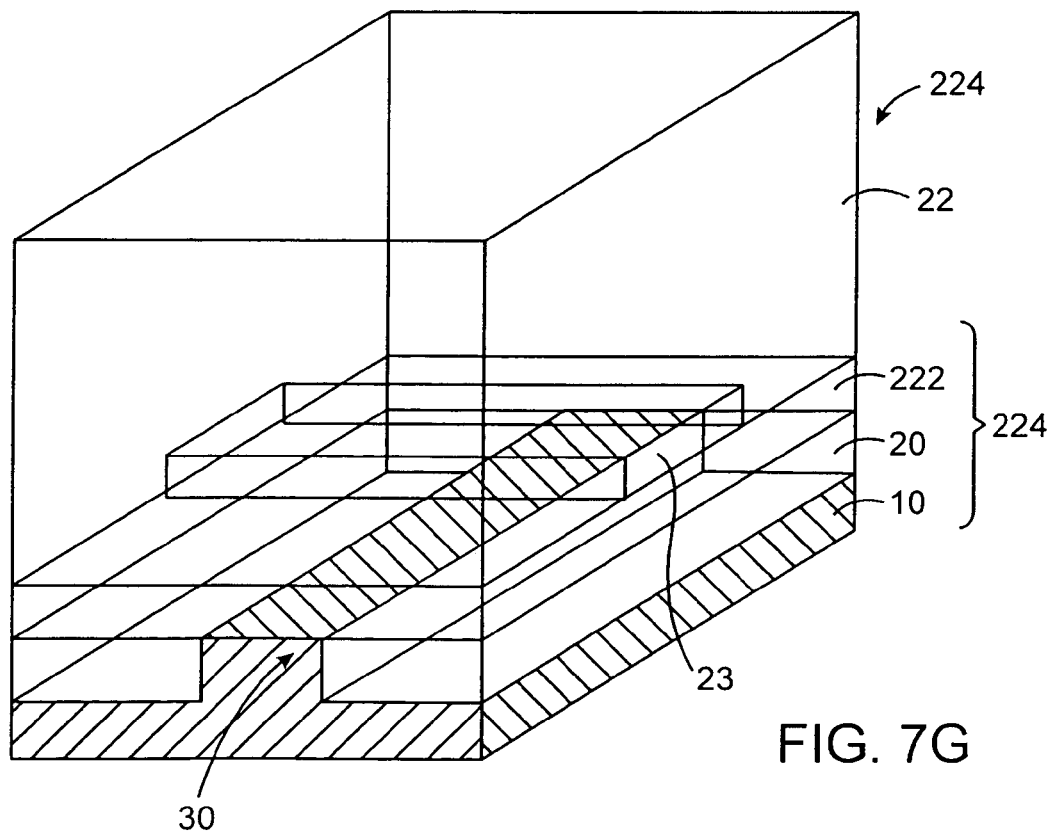

In FIG. 7G, elastomeric block 224 is placed on top of first micro-machined mold 10 and first elastomeric layer 20. Elastomeric block and first elastomeric layer 20 are then bonded together to form an integrated (i.e.: monolithic) elastomeric structure 24 having a membrane composed of a separate elastomeric layer 222.

When elastomeric structure 24 has been sealed at its bottom surface to a planar substrate in the manner described above in connection with FIG. 7A, the recess formerly occupied by raised line 11 will form flow channel 30.

The variant fabrication method illustrated above in conjunction with FIGS. 7C-7G offers the advantage of permitting the membrane portion to be composed of a separate material than the elastomeric material of the remainder of the structure. This is important because the thickness and elastic properties of the membrane play a key role in operation of the device. Moreover, this method allows the separate elastomer layer to readily be subjected to conditioning prior to incorporation into the elastomer structure. As discussed in detail below, examples of potentially desirable condition include the introduction of magnetic or electrically conducting species to permit actuation of the membrane, and/or the introduction of dopant into the membrane in order to alter its elasticity.

While the above method is illustrated in connection with forming various shaped elastomeric layers formed by replication molding on top of a micromachined mold, the present invention is not limited to this technique. Other techniques could be employed to form the individual layers of shaped elastomeric material that are to be bonded together. For example, a shaped layer of elastomeric material could be formed by laser cutting or injection molding, or by methods utilizing chemical etching and/or sacrificial materials as discussed below in conjunction with the second exemplary method.

An alternative method fabricates a patterned elastomer structure utilizing development of photoresist encapsulated within elastomer material. However, the methods in accordance with the present invention are not limited to utilizing photoresist. Other materials such as metals could also serve as sacrificial materials to be removed selective to the surrounding elastomer material, and the method would remain within the scope of the present invention. For example, gold metal may be etched selective to RTV 615 elastomer utilizing the appropriate chemical mixture.

2. Layer and Channel Dimensions

Microfabricated refers to the size of features of an elastomeric structure fabricated in accordance with an embodiment of the present invention. In general, variation in at least one dimension of microfabricated structures is controlled to the micron level, with at least one dimension being microscopic (i.e. below 1000 μm). Microfabrication typically involves semiconductor or MEMS fabrication techniques such as photolithography and spincoating that are designed for to produce feature dimensions on the microscopic level, with at least some of the dimension of the microfabricated structure requiring a microscope to reasonably resolve/image the structure.

In preferred aspects, flow channels 30, 32, 60 and 62 preferably have width-to-depth ratios of about 10:1. A non-exclusive list of other ranges of width-to-depth ratios in accordance with embodiments of the present invention is 0.1:1 to 100:1, more preferably 1:1 to 50:1, more preferably 2:1 to 20:1, and most preferably 3:1 to 15:1. In an exemplary aspect, flow channels 30, 32, 60 and 62 have widths of about 1 to 1000 microns. A non-exclusive list of other ranges of widths of flow channels in accordance with embodiments of the present invention is 0.01 to 1000 microns, more preferably 0.05 to 1000 microns, more preferably 0.2 to 500 microns, more preferably 1 to 250 microns, and most preferably 10 to 200 microns. Exemplary channel widths include 0.1 μm, 1 μm, 2 μm, 5 μm, 10 μm, 20 μm, 30 μm, 40 μm, 50 μm, 60 μm, 70 μm, 80 μm, 90 μm, 100 μm, 110 μm, 120 μm, 130 μm, 140 μm, 150 μm, 160 μm, 170 μm, 180 μm, 190 μm, 200 μm, 210 μm, 220 μm, 230 μm, 240 μm, and 250 μm.

Flow channels 30, 32, 60, and 62 have depths of about 1 to 100 microns. A non-exclusive list of other ranges of depths of flow channels in accordance with embodiments of the present invention is 0.01 to 1000 microns, more preferably 0.05 to 500 microns, more preferably 0.2 to 250 microns, and more preferably 1 to 100 microns, more preferably 2 to 20 microns, and most preferably 5 to 10 microns. Exemplary channel depths include including 0.01 μm, 0.02 μm, 0.05 μm, 0.1 μm, 0.2 μm, 0.5 μm, 1 μm, 2 μm, 3 μm, 4 μm, 5 μm, 7.5 μm, 10 μm, 12.5 μm, 15 μm, 17.5 μm, 20 μm, 22.5 μm, 25 μm, 30 μm, 40 μm, 50 μm, 75 μm, 100 μm, 150 μm, 200 μm, and 250 μm.

The flow channels are not limited to these specific dimension ranges and examples given above, and may vary in width in order to affect the magnitude of force required to deflect the membrane as discussed at length below in conjunction with FIG. 27. For example, extremely narrow flow channels having a width on the order of 0.01 μm may be useful in optical and other applications, as discussed in detail below. Elastomeric structures which include portions having channels of even greater width than described above are also contemplated by the present invention, and examples of applications of utilizing such wider flow channels include fluid reservoir and mixing channel structures.

The elastomeric layers may be cast thick for mechanical stability. In an exemplary embodiment, elastomeric layer 22 of FIG. 1 is 50 microns to several centimeters thick, and more preferably approximately 4 mm thick. A non-exclusive list of ranges of thickness of the elastomer layer in accordance with other embodiments of the present invention is between about 0.1 micron to 10 cm, 1 micron to 5 cm, 10 microns to 2 cm, 100 microns to 10 mm.

Accordingly, membrane 25 of FIG. 7B separating flow channels 30 and 32 has a typical thickness of between about 0.01 and 1000 microns, more preferably 0.05 to 500 microns, more preferably 0.2 to 250, more preferably 1 to 100 microns, more preferably 2 to 50 microns, and most preferably 5 to 40 microns. As such, the thickness of elastomeric layer 22 is about 100 times the thickness of elastomeric layer 20. Exemplary membrane thicknesses include 0.01 μm, 0.02 μm, 0.03 μm, 0.05 μm, 0.1 μm, 0.2 μm, 0.3 μm, 0.5 μm, 1 μm, 2 μm, 3 μm, 5 μm, 7.5 μm, 10 μm, 12.5 μm, 15 μm, 17.5 μm, 20 μm, 22.5 μm, 25 μm, 30 μm, 40 μm, 50 μm, 75 μm, 100 μm, 150 μm, 200 μm, 250 μm, 300 μm, 400 μm, 500 μm, 750 μm, and 1000 μm.

3. Soft Lithographic Bonding

Preferably, elastomeric layers are bonded together chemically, using chemistry that is intrinsic to the polymers comprising the patterned elastomer layers. Most preferably, the bonding comprises two component "addition cure" bonding.

In a preferred aspect, the various layers of elastomer are bound together in a heterogeneous bonding in which the layers have a different chemistry. Alternatively, a homogenous bonding may be used in which all layers would be of the same chemistry. Thirdly, the respective elastomer layers may optionally be glued together by an adhesive instead. In a fourth aspect, the elastomeric layers may be thermoset elastomers bonded together by heating.

In one aspect of homogeneous bonding, the elastomeric layers are composed of the same elastomer material, with the same chemical entity in one layer reacting with the same chemical entity in the other layer to bond the layers together. In one embodiment, bonding between polymer chains of like elastomer layers may result from activation of a crosslinking agent due to light, heat, or chemical reaction with a separate chemical species.

Alternatively in a heterogeneous aspect, the elastomeric layers are composed of different elastomeric materials, with a first chemical entity in one layer reacting with a second chemical entity in another layer. In one exemplary heterogeneous aspect, the bonding process used to bind respective elastomeric layers together may comprise bonding together two layers of RTV 615 silicone. RTV 615 silicone is a two-part addition-cure silicone rubber. Part A contains vinyl groups and catalyst; part B contains silicon hydride (Si—H) groups. The conventional ratio for RTV 615 is 10A:1B. For bonding, one layer may be made with 30A:1B (i.e. excess vinyl groups) and the other with 3A:1B (i.e. excess Si—H groups). Each layer is cured separately. When the two layers are brought into contact and heated at elevated temperature, they bond irreversibly forming a monolithic elastomeric substrate.

In an exemplary aspect of the present invention, elastomeric structures are formed utilizing Sylgard 182, 184 or 186, or aliphatic urethane diacrylates such as (but not limited to) Ebecryl 270 or Irr 245 from UCB Chemical.

In one embodiment in accordance with the present invention, two-layer elastomeric structures were fabricated from pure acrylated Urethane Ebe 270. A thin bottom layer was spin coated at 8000 rpm for 15 seconds at 170° C. The top and bottom layers were initially cured under ultraviolet light for 10 minutes under nitrogen utilizing a Model ELC 500 device manufactured by Electrolite corporation. The assembled layers were then cured for an additional 30 minutes. Reaction was catalyzed by a 0.5% vol/vol mixture of Irgacure 500 manufactured by Ciba-Geigy Chemicals. The resulting elastomeric material exhibited moderate elasticity and adhesion to glass.

In another embodiment in accordance with the present invention, two-layer elastomeric structures were fabricated from a combination of 25% Ebe 270/50% Irr245/25% isopropyl alcohol for a thin bottom layer, and pure acrylated Urethane Ebe 270 as a top layer. The thin bottom layer was initially cured for 5 min, and the top layer initially cured for 10 minutes, under ultraviolet light under nitrogen utilizing a Model ELC 500 device manufactured by Electrolite corporation. The assembled layers were then cured for an additional 30 minutes. Reaction was catalyzed by a 0.5% vol/vol mixture of Irgacure 500 manufactured by Ciba-Geigy Chemicals. The resulting elastomeric material exhibited moderate elasticity and adhered to glass.

Alternatively, other bonding methods may be used, including activating the elastomer surface, for example by plasma exposure, so that the elastomer layers/substrate will bond when placed in contact. For example, one possible approach to bonding together elastomer layers composed of the same material is set forth by Duffy et al, "Rapid Prototyping of Microfluidic Systems in Poly (dimethylsiloxane)", *Analytical Chemistry* (1998), 70, 4974-4984, incorporated herein by reference. This paper discusses that exposing polydimethylsiloxane (PDMS) layers to oxygen plasma causes oxidation of the surface, with irreversible bonding occurring when the two oxidized layers are placed into contact.

Yet another approach to bonding together successive layers of elastomer is to utilize the adhesive properties of uncured elastomer. Specifically, a thin layer of uncured elastomer such as RTV 615 is applied on top of a first cured elastomeric layer. Next, a second cured elastomeric layer is placed on top of the uncured elastomeric layer. The thin middle layer of uncured elastomer is then cured to produce a monolithic elastomeric structure. Alternatively, uncured elastomer can be applied to the bottom of a first cured elastomer layer, with the first cured elastomer layer placed on top of a second cured elastomer layer. Curing the middle thin elastomer layer again results in formation of a monolithic elastomeric structure.

Where encapsulation of sacrificial layers is employed to fabricate the elastomer structure, bonding of successive elastomeric layers may be accomplished by pouring uncured elastomer over a previously cured elastomeric layer and any sacrificial material patterned thereupon. Bonding between elastomer layers occurs due to interpenetration and reaction of the polymer chains of an uncured elastomer layer with the polymer chains of a cured elastomer layer. Subsequent curing of the elastomeric layer will create a bond between the elastomeric layers and create a monolithic elastomeric structure.

Referring to the first method of FIGS. 1 to 7B, first elastomeric layer 20 may be created by spin-coating an RTV mixture on microfabricated mold 12 at 2000 rpm's for 30 seconds yielding a thickness of approximately 40 microns. Second elastomeric layer 22 may be created by spin-coating an RTV mixture on microfabricated mold 11. Both layers 20 and 22 may be separately baked or cured at about 80° C. for 1.5 hours. The second elastomeric layer 22 may be bonded onto first elastomeric layer 20 at about 80° C. for about 1.5 hours.

Micromachined molds 10 and 12 may be patterned photoresist on silicon wafers. In an exemplary aspect, a Shipley SJR 5740 photoresist was spun at 2000 rpm patterned with a high resolution transparency film as a mask and then developed yielding an inverse channel of approximately 10 microns in height. When baked at approximately 200° C. for about 30 minutes, the photoresist reflows and the inverse channels become rounded. In preferred aspects, the molds may be treated with trimethylchlorosilane (TMCS) vapor for about a minute before each use in order to prevent adhesion of silicone rubber.

4. Suitable Elastomeric Materials

Allcock et al, Contemporary Polymer Chemistry, $2^{nd}$ Ed. describes elastomers in general as polymers existing at a temperature between their glass transition temperature and liquefaction temperature. Elastomeric materials exhibit elastic properties because the polymer chains readily undergo torsional motion to permit uncoiling of the backbone chains in response to a force, with the backbone chains recoiling to assume the prior shape in the absence of the force. In general, elastomers deform when force is applied, but then return to their original shape when the force is removed. The elasticity exhibited by elastomeric materials may be characterized by a Young's modulus. Elastomeric materials having a Young's modulus of between about 1 Pa-1 TPa, more preferably between about 10 Pa-100 GPa, more preferably between about 20 Pa-1 GPa, more preferably between about 50 Pa-10 MPa, and more preferably between about 100 Pa-1 MPa are useful in accordance with the present invention, although elastomeric materials having a Young's modulus outside of these ranges could also be utilized depending upon the needs of a particular application.

The systems of the present invention may be fabricated from a wide variety of elastomers. In an exemplary aspect, the elastomeric layers may preferably be fabricated from silicone rubber. However, other suitable elastomers may also be used.

In an exemplary aspect of the present invention, the present systems are fabricated from an elastomeric polymer such as GE RTV 615 (formulation), a vinyl-silane crosslinked (type) silicone elastomer (family). However, the present systems are not limited to this one formulation, type or even this family of polymer; rather, nearly any elastomeric polymer is suitable. An important requirement for the preferred method of fabrication of the present microvalves is the ability to bond multiple layers of elastomers together. In the case of multilayer soft lithography, layers of elastomer are cured separately and then bonded together. This scheme requires that cured layers possess sufficient reactivity to bond together. Either the layers may be of the same type, and are capable of bonding to themselves, or they may be of two different types, and are capable of bonding to each other. Other possibilities include the use an adhesive between layers and the use of thermoset elastomers.

Given the tremendous diversity of polymer chemistries, precursors, synthetic methods, reaction conditions, and potential additives, there are a huge number of possible elastomer systems that could be used to make monolithic elastomeric microvalves and pumps. Variations in the materials used will most likely be driven by the need for particular material properties, i.e. solvent resistance, stiffness, gas permeability, or temperature stability.

There are many, many types of elastomeric polymers. A brief description of the most common classes of elastomers is presented here, with the intent of showing that even with relatively "standard" polymers, many possibilities for bonding exist. Common elastomeric polymers include polyisoprene, polybutadiene, polychloroprene, polyisobutylene, poly(styrene-butadiene-styrene), the polyurethanes, and silicones.

Polyisoprene, polybutadiene, polychloroprene:

Polyisoprene, polybutadiene, and polychloroprene are all polymerized from diene monomers, and therefore have one double bond per monomer when polymerized. This double bond allows the polymers to be converted to elastomers by vulcanization (essentially, sulfur is used to form crosslinks between the double bonds by heating). This would easily allow homogeneous multilayer soft lithography by incomplete vulcanization of the layers to be bonded; photoresist encapsulation would be possible by a similar mechanism.

Polyisobutylene:

Pure Polyisobutylene has no double bonds, but is crosslinked to use as an elastomer by including a small amount (~1%) of isoprene in the polymerization. The isoprene monomers give pendant double bonds on the Polyisobutylene backbone, which may then be vulcanized as above.

Poly(styrene-butadiene-styrene):

Poly(styrene-butadiene-styrene) is produced by living anionic polymerization (that is, there is no natural chain-terminating step in the reaction), so "live" polymer ends can exist in the cured polymer. This makes it a natural candidate for the present photoresist encapsulation system (where there will be plenty of unreacted monomer in the liquid layer poured on top of the cured layer). Incomplete curing would allow homogeneous multilayer soft lithography (A to A bonding). The chemistry also facilitates making one layer with extra butadiene ("A") and coupling agent and the other layer ("B") with a butadiene deficit (for heterogeneous multilayer soft lithography). SBS is a "thermoset elastomer", meaning that above a certain temperature it melts and becomes plastic (as opposed to elastic); reducing the temperature yields the elastomer again. Thus, layers can be bonded together by heating.

Polyurethanes:

Polyurethanes are produced from di-isocyanates (A-A) and di-alcohols or di-amines (B-B); since there are a large variety of di-isocyanates and di-alcohols/amines, the number of different types of polyurethanes is huge. The A vs. B nature of the polymers, however, would make them useful for heterogeneous multilayer soft lithography just as RTV 615 is: by using excess A-A in one layer and excess B-B in the other layer.

Silicones:

Silicone polymers probably have the greatest structural variety, and almost certainly have the greatest number of commercially available formulations. The vinyl-to-(Si—H) crosslinking of RTV 615 (which allows both heterogeneous multilayer soft lithography and photoresist encapsulation) has already been discussed, but this is only one of several crosslinking methods used in silicone polymer chemistry.

5. Operation of Device

FIGS. 7B and 7H together show the closing of a first flow channel by pressurizing a second flow channel, with FIG. 7B (a front sectional view cutting through flow channel 32 in corresponding FIG. 7A), showing an open first flow channel 30; with FIG. 7H showing first flow channel 30 closed by pressurization of the second flow channel 32.

Referring to FIG. 7B, first flow channel 30 and second flow channel 32 are shown. Membrane 25 separates the flow channels, forming the top of first flow channel 30 and the bottom of second flow channel 32. As can be seen, flow channel 30 is "open".

As can be seen in FIG. 7H, pressurization of flow channel 32 (either by gas or liquid introduced therein) causes membrane 25 to deflect downward, thereby pinching off flow F passing through flow channel 30. Accordingly, by varying the pressure in channel 32, a linearly actuable valving system is provided such that flow channel 30 can be opened or closed by moving membrane 25 as desired. (For illustration purposes only, channel 30 in FIG. 7G is shown in a "mostly closed" position, rather than a "fully closed" position).

Since such valves are actuated by moving the roof of the channels themselves (i.e.: moving membrane 25) valves and pumps produced by this technique have a truly zero dead volume, and switching valves made by this technique have a dead volume approximately equal to the active volume of the valve, for example about 100×100×10 µm=100 µL. Such dead volumes and areas consumed by the moving membrane are approximately two orders of magnitude smaller than known conventional microvalves. Smaller and larger valves and switching valves are contemplated in the present invention, and a non-exclusive list of ranges of dead volume includes 1 aL to 1 uL, 100 aL to 100 nL, 1 fl, to 10 nL, 100 fL to 1 nL, and 1 pL to 100 pL.

The extremely small volumes capable of being delivered by pumps and valves in accordance with the present invention represent a substantial advantage. Specifically, the smallest known volumes of fluid capable of being manually metered is around 0.1 µl. The smallest known volumes capable of being metered by automated systems is about ten-times larger (1 µl). Utilizing pumps and valves in accordance with the present invention, volumes of liquid of 10 nl or smaller can routinely be metered and dispensed. The accurate metering of extremely small volumes of fluid enabled by the present invention would be extremely valuable in a large number of biological applications, including diagnostic tests and assays.

Equation 1 represents a highly simplified mathematical model of deflection of a rectangular, linear, elastic, isotropic plate of uniform thickness by an applied pressure:

$$w=(BPb^4)/(Eh^3), \quad (1)$$

where:

w=deflection of plate;

B=shape coefficient (dependent upon length vs. width and support of edges of plate);

P=applied pressure;

b=plate width

E=Young's modulus; and h=plate thickness.

Thus even in this extremely simplified expression, deflection of an elastomeric membrane in response to a pressure will be a function of: the length, width, and thickness of the membrane, the flexibility of the membrane (Young's modulus), and the applied actuation force. Because each of these parameters will vary widely depending upon the actual dimensions and physical composition of a particular elastomeric device in accordance with the present invention, a wide range of membrane thicknesses and elasticity's, channel widths, and actuation forces are contemplated by the present invention.

It should be understood that the formula just presented is only an approximation, since in general the membrane does not have uniform thickness, the membrane thickness is not necessarily small compared to the length and width, and the deflection is not necessarily small compared to length, width, or thickness of the membrane. Nevertheless, the equation serves as a useful guide for adjusting variable parameters to achieve a desired response of deflection versus applied force.

Figure 8A:
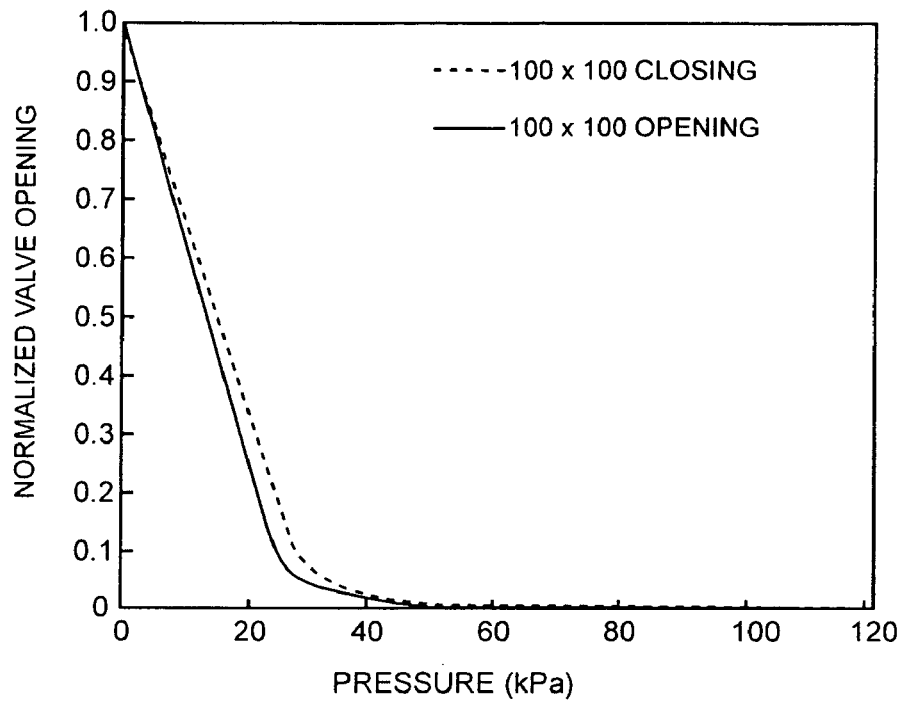
FIGS. 8A and 8B illustrates valve opening vs. applied pressure for various flow channels.
Figure 8B:
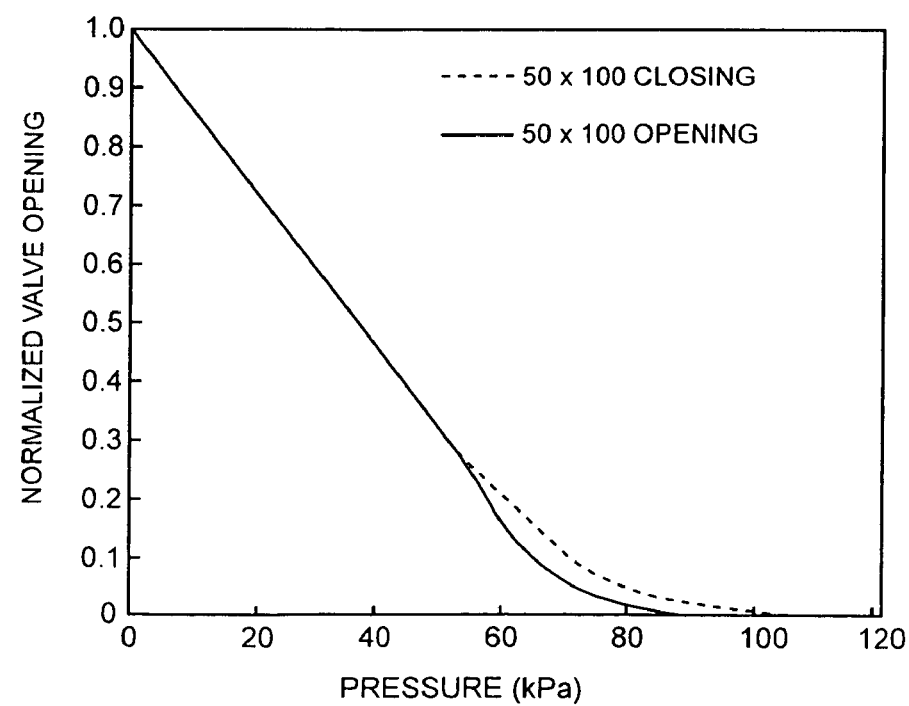

FIGS. 8A and 8B illustrate valve opening vs. applied pressure for a 100 µm wide first flow channel 30 and a 50 µm wide second flow channel 32. The membrane of this device was formed by a layer of General Electric Silicones RTV 615 having a thickness of approximately 30 µm and a Young's modulus of approximately 750 kPa. FIGS. 21a and 21b show the extent of opening of the valve to be substantially linear over most of the range of applied pressures.

Air pressure was applied to actuate the membrane of the device through a 10 cm long piece of plastic tubing having an outer diameter of 0.025" connected to a 25 mm piece of stainless steel hypodermic tubing with an outer diameter of 0.025" and an inner diameter of 0.013". This tubing was placed into contact with the control channel by insertion into the elastomeric block in a direction normal to the control channel. Air pressure was applied to the hypodermic tubing from an external LHDA miniature solenoid valve manufactured by Lee Co.

While control of the flow of material through the device has so far been described utilizing applied gas pressure, other fluids could be used.

For example, air is compressible, and thus experiences some finite delay between the time of application of pressure by the external solenoid valve and the time that this pressure is experienced by the membrane. In an alternative embodiment of the present invention, pressure could be applied from an external source to a noncompressible fluid such as water or hydraulic oils, resulting in a near-instantaneous transfer of applied pressure to the membrane. However, if the displaced volume of the valve is large or the control channel is narrow, higher viscosity of a control fluid may contribute to delay in actuation. The optimal medium for transferring pressure will therefore depend upon the particular application and device configuration, and both gaseous and liquid media are contemplated by the invention.

While external applied pressure as described above has been applied by a pump/tank system through a pressure regulator and external miniature valve, other methods of applying external pressure are also contemplated in the present invention, including gas tanks, compressors, piston systems, and columns of liquid. Also contemplated is the use of naturally occurring pressure sources such as may be found inside living organisms, such as blood pressure, gastric pressure, the pressure present in the cerebrospinal fluid, pressure present in the intra-ocular space, and the pressure exerted by muscles during normal flexure. Other methods of regulating external pressure are also contemplated, such as miniature valves, pumps, macroscopic peristaltic pumps, pinch valves, and other types of fluid regulating equipment such as is known in the art.

As can be seen, the response of valves in accordance with embodiments of the present invention have been experimentally shown to be almost perfectly linear over a large portion of its range of travel, with minimal hysteresis. Accordingly, the present valves are ideally suited for microfluidic metering and fluid control. The linearity of the valve response demonstrates that the individual valves are well modeled as Hooke's Law springs. Furthermore, high pressures in the flow channel (i.e.: back pressure) can be countered simply by increasing the actuation pressure. Experimentally, the present inventors have achieved valve closure at back pressures of 70 kPa, but higher pressures are also contemplated. The following is a nonexclusive list of pressure ranges encompassed by the present invention: 10 Pa-25 MPa; 100 Pa-10 Mpa, 1 kPa-1 MPa, 1 kPa-300 kPa, 5 kPa-200 kPa, and 15 kPa-100 kPa.

While valves and pumps do not require linear actuation to open and close, linear response does allow valves to more easily be used as metering devices. In one embodiment of the invention, the opening of the valve is used to control flow rate by being partially actuated to a known degree of closure. Linear valve actuation makes it easier to determine the amount of actuation force required to close the valve to a desired degree of closure. Another benefit of linear actuation is that the force required for valve actuation may be easily determined from the pressure in the flow channel. If actuation is linear, increased pressure in the flow channel may be countered by adding the same pressure (force per unit area) to the actuated portion of the valve.

Linearity of a valve depends on the structure, composition, and method of actuation of the valve structure. Furthermore, whether linearity is a desirable characteristic in a valve depends on the application. Therefore, both linearly and non-linearly actuable valves are contemplated in the present invention, and the pressure ranges over which a valve is linearly actuable will vary with the specific embodiment.

Figure 9:
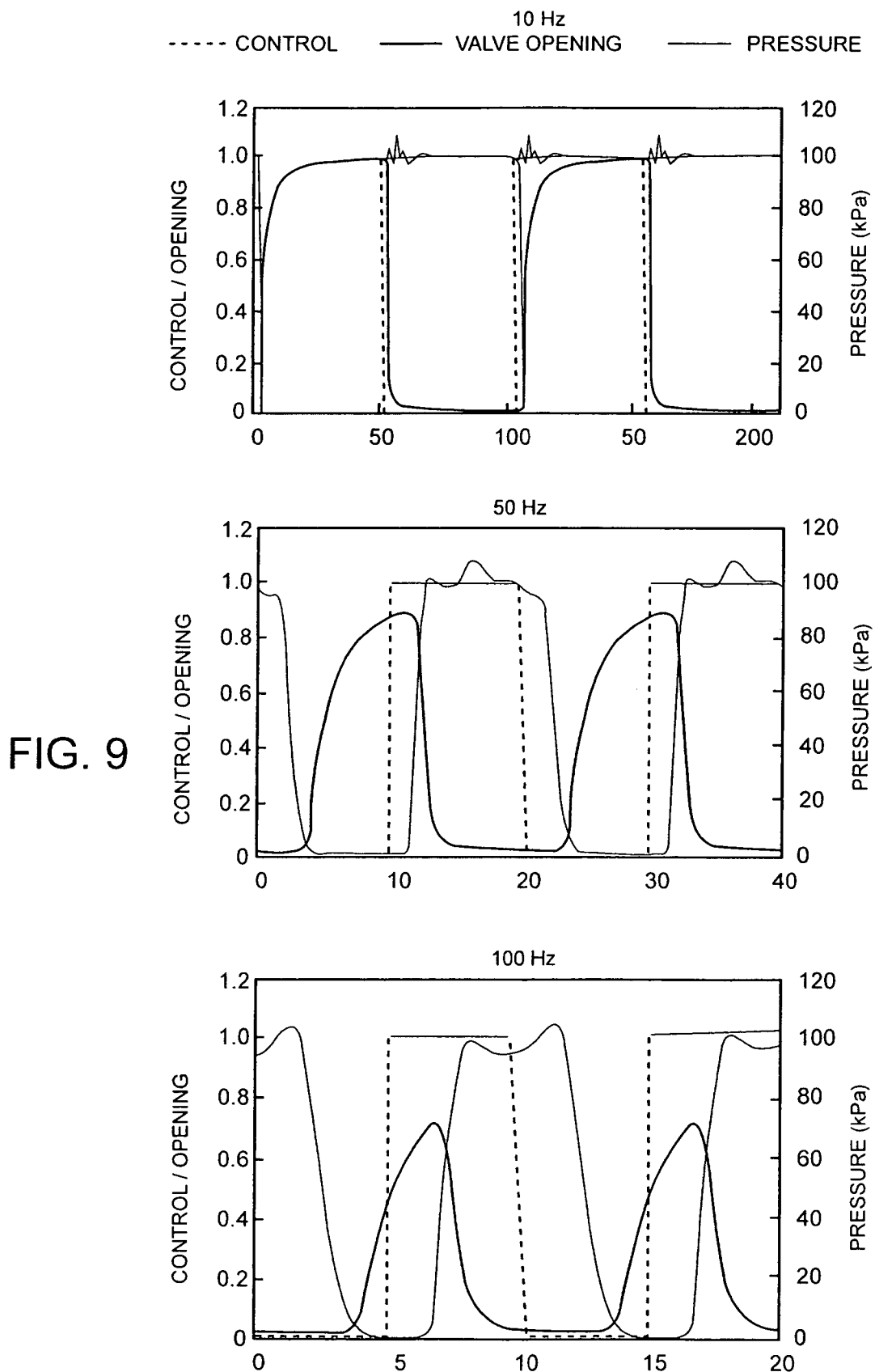
FIG. 9 illustrates time response of a 100 µm×100 µm×10 µm RTV microvalve.

FIG. 9 illustrates time response (i.e.: closure of valve as a function of time in response to a change in applied pressure) of a 100 μm×100 μm×10 μm RTV microvalve with 10-cm-long air tubing connected from the chip to a pneumatic valve as described above.

Two periods of digital control signal, actual air pressure at the end of the tubing and valve opening are shown in FIG. 9. The pressure applied on the control line is 100 kPa, which is substantially higher than the ~40 kPa required to close the valve. Thus, when closing, the valve is pushed closed with a pressure 60 kPa greater than required. When opening, however, the valve is driven back to its rest position only by its own spring force ($\leq$40 kPa). Thus, close is expected to be smaller than τopen. There is also a lag between the control signal and control pressure response, due to the limitations of the miniature valve used to control the pressure. Calling such lags t and the l/e time constants τ, the values are: topen=3.63 ms, τopen=1.88 ms, tclose=2.15 ms, τclose=0.51 ms. If 3τ each are allowed for opening and closing, the valve runs comfortably at 75 Hz when filled with aqueous solution.

If one used another actuation method which did not suffer from opening and closing lag, this valve would run at ~375 Hz. Note also that the spring constant can be adjusted by changing the membrane thickness; this allows optimization for either fast opening or fast closing. The spring constant could also be adjusted by changing the elasticity (Young's modulus) of the membrane, as is possible by introducing dopant into the membrane or by utilizing a different elastomeric material to serve as the membrane (described above in conjunction with FIGS. 7C-7H.)

When experimentally measuring the valve properties as illustrated in FIG. 9 the valve opening was measured by fluorescence. In these experiments, the flow channel was filled with a solution of fluorescein isothiocyanate (FITC) in buffer (pH$\geq$8) and the fluorescence of a square area occupying the center ~⅓ of the channel is monitored on an epi-fluorescence microscope with a photomultiplier tube with a 10 kHz bandwidth. The pressure was monitored with a Wheatstone-bridge pressure sensor (SenSym SCC15GD2) pressurized simultaneously with the control line through nearly identical pneumatic connections.

6. Flow Channel Cross Sections

The flow channels of the present invention may optionally be designed with different cross sectional sizes and shapes, offering different advantages, depending upon their desired application. For example, the cross sectional shape of the lower flow channel may have a curved upper surface, either along its entire length or in the region disposed under an upper cross channel). Such a curved upper surface facilitates valve sealing, as follows.

Figure 10:
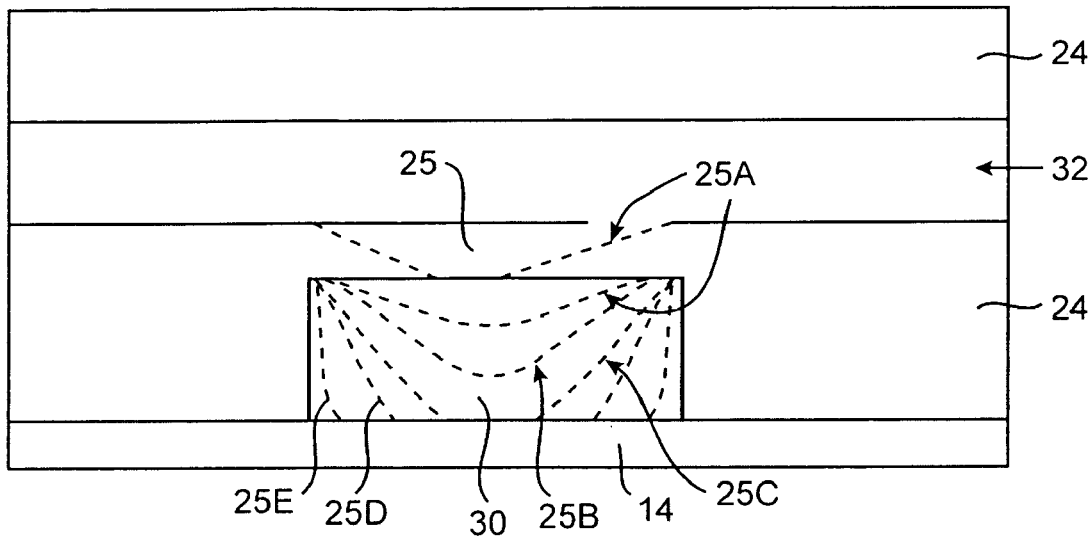
FIG. 10 is a front sectional view of the valve of FIG. 7B showing actuation of the membrane.

Referring to FIG. 10, a cross sectional view (similar to that of FIG. 7B) through flow channels 30 and 32 is shown. As can be seen, flow channel 30 is rectangular in cross sectional shape. In an alternate preferred aspect of the invention, as shown in FIG. 10, the cross-section of a flow channel 30 instead has an upper curved surface.

Referring first to FIG. 10, when flow channel 32 is pressurized, the membrane portion 25 of elastomeric block 24 separating flow channels 30 and 32 will move downwardly to the successive positions shown by the dotted lines 25A, 25B, 25C, 25D, and 25E. As can be seen, incomplete sealing may possibly result at the edges of flow channel 30 adjacent planar substrate 14.

Figure 11:
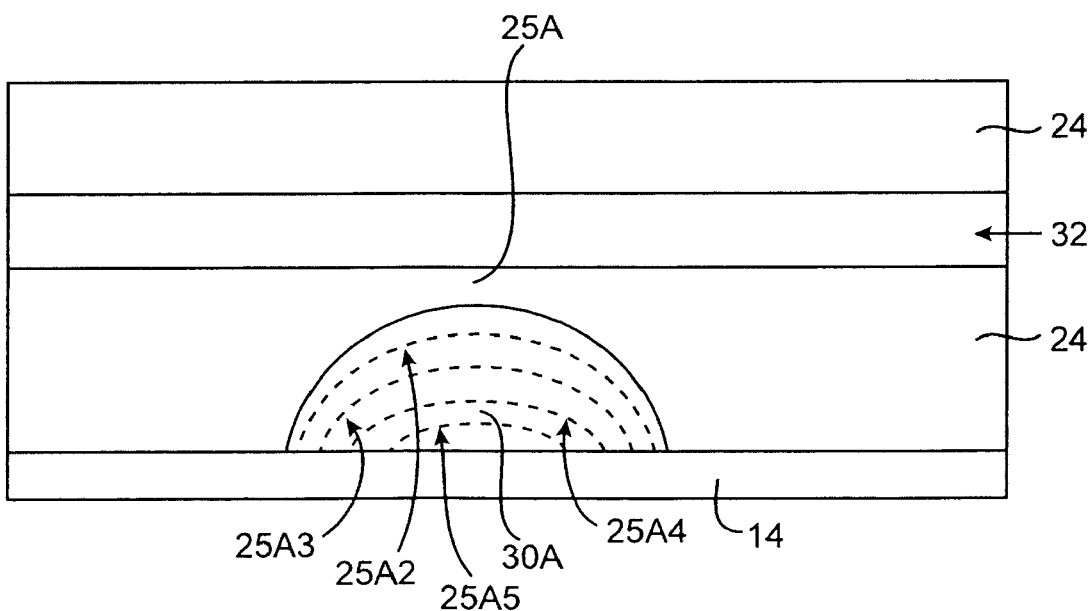
FIG. 11 is a front sectional view of an alternative embodiment of a valve having a flow channel with a curved upper surface.

In the alternate preferred embodiment of FIG. 11, flow channel 30a has a curved upper wall 25A. When flow channel 32 is pressurized, membrane portion 25 will move downwardly to the successive positions shown by dotted lines 25A2, 25A3, 25A4 and 25A5, with edge portions of the membrane moving first into the flow channel, followed by top membrane portions. An advantage of having such a curved upper surface at membrane 25A is that a more complete seal will be provided when flow channel 32 is pressurized. Specifically, the upper wall of the flow channel 30 will provide a continuous contacting edge against planar substrate 14, thereby avoiding the "island" of contact seen between wall 25 and the bottom of flow channel 30 in FIG. 10.

Another advantage of having a curved upper flow channel surface at membrane 25A is that the membrane can more readily conform to the shape and volume of the flow channel in response to actuation. Specifically, where a rectangular flow channel is employed, the entire perimeter (2× flow channel height, plus the flow channel width) must be forced into the flow channel. However where an arched flow channel is used, a smaller perimeter of material (only the semi-circular arched portion) must be forced into the channel. In this manner, the membrane requires less change in perimeter for actuation and is therefore more responsive to an applied actuation force to block the flow channel In an alternate aspect, (not illustrated), the bottom of flow channel 30 is rounded such that its curved surface mates with the curved upper wall 25A as seen in FIG. 20 described above.

In summary, the actual conformational change experienced by the membrane upon actuation will depend upon the configuration of the particular elastomeric structure. Specifically, the conformational change will depend upon the length, width, and thickness profile of the membrane, its attachment to the remainder of the structure, and the height, width, and shape of the flow and control channels and the material properties of the elastomer used. The conformational change may also depend upon the method of actuation, as actuation of the membrane in response to an applied pressure will vary somewhat from actuation in response to a magnetic or electrostatic force.

Moreover, the desired conformational change in the membrane will also vary depending upon the particular application for the elastomeric structure. In the simplest embodiments described above, the valve may either be open or closed, with metering to control the degree of closure of the valve. In other embodiments however, it may be desirable to alter the shape of the membrane and/or the flow channel in order to achieve more complex flow regulation. For instance, the flow channel could be provided with raised protrusions beneath the membrane portion, such that upon actuation the membrane shuts off only a percentage of the flow through the flow channel, with the percentage of flow blocked insensitive to the applied actuation force.

Many membrane thickness profiles and flow channel cross-sections are contemplated by the present invention, including rectangular, trapezoidal, circular, ellipsoidal, parabolic, hyperbolic, and polygonal, as well as sections of the above shapes. More complex cross-sectional shapes, such as the embodiment with protrusions discussed immediately above or an embodiment having concavities in the flow channel, are also contemplated by the present invention.

In addition, while the invention is described primarily above in conjunction with an embodiment wherein the walls and ceiling of the flow channel are formed from elastomer, and the floor of the channel is formed from an underlying substrate, the present invention is not limited to this particular orientation. Walls and floors of channels could also be formed in the underlying substrate, with only the ceiling of the flow channel constructed from elastomer. This elastomer flow channel ceiling would project downward into the channel in response to an applied actuation force, thereby controlling the flow of material through the flow channel. In general, monolithic elastomer structures as described elsewhere in the instant application are preferred for microfluidic applications. However, it may be useful to employ channels formed in the substrate where such an arrangement provides advantages. For instance, a substrate including optical waveguides could be constructed so that the optical waveguides direct light specifically to the side of a microfluidic channel.

7. Networked Systems

Figure 12A:
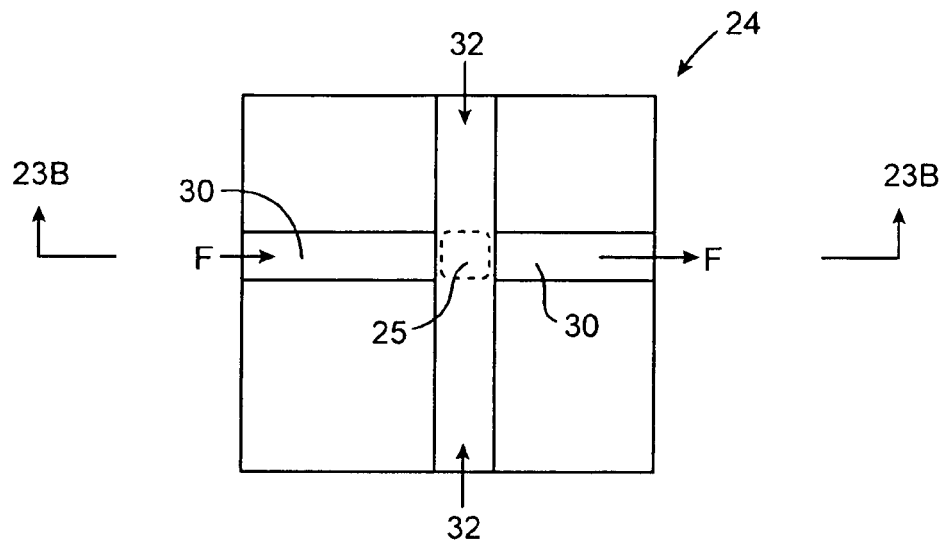
FIG. 12A is a top schematic view of an on/off valve.
Figure 13A:
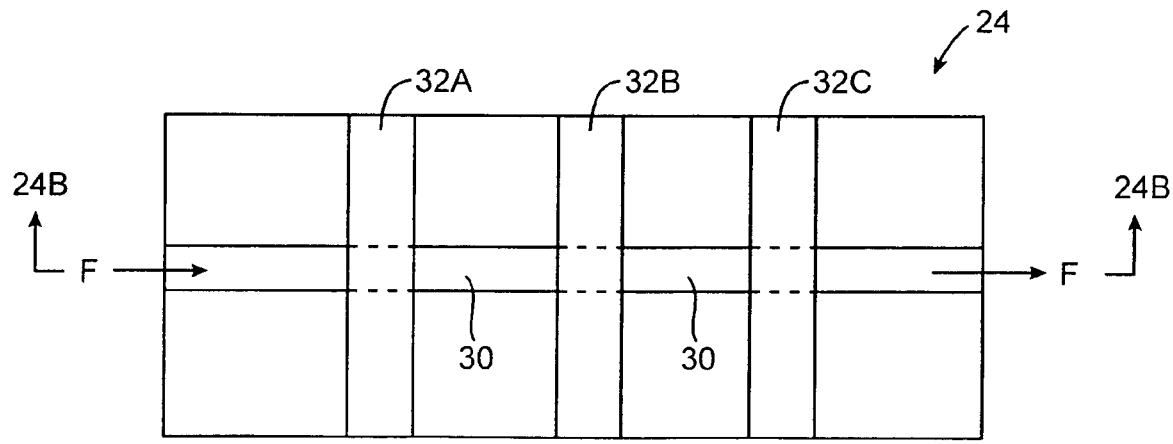
FIG. 13A is a top schematic view of a peristaltic pumping system.
Figure 12B:
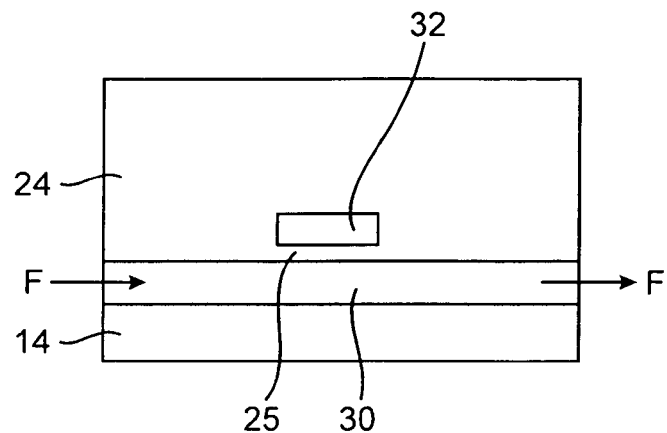
FIG. 12B is a sectional elevation view along line 23B-23B in FIG. 12A
Figure 13B:
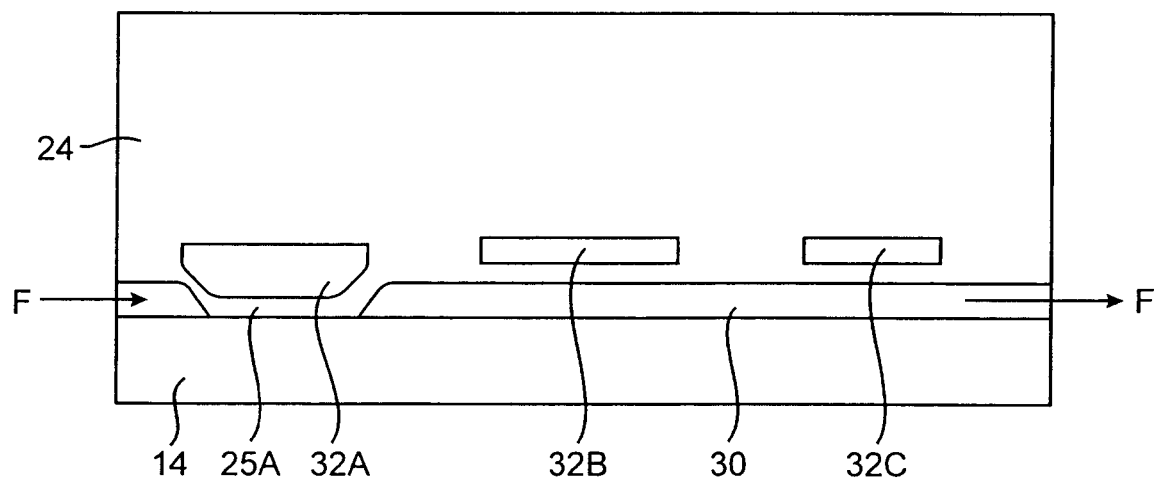
FIG. 13B is a sectional elevation view along line 24B-24B in FIG. 13A
Figure 14:
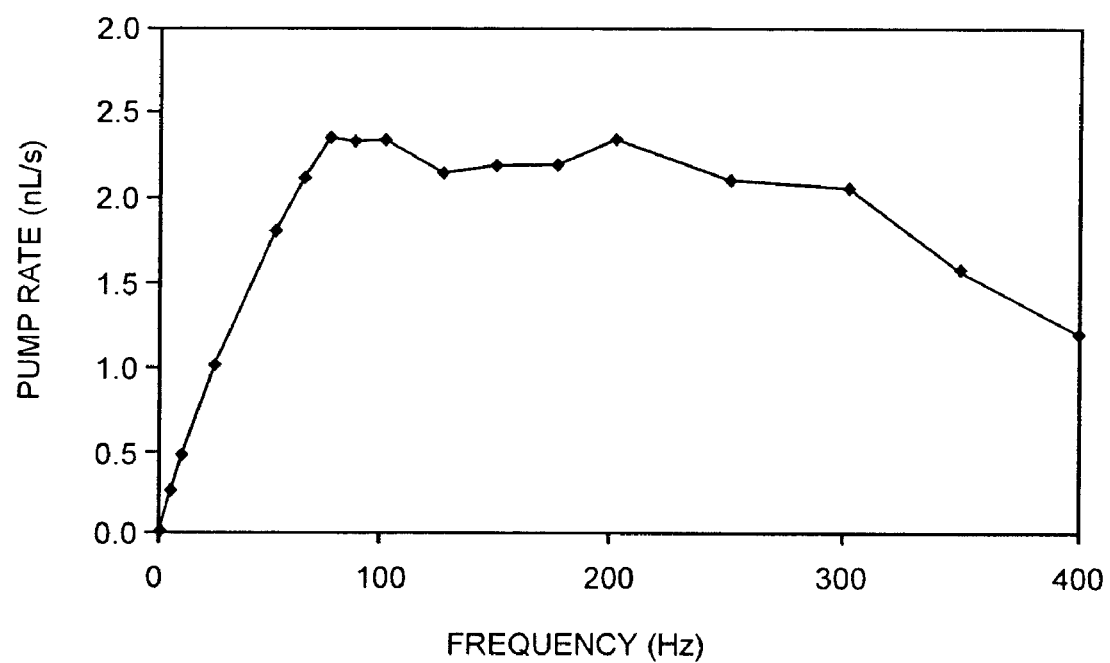
FIG. 14 is a graph showing experimentally achieved pumping rates vs. frequency for an embodiment of the peristaltic pumping system of FIG. 13.
Figure 15A:
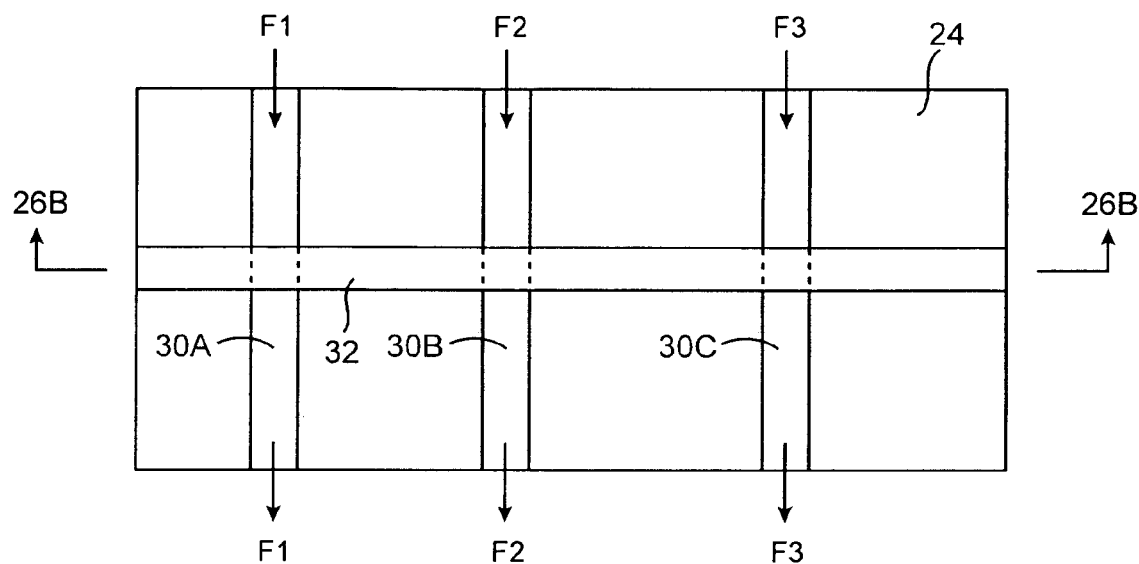
FIG. 15A is a top schematic view of one control line actuating multiple flow lines simultaneously.
Figure 15B:
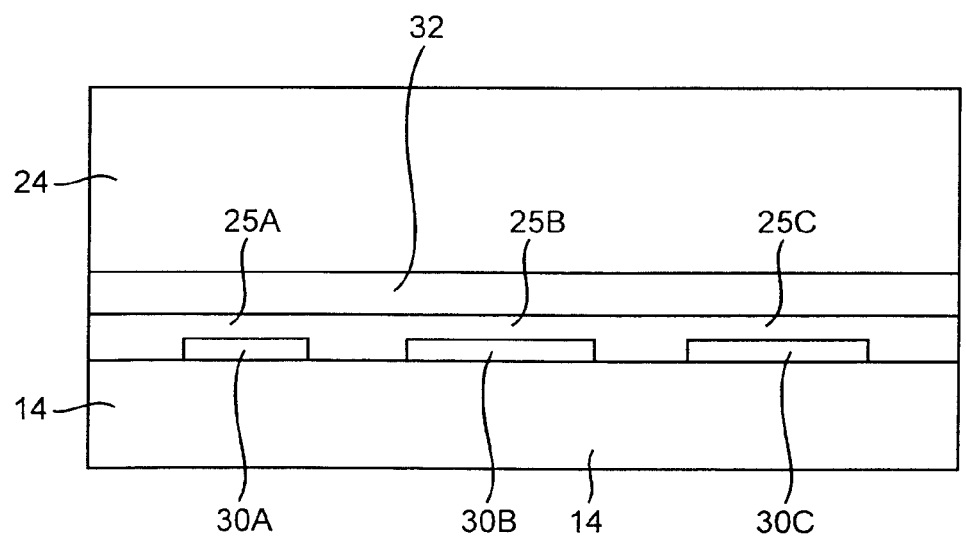
FIG. 15B is a sectional elevation view along line 26B-26B in FIG. 15A
Figure 16:
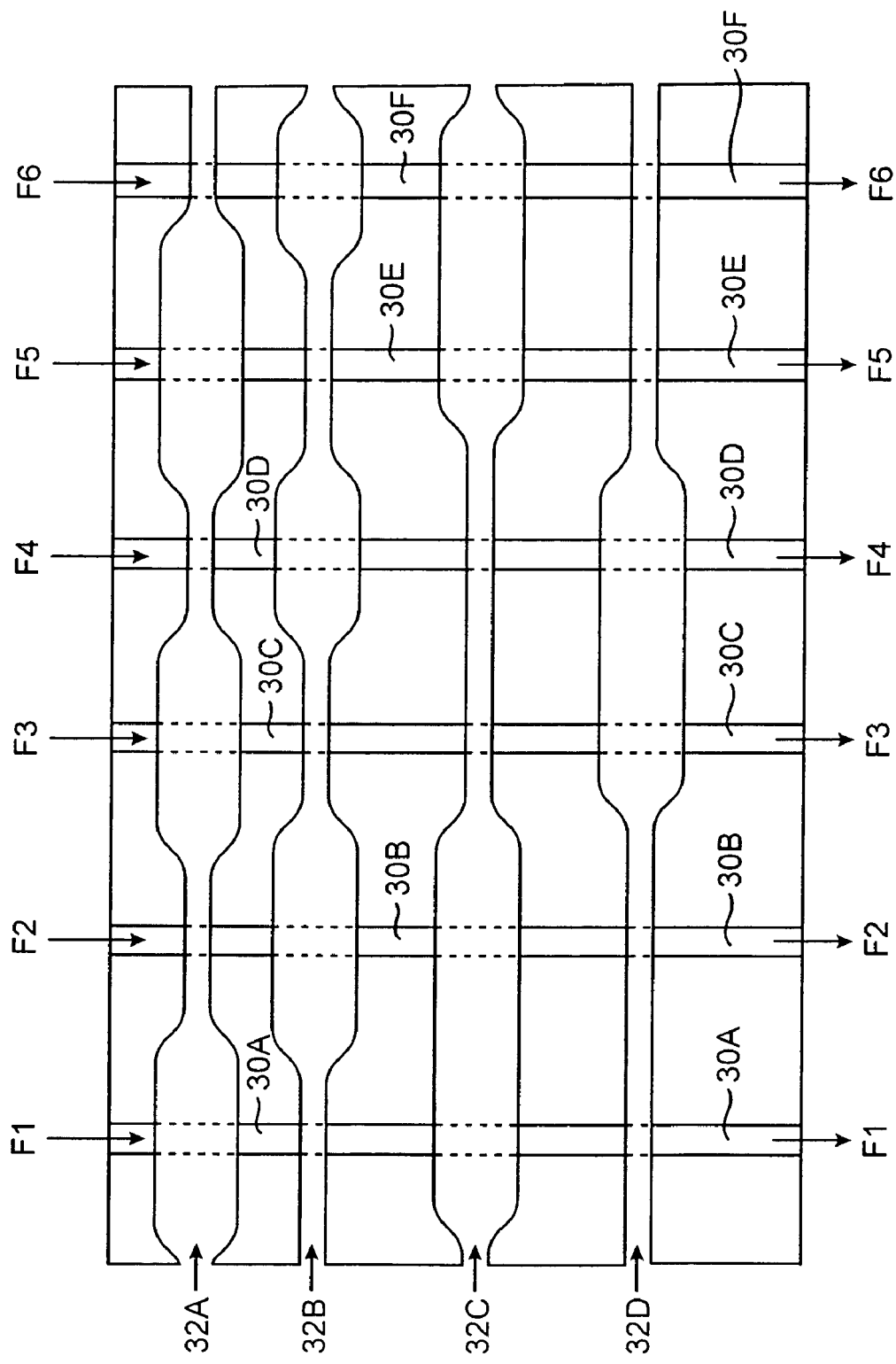
FIG. 16 is a schematic illustration of a multiplexed system adapted to permit flow through various channels.

FIGS. 12A and 12B show a views of a single on/off valve, identical to the systems set forth above, (for example in FIG. 7A). FIGS. 13A and 13B shows a peristaltic pumping system comprised of a plurality of the single addressable on/off valves as seen in FIG. 12, but networked together. FIG. 14 is a graph showing experimentally achieved pumping rates vs. frequency for the peristaltic pumping system of FIG. 13. FIGS. 15A and 15B show a schematic view of a plurality of flow channels which are controllable by a single control line. This system is also comprised of a plurality of the single addressable on/off valves of FIG. 12, multiplexed together, but in a different arrangement than that of FIG. 12. FIG. 16 is a schematic illustration of a multiplexing system adapted to permit fluid flow through selected channels, comprised of a plurality of the single on/off valves of FIG. 12, joined or networked together.

Referring first to FIGS. 12A and 12B, a schematic of flow channels 30 and 32 is shown. Flow channel 30 preferably has a fluid (or gas) flow F passing therethrough. Flow channel 32, (which crosses over flow channel 30, as was already explained herein), is pressurized such that membrane 25 separating the flow channels may be depressed into the path of flow channel 30, shutting off the passage of flow F therethrough, as has been explained. As such, "flow channel" 32 can also be referred to as a "control line" which actuates a single valve in flow channel 30. In FIGS. 12 to 15, a plurality of such addressable valves are joined or networked together in various arrangements to produce pumps, capable of peristaltic pumping, and other fluidic logic applications.

Referring to FIGS. 13A and 13B, a system for peristaltic pumping is provided, as follows. A flow channel 30 has a plurality of generally parallel flow channels (i.e.: control lines) 32A, 32B and 32C passing thereover. By pressurizing control line 32A, flow F through flow channel 30 is shut off under membrane 25A at the intersection of control line 32A and flow channel 30. Similarly, (but not shown), by pressurizing control line 32B, flow F through flow channel 30 is shut off under membrane 25B at the intersection of control line 32B and flow channel 30, etc.

Each of control lines 32A, 32B, and 32C is separately addressable. Therefore, peristalsis may be actuated by the pattern of actuating 32A and 32C together, followed by 32A, followed by 32A and 32B together, followed by 32B, followed by 32B and C together, etc. This corresponds to a successive "101, 100, 110, 010, 011, 001" pattern, where "0" indicates "valve open" and "1" indicates "valve closed." This peristaltic pattern is also known as a 120° pattern (referring to the phase angle of actuation between three valves). Other peristaltic patterns are equally possible, including 60° and 90° patterns.

In experiments performed by the inventors, a pumping rate of 2.35 nL/s was measured by measuring the distance traveled by a column of water in thin (0.5 mm i.d.) tubing; with 100×100×10 µm valves under an actuation pressure of 40 kPa. The pumping rate increased with actuation frequency until approximately 75 Hz, and then was nearly constant until above 200 Hz. The valves and pumps are also quite durable and the elastomer membrane, control channels, or bond have never been observed to fail. In experiments performed by the inventors, none of the valves in the peristaltic pump described herein show any sign of wear or fatigue after more than 4 million actuations. In addition to their durability, they are also gentle. A solution of *E. Coli* pumped through a channel and tested for viability showed a 94% survival rate.

FIG. 14 is a graph showing experimentally achieved pumping rates vs. frequency for the peristaltic pumping system of FIG. 13.

FIGS. 15A and 15B illustrates another way of assembling a plurality of the addressable valves of FIG. 12. Specifically, a plurality of parallel flow channels 30A, 30B, and 30C are provided. Flow channel (i.e.: control line) 32 passes thereover across flow channels 30A, 30B, and 30C. Pressurization of control line 32 simultaneously shuts off flows F1, F2 and F3 by depressing membranes 25A, 25B, and 25C located at the intersections of control line 32 and flow channels 30A, 30B, and 30C.

FIG. 16 is a schematic illustration of a multiplexing system adapted to selectively permit fluid to flow through selected channels, as follows. The downward deflection of membranes separating the respective flow channels from a control line passing thereabove (for example, membranes 25A, 25B, and 25C in FIGS. 15A and 15B) depends strongly upon the membrane dimensions. Accordingly, by varying the widths of flow channel control line 32 in FIGS. 15A and 15B, it is possible to have a control line pass over multiple flow channels, yet only actuate (i.e.: seal) desired flow channels. FIG. 16 illustrates a schematic of such a system, as follows.

A plurality of parallel flow channels 30A, 30B, 30C, 30D, 30E and 30F are positioned under a plurality of parallel control lines 32A, 32B, 32C, 32D, 32E and 32F. Control channels 32A, 32B, 32C, 32D, 32E and 32F are adapted to shut off fluid flows F1, F2, F3, F4, F5 and F6 passing through parallel flow channels 30A, 30B, 30C, 30D, 30E and 30F using any of the valving systems described above, with the following modification.

Each of control lines 32A, 32B, 32C, 32D, 32E and 32F have both wide and narrow portions. For example, control line 32A is wide in locations disposed over flow channels 30A, 30C and 30E. Similarly, control line 32B is wide in locations disposed over flow channels 30B, 30D and 30F, and control line 32C is wide in locations disposed over flow channels 30A, 30B, 30E and 30F.

At the locations where the respective control line is wide, its pressurization will cause the membrane (25) separating the flow channel and the control line to depress significantly into the flow channel, thereby blocking the flow passage therethrough. Conversely, in the locations where the respective control line is narrow, membrane (25) will also be narrow. Accordingly, the same degree of pressurization will not result in membrane (25) becoming depressed into the flow channel (30). Therefore, fluid passage thereunder will not be blocked.

For example, when control line 32A is pressurized, it will block flows F1, F3 and F5 in flow channels 30A, 30C and 30E. Similarly, when control line 32C is pressurized, it will block flows F1, F2, F5 and F6 in flow channels 30A, 30B, 30E and 30F. As can be appreciated, more than one control line can be actuated at the same time. For example, control lines 32A and 32C can be pressurized simultaneously to block all fluid flow except F4 (with 32A blocking F1, F3 and F5; and 32C blocking F1, F2, F5 and F6).

By selectively pressurizing different control lines (32) both together and in various sequences, a great degree of fluid flow control can be achieved. Moreover, by extending the present system to more than six parallel flow channels (30) and more than four parallel control lines (32), and by varying the positioning of the wide and narrow regions of the control lines, very complex fluid flow control systems may be fabricated. A property of such systems is that it is possible to turn on any one flow channel out of n flow channels with only 2(log 2n) control lines.

8. Switchable Flow Arrays

Figure 20A:
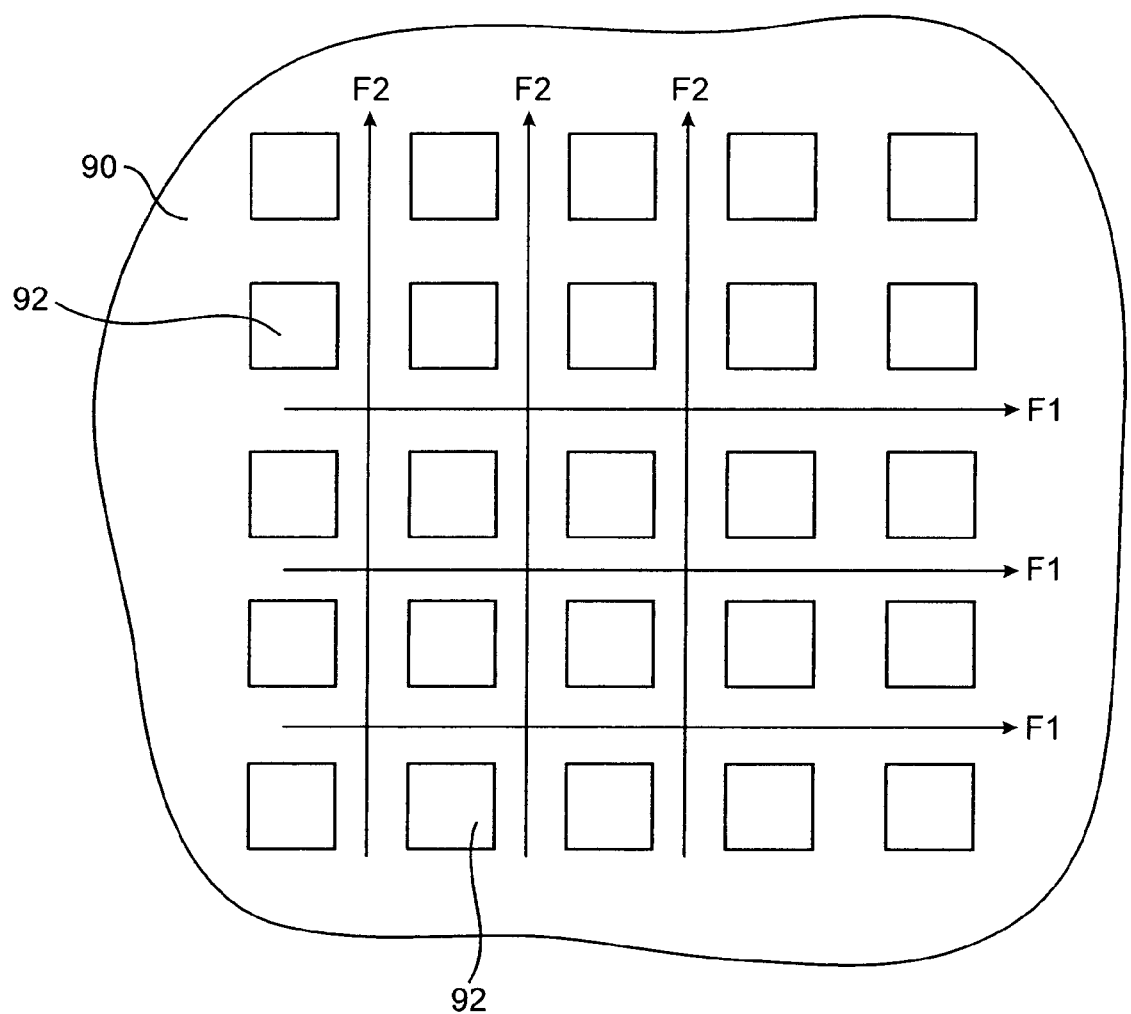
FIG. 20A is a bottom plan view of first layer (i.e.: the flow channel layer) of elastomer of a switchable flow array.
Figure 20B:
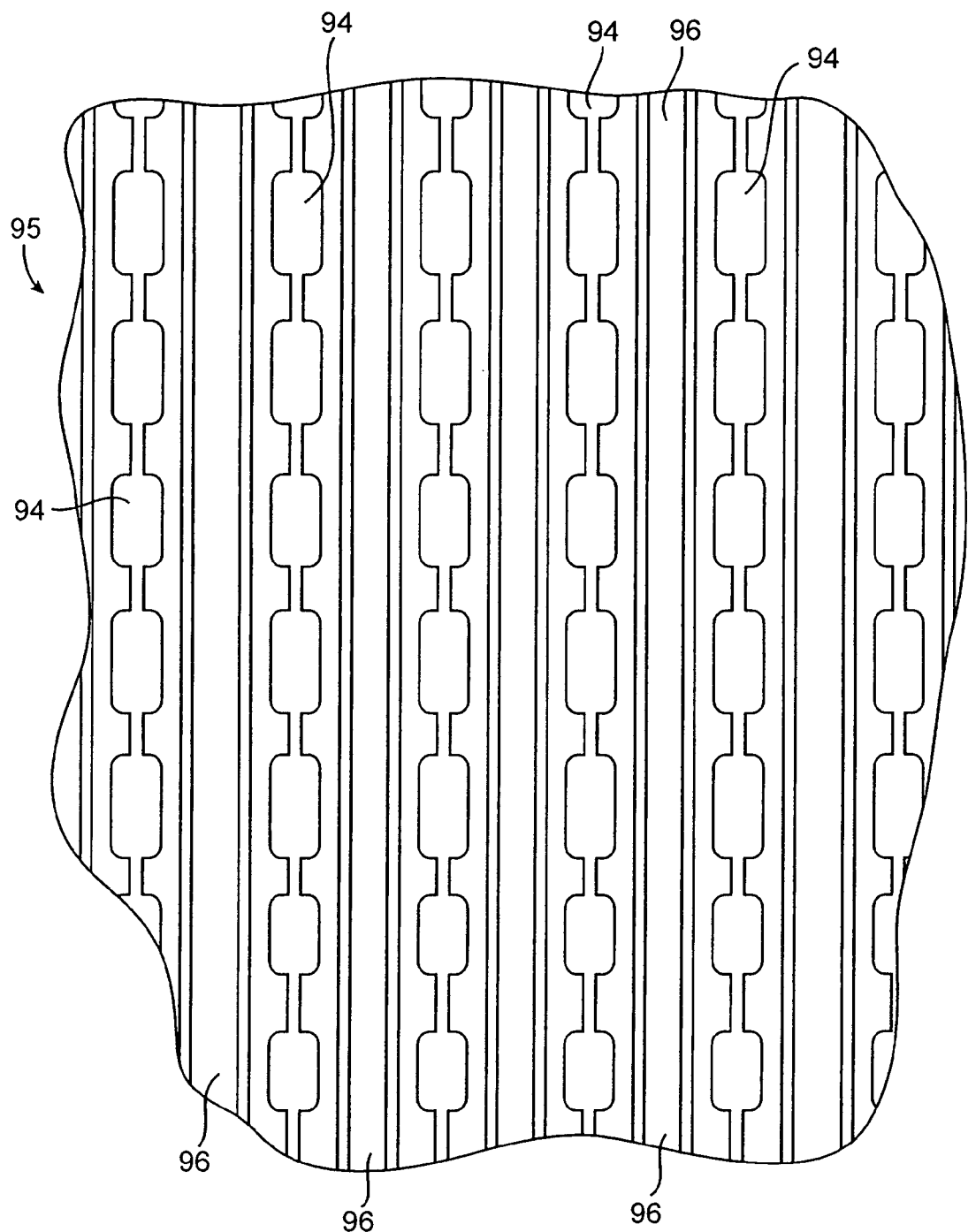
FIG. 20B is a bottom plan view of a control channel layer of a switchable flow array.

In yet another novel embodiment, fluid passage can be selectively directed to flow in either of two perpendicular directions. An example of such a "switchable flow array" system is provided in FIGS. 20A to 20D. FIG. 20A shows a bottom view of a first layer of elastomer 90, (or any other suitable substrate), having a bottom surface with a pattern of recesses forming a flow channel grid defined by an array of solid posts 92, each having flow channels passing therearound.

In preferred aspects, an additional layer of elastomer is bound to the top surface of layer 90 such that fluid flow can be selectively directed to move either in direction F1, or perpendicular direction F2. FIG. 20 is a bottom view of the bottom surface of the second layer of elastomer 95 showing recesses formed in the shape of alternating "vertical" control lines 96 and "horizontal" control lines 94. "Vertical" control lines 96 have the same width therealong, whereas "horizontal" control lines 94 have alternating wide and narrow portions, as shown.

Figure 20C:
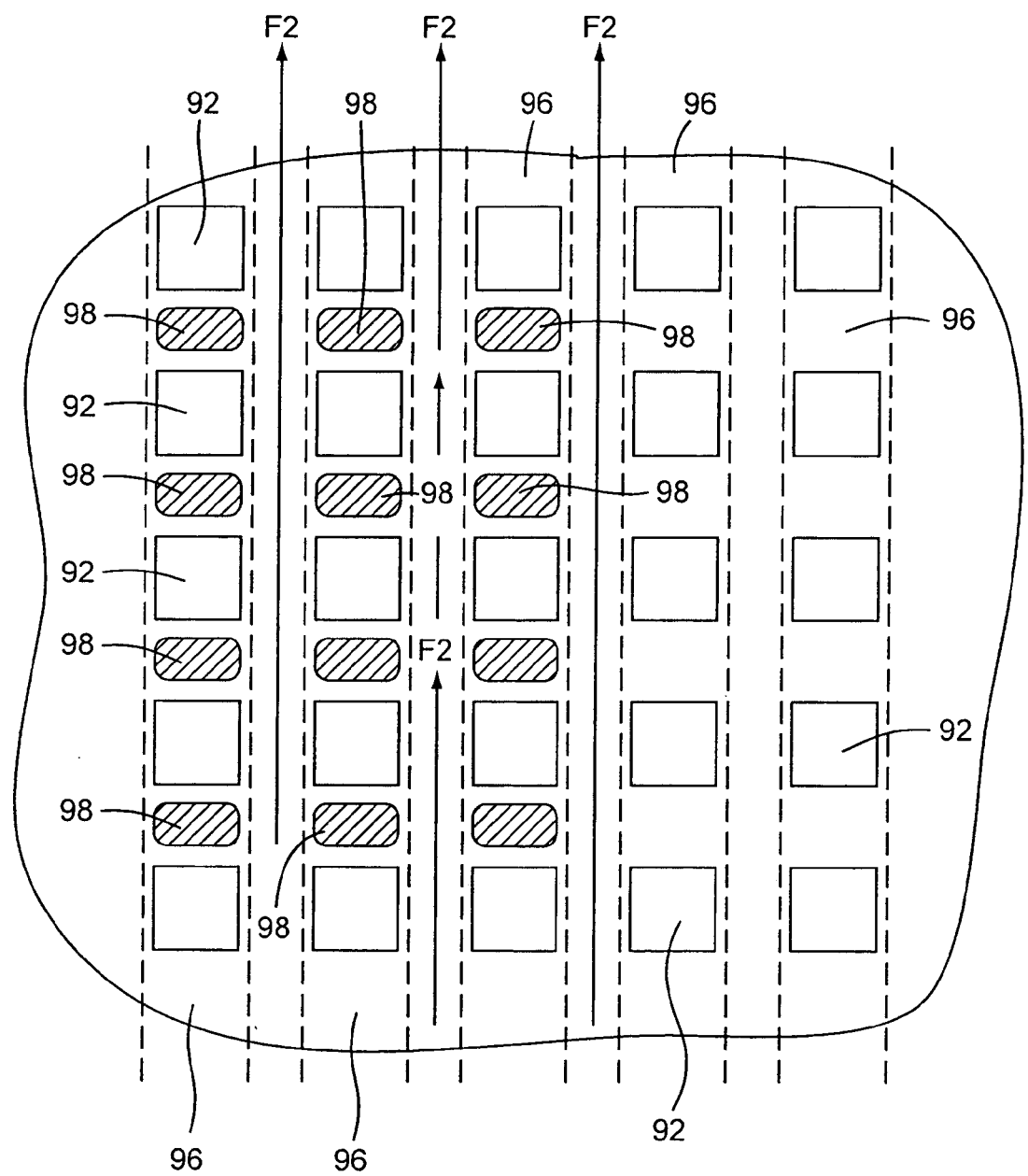
FIG. 20C shows the alignment of the first layer of elastomer of FIG. 20A with one set of control channels in the second layer of elastomer of FIG. 20B.
Figure 20D:
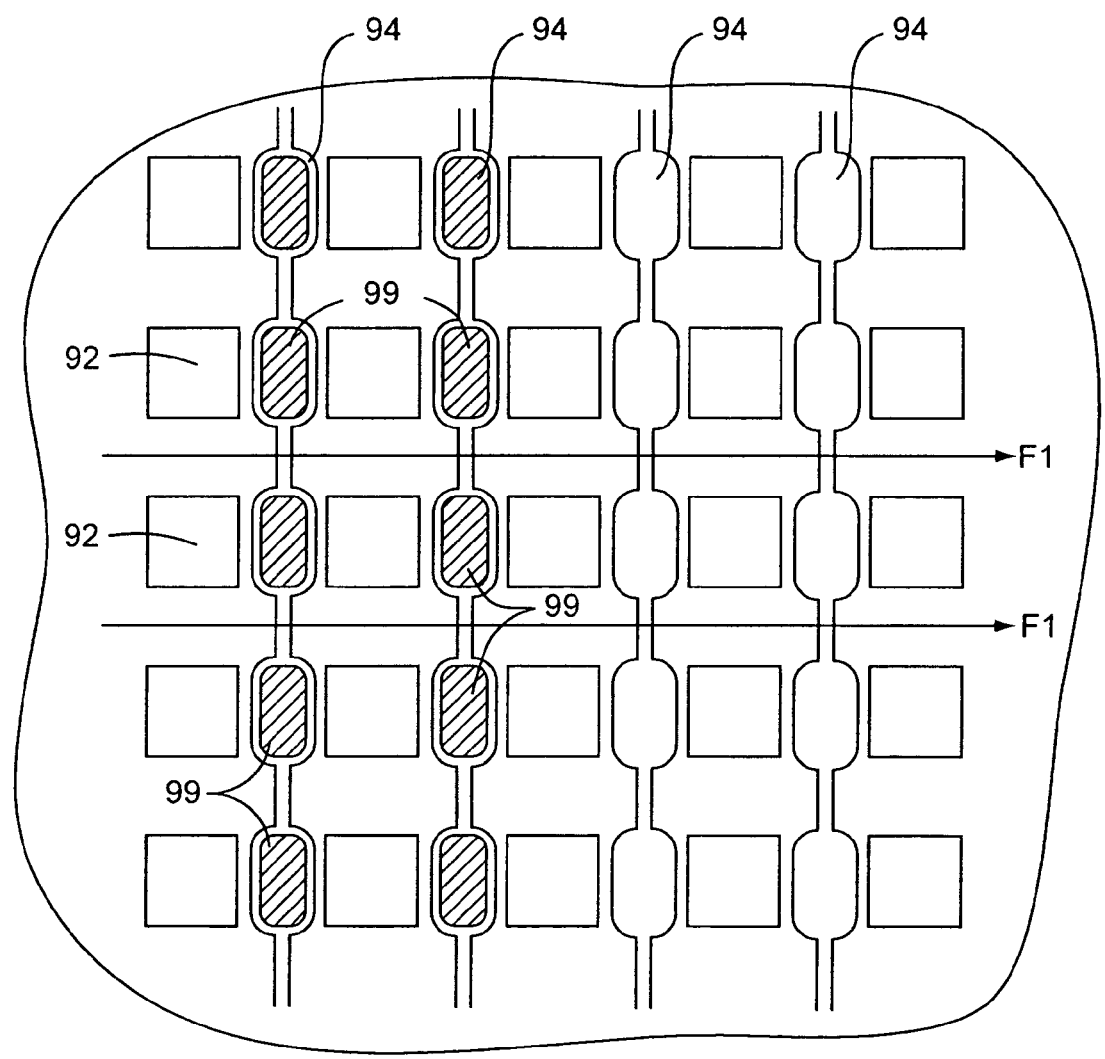
FIG. 20D also shows the alignment of the first layer of elastomer of FIG. 20A with the other set of control channels in the second layer of elastomer of FIG. 20B.

Elastomeric layer 95 is positioned over top of elastomeric layer 90 such that "vertical" control lines 96 are positioned over posts 92 as shown in FIG. 20C and "horizontal" control lines 94 are positioned with their wide portions between posts 92, as shown in FIG. 20D.

As can be seen in FIG. 20C, when "vertical" control lines 96 are pressurized, the membrane of the integrated structure formed by the elastomeric layer initially positioned between layers 90 and 95 in regions 98 will be deflected downwardly over the array of flow channels such that flow in only able to pass in flow direction F2 (i.e.: vertically), as shown.

As can be seen in FIG. 20D, when "horizontal" control lines 94 are pressurized, the membrane of the integrated structure formed by the elastomeric layer initially positioned between layers 90 and 95 in regions 99 will be deflected downwardly over the array of flow channels, (but only in the regions where they are widest), such that flow in only able to pass in flow direction F1 (i.e.: horizontally), as shown.

The design illustrated in FIGS. 20A-D allows a switchable flow array to be constructed from only two elastomeric layers, with no vertical vias passing between control lines in different elastomeric layers required. If all vertical flow control lines 94 are connected, they may be pressurized from one input. The same is true for all horizontal flow control lines 96.

9. Cell Pen/Cell Cage

In yet a further application of the present invention, an elastomeric structure can be utilized to manipulate organisms or other biological material. FIGS. 26A-26D show plan views of one embodiment of a cell pen structure in accordance with the present invention.

Cell pen array 4400 features an array of orthogonally-oriented flow channels 4402, with an enlarged "pen" structure 4404 at the intersection of alternating flow channels. Valve 4406 is positioned at the entrance and exit of each pen structure 4404. Peristaltic pump structures 4408 are positioned on each horizontal flow channel and on the vertical flow channels lacking a cell pen structure.

Figure 26A:
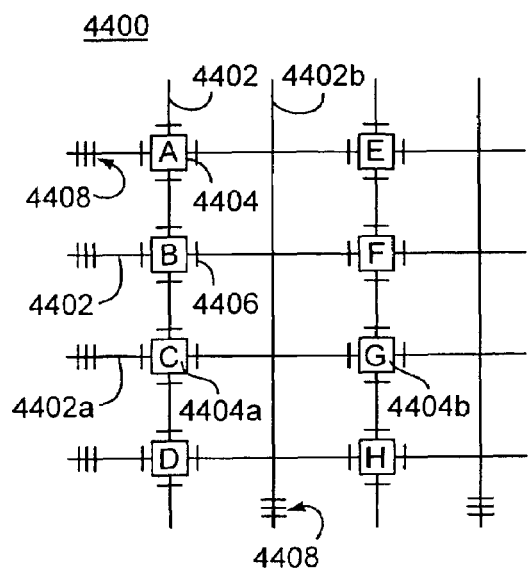
FIGS. 26A-26D show plan views illustrating operation of one embodiment of a cell pen structure in accordance with the present invention.
Figure 26C:
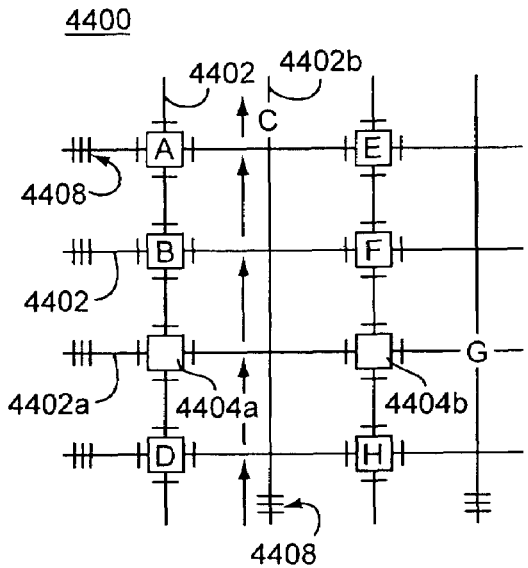
Figure 26B:
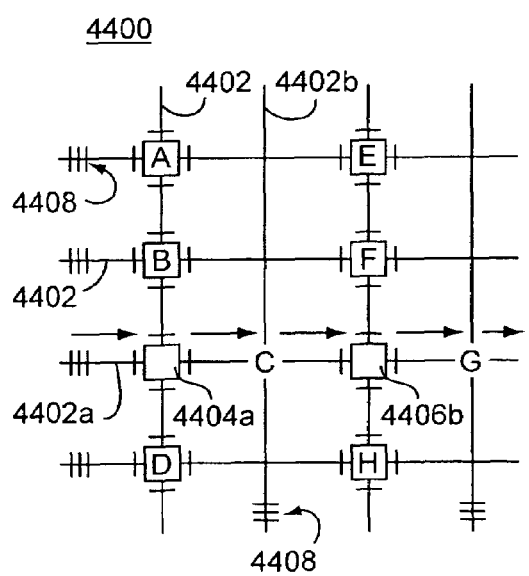
Figure 26D:
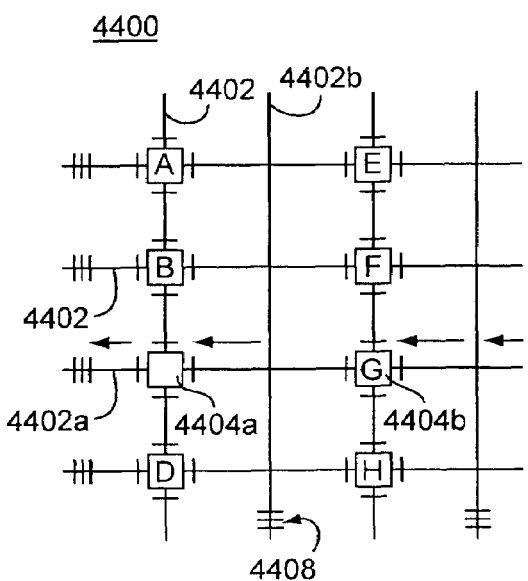

Cell pen array 4400 of FIG. 26A has been loaded with cells A-H that have been previously sorted. FIGS. 26B-26C show the accessing and removal of individually stored cell C by 1) opening valves 4406 on either side of adjacent pens 4404a and 4404b, 2) pumping horizontal flow channel 4402a to displace cells C and G, and then 3) pumping vertical flow channel 4402b to remove cell C. FIG. 26D shows that second cell G is moved back into its prior position in cell pen array 4400 by reversing the direction of liquid flow through horizontal flow channel 4402a.

Figure 27A:
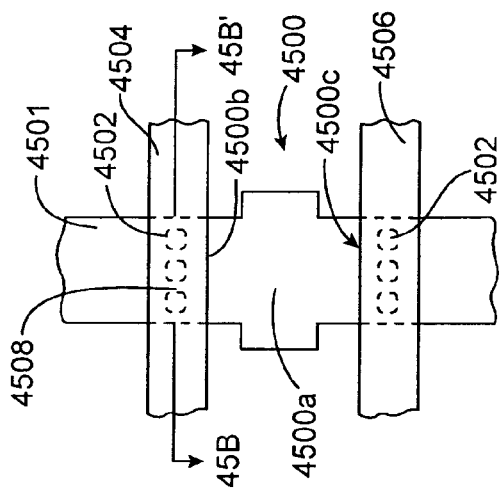
FIGS. 27A-27B show plan and cross-sectional views illustrating operation of one embodiment of a cell cage structure in accordance with the present invention.
Figure 27B:
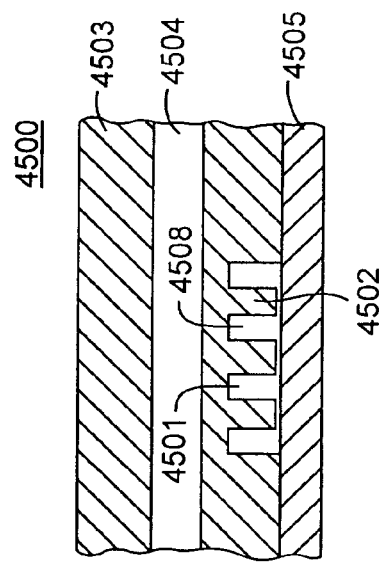

The cell pen array 4404 described above is capable of storing materials within a selected, addressable position for ready access. However, living organisms such as cells may require a continuous intake of foods and expulsion of wastes in order to remain viable. Accordingly, FIGS. 27A and 27B show plan and cross-sectional views (along line 45B-45B') respectively, of one embodiment of a cell cage structure in accordance with the present invention.

Cell cage 4500 is formed as an enlarged portion 4500a of a flow channel 4501 in an elastomeric block 4503 in contact with substrate 4505. Cell cage 4500 is similar to an individual cell pen as described above in FIGS. 26A-26D, except that ends 4500b and 4500c of cell cage 4500 do not completely enclose interior region 4500a. Rather, ends 4500a and 4500b of cage 4500 are formed by a plurality of retractable pillars 4502.

Specifically, control channel 4504 overlies pillars 4502. When the pressure in control channel 4504 is reduced, elastomeric pillars 4502 are drawn upward into control channel 4504, thereby opening end 4500b of cell cage 4500 and permitting a cell to enter. Upon elevation of pressure in control channel 4504, pillars 4502 relax downward against substrate 4505 and prevent a cell from exiting cage 4500.

Elastomeric pillars 4502 are of a sufficient size and number to prevent movement of a cell out of cage 4500, but also include gaps 4508 which allow the flow of nutrients into cage interior 4500a in order to sustain cell(s) stored therein. Pillars 4502 on opposite end 4500c are similarly configured beneath second control channel 4506 to permit opening of the cage and removal of the cell as desired.

The cross-flow channel architecture illustrated shown in FIGS. 26A-26D can be used to perform functions other than the cell pen just described. For example, the cross-flow channel architecture can be utilized in mixing applications.

This is shown in FIGS. 28A-E, which illustrate a plan view of mixing steps performed by a microfabricated structures in accordance another embodiment of the present invention. Specifically, portion 7400 of a microfabricated mixing structure comprises first flow channel 7402 orthogonal to and intersecting with second flow channel 7404. Control channels 7406 overlie flow channels 7402 and 7404 and form valve pairs 7408a-b and 7408c-d that surround each intersection 7412.

Figure 28C:
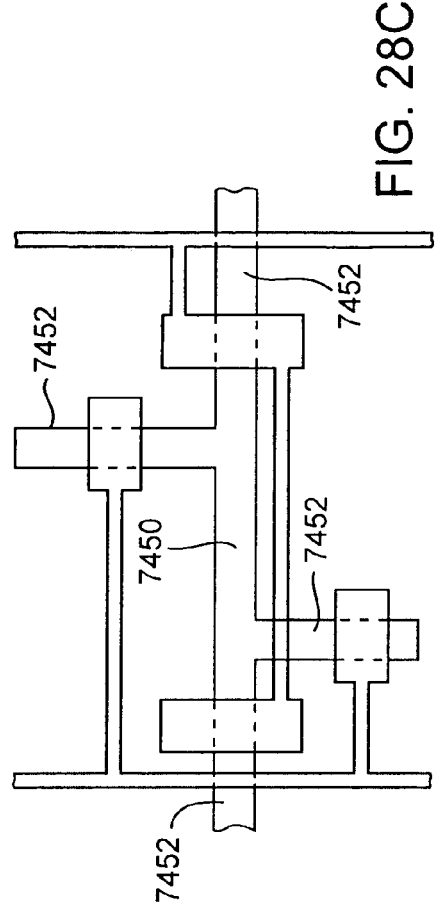
FIGS. 28A-28D show plan views of operation of a structure utilizing cross-channel injection in accordance with the embodiment of the present invention.
Figure 28D:
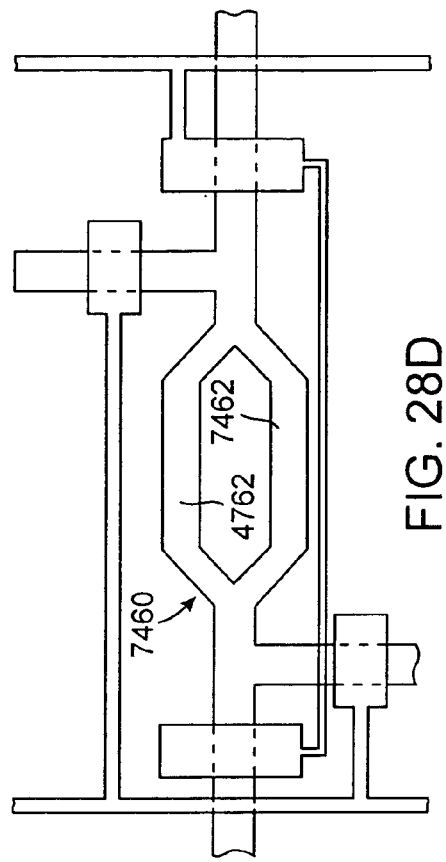
Figure 28A:
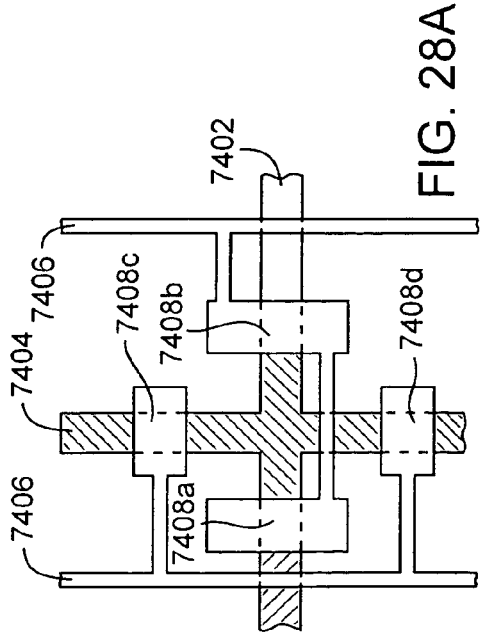

As shown in FIG. 28A, valve pair 7408c-d is initially opened while valve pair 7408a-b is closed, and fluid sample 7410 is flowed to intersection 7412 through flow channel 7404. Valve pair 7408a-b is then actuated, trapping fluid sample 7410 at intersection 7412.

Figure 28B:
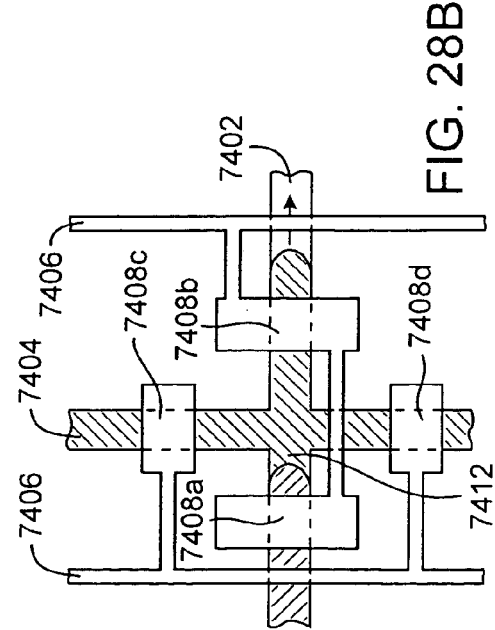
Figure 29A:
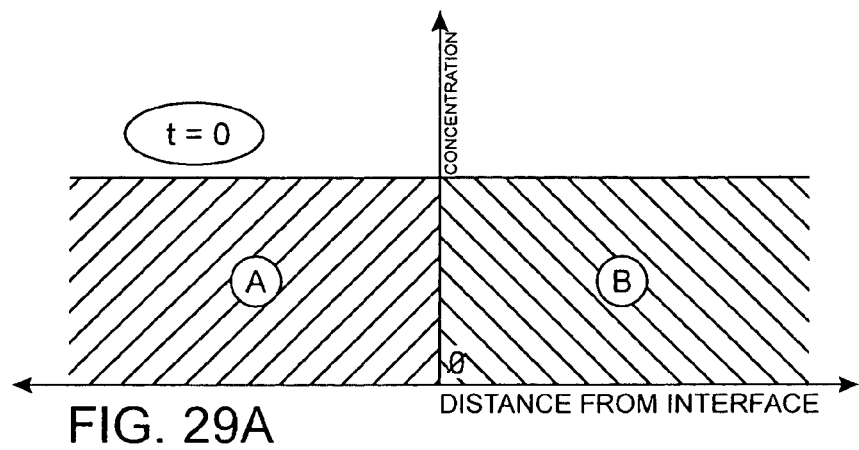
FIGS. 29A-D are simplified schematic diagrams plotting concentration versus distance for two fluids in diffusing across a microfluidic free interface in accordance with an embodiment of the present invention.
Figure 29B:
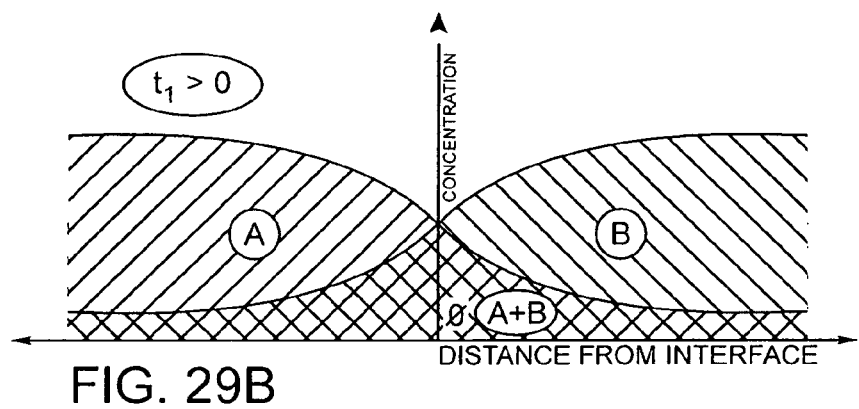
Figure 29C:
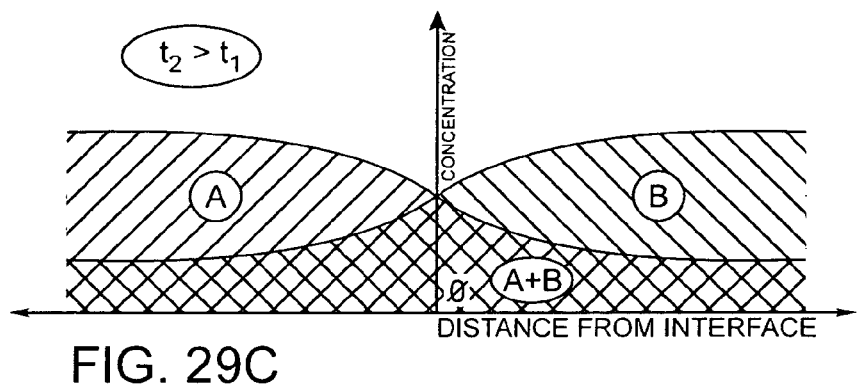
Figure 29D:
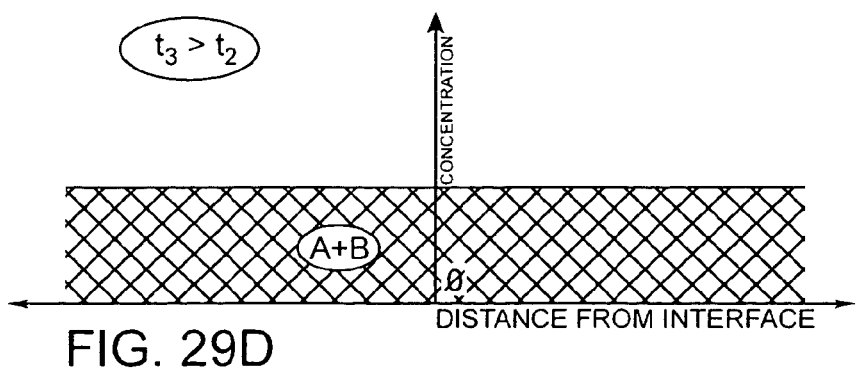

Next, as shown in FIG. 28B, valve pairs 7408c-d are closed and 7408a-b are opened, such that fluid sample 7410 is injected from intersection 7412 into flow channel 7402 bearing a cross-flow of fluid. The process shown in FIGS. 28A-B can be repeated to accurately dispense any number of fluid samples down cross-flow channel 7402.

While the embodiment of a process-channel flow injector structure shown in FIGS. 28A-B feature channels intersecting at a single junction, this is not required by the present invention. Thus FIG. 28C shows a simplified plan view of another embodiment of an injection structure in accordance with the present invention, wherein junction 7450 between intersecting flow channels 7452 is extended to provide additional volume capacity. FIG. 28D shows a simplified plan view of yet another embodiment of an injection structure in accordance with the present invention, wherein elongated junction 7460 between intersecting flow channels 7462 includes branches 7464 to provide still more injection volume capacity.

And while the embodiment shown and described above in connection with FIGS. 28A-28D utilizes linked valve pairs on opposite sides of the flow channel intersections, this is not required by the present invention. Other configurations, including linking of adjacent valves of an intersection, or independent actuation of each valve surrounding an intersection, are possible to provide the desired flow characteristics. With the independent valve actuation approach however, it should be recognized that separate control structures would be utilized for each valve, complicating device layout.

Figure 50:
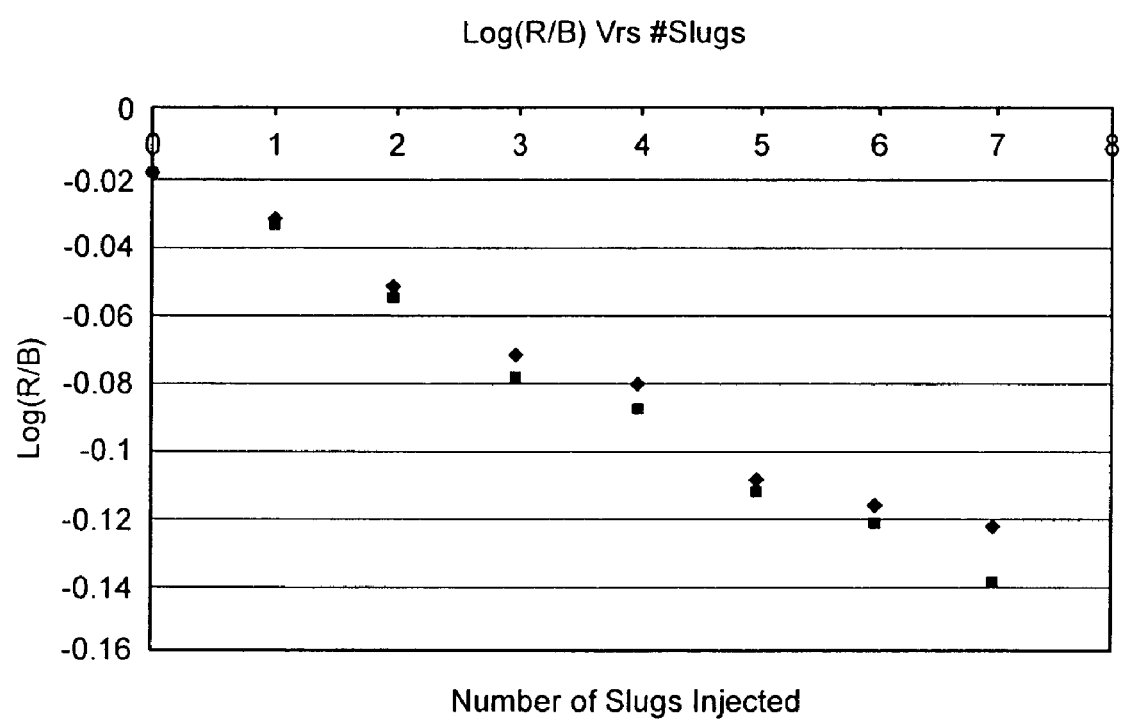
FIG. 50 plots Log(RIB) vs. number of slugs injected for one embodiment of a cross-flow injection system in accordance with the present invention.
Figure 51:
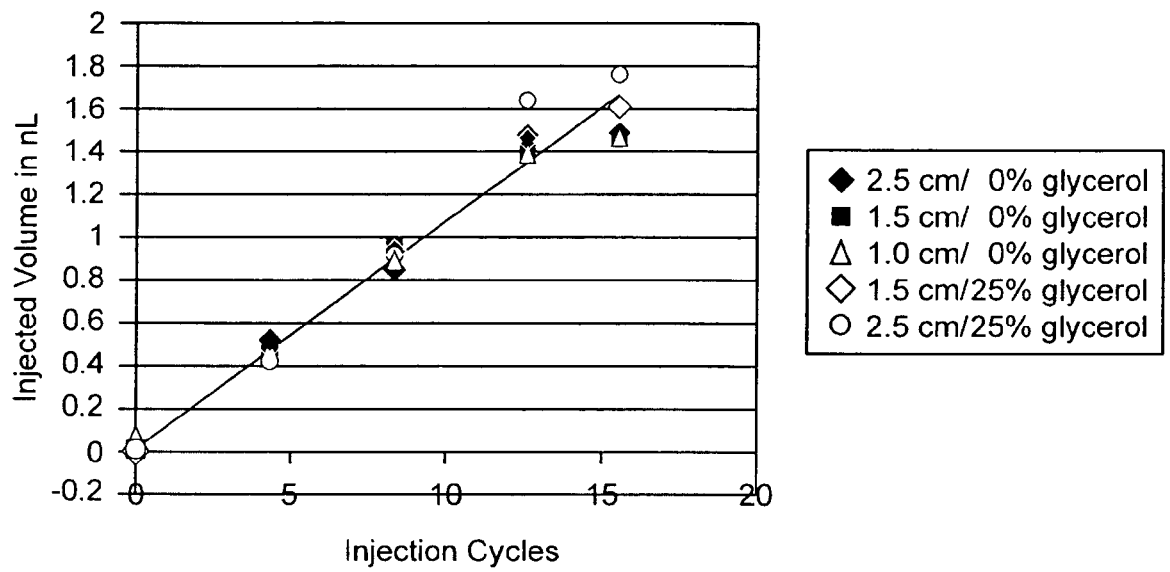
FIG. 51 plots injected volume versus injection cycles during operation of one embodiment of a cross-flow injection structure in accordance with the present invention.

FIG. 50 plots Log(R/B) vs. number of slugs injected for one embodiment of a cross-flow injection system in accordance with the present invention. The reproducibility and relative independence of metering by cross-flow injection from process parameters such as flow resistance is further evidenced by FIG. 51, which plots injected volume versus number of injection cycles for cross-channel flow injection under a variety of flow conditions. FIG. 51 shows that volumes metered by cross-flow injection techniques increase on a linear basis over a succession of injection cycles. This linear relationship between volume and number of injection cycles is relatively independent of flow resistance parameters such as elevated fluid viscosity (imparted by adding 25% glycerol) and the length of the flow channel (1.0-2.5 cm).

10. Rotary Mixing Structure

Microfluidic control and flow channels in accordance with embodiments of the present invention may be oriented to rotary pump design which circulates fluid through a closed circuit flow channel. As used herein the term "closed circuit" has the meaning known in the art and refers to configurations that are circular and variations thereof such as ellipsoids and ovals, as well as flow circuit paths having corners as are created by triangular, rectangular, or more complex shapes.

Figure 21:
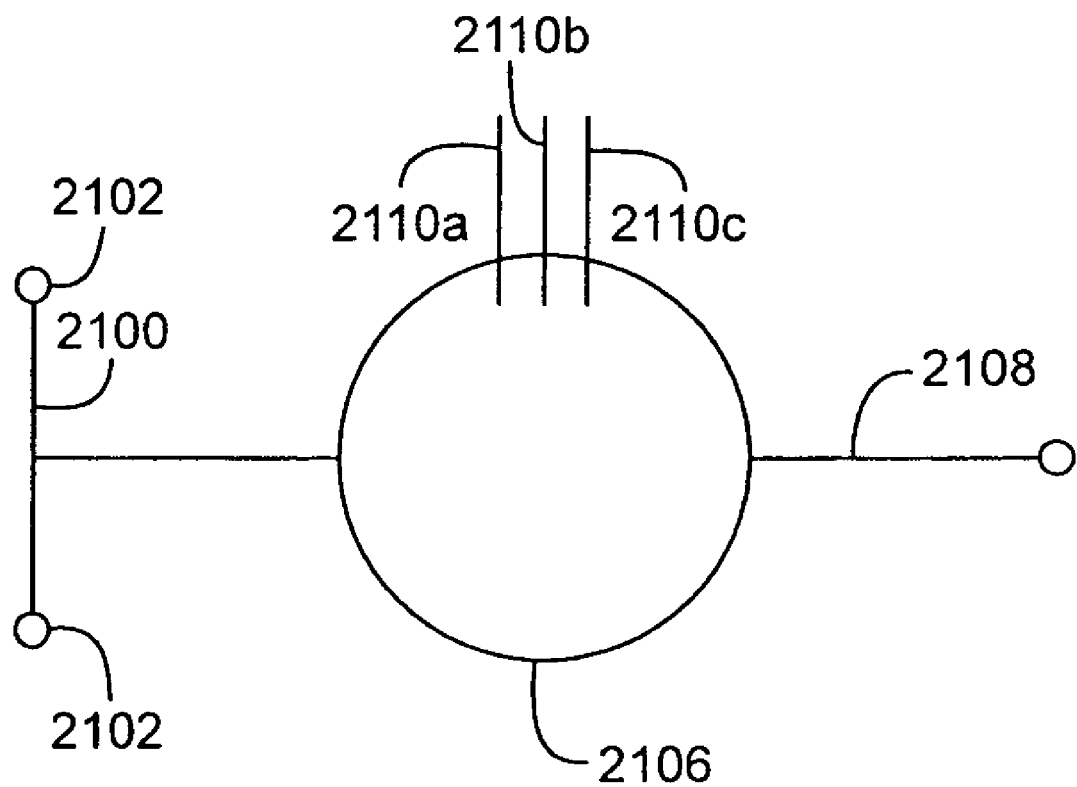
FIG. 21 shows a plan view of one embodiment of a rotary mixing structure in accordance with the present invention.

As illustrated in FIG. 21, a layer with flow channels 2100 has a plurality of sample inputs 2102, a mixing T-junction 2104, a central circulation loop 2106 (i.e., the substantially circular flow channel), and an output channel 2108. The overlay of control channels with a flow channel can form a microvalve. This is so because the control and flow channels are separated by a thin elastomeric membrane that can be deflected into the flow channel or retracted therefrom.

The substantially circular central loop and the control channels that intersect with it form the central part of the rotary pump. The pump(s) which cause solution to be flowed through the substantially circular flow channel consist of a set of at least three control channels 2110a-c that are adjacent to one another and which intersect the substantially circular branch flow channel 2106 (i.e., the central loop).

When a series of on/off actuation sequences, such a 001, 011, 010, 110, 100, 101, are applied to the control channels, the fluid in the central loop can be peristaltically pumped in a chosen direction, either clockwise or counterclockwise. The peristaltic pumping action results from the sequential deflection of the membranes separating the control channels and flow channel into or out of the flow channel.

In general, the higher the actuation frequency, the faster the fluid rotates through the central loop. However, a point of saturation may eventually be reached at which increased frequency does not result in faster fluid flow. This is primarily due to limitations in the rate at which the membrane can return to an unactuated position. As described below in connection with the combination mixing device shown in FIGS. 17A-B, various techniques may be adopted to maintain the connection between faster activation and flow/mixing at higher frequencies.

While the system shown in FIG. 21 shows two sets of pumps (i.e., two sets of three control channels that overlay the substantially circular flow channel) a single pump can be utilized (i.e., a single set of three control channels overlaying the substantially circular flow channel). Furthermore, while each pump is shown as including three control channels, a different number of control channels can be utilized, for example, a single serpentine control channel having multiple cross-over points could be used.

A variety of different auxiliary flow channels which are in fluid communication with the central loop can be utilized to introduce and withdrawn sample and reactant solutions from the central loop. Similarly, one or more exit or outlet flow channels in fluid communication with the central loop can be utilized to remove solution from the central loop. For example, control valves can be utilized at the inlet(s) and the outlet(s) to prevent solution flow into or out from the central loop.

Flow channel sizes and shapes can vary. With certain devices, the diameter of the channel tends to range from about 1 mm to 2 cm, although the diameter can be considerably larger in certain devices (e.g., 4, 6, 8, or 10 cm). Limits on how small the diameter of the circular flow channel can be are primarily a function of the limits imposed by the multilayer soft lithography processes. Channel widths (either flow or control) usually vary between 30 µm and 250 µm. However, channel width in some devices is as narrow as 1 um. Channels of larger widths can also be utilized, but generally require some type of structural support within the flow channel. Channel height generally varies between 5 and 50 µm. In flow channels having a width of 100 µm or less, the channel height may be 1 µm or smaller. The flow channel is typically rounded to allow for complete blockage of the channel once the membrane is deflected into the channel. In some devices, the channels have shapes such as octagons or hexagons. In certain devices, the flow channels are rounded and 100 µm wide and 10 µm high and control channels are 100 µm wide and 10 µm high. One system that has been utilized in certain studies has utilized a central loop having a diameter of 2 cm, a flow channel width of 100 µm and a depth of 10 µm.

While the channels typically have the foregoing sizes and shapes, it should be recognized that the devices provided herein are not limited to these particular sizes and shapes. For example, branches present in a closed circuit flow channel may serve to control the dispersion and hence mixing of materials flowed therein.

II. Combinatoric Mixing

The various microfluidic elements described above can be combined together to create a microfluidic device enabling accurate and rapid mixing of arbitrary combinations of input solutions on a microfluidic chip, thus enabling the creation of many thousands of different solutions from relatively few basic components.

1. Combinatoric Mixing Structure

Figure 17A:
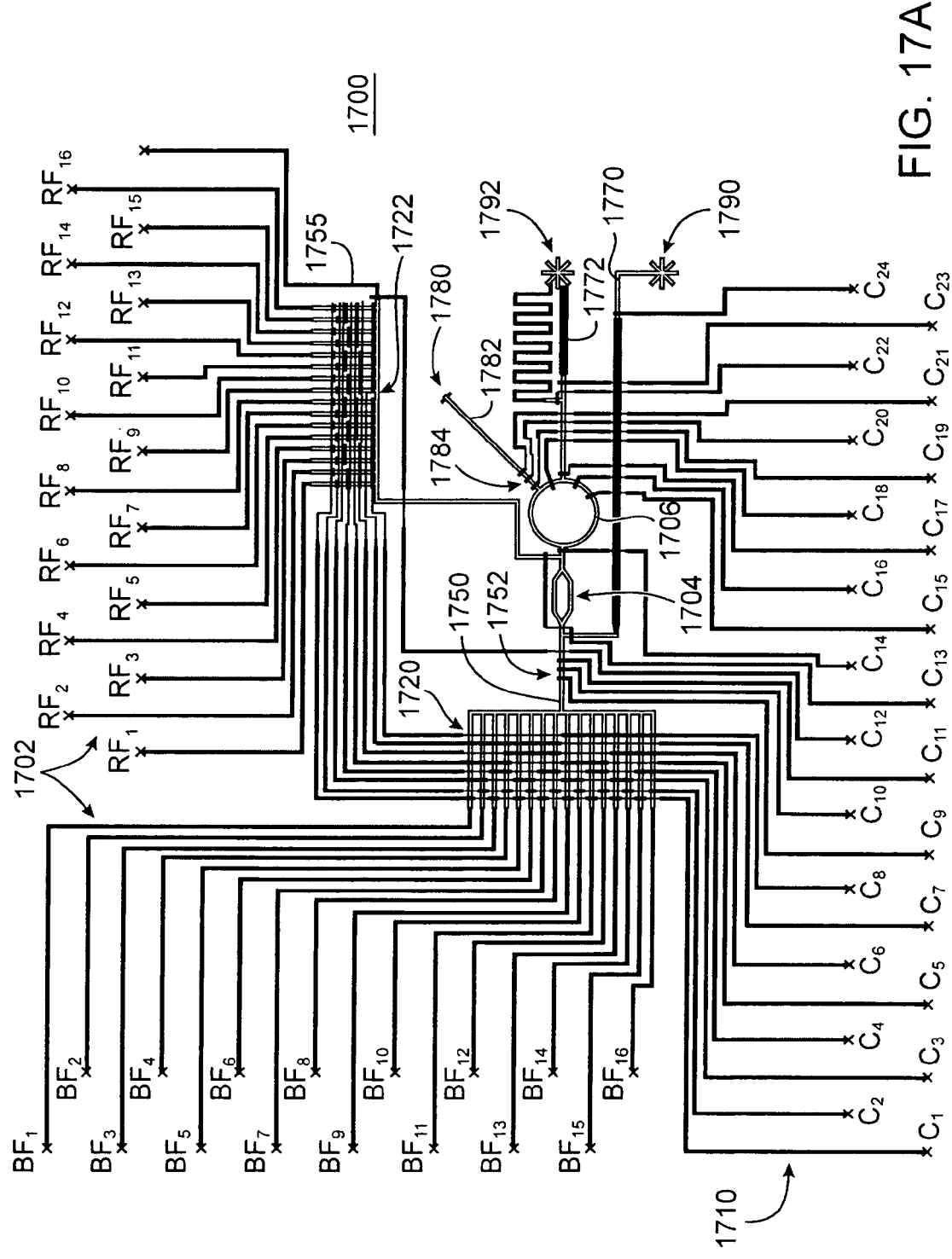
FIG. 17A shows a plan view of one embodiment of a combinatoric mixing device in accordance with the present invention.
Figure 17B:
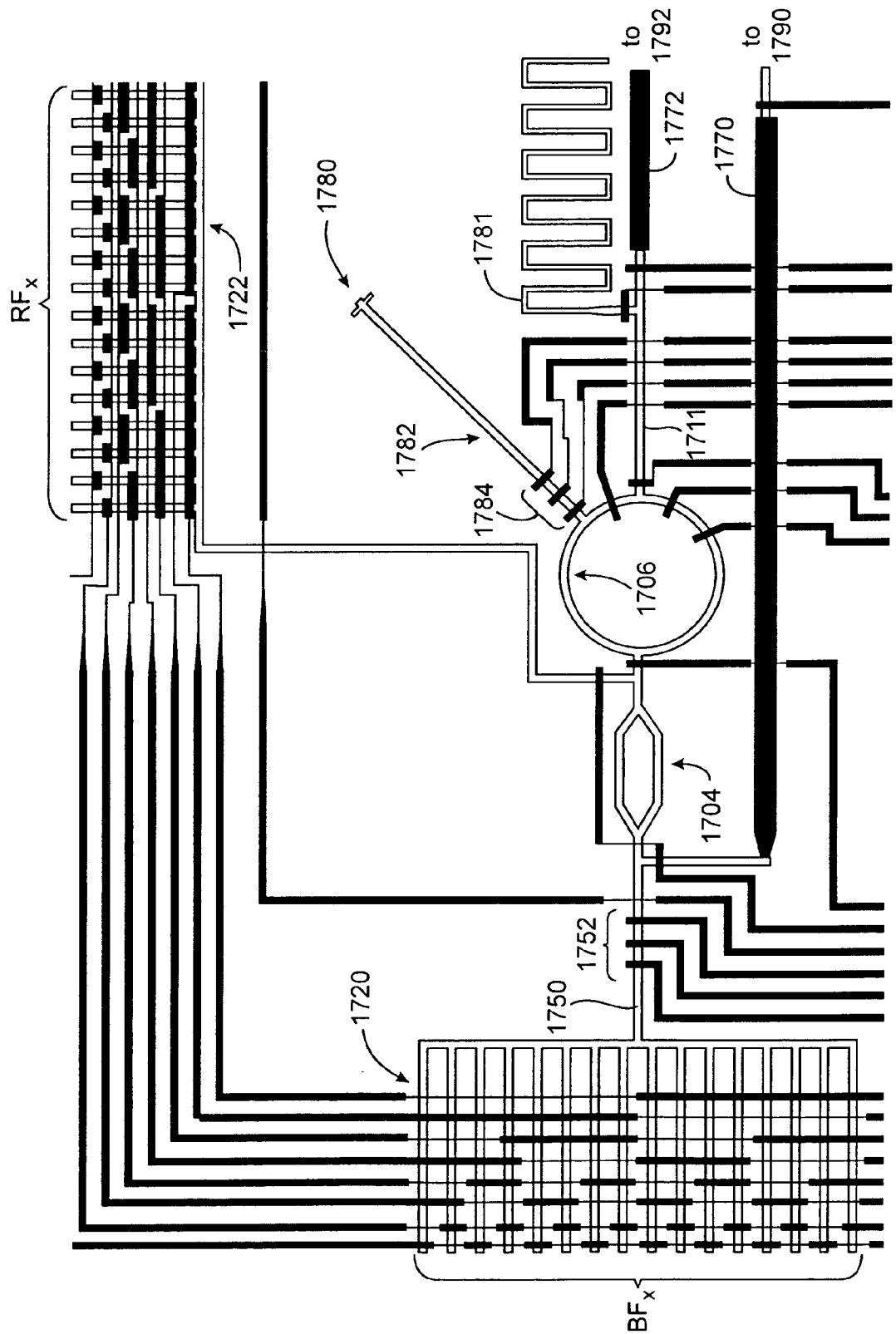
FIG. 17B shows an enlarged plan view of a portion of the combinatoric mixing device of FIG. 17A.

FIG. 17A shows a plan view of one embodiment of a combinatoric mixing device in accordance with the present invention. FIG. 17B shows an enlarged view of one region of the combinatoric mixing device of FIG. 17A.

Combination mixing device 1700 comprises flow channel network 1702 comprising buffer import flow lines ($BF_1$-$BF_{16}$) and reagent input flow lines ($RF_1$-$RF_{16}$), which intersect at branched cross-flow injector structure 1704, which is in turn in fluid communication with rotary mixing structure 1706.

Control channel network 1710 comprises control lines $C_1$-$C_{24}$. Control lines $C_1$-$C_8$ interact with buffer input flow lines $BF_1$-$BF_{16}$ to create first multiplexer structure 1720 governing metering of buffer to cross-flow injector 1704. Control lines $C_1$-$C_8$ also interact with reagent input flow lines $RF_1$-$RF_{16}$ to create second multiplexer structure 1722 governing metering of reagent to cross-flow injector 1704.

Control lines $C_9$-$C_{11}$ interact with main flow channel 1750 to create first peristaltic pump 1752 responsible for flowing buffer into the cross-flow injection structure 1704. Reagent is flowed through input flow lines $RF_1$-$RF_{16}$ under the influence of external pressure.

The right-most flow channel 1755 is controlled by a separate control line ($C_{12}$) and is used to flush water/buffer past the multiplexer inlet to avoid cross-contamination and subsequent insoluble salt formation in the channels. Prior to this washing process, the pressure within control lines $C_1$-$C_8$ may be varied to provide a pumping action.

Specifically, by selectively actuating these lines it is possible to pump only a selected channel, or to simultaneously pump all channels together. Furthermore, the pumping sequence may be designed to pump a specified volume of fluid either forward or backward. Backward fluid pumping may be used to prevent the unwanted mixing of two fluids belonging to different lines.

One instance where backward fluid pumping may be important is to prevent the unwanted mixture of different soluble salts in adjacent lines to form insoluble salts blocking the flow channels. Such unwanted mixing may be prevented in the following manner.

At the beginning of an experiment, buffer is pumped back into the multiplexer so that injected solutions are located a finite distance downstream from the multiplexer inlet. After a channel containing a first salt is selected from the multiplexer and the cross-injection junction has been flushed, a control line such as $C_{12}$ is released to flush water or buffer past the multiplexer outlet. This flushing eliminates most of the salt from the vicinity of the multiplexer outlet. However, small amounts of salt may have diffused from the nearby inlets.

Thus the multiplexer is then used to pump forward all the inlet lines simultaneously, causing any remaining salt solution to be swept away by the buffer/water moving past the multiplexer outlet. The multiplexer is then next used to pump backwards, so that fresh buffer is brought back into all the lines. In this way buffer solution is present in each line of the multiplexer until the line is selected and desired reagent is flushed through the selected line. This flow process ensures against unwanted mixing of the reagents. Continuous operation for more than a week using the flush/backflow method just described has shown that incompatible salts, for example potassium phosphate and magnesium chloride, may be used in adjacent lines without any unwanted mixing or formation of insoluble salts.

Control line $C_{13}$ gates the flow of reagent into cross-flow injector 1704. Control lines $C_{14}$ and $C_{17}$ gate the flow into and out of rotary mixer 1706. Control lines $C_{15}$, $C_{16}$, and $C_{18}$ interact with rotary mixer 1706 to form a third peristaltic pump responsible for creating the circular flow within the mixer.

First outlet flow channel 1770 is in direct fluid communication with cross-flow injector 1704 and typically conveys waste material to first outlet 1790. Second outlet flow channel 1772 is in fluid communication with the cross-flow injector structure 1704 through rotary mixer 1706, and thus conveys waste material to second outlet 1792.

The combinatoric mixer shown in FIGS. 17A-B further includes a serpentine alternative outlet channel 1781 proximate to second outlet flow channel 1772. The purpose of serpentine channel 1781 is as follows. Since the inlet, cross-junction, mixing ring, and outlet are in fluidic series, the fluidic impedance is the sum of the component impedance. If the impedance of the cross-injector is small compared to the inlet/outlet impedance, then changing the viscosity of the fluid in the cross-injective should have a minimal effect, thereby desirably resulting in a decrease in metering sensitivity. For this reason, channel 1781 is long (with many bends) and of smaller diameter. The outlet for the combinatoric mixer is switched to the serpentine channel 1781 during injection cycles.

Typical operation of the device shown in FIGS. 17A-B is as follows. Flow is directed horizontally through cross injection area 1704. First multiplexer 1720 is used to select a flow line from buffer flow channel inputs ($BF_1$-$BF_{16}$) that flush through branched-cross injector 1704, through rotary mixer 1706, out second outlet channel 1772.

The flow of buffer through the device is then stopped by closing the valves of peristaltic pump 1752, and flow is directed vertically through the cross-injector 1704. A reagent is then selected from the reagent flow channel inputs ($RF_1$-$RF_{16}$) using second multiplexer 1722. This reagent flushes through cross-injection area 1704 and then out through first outlet channel 1770.

Flow is then once again directed horizontally through cross-injector 1704, and the peristaltic pump 1752 is used to push an exact amount of reagent into rotary mixing ring 1706. Every cycle of peristaltic pump 1752 injects a well-defined volume (approximately 80 pL) into the rotary mixer 1706, so that the total amount injected into the ring may be controlled by number of injection cycles.

Once the desired amount of the first reagent is injected into rotary mixer 1706, another reagent flow channel line ($RF_x$) is selected and the injection process is repeated. In this way, arbitrary combinations of the reagents may be introduced into the rotary mixer 1706. The rotary mixer has a total volume of 5 nL so that the rotary mixer may accommodate approximately 60 injection volumes.

Once the ingredients have been injected into the rotary mixer 1706, diffusive mixing occurs by Poiseuille flow resulting from peristaltic pumping of the mixture around mixer 1706. Once mixing is complete, the mixture is flowed through flow channel 1711 to second outlet channel 1772, which can be in fluid communication with another region of the chip or another chip entirely (neither of which is shown in FIGS. 17A-B) for storage, analysis and/or further processing. These steps may be repeated for serial processing.

The specific embodiment of the combinatoric mixing device 1700 shown in FIGS. 17A-B also includes sample port 1780 in fluid communication with rotary mixer 1706 through flow channel 1782 in pressure communication with the peristaltic pump 1784 defined by the presence of control channels $C_{19-21}$. If desired, a sample, may be introduced through the sample input port and then injected into the mixer using peristaltic pump. As described at length below, one potential application utilizing this sample injector is to conduct high throughput mapping of phase space by precipitation.

The above described mixing chip may be used on its own or incorporated as key component in a larger microfluidic device. The chip may be used to mix and meter arbitrary combinations of fluids that can be delivered to downstream measurement or storage systems. By adding storage or memory elements this mixing functionality allows for large scale screening and processing of samples. For example, as discussed below, the outlet of the ring may be used to serially mix reagents and then send them to fill an array of several thousand reaction chambers for storage/screening purposes.

The combintoric mixing structure described prepares a mixed volume of about 5 nL. However, embodiments in accordance with the present invention are not limited to mixing at this or any other volume. Mixing volumes achievable by microfluidic devices may range from over 1 µL, to between about 1 µL and 100 µL. The mixing volumes utilized for crystallization studies may thus include 1 µL or less, 100 nL or less, 10 nL or less, 1 nL or less, or 100 pL or less.

Figure 22:
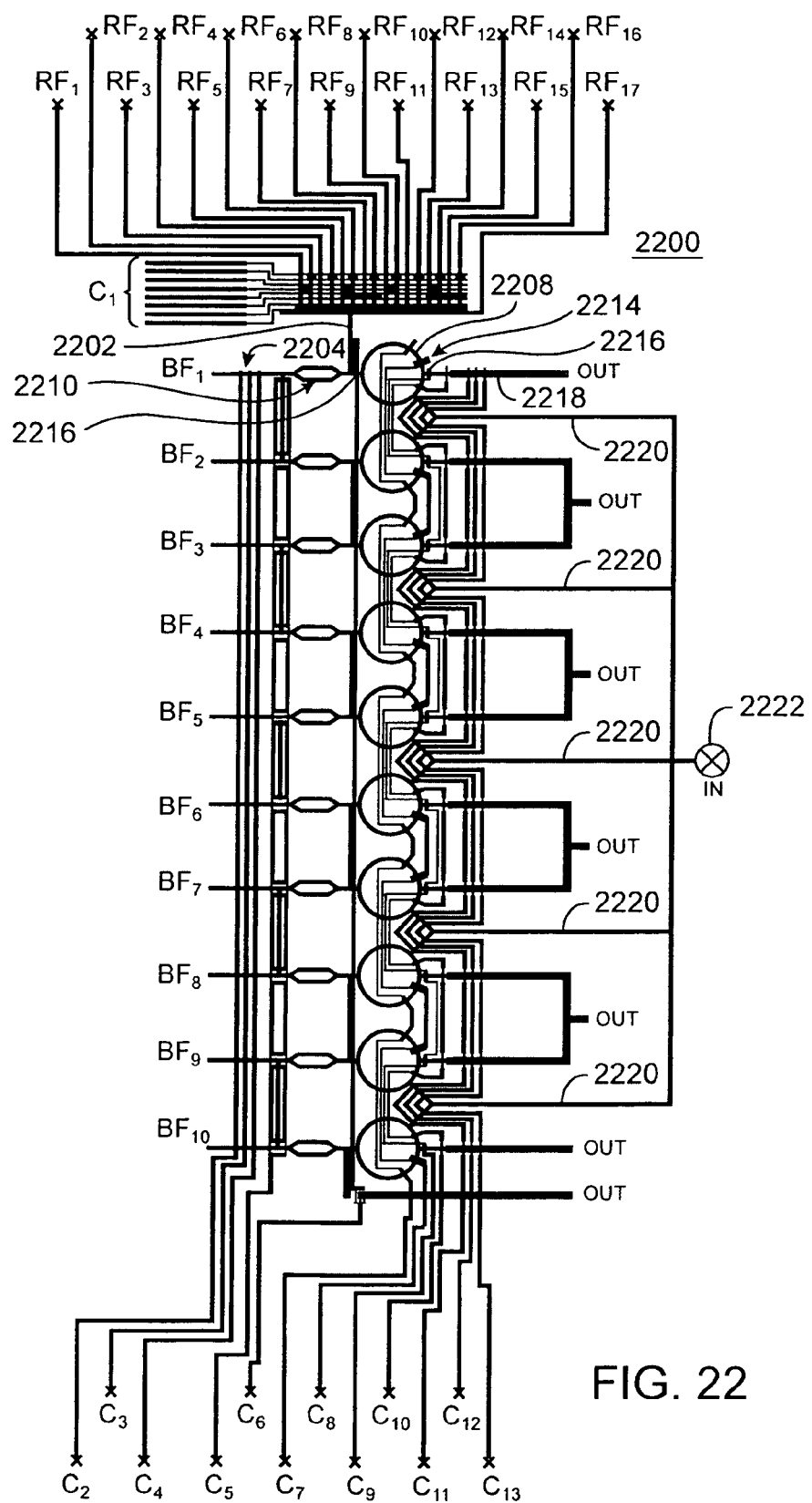
FIG. 22 shows a plan view of an array of combinatoric mixing structures in accordance with the present invention.
Figure 23:
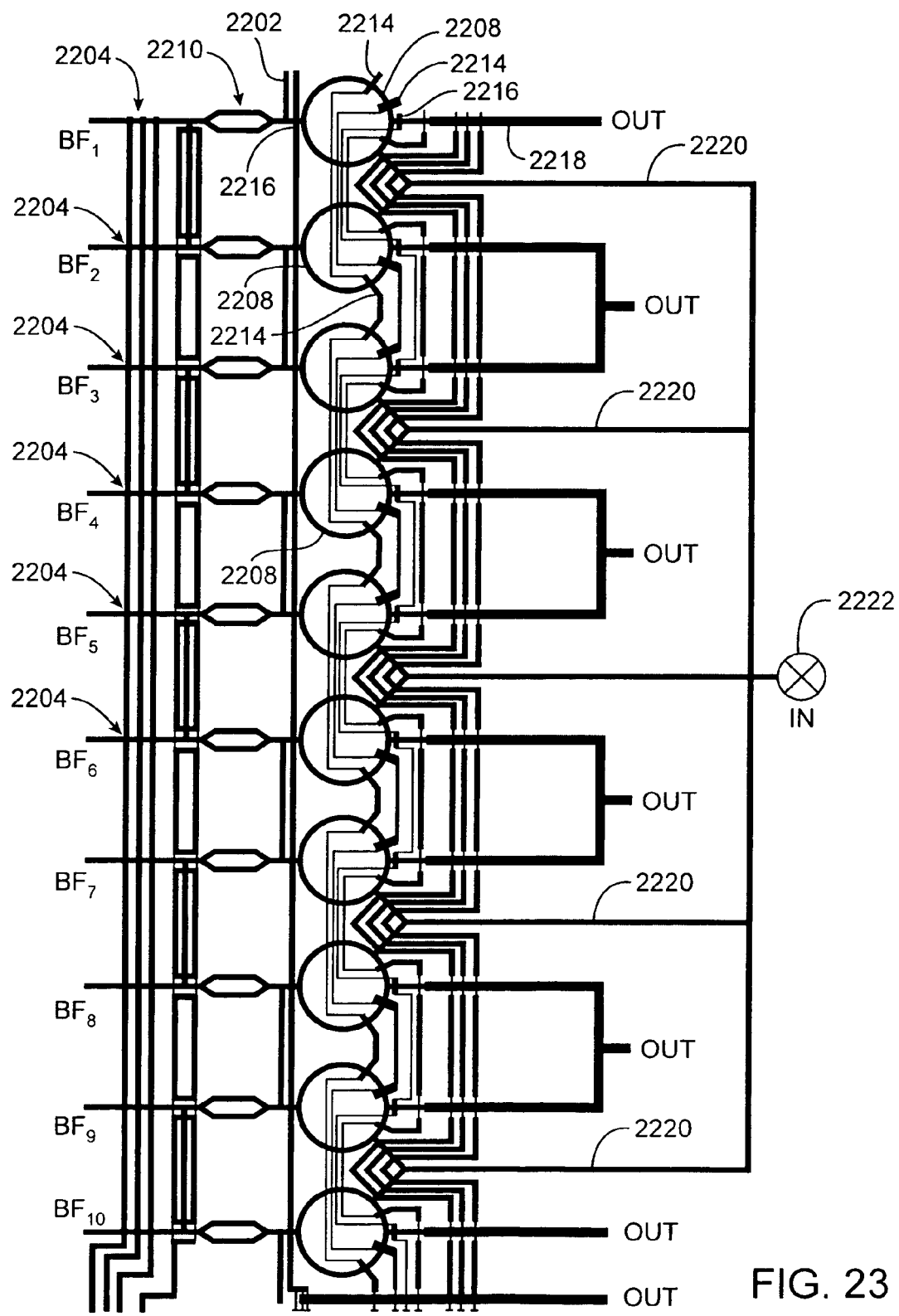
FIG. 23 shows a enlarged view of the array of combinatoric mixing structures of FIG. 22.

While the above description relates to serial implementation of combinatoric mixing, parallel implementations of the basic mixing elements are also possible. For example, an array of multiple fluidic structures such as that shown in FIGS. 17A-B may be incorporated onto a single chip For example, FIG. 22 shows an overall plan view, and FIG. 23 shows an enlarged view, of a column of combinatoric mixers in accordance with an embodiment of the present invention. Combinatoric mixing device 2200 comprises flow channel network 2202 including buffer input flow channels $BF_1$-$BF_{10}$ controlled by the peristaltic pump structures 2204 formed by the overlay of control channels $C_2$-$C_4$. Buffer input flow channels $BF_1$-$BF_{10}$ are in fluid communication with mixing structures 2208 through respective branched cross-channel injectors 2210. Reagents selected from reagent flow lines $RF_1$-$RF_{16}$ may be selected utilizing the multiplexer 2212 created from the overlap of control channel network $C_1$, and then flowed into cross-flow injectors 2210.

The overlap of control channels $C_7$, $C_8$, and $C_{10}$ over the closed circuit mixing structure defines peristaltic mixing pumps 2214. The overlap of control lines $C_6$ and $C_9$ create respective gate valves 2216 for the mixing structures. Materials outlet from the mixing structures flows through outlet lines 2218 for disposal.

Macromolecule samples may be injected from sample inlet lines 2220 in common fluid communication with sample reservoir 2222, specifically utilizing peristaltic pumping structures defined by the overlap of control lines $C_{11}$-$C_{13}$. Once macromolecule samples have been injected into the mixing structure, the formation of the solid phase can be monitored by optical interrogation, utilizing a common light source and a bank of detectors appropriately positioned proximate to the mixing structures. Alternatively, a plurality of mixing structures on the chip may be scanned over a single detector utilizing a motorized stage.

As shown in FIGS. 22-23, the control lines for each mixing component may be connected so that the entire array of mixing elements may be operated with no increase in control complexity. In one embodiment, all the buffers may be used at the same time with identical reagents. Alternatively, every ring may be prepared in an identical fashion but with a different sample. Thus, a parallel architecture would allow for the simultaneous screening of one sample against the same reagents, but with different buffers (having different pH), or the screening of many different samples against identical conditions. In this way the throughput of this system can be increased proportionally to the degree of parallelization.

For example, a combinatoric mixing structure in accordance with an embodiment of the present invention is currently able to perform approximately 3000 protein solubility assays per day, so that the design of FIGS. 22-23, having 10 parallel mixing structures, can perform 30,000 experiments per day. Each of these experiments requires an average of 1 nL of protein sample so that a total of 100,000 experiments can be conducted in a little over three days using a total volume of approximately 100 uL of protein sample.

Another method of increasing throughput is to couple the combinatoric mixing structure to another fluidic structure that is designed to perform a fixed mixing function. For example, the combinatoric mixing structure can be coupled via a multiplexer to a fluidic mixing matrix. The combinatoric mixing structure can be used to fill the N rows of the matrix with unique solutions, while the columns are connected to N different samples. In this way N mixing operations may be used to create $N^2$ unique reactions.

In one approach, such a combinatoric mixing chip could be placed into fluid communication with a flow channel pattern suitable for performing the polymerase chain reaction (PCR). Alternatively, a fluidic structure may be designed to allow for a broad range of mixing ratios to be simultaneously implemented based on geometric metering schemes previously described.

The combinatoric mixing design has been implemented and used to demonstrate ultra-precise metering of a wide range of fluids having different physical properties (ionic strength, pH, viscosity, surface tension). It has been determined that this metering and mixing system is extremely accurate, robust, and insensitive to the fluid properties. Fluid may be injected into the ring in volume increments of approximately 80 pL and with less than 1% error. The system is able to meter fluids with viscosities ranging from 1 to 400 cP with only a 5% variation in injected volume.

The speed of metering fluids through channels of the embodiments of microfluidic structures in accordance with embodiments of the present invention is well approximated by Equation (2) below, which describes the volume flux through a channel of circular cross-section:

$$Q = \frac{\pi a^4 \Delta P}{8 \mu L}; \text{ where:} \qquad (2)$$

Q=volume flux in channel (vol/s)
a=dimension of channel;
L=length of channel;
$\Delta P$=changed pressure within channel; and
$\mu$=viscosity of actuation fluid within channel.

Equation (2) essentially describes the ability to effect a change in volume of fluid in a microfluidic channel. Where the fluid is actuation fluid and the microfluidic channel is a control channel, this volume flux dictates the rate at which material may be flowed through a flow channel adjacent to the control channel.

Per Equation (2), one way of achieving more rapid actuation/mixing is to increase the dimension (a) of the control channel. In the embodiment of the combinatoric mixing device of FIGS. 17A-B, this has been accomplished by enlarging dimensions of the control channels to reduce the flow resistance of volumes of actuating fluid moving in and out of the actuated/deactuated control channels, respectively. Specifically, the height dimension of the control channels has been increased to 30 µm from 10 µm.

Another way of achieving more rapid actuation is to raise the baseline (ground) pressure above atmospheric. Specifically, the rebound of the actuated membrane may be a rate limiting factor since the pressure driving retraction may only be the channel pressure which typically is near atmospheric. The rebound thus may often be solely due to the elastic properties of the membrane. By raising the ground pressure, in accordance with embodiments of the present invention, the membrane may also back up into the control channel by the flowed fluid. In certain embodiments, the base pressure is around 6 psi, however the higher this baseline pressure, the faster the valve response.

Further per Equation (2), still another way of achieving more rapid actuation is to reduce the viscosity (µ) of the actuation fluid. Generally, water having a viscosity of 0.001 kg/m·s, or air having a viscosity of 0.000018 kg/m·s, may be utilized as the actuation fluid. Water rather than air has been used as the actuation fluid due to the desire to avoid the formation of air bubbles in the flow channels. However, the embodiment of the combinatoric mixing device shown in FIGS. 17A-B utilizes air-filled control channels to increase actuation speed. Moreover, it has been discovered that the use of an elevated baseline pressure substantially reduces the incidence of bubble formation.

To summarize, combination of 1) larger peripheral control channel dimensions, 2) elevated baseline pressure, and 3) the use of air as an actuation fluid, has increased the maximum frequency of actuation of valves of the microfluidic combinatoric mixing device of FIGS. 17A-B from about 10 Hz to about 100 Hz, with a resulting frequency of movement of fluid through the closed circuit mixer of about 4 Hz.

The metering and mixing performed by the combinatoric mixing chip was found to be correspondingly fast. A single mixing configuration is capable of processing 3000 samples per day. By the parallel integration of 20 such mixers on a single chip it is possible to process approximately 60,000 reactions a day, making this device suitable for high throughput screening applications.

Figure 18:
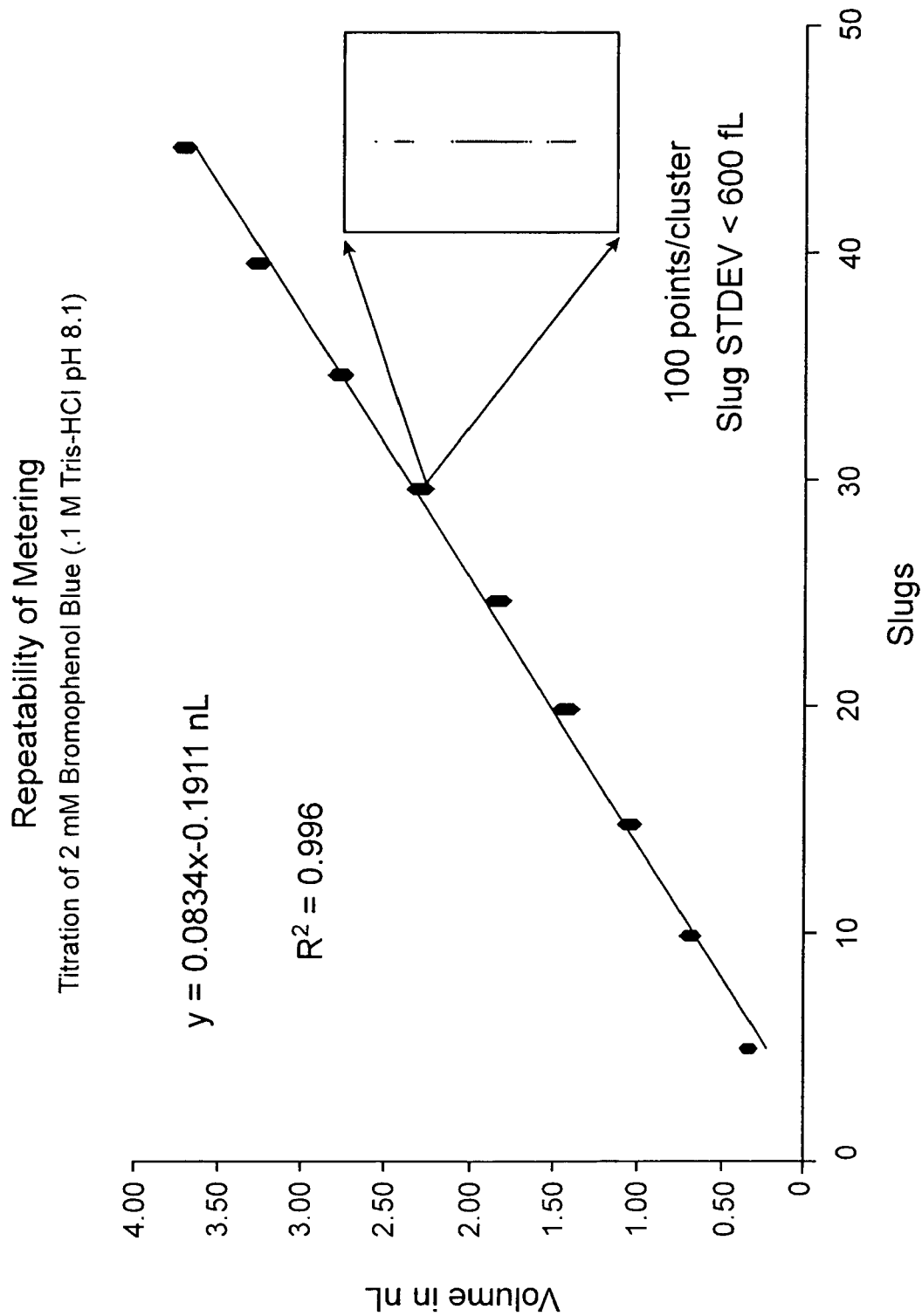
FIG. 18 plots injection volume for a number of injection slugs.
Figure 19:
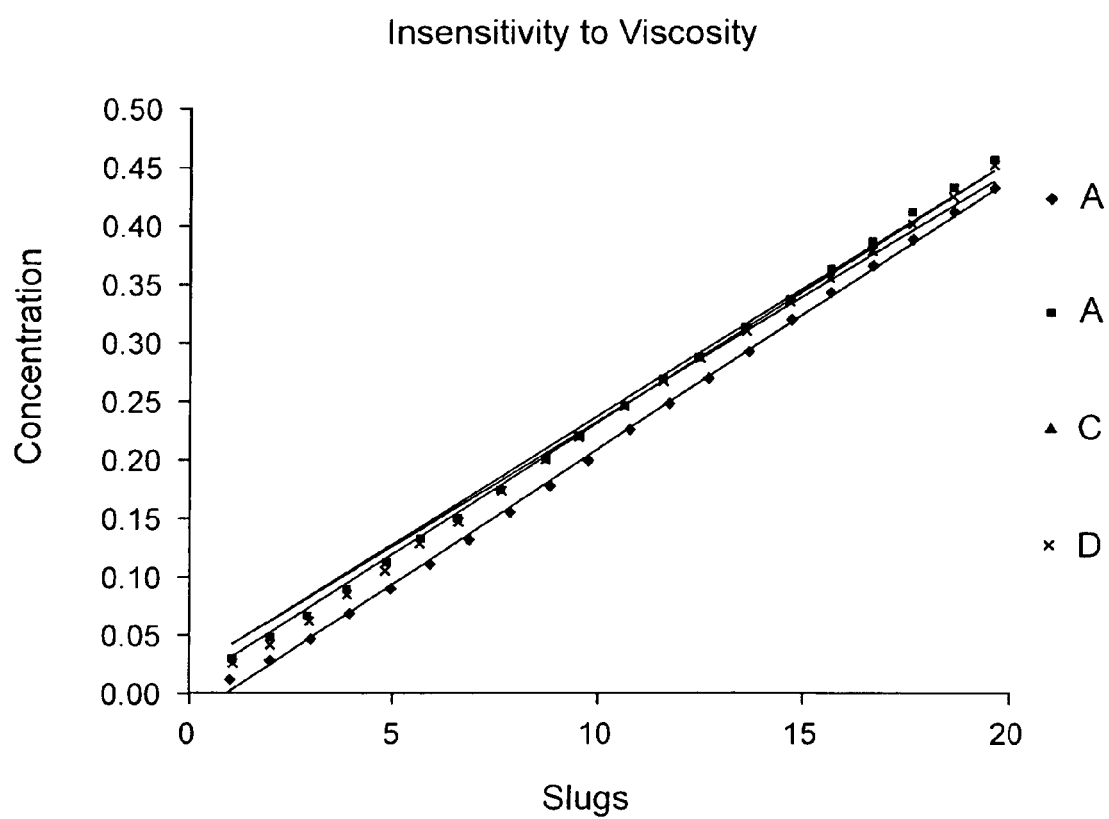
FIG. 19 plots concentration for a number of injection slugs.

FIGS. 18 and 19 below show the results of some metering experiments performed on chip. FIG. 18 plots injection volume versus injected slug number for titration of 2 mM Bromphenol Blue (0.1 M Tus-HCl @ pH 8.1). Absorption measurements of FIG. 18 evidence the precision and repeatability of metering. Each of the nine clusters consists of one hundred independent metering experiments conducted over the period of ten hours.

FIG. 19 plots concentration versus injected slug number for samples exhibiting four different viscosities, as summarized in the following TABLE 1.

TABLE 1

| SAMPLE | GLYCEROL (%) | VISCOSITY (cP) | SLUG VOL. (pL) | R2 |
|---|---|---|---|---|
| A | 0 | 1 | 90.72 | 0.999 |
| B | 76 | 40 | 88.2 | 0.997 |
| C | 84 | 100 | 84.84 | 0.998 |
| D | 92 | 400 | 86.52 | 0.998 |

The narrow deviation evidenced by the injected volumes in FIG. 19 evidences absorption measurements showing the insensitivity of metering to fluid properties, and in particular to a wide range of viscosities.

The combinatoric mixing device may find a variety of applications as a formulation tool to address problems in biology, chemistry, chemical engineering and so forth in which it is necessary to find the optimal combination of components in a recipe. This device chip and variants thereof can be used to systematically screen through many variations in the parameters of these recipes, thus providing a quick and inexpensive means to optimize recipes and formulations. Potential fields of use include microbiology, chemical synthesis, high throughput screening, drug discovery, medical diagnostics, pathogen identification, and enzymatic reactions (including but not limited to the polymerase chain reaction and all of its variants). The device can also serve to formulate a variety of lotions, creams, or food products, chemical synthesis, and so forth.

Embodiments of microfluidic structures in accordance with the present invention may be employed for applications as are more completely described in PCT application PCT/US01/44869, filed Nov. 16, 2001 and entitled "Cell Assays and High Throughput Screening", hereby incorporated by reference for all purposes. Examples of microfluidic structures suitable for performing such applications include those described herein, as well as others described in U.S. nonprovisional patent application Ser. No. 10/118,466, "Nucleic Acid Amplification Utilizing Microfluidic Devices", filed Apr. 5, 2002 as Atty Docket No. 20174C-004430, hereby incorporated by reference for all purposes.

One promising application for the combinatoric device shown and described in connection with FIGS. 17A-B is the solubilization of membrane proteins.

Membrane proteins are typically expressed in eukaryotic cells, where they are incorporated within the cell membranes. The three-dimensional structure of these membrane proteins can be determined by x-ray diffractometry of them in crystalline form.

Before such crystals can be formed, however, it is first often necessary to stabilize the proteins in solution with the three-dimensional folded shape that they possess when incorporated into the cell membrane. This is typically accomplished by addition of a detergent, which encloses the membrane protein in a small envelope of amphiphilic molecules (the detergents) that emulate the environment of the cell membrane and prevent denaturation. Solubilizing the membrane proteins in this manner typically requires experimentation with different buffers at different pH values, ionic strengths, and including different detergents. The solubilization of membrane proteins is thus at heart a formulation problem.

Since the membrane proteins are typically available to the researcher in only small quantities, it is desirable to perform solubility studies in small volumes, and in an automated fashion. Accordingly, the combinatoric mixing device just described is well-suited to this task.

FIGS. 61A-G are schematic views of an assay by which screening conditions may be assessed for success in solubilizing membrane proteins. This technique is appropriate for solubilization of membrane proteins for which a corresponding receptor or antibody is known.

Figure 61A:
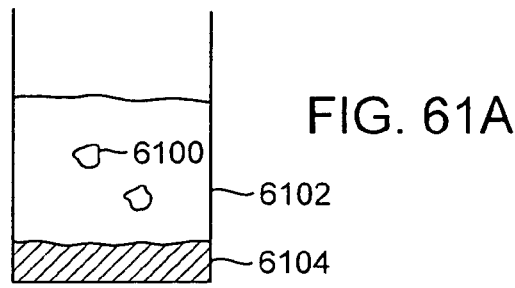
FIGS. 61A-F illustrate schematic views of an embodiment of a method in accordance with the present invention for solubilizing a membrane protein.

FIG. 61A shows a first step of the method, wherein cells 6100 in test tube 6102 are lysed centrifuged to concentrate membranes containing the membrane proteins in a pellet 6104 at a bottom of the test tube. Pellet 6104 is referred to as the lysate.

Figure 61B:
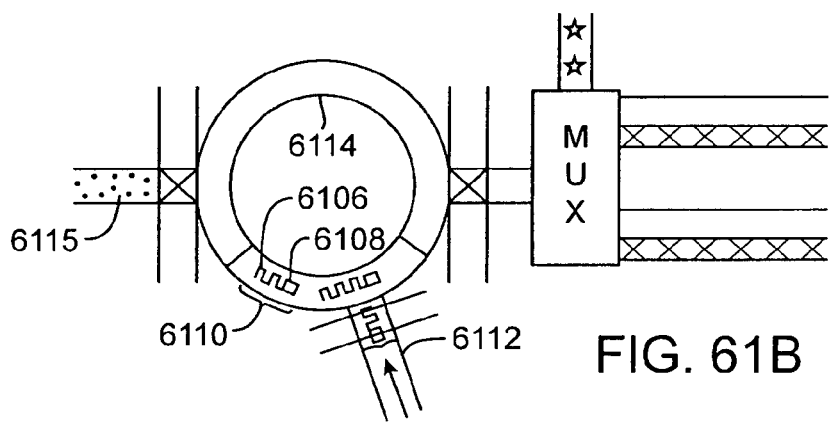
Figure 61C:
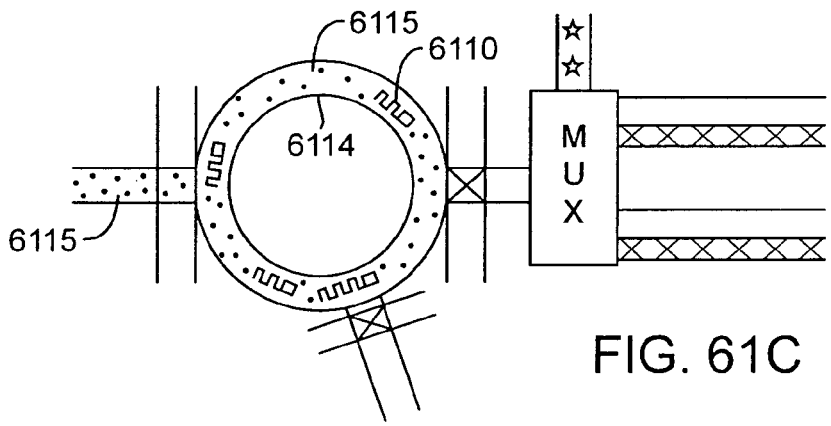

FIG. 61B shows a second step of the method, wherein membrane proteins 6106 within the lysate are tagged with histadine (HIS) 6108 and a sample containing the HIS-tagged membrane proteins 6110 is flowed into microfluidic inlet channel 6112 into closed circuit mixing structure 6114. FIG. 61C shows a third step, wherein mixture 6115 of detergent, buffers, and salts are injected into the mixing structure 6114 and mixed with the HIS-tagged membrane proteins 6110 to solubilize the membrane protein. At this stage the solubilized membrane proteins may or may not exhibit the folded three-dimensional shape exhibited in the cell membrane.

Figure 61D:
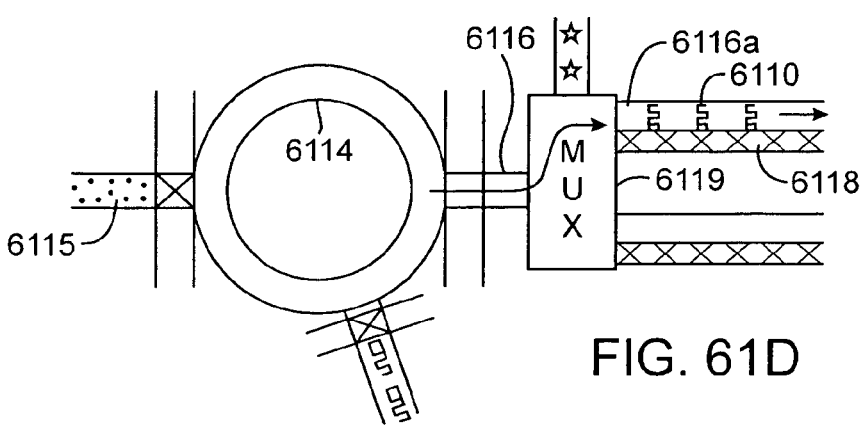
Figure 61E:
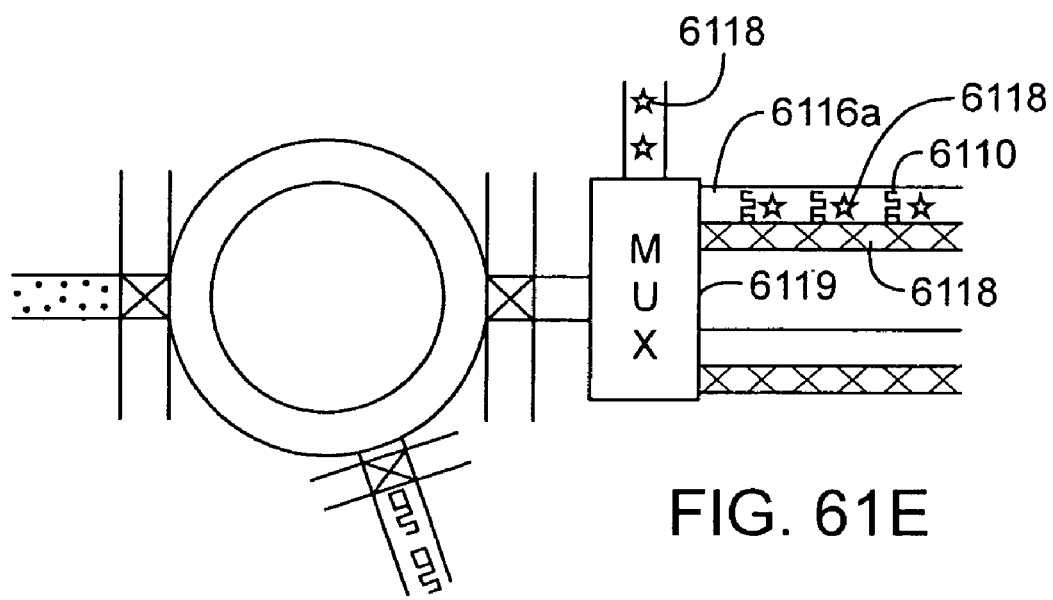

FIG. 61D shows a fourth step, wherein the solubilized membrane protein mixture is flowed out of the mixing structure 6114 through multiplexer 6119 to first flow channel 6116a over a nickel substrate 6118 to immobilize the proteins. FIG. 61E shows a fifth step, wherein a fluorescently tagged ligand or antibody 6118 is flowed over the immobilized HIS-tagged protein sample 6110. The corresponding tagged ligand/antibody will bind only to those immobilized proteins exhibiting the same folded shape as in the cell membrane.

Figure 61F:
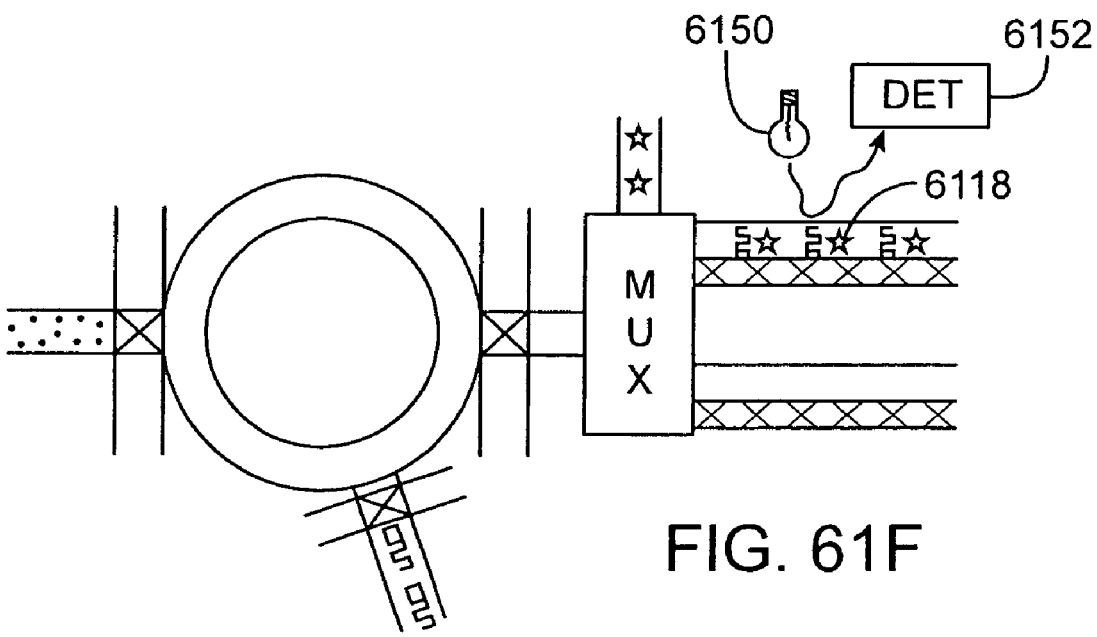

As shown in FIG. 61F, the flow channel containing the nickel is washed and a fluorescence measurement taken by irradiating the contents of channel 6118 from source 6150 and detecting at detector 6152 the resulting emitted fluorescence. Intensity of the detected fluorescent signal may reveal the number of solubilized proteins exhibiting desired naturally-occurring folded three-dimensional shape that allows binding of the complementary fluorescent ligand/antibody. Subsequent variation of the solubilization conditions can optimize the number of protein molecules entering solution with the desired three-dimensional folded shape. Optimization of the solubilization process can be achieved by comparing the magnitude of signals detected from mixtures having different concentrations/identities of amphiphilic moieties or other solution components.

At the conclusion of one solubilization process, the closed circuit mixing structure may be washed with a low pH buffer to elute the bound and labeled protein, and another solubilization experiment conducted. If a fresh nickel surface is needed, the next mixture can be directed from the mixing structure to another flow channel by the multiplexer.

While the embodiment illustrated and discussed in connection with FIGS. 61A-F above involves exposing the solubilized membrane protein to the complementary detectable ligand after mixing in the closed circuit microfluidic mixing structure, this is not required by the present invention. In accordance with an alternative embodiment, the complementary ligand/antibody may be mixed directly with the tagged protein in the mixing structure. This alternative embodiment may offer more accurate results where binding of the tagged protein to the nickel substrate may inhibit binding between the protein and its complementary ligand.

And while the embodiment illustrated and discussed in connection with FIGS. 61A-F above involves immobilizing the solubilized protein on a planar nickel substrate, this is also not required by the present invention. Alternative embodiments could utilize a flow channel packed with beads having surfaces exhibiting the desired immobilization functionality.

And while the embodiment illustrated and discussed in connection with FIGS. 61A-F above involves the use of a ligand detectable by its fluorescent properties, this is also not required by the present invention. Alternative embodiments could utilize radio-type ligands detectable utilizing a PET detector.

Another particularly promising application for the combinatoric device shown and described in connection with FIGS. 17A-B is crystallization of macromolecules, for example the membrane proteins whose solubilization was just discussed. Such crystallization requires the large scale screening of many different reagents against a concentrated and purified protein or macromolecule sample. Since protein is generally difficult to obtain and purify in large quantities, it is of the utmost importance to minimize sample consumption in screening trials. While conventional means require microliter sample volumes per assay, the current invention is capable of realizing sub-nanoliter reaction volumes.

Furthermore, since many thousands of unique solutions may be mixed directly on chip, the present invention may be used to do exhaustive screening of protein crystallization conditions. This screening may be done in a random or systematic way. Once mixed, crystallization reactions may be routed to a locations device for storage and inspection, for example as is described in detail below.

2. Storage Structures

Combining the basic metering and mixing functionality of the combinatoric mixing structure with a fluidic storage structure, allows for a complete protein crystallization workstation to be implemented on chip. In this way a researcher may explore the solubility of a protein in various chemistries, decide which are the most promising crystallization conditions, and then set and incubate reactions for crystal growth. In this way, screening, phase space exploration, optimization, and incubation may be achieved on a single microfluidic workstation. A non-exclusive list of possible methods of storage is provided below.

Figure 58A:
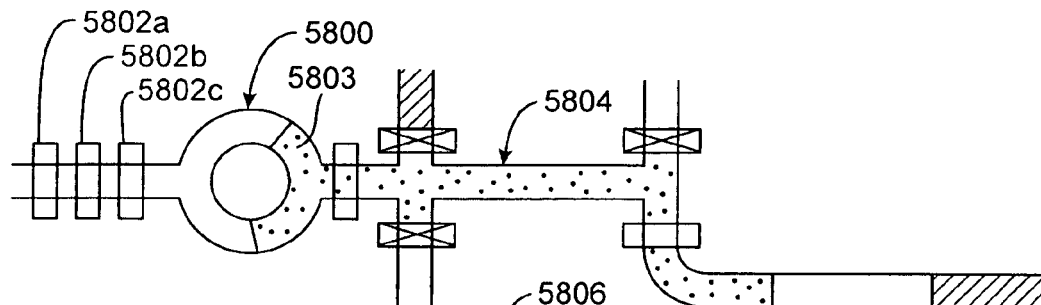
FIG. 58A-D illustrates a schematic view of storage technique utilizing a gated serpentine storage line.
Figure 58B:
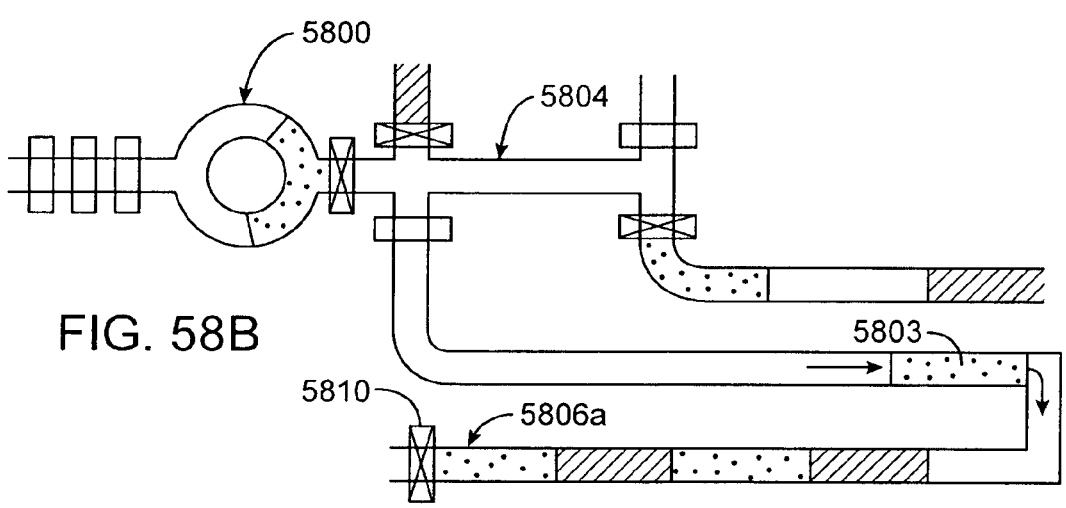
Figure 58C:
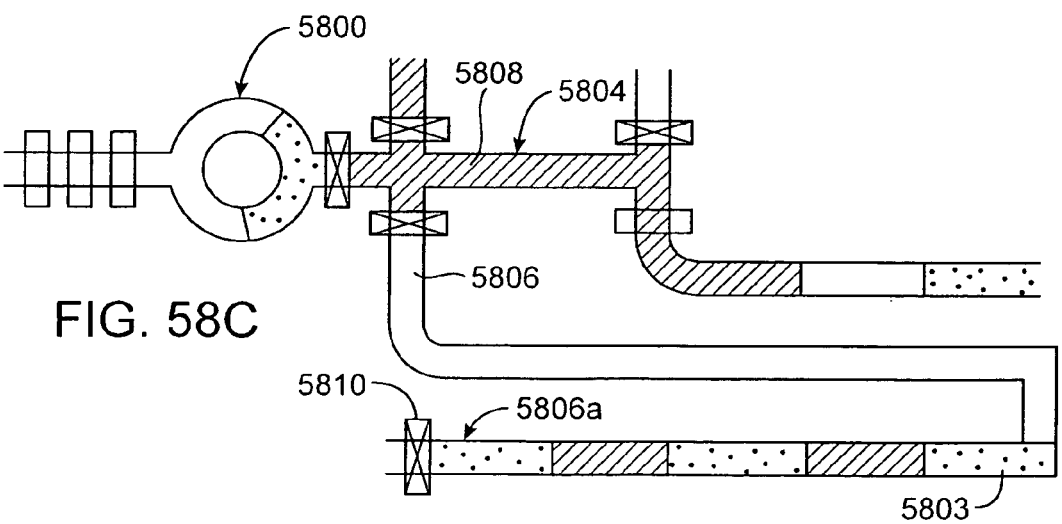

In accordance with one embodiment of the present invention, reactions may be stored by pumping pre-mixed reagent (crystallizing agents, additives, cryo-protectants . . . , sample) into a storage channel and separating the experiments by an immiscible fluid (eg. Paraffin oil). FIGS. 58A-C are schematic views of one implementation of this storage technique.

Figure 58D:
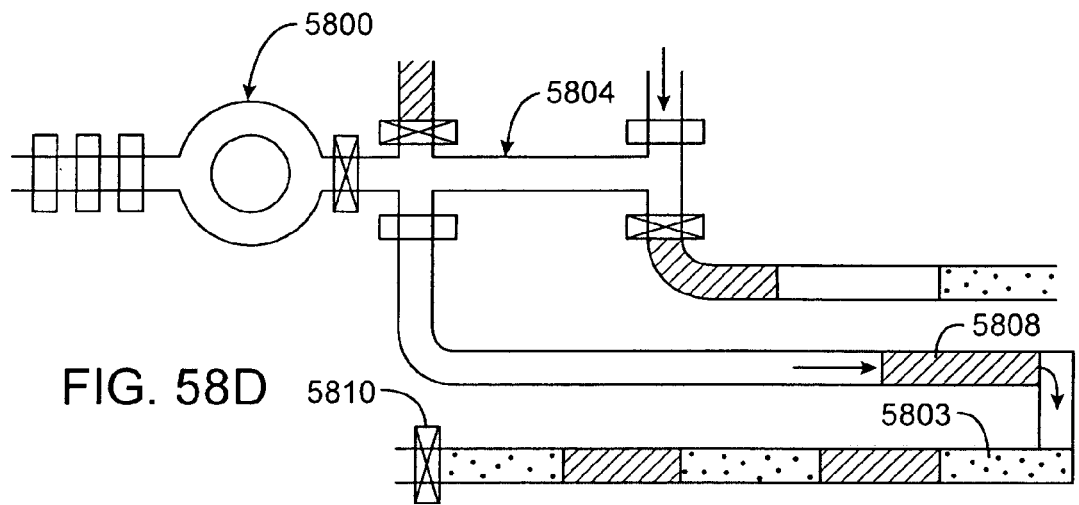

In FIG. 58A, a sample is flowed into circular mixing device 5800 through the peristaltic pumping action of serial valves 5802a-c. Mixture 5803 is then created and flowed into cross-junction 5804. In FIG. 58B, the sample within cross-junction 5804 is routed to serpentine, storage channel 5806 having end 5806a controlled by valve 5810. In FIG. 58C, the valve configuration is changed, and an inert separating fluid 5808 such as oil is flowed into cross-junction 5804. In FIG. 58D, the separating fluid 5808 is flowed into storage channel 5806. The cycle illustrated in FIGS. 58A-D may then be repeated to provide a new sample volume within storage line 5806. Samples stored within channel 5806 may be recovered through end 5806a through gate valve 5810.

Assuming that the storage channel has dimensions 100 µm wide*100 µm tall, a 1 nL sample would fill a length of channel equal to 100 µm. Assuming that the channel is serpentine and that adjacent legs are separated by 100 µm, the total length of channel that would fit on a 1 cm square storage area is approximately 1 cm*100/2=0.5 m. This would allow the storage of 0.5 m/100 µm=5000 reactions.

Figure 59:
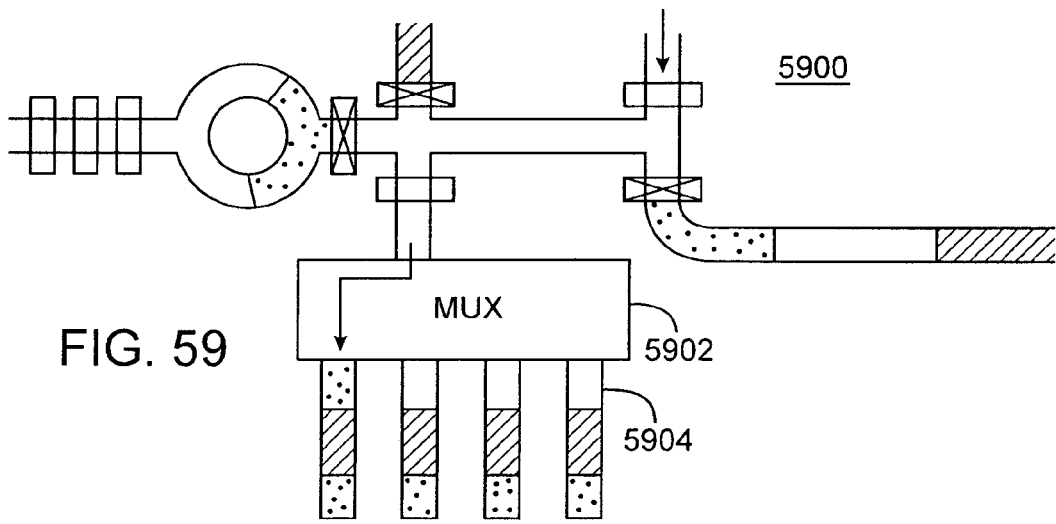
FIG. 59 illustrates a schematic view of an embodiment wherein a multiplexer could be used to direct each experimental condition into parallel storage channels.

Since the entire length of fluid must be advanced for every addition, it may prove difficult to pump this long length of fluid. To avoid this problem, FIG. 59 shows a schematic view of embodiment 5900 of a reaction/storage scheme wherein multiplexer 5902 could be used to direct an experimental sample and inert separating fluid into one of a plurality of parallel storage channels 5904.

Figure 60:
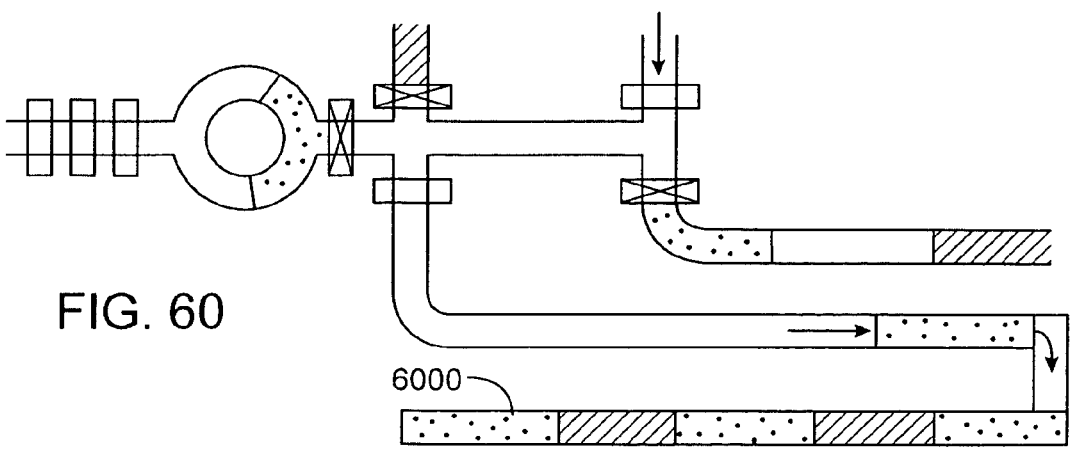
FIG. 60 illustrates a schematic view of an embodiment wherein each reaction condition is dead-end filled to the end of a storage line.

In accordance with still another alternative embodiment, each reaction could be dead-end filled to the end of the storage line so that the entire column of fluid need never be moved together. FIG. 60 shows a simplified schematic view of such an approach, wherein storage channel 6000 is dead-ended.

A flow of air could be utilized to bias the samples and inert separating liquid into the storage channel, with the air ultimately diffusing out of the channel through the elastomer material. In such an embodiment, the relatively high pressures required to accomplish dead-ended filling could be achieved using an external pressure source, thereby eliminating the need for a separate pump on the oil line. This dead-end filling technique could be used to fill a single storage line as in the embodiment shown in FIGS. 58A-D, or many parallel storage lines through a multiplexer as in the embodiment shown in FIG. 59.

While FIGS. 58A-60 show the storage line as being integrated in a planar fashion as a channel on the chip, this is not required by the present invention. In accordance with alternative embodiments of the present invention the reagents may be off-loaded from the chip in the vertical direction, for example into a glass capillary.

Still another approach for storing chemicals is to utilize diffusion assays. FIGS. 54A-D show a layout of a device that combines combinatoric mixing structure 5400 with an addressable storage array 5402. Array 5402 allows for incubation on chip of 256 individual batch experiments or 128 free interface diffusion experiments.

Figure 54A:
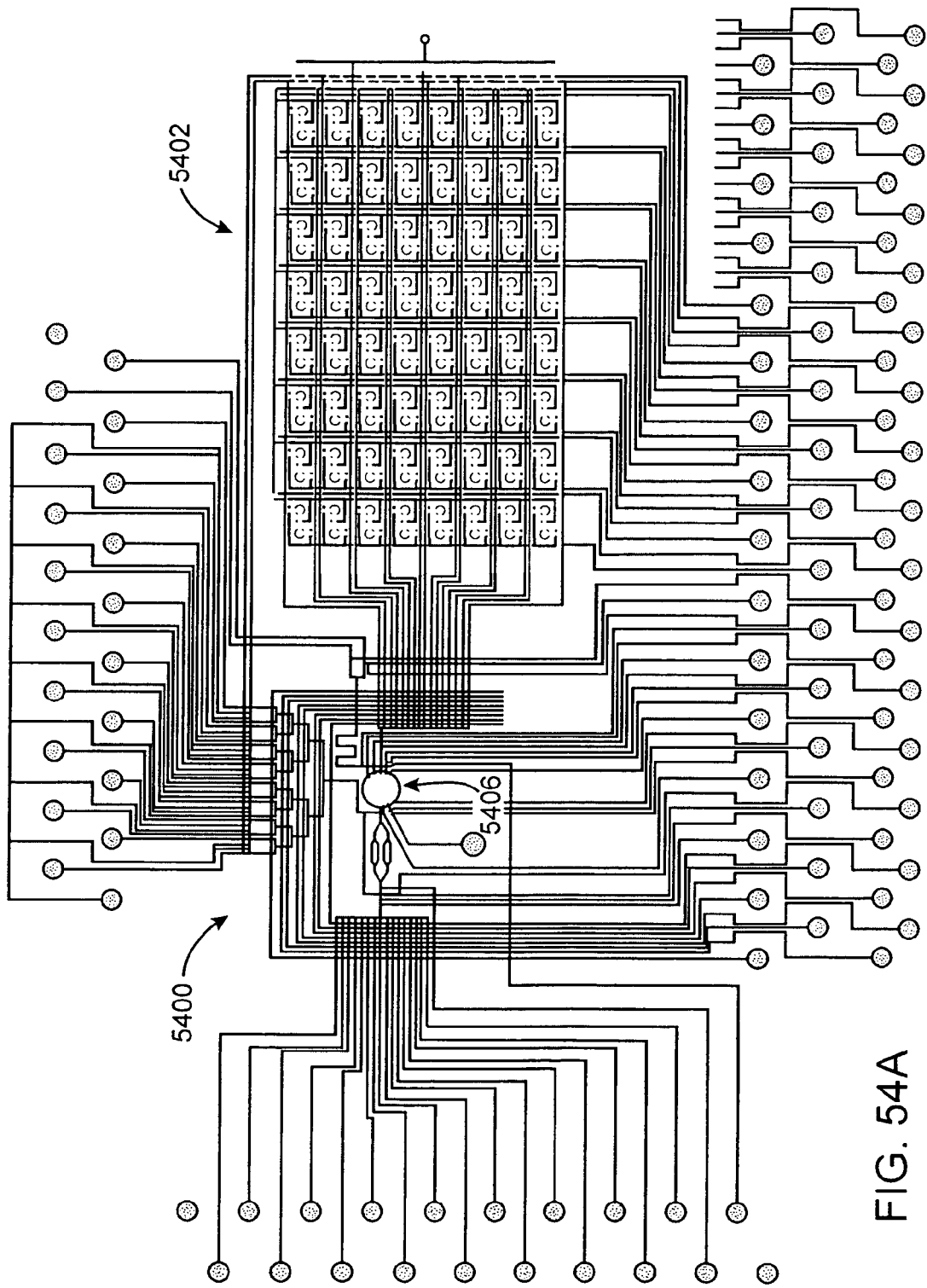
FIG. 54A shows a plan view of one embodiment of a combinatoric mixing/storage structure in accordance with the present invention.
Figure 54B:
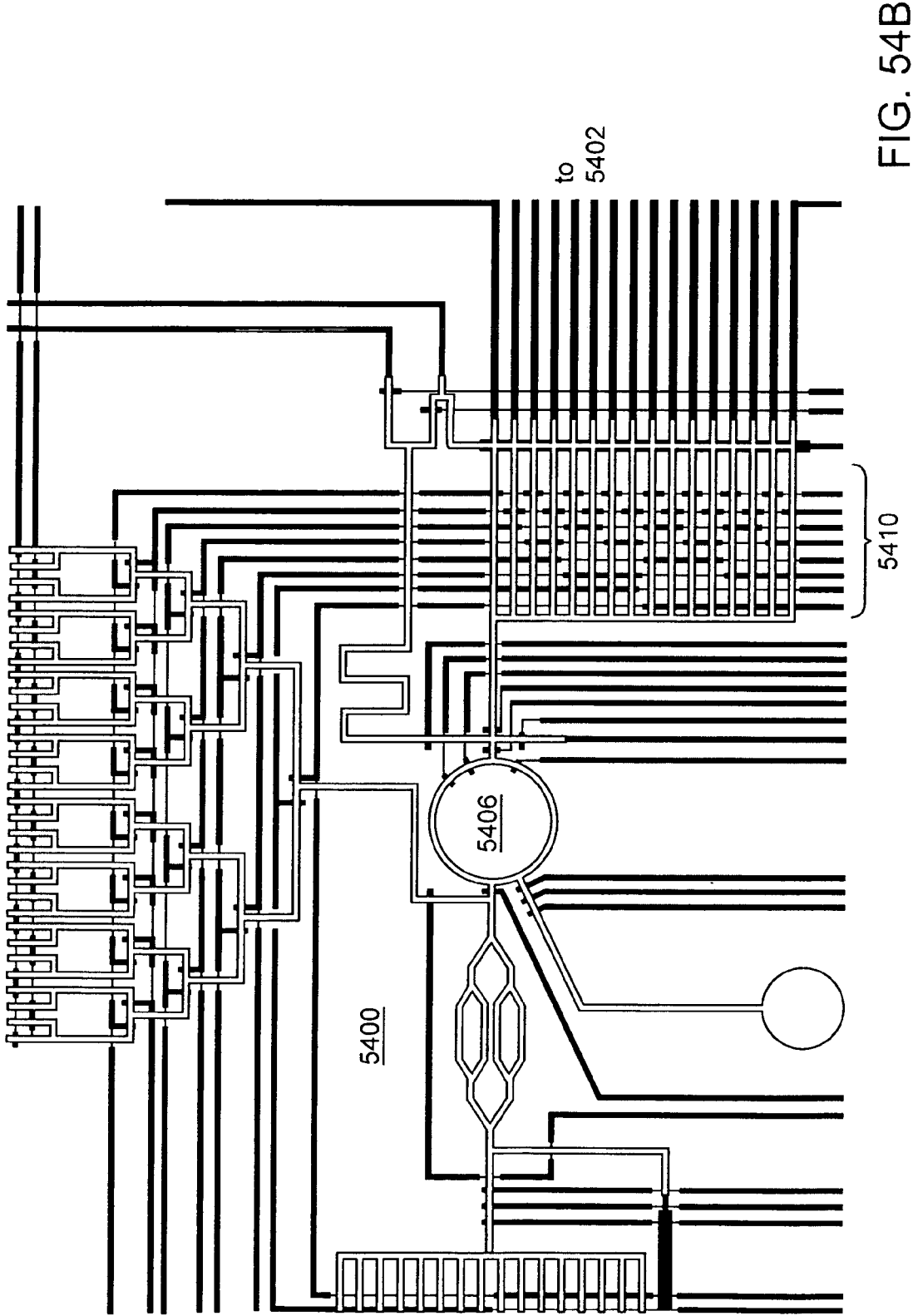
FIG. 54B shows an enlarged view of the mixing portion of the structure of FIG. 54A.

FIG. 54B shows a blow-up of the entrance to storage array 5402. Array 5402 works on the dead-end loading principal discussed above. Once the reagents are mixed in ring 5406, they are pumped into serpentine channel 5408 for temporary storage. Multiplexer 5410 at the storage array inlet is then actuated to open one of the sixteen possible inlets, thereby selecting the array row to be addressed.

Figure 54C:
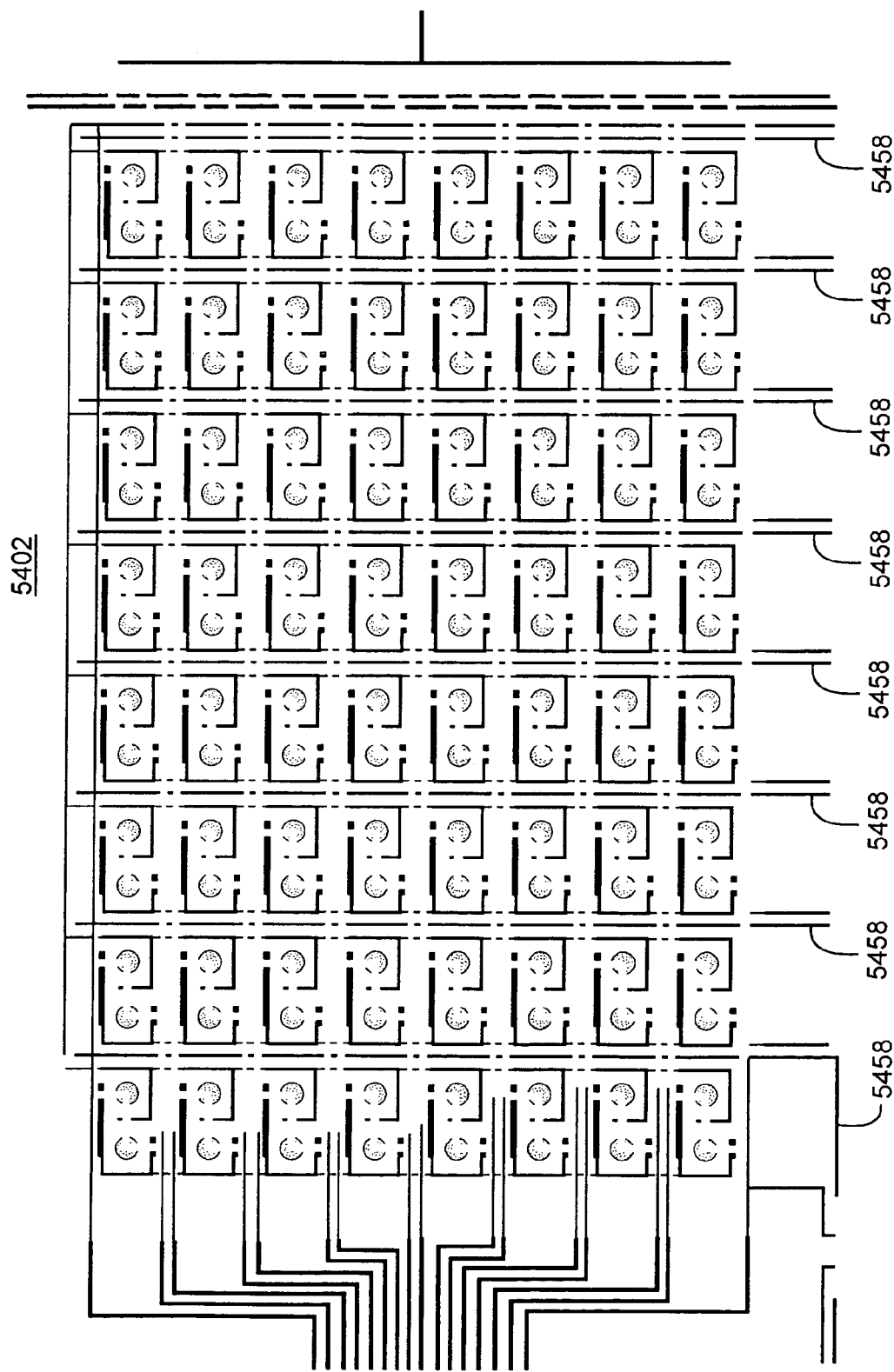
FIG. 54C shows an enlarged view of the storage array of the structure of FIG. 54A.
Figure 54D:
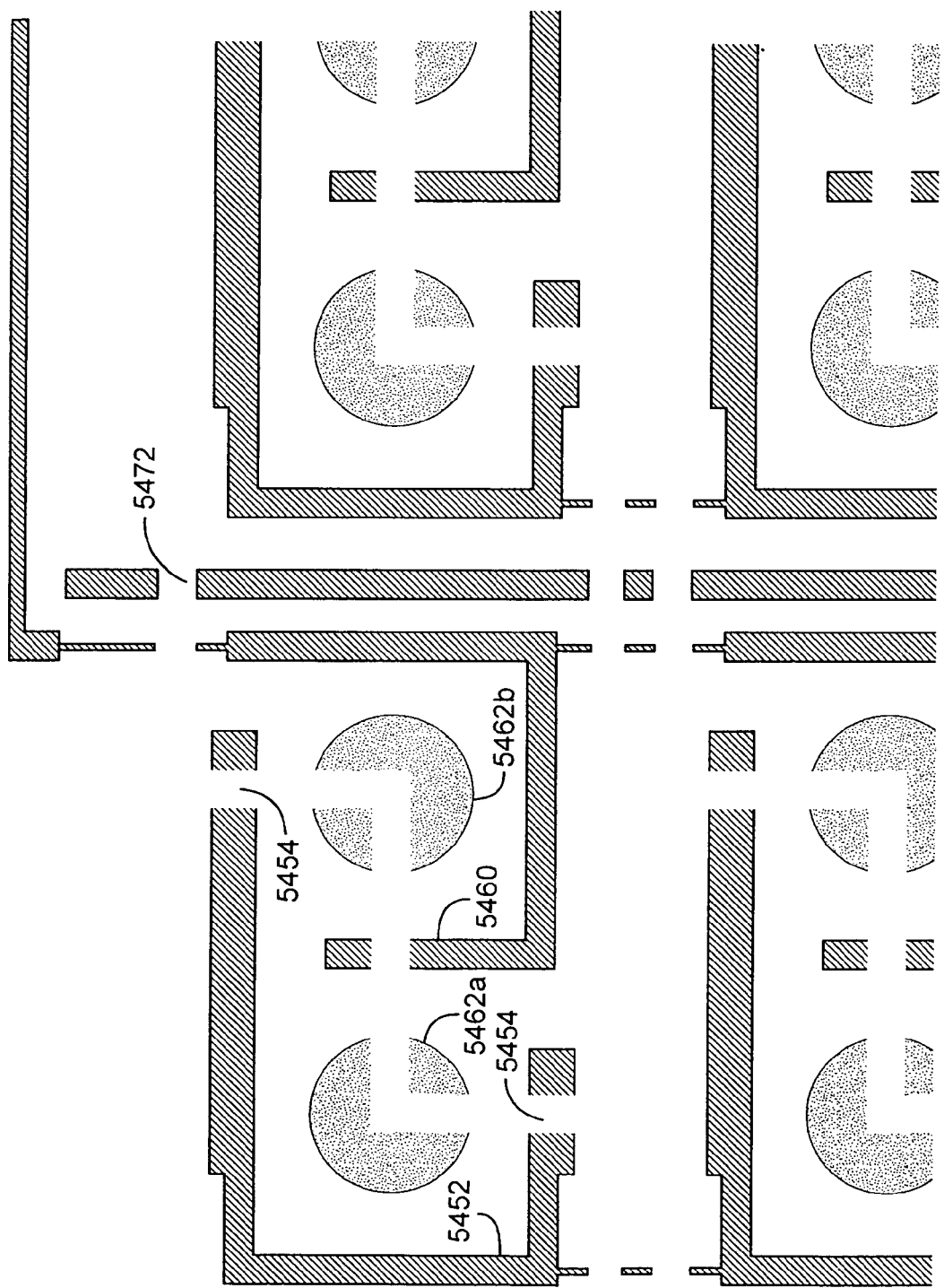
FIG. 54D shows an enlarged view of one cell of the storage array of the structure of FIG. 54C.

FIG. 54C shows an enlarged view of the storage array of FIG. 54A. FIG. 54D shows an enlarged view of a single cell in the array of FIG. 54D.

Each row of the storage array has a control line 5452 that actuates valves 5454 separating storage chambers 5456 from the channel inlets, and a control line 5458 that separates the columns of the storage array. A single control line 5460 is further routed to every pair of fluidically coupled chambers 5462a-b to separate them until it is desired to create a fluidic interface.

Once the row is selected by the multiplexer, the array column 5470 is selected by actuating a corresponding column valve 5472. In this way a single chamber of the array is selected for filling.

Valves near the outlet of the ring are actuated to connect the serpentine storage line to the multiplexer inlet, and the stored solution is pushed back out of the serpentine storage line and into the multiplexer area by pressurized air. This pressurization drives the fluid into the appropriate row of the storage array, pressurizing the air ahead of it and causing it to diffuse into the polymer.

While the chamber inlet valves remain closed, the fluid does not enter the chamber, but rather remains in the dead volume between the multiplexer and the storage array (or partly in this volume and partly in the storage array channels). A new line of the multiplexer is then selected and the column valve is temporarily opened to allow the new row to be flushed with buffer as a precaution to avoid cross contamination. Since only one line of the multiplexer is open the other rows of the storage array are held fixed.

This new row is then emptied by blowing air through it, preparing it for the next solution. These steps are repeated until all rows are filled with a unique solution.

The column valve is then actuated, and the inlet valves opened, and all rows are simultaneously pressurized. This drives the solutions into their respective chambers. This entire process can be repeated for every column until the array is filled with solutions (potentially a different solution in every chamber).

If the interface valves are held closed, the array of FIGS. 54A-D will accommodate 256 (8 columns×16 rows) batch reactions. In applications such as protein crystallography where diffusion across a microfluidic free interface is desired, the interface valves may be opened to commence the reactions. Since all solutions have previously been separately mixed in the ring, the experimenter has control over the solutions.

For example, free-interface diffusion experiments for crystallization may be conducted in which one or more of the following is varied: identity and/or initial concentration of the precipitating agent; identity and/or initial concentration of the crystallized species; identity and/or initial concentration of additives; and identity and/or initial concentration of cryoprotectants. The ability to mix a host of different agents into small volumes of protein solution prior to free interface diffusion experiments offers an important advantage over conventional crystallization approaches, where typically a standard protein stock is used against different crystallization agents. The microfluidic network described above thus offers a flexible platform for crystallization.

The array of FIGS. 54A-D also allows for sample recovery, addressable well flushing, and the reusing of reaction chambers. Specifically, to recover sample or flush a well the appropriate inlet valves are opened on the column that has the well to be emptied/flushed. One of the rows of the multiplexer that connects one of the chambers of the pair to be flushed is selected.

The array row that connects the pair that was not opened at the multiplexer is then opened at the end of the array, and the row that was opened at the multiplexer is closed at the end of the array.

This manipulation causes and open fluidic path through the selected row of the multiplexer, through the chamber pair to be emptied/flushed, and out the row selected at the outlet. In this way a single chamber pair can be addressed and flushed.

III. Crystallization Structures and Methods

High throughput screening of crystallization of a target material, or purification of small samples of target material by recrystallization, may be accomplished by simultaneously introducing a solution of the target material at known concentrations into a plurality of chambers of a microfabricated fluidic device. The microfabricated fluidic device is then manipulated to vary solution conditions in the chambers, thereby simultaneously providing a large number of crystallization environments. Control over changed solvent conditions may result from a variety of techniques, including but not limited to metering of volumes of a crystallizing agent into the chamber by volume exclusion, by entrapment of liquid volumes determined by the dimensions of the microfabricated structure, or by cross-channel injection into a matrix of junctions defined by intersecting orthogonal flow channels.

Crystals resulting from crystallization in accordance with embodiments of the present invention can be utilized for x-ray crystallography to determine three-dimensional molecular structure. Alternatively, where high throughput screening in accordance with embodiments of the present invention does not produce crystals of sufficient size for direct x-ray crystallography, the crystals can be utilized as seed crystals for further crystallization experiments. Promising screening results can also be utilized as a basis for further screening focusing on a narrower spectrum of crystallization conditions, in a manner analogous to the use of standardized sparse matrix techniques.

Systems and methods in accordance with embodiments of the present invention are particularly suited to crystallizing larger biological macromolecules or aggregates thereof, such as proteins, nucleic acids, viruses, and protein/ligand complexes. However, crystallization in accordance with the present invention is not limited to any particular type of target material.

As employed in the following discussion, the term "crystallizing agent" describes a substance that is introduced to a solution of target material to lessen solubility of the target material and thereby induce crystal formation. Crystallizing agents typically include countersolvents in which the target exhibits reduced solubility, but may also describe materials affecting solution pH or materials such as polyethylene glycol that effectively reduce the volume of solvent available to the target material. The term "countersolvent" is used interchangeably with "crystallizing agent".

1. Crystallization by Volume Entrapment

Figure 45A:
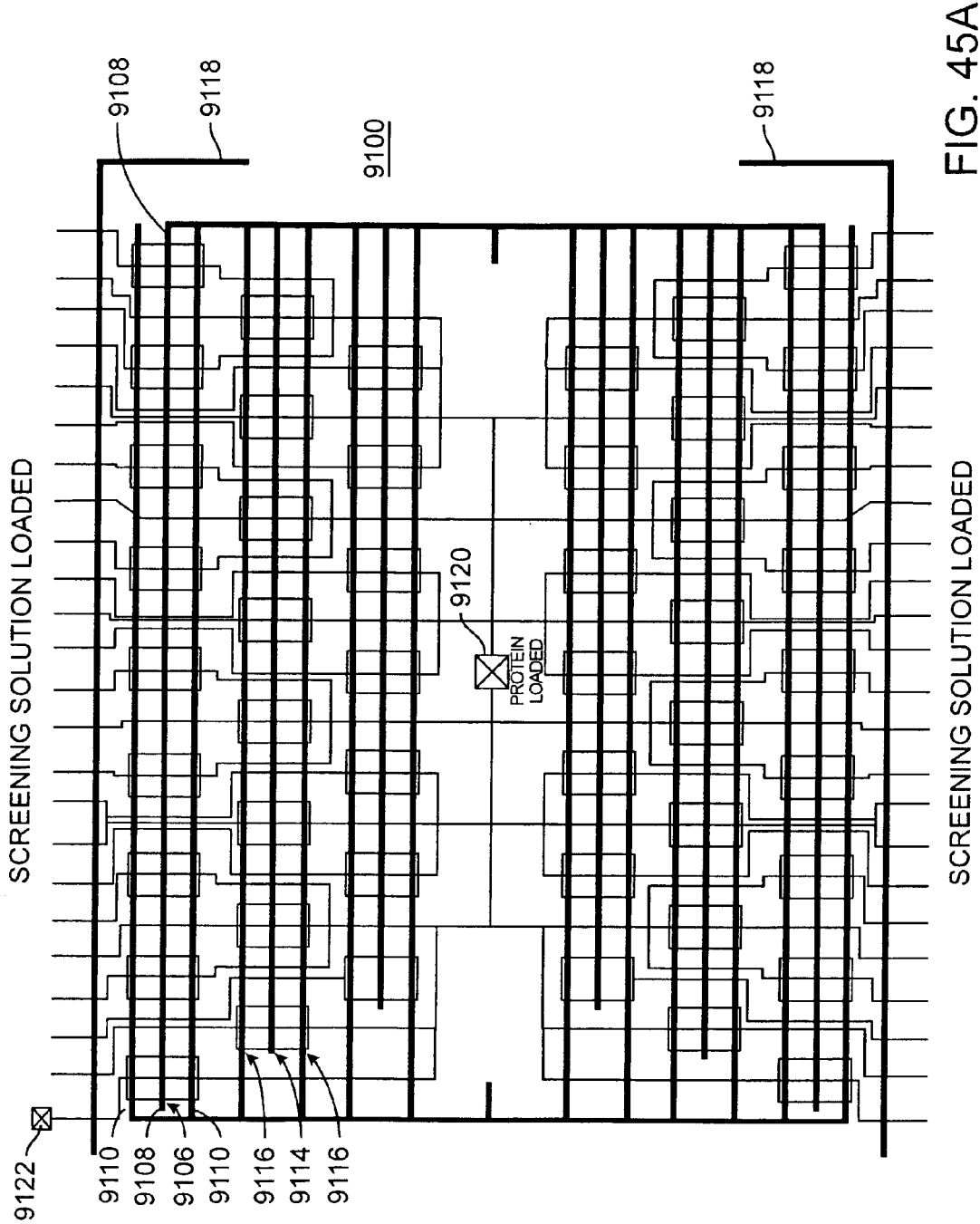
FIG. 45A shows a simplified plan view of the alternative embodiment of the chip utilized to obtain experimental results.

FIG. 45A shows a simplified plan view of an embodiment of a crystallization system wherein metering of different volumes of countersolvent is determined by photolithography during formation of the flow channels. FIG. 45B shows a simplified enlarged plan view of a set of three compound wells of the device of FIG. 45A. FIG. 45C shows a simplified cross-sectional view of the wells of FIG. 45B along line C-C'. This chip design employed metering of target solution and crystallizing agent utilizing the volume entrapment technique.

Specifically, each chip 9100 contains three compound wells 9102 for each of the 48 different screen conditions, for a total of 144 assays per chip. A compound well 9102 consists of two adjacent wells 9102a and 9102b etched in a glass substrate 9104, and in fluidic contact via a microchannel 9106 In each of the compound wells 9102, the protein solution is combined with the screen solution at a ratio that is defined by the relative size of the adjacent wells 9102a-b. In the particular embodiment shown in FIGS. 45A-C, the three ratios were (protein:solution) 4:1, 1:1, and 1:4. The total volume of each assay, including screen solution, is approximately 25 nL. However, the present invention is not limited to any particular volume or range of volumes. Alternative embodiments in accordance with the present invention may utilize total assay volumes of less than 10 nL, less than 5 nL, less than 2.5 nL, less than 1.0 nL, and less than 0.5 nL.

The chip control layer 9106 includes an interface control line 9108, a containment control line 9110 and two safety control lines 9112. Control lines 9108, 9110, and 9112 are filled with water rather than air in order to maintain a humid environment within the chip and to prevent dehydration of the flow channels and chambers in which crystallization is to be performed.

The interface valves 9114 bisect the compound wells 9102, separating the protein from the screen until completion of loading. Containment valves 9116 block the ports of each compound well 9102, isolating each condition for the duration of the experiment. The two safety valves 9118 are actuated during protein loading, and prevent spillage of protein solution in the event of a failed interface valve.

Fabrication of the microfluidic devices utilized in the experiments were prepared by standard multilayer soft lithography techniques and sealed to an etched glass slide by baking at 80° C. for 5 hours or greater. The glass substrate is masked with a 16 um layer of 5740 photoresist, and is patterned using standard photolithography. The glass substrate is then etched in a solution of 1:1:1 (BOE:$H_2O$:2N HCl) for 60 minutes, creating micro-wells with a maximum depth of approximately 80 μm.

The chip fabrication protocol just described is only one example of a possible embodiment of the present invention. In accordance with alternative embodiments, the crystallization chambers and flow channels could be defined between a planar substrate and a pattern of recesses formed entirely in the lower surface of the elastomer portion. Still further alternatively, the crystallization chambers and flow channels could be defined between a planar, featureless lower surface of the elastomer portion and a pattern of recesses formed entirely in the substrate.

Crystallization on chip is set up as follows. All control lines in chip control layer 9106 are loaded with water at a pressure of 15-17 psi. Once the control lines are filled and valves 9114 and 9116 are completely actuated, the containment valve 9116 is released, and protein is loaded through the center via 9120 using about 5-7 psi. The protein solution completely fills the protein side of each compound well 9102. Failed valves, if present, are then identified, and vacuum grease is placed over the corresponding screen via to prevent subsequent pressurization, and possible contamination of the remaining conditions. 2.5 to 4 μL of a sparse matrix screen (typically Hampton Crystal Screen I, 1-48) are then pipetted into the screen vias 9122. The safety valves 9118 are released, and a specially designed chip holder (described below) is used to create a pressurized (5-7 psi) seal over all 48 screen vias 9122. The screen solutions are dead end loaded, filling the screen side of each compound well. Protein and crystal screen reagents are kept separate with the interface valve until all wells are loaded, at which point the containment valve is closed and the interface valve opened to allow diffusion between liquid volumes present in the two halves of the compound wells 9102.

For these experiments, the average time spent setting up an experiment, including filling control lines, was approximately 35 min, with the fastest experiment taking only 20 minutes to set up. This set up time could potentially be reduced even further through the use of robotic pipetting of solutions to the chip, or through the use of pressures to load and prime delivered solutions, or through use of a microfluidic metering device, for example the combinatorial mixing structure previously described.

As previously illustrated, embodiments of microfluidic devices in accordance with the present invention may utilize on-chip reservoirs or wells. However, in a microfluidic device requiring the loading of a large number of solutions, the use of a corresponding large number of input tubes with separate pins for interfacing each well may be impractical given the relatively small dimensions of the fluidic device. In addition, the automated use of pipettes for dispensing small volumes of liquid is known, and thus it therefore may prove easiest to utilize such techniques to pipette solutions directly on to wells present on the face of a chip.

Capillary action may not be sufficient to draw solutions from on-chip wells into active regions of the chip, particularly where dead-ended chambers are to be primed with material. In such embodiments, one way of loading materials into the chip is through the use of external pressurization. Again however, the small dimensions of the device coupled with a large number of possible material sources may render impractical the application of pressure to individual wells through pins or tubing.

Figure 44:
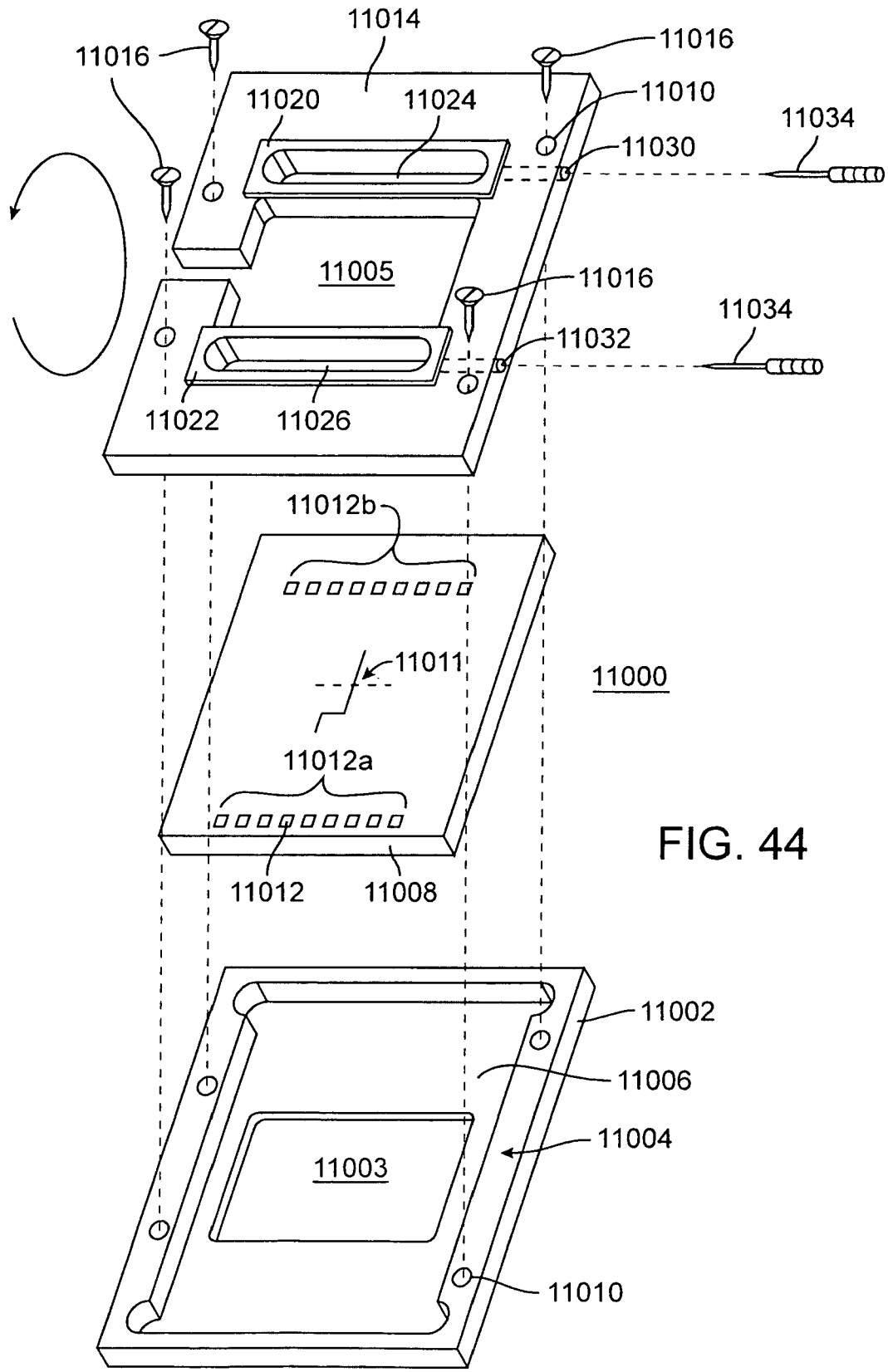
FIG. 44 shows an enlarged view of one embodiment of a chip holder in accordance with the present invention.

Accordingly, FIG. 44 shows an exploded view of a chip holder 11000 in accordance with one embodiment of the present invention. Bottom portion 11002 of chip holder 11000 includes raised peripheral portion 11004 surrounding recessed area 11006 corresponding in size to the dimensions of chip 11008, allowing microfluidic chip 11008 to be positioned therein. Peripheral region 11004 further defines screw holes 11010.

Microfluidic device 11008 is positioned within recessed area 11006 of bottom portion 11002 of chip holder 11000. Microfluidic device 11008 comprises an active region 11011 that is in fluidic communication with peripheral wells 11012 configured in first and second rows 11012a and 11012b, respectively. Wells 11012 hold sufficient volumes of material to allow device 11008 to function. Wells 11012 may contain, for example, solutions of crystallizing agents, solutions of target materials, or other chemical reagents such as stains. Bottom portion 11002 contains a window 11003 that enables active region 11011 of chip 11008 to be observed.

Top portion 11014 of chip holder 11000 fits over bottom chip holder portion 11002 and microfluidic chip 11008 positioned therein. For ease of illustration, in FIG. 44 top chip holder portion 11014 is shown inverted relative to its actual position in the assembly. Top chip holder portion 11014 includes screw holes 11010 aligned with screw holes 11010 of lower holder portion 11002, such that screws 11016 may be inserted through holes 11010 secure chip between portions 11002 and 11014 of holder 11000. Chip holder upper portion 11014 contains a window 11005 that enables active region 11011 of chip 11008 to be observed.

Lower surface 11014a of top holder portion 11014 includes raised annular rings 11020 and 11022 surrounding recesses 11024 and 11026, respectively. When top portion 11014 of chip holder 11000 is pressed into contact with chip 11008 utilizing screws 11016, rings 11020 and 11022 press into the soft elastomeric material on the upper surface of chip 11008, such that recess 11024 defines a first chamber over top row 11012a of wells 11012, and recess 11026 defines a second chamber over bottom row 11012b of wells 11012. Holes 11030 and 11032 in the side of top holder portion 11014 are in communication with recesses 11024 and 11026 respectively, to enable a positive pressure to be applied to the chambers through pins 11034 inserted into holes 11030 and 11032, respectively. A positive pressure can thus simultaneously be applied to all wells within a row, obviating the need to utilize separate connecting devices to each well.

In operation, solutions are pipetted into the wells 11012, and then chip 11008 is placed into bottom portion 11002 of holder 11000. The top holder portion 11014 is placed over chip 11008, and is pressed down by screws. Raised annular rings 11020 and 11022 on the lower surface of top holder portion 11014 make a seal with the upper surface of the chip where the wells are located. Solutions within the wells are exposed to positive pressures within the chamber, and are thereby pushed into the active area of microfluidic device.

The downward pressure exerted by the chip holder may also pose the advantage of preventing delamination of the chip from the substrate during loading. This prevention of delamination may enable the use of higher priming pressures.

The chip holder shown in FIG. 44 represents only one possible embodiment of a structure in accordance with the present invention.

2. Control Over Other Factors Influencing Crystallization

While the above crystallization structures describe altering the environment of the target material through introduction of volumes of an appropriate crystallization agent, many other factors are relevant to crystallization. Such additional factors include, but are not limited to, temperature, pressure, concentration of target material in solution, equilibration dynamics, and the presence of seed materials.

In specific embodiments of the present invention, control over temperature during crystallization may be accomplished utilizing a composite elastomer/silicon structure previously described. Specifically, a Peltier temperature control structure may be fabricated in an underlying silicon substrate, with the elastomer aligned to the silicon such that a crystallization chamber is proximate to the Peltier device. Application of voltage of an appropriate polarity and magnitude to the Peltier device may control the temperature of solvent and countersolvent within the chamber.

Alternatively, as described by Wu et al. in "MEMS Flow Sensors for Nano-fluidic Applications", *Sensors and Actuators A* 89 152-158 (2001), crystallization chambers could be heated and cooled through the selective application of current to a micromachined resistor structure resulting in ohmic heating. Moreover, the temperature of crystallization could be detected by monitoring the resistance of the heater over time. The Wu et al. paper is hereby incorporated by reference for all purposes.

It may also be useful to establish a temperature gradient across a microfabricated elastomeric crystallization structure in accordance with the present invention. Such a temperature gradient would subject target materials to a broad spectrum of temperatures during crystallization, allowing for extremely precise determination of optimum temperatures for crystallization.

With regard to controlling pressure during crystallization, embodiments of the present invention employing metering of countersolvent by volume exclusion are particularly advantageous. Specifically, once the chamber has been charged with appropriate volumes of solvent and countersolvent, a chamber inlet valve may be maintained shut while the membrane overlying the chamber is actuated, thereby causing pressure to increase in the chamber. Structures in accordance with the present invention employing techniques other than volume exclusion could exert pressure control by including flow channels and associated membranes adjacent to the crystallization chamber and specifically relegated to controlling pressure within the channel.

Another factor influencing crystallization is the amount of target material available in the solution. As a crystal forms, it acts as a sink to target material available in solution, to the point where the amount of target material remaining in solution may be inadequate to sustain continued crystal growth. Therefore, in order to grow sufficiently large crystals it may be necessary to provide additional target material during the crystallization process.

Accordingly, the cell pen structure previously described in connection with FIGS. 27A-27B may be advantageously employed in crystallization structures in accordance with embodiments of the present invention to confine growing crystals within a chamber. This obviates the danger of washing growing crystals down a flow channel that is providing additional target material, causing the growing crystals to be lost in the waste.

Moreover, the cell cage structure of FIGS. 27A-27B may also be useful during the process of crystal identification. Specifically, salts are often present in the sample or countersolvent, and these salts may form crystals during crystallization attempts. One popular method of distinguishing the growth of salt crystals from the target crystals of interest is through exposure to a staining dye such as IZIT™, manufactured by Hampton Research of Laguna Niguel, Calif. This IZIT™ dye stains protein crystals blue, but does not stain salt crystals.

However, in the process of flowing the IZIT™ dye to the crystallization chamber holding the crystals, the crystals may be dislodged, swept away, and lost. Therefore, the cell pen structure can further be employed in crystallization structures and methods in accordance with the present invention to secure crystals in place during the staining process.

Figure 49:
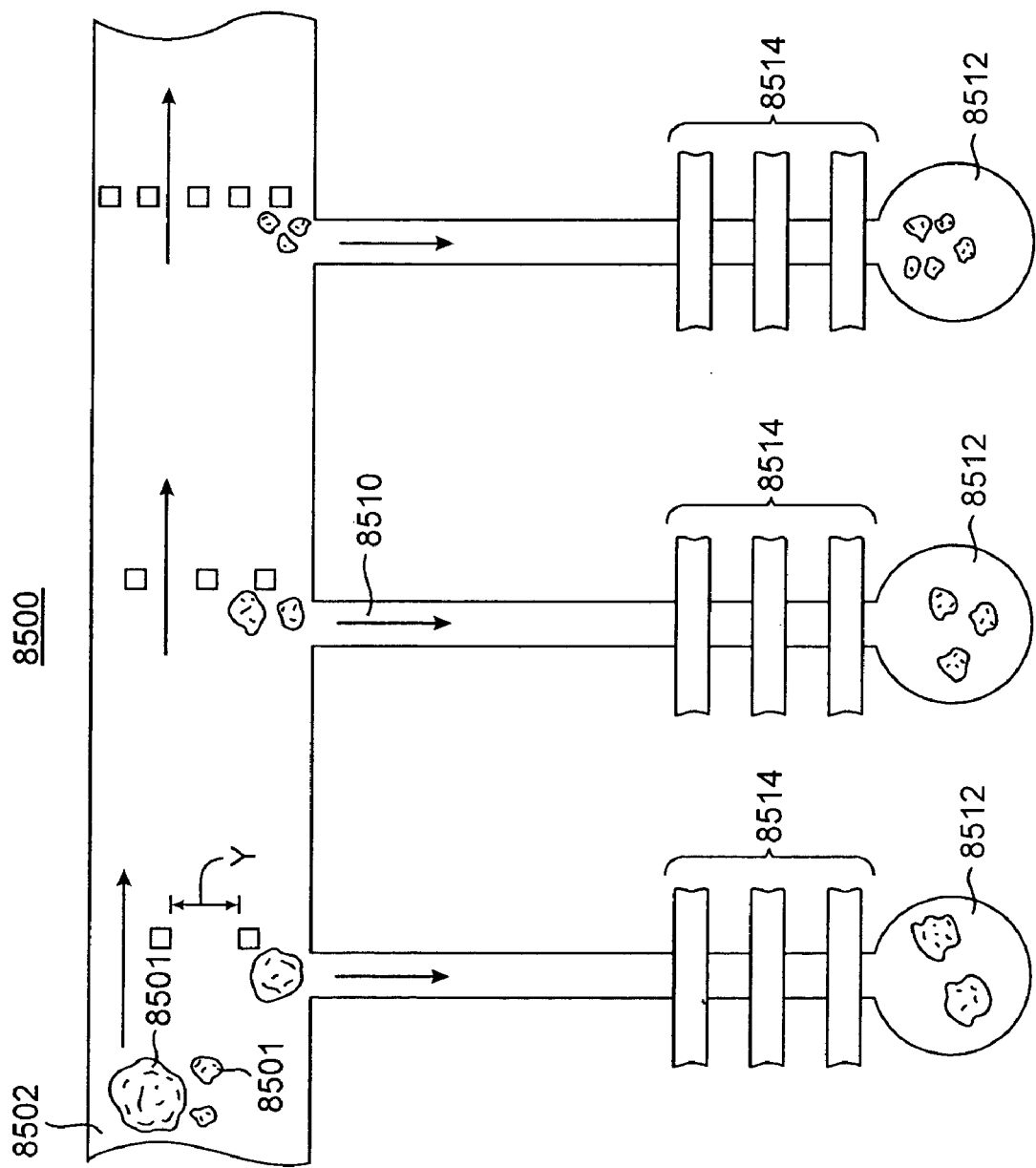
FIG. 49 shows a simplified plan view of a sorting device in accordance with an embodiment of the present invention.

FIG. 49 shows an embodiment of a sorting device for crystals based upon the cell cage concept. Specifically, crystals 8501 of varying sizes may be formed in flow channel 8502 upstream of sorting device 8500. Sorting device 8500 comprises successive rows 8504 of pillars 8506 spaced at different distances. Inlets 8508 of branch channels 8510 are positioned in front of rows 8504. As crystals 8501 flow down channel 8502, they encounter rows 8504 of pillars 8506. The largest crystals are unable to pass between gap Y between pillars 8506 of first row 8504a, and accumulate in front of row 8504a. Smaller sized crystals are gathered in front of successive rows having successively smaller spacings between pillars. Once sorted in the manner described above, the crystals of various sizes can be collected in chambers 8512 by pumping fluid through branch channels 8510 utilizing peristaltic pumps 8514 as previously described. Larger crystals collected by the sorting structure may be subjected to x-ray crystallographic analysis. Smaller crystals collected by the sorting structure may be utilized as seed crystals in further crystallization attempts.

Another factor influencing crystal growth is seeding. Introduction of a seed crystal to the target solution can greatly enhance crystal formation by providing a template to which molecules in solution can align. Where no seed crystal is available, embodiments of microfluidic crystallization methods and systems in accordance with the present invention may utilize other structures to perform a similar function.

For example, as discussed above, flow channels and chambers of structures in accordance with the present invention are typically defined by placing an elastomeric layer containing microfabricated features into contact with an underlying substrate such as glass. This substrate need not be planar, but rather may include projections or recesses of a size and/or shape calculated to induce crystal formation. In accordance with one embodiment of the present invention, the underlying substrate could be a mineral matrix exhibiting a regular desired morphology. Alternatively, the underlying substrate could be patterned (i.e. by conventional semiconductor lithography techniques) to exhibit a desired morphology or a spectrum of morphologies calculated to induce crystal formation. The optimal form of such a substrate surface morphology could be determined by prior knowledge of the target crystals.

Embodiments of crystallization structures and methods in accordance with the present invention offer a number of advantages over conventional approaches. One advantage is that the extremely small volumes (nanoliter/sub-nanoliter) of sample and crystallizing agent permit a wide variety of recrystallization conditions to be employed utilizing a relatively small amount of sample.

Another advantage of crystallization structures and methods in accordance with embodiments of the present invention is that the small size of the crystallization chambers allows crystallization attempts under hundreds or even thousands of different sets of conditions to be performed simultaneously. The small volumes of sample and crystallizing agent employed in recrystallization also result in a minimum waste of valuable purified target material.

A further advantage of crystallization in accordance with embodiments of the present invention is relative simplicity of operation. Specifically, control over flow utilizing parallel actuation requires the presence of only a few control lines, with the introduction of sample and crystallizing agent automatically performed by operation of the microfabricated device permits very rapid preparation times for a large number of samples with the added advantages of parsimonious use of sample solutions, ease of set-up, creation of well defined fluidic interfaces, control over equilibration dynamics, and the ability to conduct high-throughput parallel experimentation. These advantages are made possible by a number of features of the instant invention.

Microfluidics enables the handling of fluids on the sub-nanoliter scale. Consequently, there is no need to use large containment chambers, and hence, assays may be performed on the nanoliter, or subnanoliter scale. The utilization of extremely small volumes allows for thousands of assays to be performed to consume the same sample volume required for one macroscopic free-interface diffusion experiment. This reduces costly and time-consuming amplification and purification steps, and makes possible the screening of proteins that are not easily expressed, and hence must be purified from a bulk sample.

Microfluidics further offers savings in preparation times, as hundreds, or even thousands of assays may be performed simultaneously. The use of scaleable metering techniques as previously described, allow for parallel experimentation to be conducted without increased complexity in control mechanisms.

Still another advantage of crystallization systems in accordance with embodiments of the present invention is the ability to control solution equilibration rates. Crystal growth is often very slow, and no crystals will be formed if the solution rapidly passes through an optimal concentration on the way to equilibrium. It may therefore be advantageous to control the rate of equilibration and thereby promote crystal growth at intermediate concentrations. In conventional approaches to crystallization, slow-paced equilibrium is achieved using such techniques as vapor diffusion, slow dialysis, and very small physical interfaces.

However, crystallization in accordance with embodiments of the present invention allows for control over the rate of solution equilibrium. In systems metering crystallizing agent by volume exclusion, the overlying membrane can be repeatedly deformed, with each deformation giving rise to the introduction of additional crystallizing agent. In systems that meter crystallizing agent by volume entrapment, the valves separating sample from crystallizing agent may be opened for a short time to allow for partial diffusive mixing, and then closed to allow chamber equilibration at an intermediate concentration. The process is repeated until the final concentration is reached. Either the volume exclusion or entrapment approaches enables a whole range of intermediate concentrations to be screened in one experiment utilizing a single reaction chamber. As discussed in detail below, control over kinetics of the crystallization process may be controlled by varying the length or cross-sectional area of a capillary connection between reservoirs containing the sample and crystallizing agent, respectively.

The manipulation of solution equilibrium over time also exploits differential rates of diffusion of macromolecules such as proteins versus much smaller crystallizing agents such as salts. As large protein molecules diffuse much more slowly than the salts, rapidly opening and closing interface valves allows the concentration of crystallizing agent to be significantly changed, while at the same time very little sample is lost by diffusion into the larger volume of crystallizing agent. Moreover, as described above, many crystallization structures described readily allow for introduction of different crystallizing agents at different times to the same reaction chamber. This allows for crystallization protocols prescribing changed solvent conditions over time. Temperature control over equilibration is discussed in detail below.

3. Analysis of Crystal Structure from Protein on Chip

The utility of the chip is ultimately dependent on its' ability to quickly generate high quality diffraction patterns at a reduced cost. A clear path from the chip-to-protein structure is therefore invaluable. Several paths from in-chip crystals to diffraction data are discussed below.

One possible application for a chip is determination of favorable crystallization conditions that can subsequently be reproduced using conventional techniques. Correspondence between the chip and two conventional techniques (micro batch and hanging drop) has been shown to be variable (between 45% and 80%). However, this variation is not a feature unique to the chip. These widely used crystallization techniques show only marginal correspondence (e.g. 14 of 16 hanging drop hits for lysozyme do not occur in microbatch), and often show variation within themselves. As a tool for screening initial crystallization conditions, the chip may be able to identify as many promising conditions.

Figure 52:
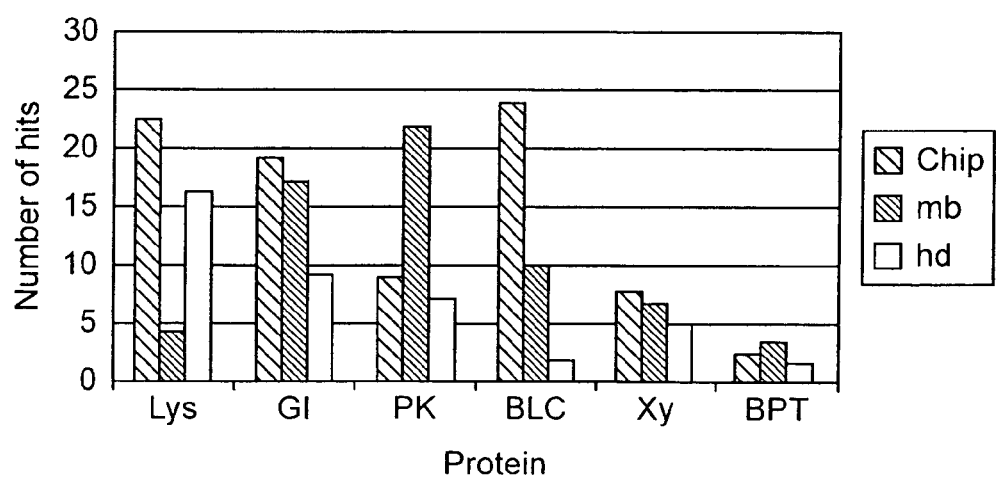
FIG. 52 plots crystallization hits utilizing a microfluidic chip in accordance with the present invention.

FIG. 52 shows a comparison of the number of hits generated on six different protein samples (lysozyme, glucose isomerase, proteinase K, B subunit of topoisomerase VI, xylanase, and bovine pancrease trypsin) using the three different technologies. In FIG. 52 only crystals, microcrystals, rods, and needles are counted as hits, while spherulites and precipitation is not counted. The data on Proteinase K is a sum of the experiments with and without PMSF, and data for the B subunit of topoisomerase VI has not been included for lack of hanging drop data (although the chip far outperformed microbatch in this case). Inspection of FIG. 52 shows that in four of the six cases, the chip produced more hits than either conventional method.

In order to understand differences between crystallization methods to identify possible reasons for productivity of the chip, we must appreciate that the three methods produce different thermodynamic conditions on both short and long time scales. In order to induce protein crystallization, one must make the crystallization energetically favorable (supersaturation condition), and maintain these conditions long enough for crystal growth to occur.

There are also different degrees of supersaturation. In low supersaturation, crystal growth tends to be supported, while nucleation of new crystals is relatively unlikely. In high supersaturation, nucleation is rapid, and many small low quality crystals may often be formed. In the three methods considered here, the condition of supersaturation is achieved through the manipulation of the relative, and absolute, concentration of protein and counter-solvent.

Figure 57:
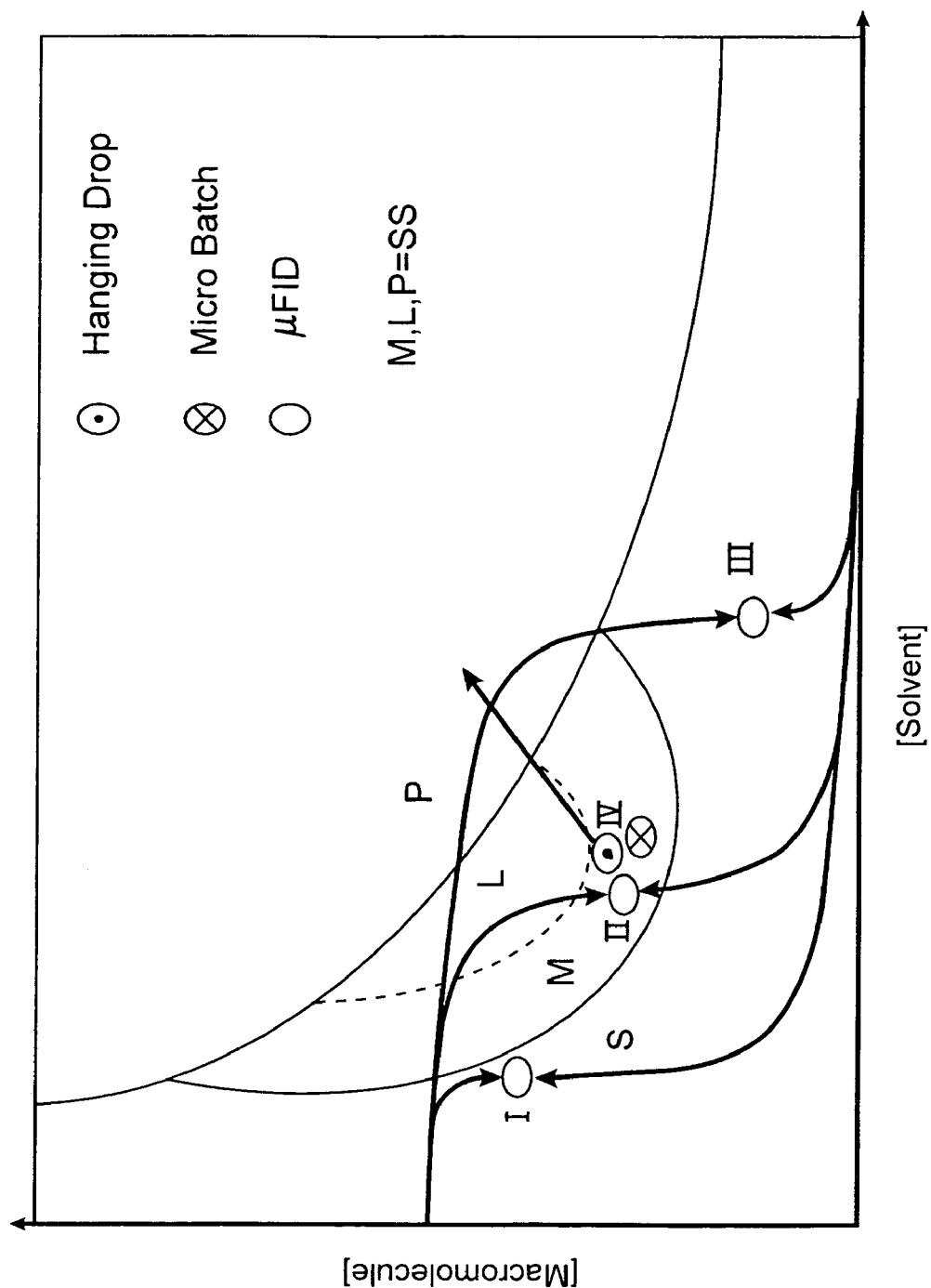
FIG. 57 plots trajectory through the phase space shown in FIG. 55 achieved by a number of crystallization approaches.

A comparison of the phase space evolution/equilibration of the three methods is shown in FIG. 57. For the micro batch technique, mixing of the two solutions is quick, and when kept under impermeable oil layers, little significant concentration occurs over time. Micro batch therefore tends to sample only a single point in phase space, maintaining approximately the same condition over time.

Hanging drop starts out like micro batch, with rapid mixing of the two solutions, but then undergoes a concentration on a longer timescale (hours to days) due to vapor equilibration with the more concentrated salt/precipitant reservoir. During the evaporative dehydration of the drop, the ratio of protein to precipitant remains constant.

As described in detail below in the description of Microfluidic Free Interface Diffusion, on the short time scale the chip dynamics most closely resemble a free interface diffusion experiment. Mixing is slow, and the rate of species equilibration (protein/precipitant/proton/salt) depends on species' diffusion constants. Small molecules such as salts have large diffusion constants, and hence equilibrate quickly. Large molecules (e.g. proteins) have small diffusion constants, and equilibrate more slowly.

The crystallization technique of free interface diffusion in capillaries may more closely emulate the chip results. Traditionally this method is not often used due to the difficulty of reliably setting up a well-defined interface. However, in microfluidic environments it is relatively easy to establish reliable free-interface diffusion experiments. Additional discussion of the formation of microfluidic free-interfaces is presented below. In another application of the crystallization chip, crystals may be grown for harvesting using conventional methods.

If high quality crystals can be grown in, and extracted from the chip, crystallization conditions need not be exported. Since the chip can be removed from the glass substrate, it is also possible to extract protein crystals.

As previously described, once a protein crystal has been formed, information about its three dimensional structure can be obtained from diffraction of x-rays by the crystal. However, application of highly energetic radiation to the protein tends to generate creates heat. X-rays are also ionizing, and can result in the production of free radicals and broken covalent bonds. Either heat or ionization may destroy or degrade the ability of a crystal to diffract incident x-rays.

Accordingly, upon formation of a crystal a cryogenic material is typically added to preserve the crystalline material in its altered state. However, the sudden addition of cryogen can also damage a crystal. Therefore, it would be advantageous for an embodiment of a crystallization chip in accordance with the present invention to enable the direct addition of cryogen to the crystallization chamber once a crystalline material is formed therein.

In addition, protein crystals are extremely delicate, and can quickly crumble or collapse in response to physical trauma. Accordingly, harvesting a crystal unharmed from the small chambers of a chip poses a potential obstacle to obtaining valuable information about the crystalline material.

Therefore, it would also be advantageous for an alternative embodiment of a crystallization chip in accordance with the present invention to allow direct interrogation by x-ray radiation of crystalline materials formed in a chip, thereby obviating entirely the need for separate crystal harvesting procedures.

Figure 53A:
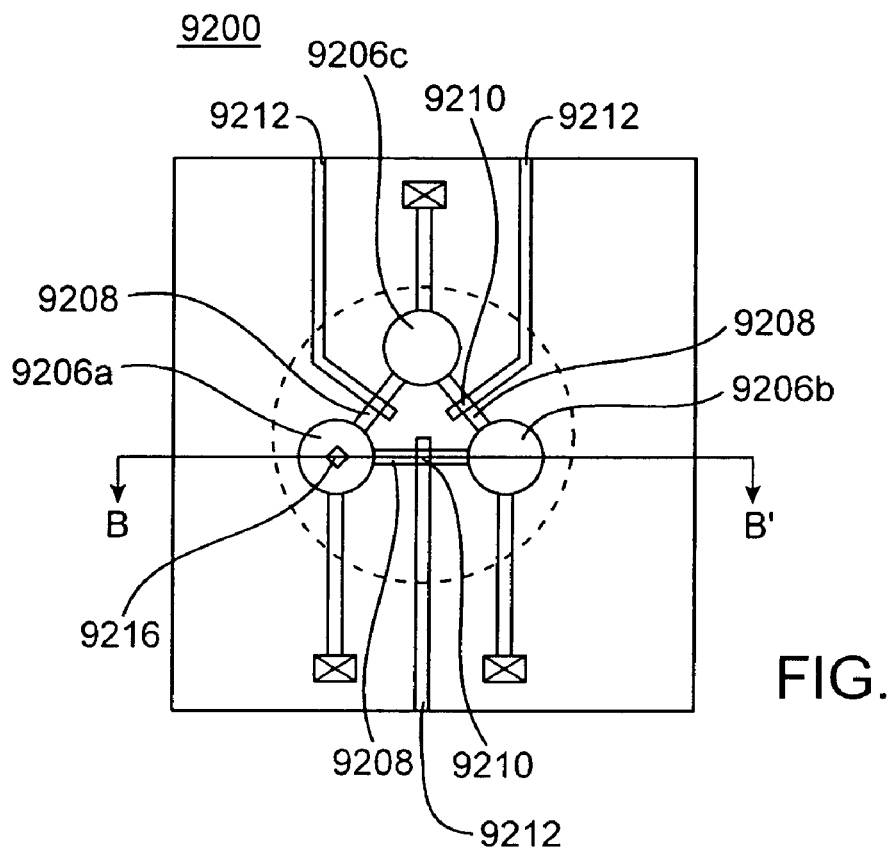
FIGS. 53A-B show plan and cross-sectional views of one embodiment of a crystal growing/harvesting chip in accordance with of one embodiment of the present invention.
Figure 53B:
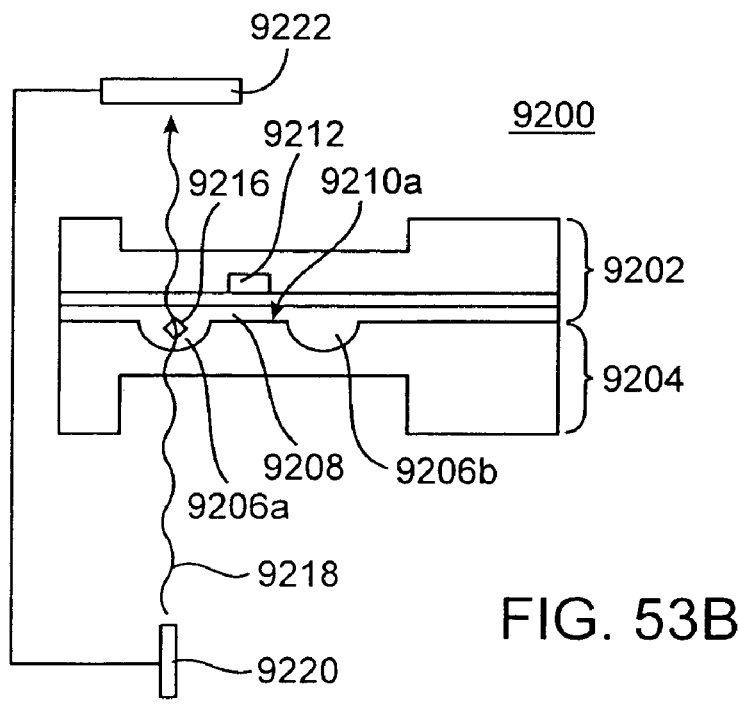

Accordingly, FIG. 53A shows a plan view of a simplified embodiment of a crystal growing chip in accordance with the present invention. FIG. 53B shows a simplified cross-sectional view of the embodiment of the crystal growing chip shown in FIG. 53A along line B-B'.

Harvesting/growing chip 9200 comprises elastomer portion 9202 overlying glass substrate 9204. Glass substrate 9204 computes three etched wells 9206a, 9206b and 9206c. Placement of elastomer portion 9202 over glass substrate 9204 thus defines three corresponding chambers in fluid communication with each other through flow channels 9208. The flow of materials through flow channels 9208 is controlled by valves 9210 defined by the overlap of control lines 9212 over control channels 9208.

During operation of growth/harvesting chip 9200, valves 9210 are initially activated to prevent contact between the contents of chambers 9206a, 9206b and 9206c. Chambers 9206a, 9206b and 9206c are then separately charged through wells 9214 with different materials for effecting crystallization. For example, chamber 9206a may be charged with a protein solution, chamber 9206b may be charged with a crystallizing agent, and chamber 9206c may be charged with a cryogen.

The first control line 9212 may then be deactivated to open valve 9210a, and thereby allowing diffusion of protein solution and crystallizing agent. Upon formation of a crystal 9216, the remaining control lines 9212 may be deactivated to allow the diffusion of cryogen from chamber 9206c to preserve the crystal 9216.

Next, the entire chip 9200 may be mounted in an x-ray diffraction apparatus, with x-ray beam 9218 applied from source 9220 against crystal 9216 with diffraction sensed by detector 9222. As shown in FIG. 53B, the general location of wells 9206 corresponds to regions of reduced thickness of both elastomer portion 9202 and underlying glass portion 9204. In this manner, radiation beam 9218 is required to traverse a minimum amount of elastomer and glass material prior to and subsequent to encountering crystal 9216, thereby reducing the deleterious effect of noise on the diffracted signal received.

While one example of a protein growth/harvesting chip has been described above in connection with FIGS. 53A-B, embodiments in accordance with the present invention are not limited to this particular structure. For example, while the embodiment of the current embodiment that is described utilizes a glass substrate in which microchambers have been etched, fabrication of microfluidic structures in accordance with the present invention is not limited to the use of glass substrates. Possible alternatives for fabricating features in a substrate include injection molding of plastics, hot embossing of plastics such as PMMA, or fabricating wells utilizing a photocurable polymer such as SU8 photoresist. In addition, features could be formed on a substrate such as glass utilizing laser ablation, or features could be formed by isotropic or aniosotropic etching of a substrate other than glass, such as silicon.

Potential advantages conferred by alternative fabrication methods include but are not limited to, more accurate definition of features allowing for more dense integration, and ease of production (e.g. hot embossing). Moreover, certain materials such as carbon based plastics impose less scattering of X-rays, thereby facilitating collection of diffraction data directly from a chip.

An additional possibility for the harvesting of crystals is to have a method of off-loading from chip. Off-loading could be performed once crystals have formed, or alternatively, prior to incubation. These off-loaded crystals could then be used to seed macroscopic reactions, or be extracted and mounted in a cryo-loop. If a method for the addition of cryogen was also developed, the crystals could be flash frozen and mounted directly into the x-ray beam.

4. Temporal Control Over Equilibration

The growth and quality of crystals is determined not only by thermodynamic conditions explored during the equilibration, but also by the rate at which equilibration takes place. It is therefore potentially valuable to control the dynamics of equilibration.

In conventional crystallization methods, course control only over the dynamics of equilibration may be available through manipulation of initial conditions. For macroscopic free interface diffusion, once diffusion begins, the experimenter has no control over the subsequent equilibration rate. For hanging drop experiments, the equilibration rate may be changed by modifying the size of the initial drop, the total size of the reservoir, or the temperature of incubation. In microbatch experiments, the rate at which the sample is concentrated may be varied by manipulating the size of the drop, and the identity and amount of the surrounding oil. Since the equilibration rates depend in a complicated manner on these parameters, the dynamics of equilibration may only be changed in a coarsely manner. Moreover, once the experiment has begun, no further control over the equilibration dynamics is available.

By contrast, the fluidic interface in a gated μ-Fib experiment may be controlled by manipulation of the dimensions of the reaction chambers and of the connecting channels. To good approximation, the time required for equilibration varies as the required diffusion length. The equilibration rate also depends on the cross-sectional area of the connecting channels. The required time for equilibration may therefore be controlled by changing both the length, and the cross-sectional area of the connecting channels.

Figure 38A:
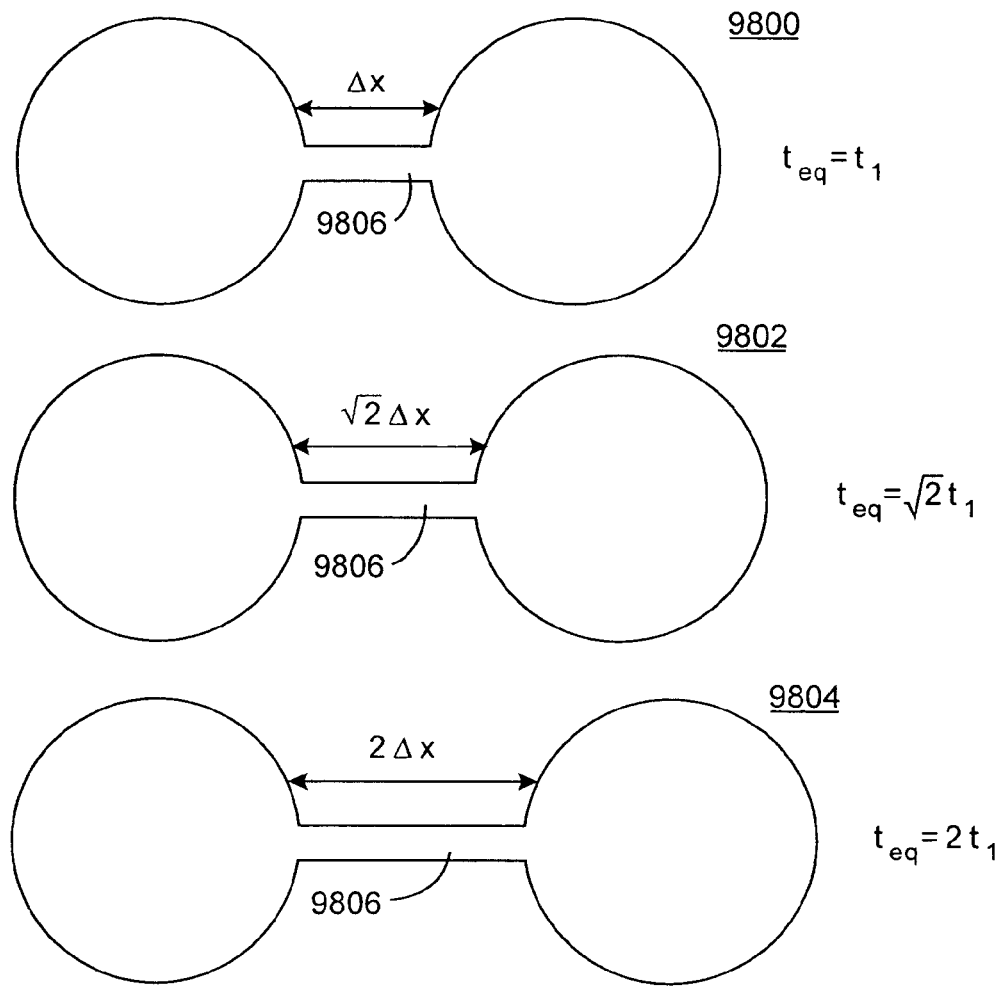
FIG. 38A shows three sets of pairs of chambers connected by microchannels of a different length.
Figure 38B:
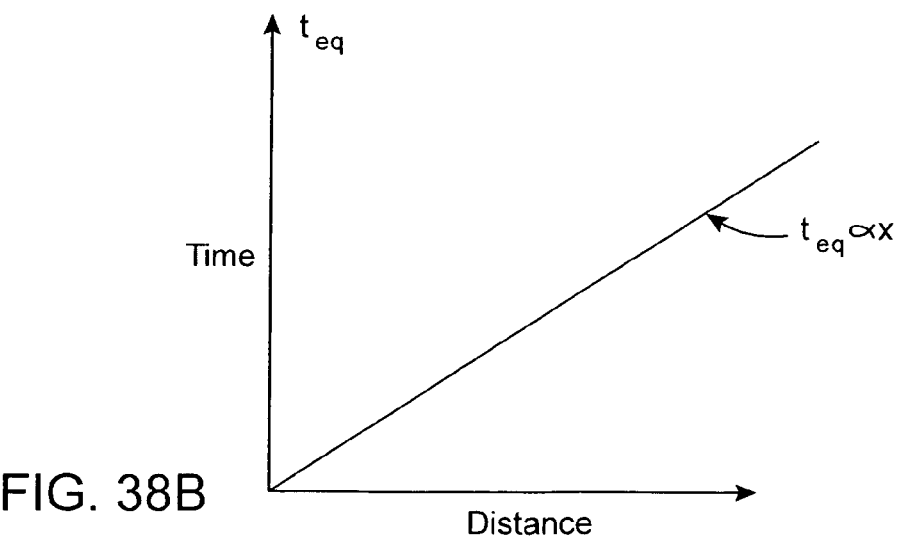
FIG. 38B plots equilibration time versus channel length.

FIG. 38A shows three sets of pairs of compound chambers 9800, 9802, and 9804, each pair connected by microchannels 9806 of a different length Δx. FIG. 38B plots equilibration time versus equilibration distance. FIG. 38B shows that the required time for equilibration of the chambers of FIG. 38A varies as the length of the connecting channels.

Figure 39:
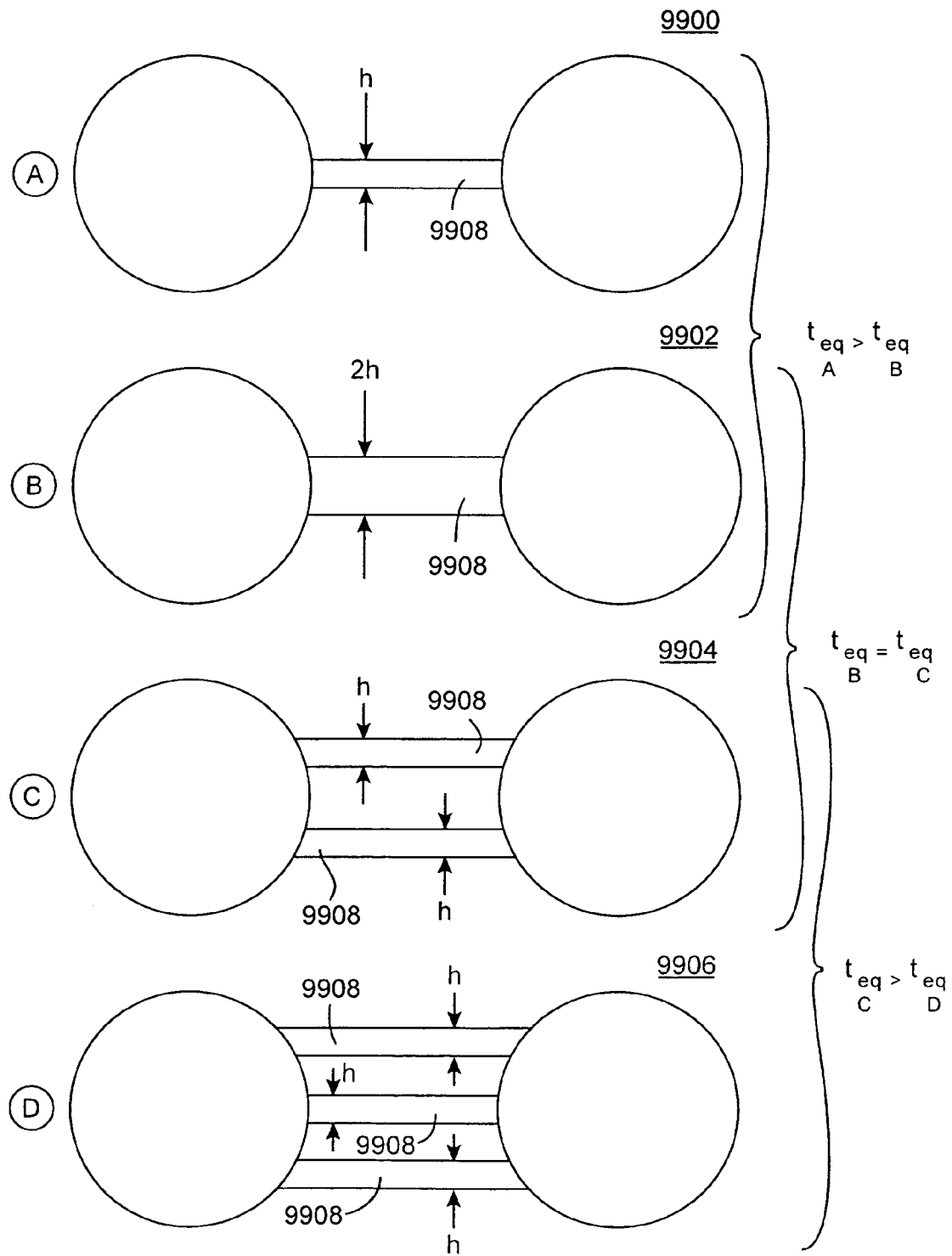
FIG. 39 shows four pairs of chambers, each having different arrangements of connecting microchannel(s).

FIG. 39 shows four compound chambers 9900, 9902, 9904, and 9906, each having different arrangements of connecting microchannel(s) 9908. Microchannels 9908 have the same length, but differ in cross-sectional area and/or number of connecting channels. The rate of equilibration may thus be increased/decreased by decreasing/increasing the cross-sectional area, for example by decreasing/increasing the number of connecting channels or the dimensions of those channels.

Varying the equilibration rate by changing the geometry of connecting channels may be used on a single device to explore the effect of equilibration dynamics on crystal growth. FIGS. 37A-D show an embodiment in which a gradient of concentrations, initially established by the partial diffusive equilibration of two solutions from a micro-free interface, can be maintained by the actuation of containment valves.

Figure 37A:
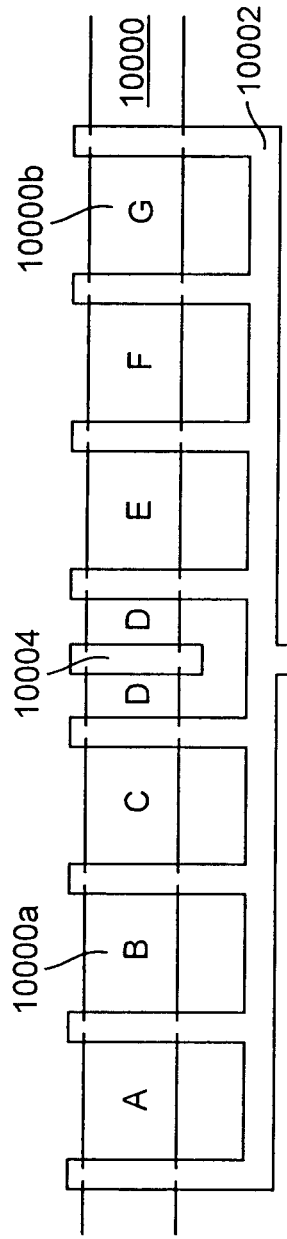
FIG. 37A shows a simplified plan view of a flow channel overlapped at intervals by a forked control channel to define a plurality of chambers (A-G) positioned on either side of a separately-actuated interface valve.
Figure 37B:
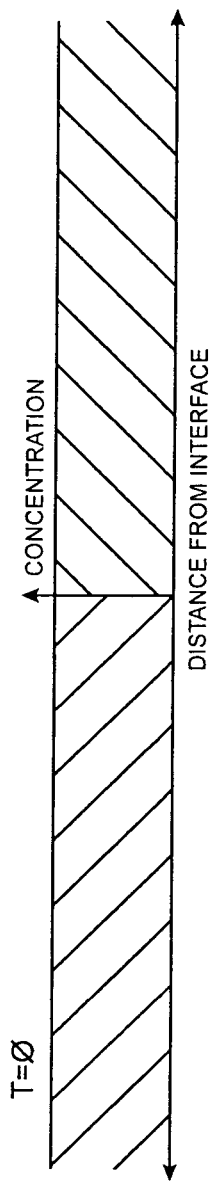
FIGS. 37B-D plot solvent concentration at different times for the flow channel shown in FIG. 37A.
Figure 37C:
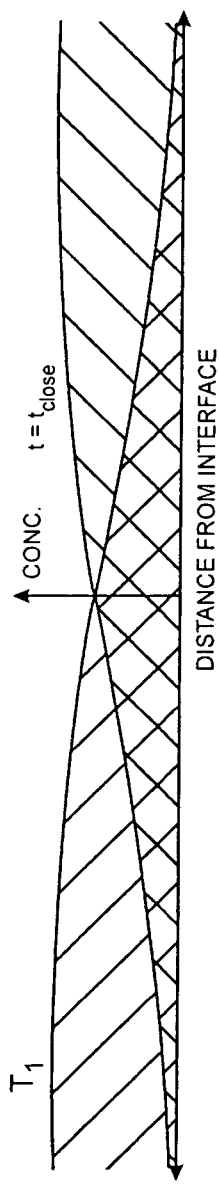
Figure 37D:
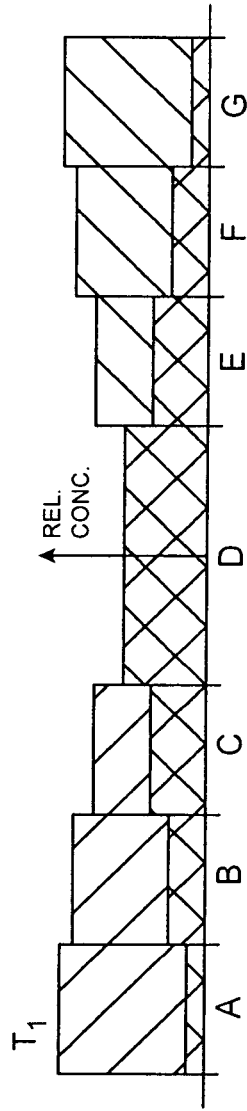

FIG. 37A shows flow channel 10000 that is overlapped at intervals by a forked control channel 10002 to define a plurality of chambers (A-G) positioned on either side of a separately-actuated interface valve 10004. FIG. 37B plots solvent concentration at an initial time, when interface valve 10004 is actuated and a first half 10000a of the flow channel has been mixed with a first solution, and a second half 10000b of the flow channel has been primed with a second solution. FIG. 37C plots solvent concentration at a subsequent time $T_1$, when control channel 10002 is actuated to define the seven chambers (A-G), which capture the concentration gradient at that particular point in time. FIG. 37D plots relative concentration of the chambers (A-G) at time $T_1$.

In the embodiment shown in FIG. 37A, actuation of the forked control channel simultaneously creates the plurality of chambers A-G. However, this is not required, and in alternative embodiments of the present invention multiple control channels could be utilized to allow independent creation of chambers A-G at different time intervals, thereby allow additional diffusion to occur after an initial set of chambers are created immediately adjacent to the free interface.

An embodiment of a method of capturing a concentration gradient between two fluids comprises providing a first fluid on a first side of an elastomer membrane present within a microfluidic flow channel, and providing a second fluid on a second side of the elastomer membrane. The elastomer membrane is displaced from the microfluidic flow channel to define a microfluidic free interface between the first fluid and the second fluid. The first fluid and the second fluid are allowed to diffuse across the microfluidic free interface. A group of elastomer valves positioned along the flow channel at increasing distances from the microfluidic free interface are actuated to define a succession of chambers whose relative concentration of the first fluid and the second fluid reflects a time of diffusion across the microfluidic free interface.

5. Target Materials

Typical targets for crystallization are diverse. A target for crystallization may include but is not limited to: 1) biological macromolecules (cytosolic proteins, extracellular proteins, membrane proteins, DNA, RNA, and complex combinations thereof), 2) pre- and post-translationally modified biological molecules (including but not limited to, phosphorylated, sulfolated, glycosylated, ubiquitinated, etc. proteins, as well as halogenated, abasic, alkylated, etc. nucleic acids); 3) deliberately derivatized macromolecules, such as heavy-atom labeled DNAs, RNAs, and proteins (and complexes thereof), selenomethionine-labeled proteins and nucleic acids (and complexes thereof), halogenated DNAs, RNAs, and proteins (and complexes thereof), 4) whole viruses or large cellular particles (such as the ribosome, replisome, spliceosome, tubulin filaments, actin filaments, chromosomes, etc.), 5) small-molecule compounds such as drugs, lead compounds, ligands, salts, and organic or metallo-organic compounds, and 6) small-molecule/biological macromolecule complexes (e.g., drug/protein complexes, enzyme/substrate complexes, enzyme/product complexes, enzyme/regulator complexes, enzyme/inhibitor complexes, and combinations thereof). Such targets are the focus of study for a wide range of scientific disciplines encompassing biology, biochemistry, material sciences, pharmaceutics, chemistry, and physics.

A nonexclusive listing of possible protein modifications is as follows: 5' dephospho; Desmosine (from Lysine); decomposed carboxymethylated Methionine; Ornithine (from Arginine); Lysinoalanine (from Cysteine); Lanthionine (from Cysteine); Dehydroalanine (from Cysteine); Homoserine formed from Met by CNBr treatment; Dehydration (—H2O); S-gamma-Glutamyl (crosslinked to Cysteine); O-gamma-Glutamyl-(Crosslink to Serine); Serine to Dehydroalanine; Alaninohistidine (Serine crosslinked to theta or pi carbon of Histidine); Pyroglutamic Acid formed from Gln;N-pyrrolidone carboxyl (N terminus); N alpha-(gamma-Glutamyl)-lysine; N-(beta-Aspartyl)-Lysine (Crosslink); 3,3',5,5'-Ter-Tyr (Crosslink); Disulphide bond formation (Cystine); S-(2-Histidyl)- (Crosslinked to Cysteine); S-(3-Tyr) (Crosslinked to Cysteine); 3,3'-BiTyr (Crosslink); IsodiTyr (Crosslink); Allysine (from Lysine); Amide formation (C terminus); Deamidation of Asparagine and Glutamine to Aspartate and Glutamate; Citruline (from Arginine); Syndesine (from Lysine); Methylation (N terminus, N epsilon of Lysine, O of Serine, Threonine or C terminus, N of Asparagine); delta-Hydroxy-allysine (from Lysine); Hydroxylation (of delta C of Lysine, beta C of Tryptophan, C3 or C4 of Proline, beta C of Aspartate); Oxidation of Methionine (to Sulphoxide); Sulfenic Acid (from Cysteine); Pyruvoyl-(Serine); 3,4-Dihydroxy-Phenylalanine (from Tyrosine) (DOPA); Sodium; Ethyl; N,N dimethylation (of Arginine or Lysine); 2,4-Bis-Trp-6,7-dione (from Tryptophan); Formylation (CHO); 6,7 Dione (from Tryptophan); 3,4,6-Trihydroxy-Phenylalanine (from Tyrosine) (TOPA); 3,4-Dihydroxylation (of Proline); Oxidation of Methionine (to Sulphone); 3-Chlorination (of Tyrosine with 35Cl); 3-Chlorination (of Tyrosine with 37Cl); Potassium; Carbamylation; Acetylation (N terminus, N epsilon of Lysine, O of Serine) (Ac); N-Trimethylation (of Lysine); gamma Carboxylation of Glutamate or beta Carboxylation of Aspartate; disodium; Nitro (NO2); t-butyl ester (OtBu) and t-butyl (tBu); Glycyl (-G-, -Gly-); Carboxymethyl (on Cystine); sodium+potassium; Selenocysteine (from Serine); 3,5-Dichlorination (of Tyrosine with 35Cl); Dehydroalanine (Dha); 3,5-Dichlorination (of Tyrosine with mixture of 35Cl and 37Cl)); Pyruvate; Acrylamidyl or Acrylamide adduct; Sarcosyl; Alanyl (-A-, -Ala-); Acetamidomethyl (Acm); 3,5-Dichlorination (of Tyrosine with 37Cl); S-(sn-1-Glyceryl) (on Cysteine); Glycerol Ester (on Glutamic acid side chain); Glycine (G, Gly); Beta mercaptoethanol adduct; Phenyl ester (OPh) (on acidic); 3-Bromination (of Tyrosine with 79Br); Phosphorylation (O of Serine, Threonine, Tyrosine and Aspartate, N epsilon of Lysine); 3-Bromination (of Tyrosine with 81Br); Sulphonation (SO3H) (of PMC group); Sulphation (of O of Tyrosine); Cyclohexyl ester (OcHex); Homoseryl lactone; Dehydroamino butyric acid (Dhb); Gamma Aminobutyryl; 2-Aminobutyric acid (Abu); 2-Aminoisobutyric acid (Aib); Diaminopropionyl; t-butyloxymethyl (Bum); N-(4-NH2-2-OH-butyl)- (of Lysine) (Hypusine); Seryl (—S—, -Ser-); t-butylsulfenyl (StBu); Alanine (A, Ala); Sarcosine (Sar); Anisyl; Benzyl (Bzl) and benzyl ester (OBzl); 1,2-ethanedithiol (EDT); Dehydroprolyl; Triflouroacetyl (TFA); N-hydroxysuccinimide (ONSU, OSu); Prolyl (-P-, -Pro-); Valyl (-V-, -Val-); Isovalyl (-I-,-Iva-); t-Butyloxycarbonyl (tBoc); Threoyl (-T-, -Thr-); Homoseryl (-Hse-); Cystyl (-C-, -Cys-); Benzoyl (Bz); 4-Methylbenzyl (Meb); Serine (S, Ser); HMP (hydroxymethylphenyl) linker; Thioanisyl; Thiocresyl; Diphthamide (from Histidine); Pyroglutamyl; 2-Piperidinecarboxylic acid (Pip); Hydroxyprolyl (-Hyp-); Norleucyl (-Nle-); Isoleucyl (-I-, -Ile-); Leucyl (-L-, -Leu-); Ornithyl (-Orn-); Asparagyl (-N-, -Asn-); t-amyloxycarbonyl (Aoc); Proline (P, Pro); Aspartyl (-D-, -Asp-); Succinyl; Valine (V, Val); Hydroxybenzotriazole ester (HOBt); Dimethylbenzyl (diMeBzl); Threonine (T, Thr); Cysteinylation; Benzyloxymethyl (Bom); p-methoxybenzyl (Mob, Mbzl); 4-Nitrophenyl, p-Nitrophenyl (ONp); Cysteine (C, Cys); Chlorobenzyl (ClBzl); Iodination (of Histidine[C4] or Tyrosine[C3]); Glutamyl (-Q-, -Gln-); N-methyl Lysyl; Lysyl (-K-, -Lys-); O-Methyl Aspartamyl; Glutamyl (-E-, -Glu-); N alpha-(gamma-Glutamyl)-Glu; Norleucine (Nle); Hydroxy Aspartamyl; Hydroxyproline (Hyp); bb-dimethyl Cystenyl; Isoleucine (I, Ile); Leucine (L, Leu); Methionyl (-M-, -Met-); Asparagine (N, Asn); Pentoses (Ara, Rib, Xyl); Aspartic Acid (D, Asp); Dmob (Dimethoxybenzyl); Benzyloxycarbonyl (Z); Adamantyl (Ada); p-Nitrobenzyl ester (ONb); Histidyl (-H-, -His-); N-methyl Glutamyl; O-methyl Glutamyl; Hydroxy Lysyl (-Hyl-); Methyl Methionyl; Glutamine (Q, Gln); Aminoethyl Cystenyl; Pentosyl; Deoxyhexoses (Fuc, Rha); Lysine (K, Lys); Aminoethyl cystenyl (-AECys-); 4-Glycosyloxy- (pentosyl,C5) (of Proline); Methionyl Sulfoxide; Glutamic Acid (E, Glu); Phenylalanyl- (-F-, -Phe-); Pyridyl Alanyl; Flourophenylalanyl; 2-Nitrobenzoyl (NBz); Methionine (M, Met); 3-methyl Histidyl; 2-Nitrophenylsulphenyl (Nps); 4-Toluenesulphonyl (Tosyl, Tos); 3-nitro-2-pyridinesulfenyl (Npys); Histidine (H, His); 3,5-Dibromination (of Tyrosine with 79Br); Arginyl (-R-, -Arg-); Citrulline; 3,5-Dibromination (of Tyrosine with mixture of 79Br and 81Br); Dichlorobenzyl (Dcb); 3,5-Dibromination (of Tyrosine with 81Br); Carboxyamidomethyl Cystenyl; Carboxymethyl Cystenyl; Methylphenylalanyl; Hexosamines (GaiN, GlcN); Carboxymethyl cysteine (Cmc); N-Glucosyl (N terminus or N epsilon of Lysine) (Aminoketose); O-Glycosyl- (to Serine or Threonine); Hexoses (Fru, Gal, Glc, Man); Inositol; MethionylSulphone; Tyrosinyl (-Y-, -Tyr-); Phenylalanine (F, Phe); 2,4-dinitrophenyl (Dnp); Pentaflourophenyl (Pfp); Diphenylmethyl (Dpm); Phospho Seryl; 2-Chlorobenzyloxycarbonyl (ClZ); Napthyl acetyl; Isopropyl Lysyl; N-methyl Arginyl; Ethaneditohiol/TFA cyclic adduct; Carboxy Glutamyl (Gla); Acetamidomethyl Cystenyl; Acrylamidyl Cystenyl; Arginine (R, Arg); N-Glucuronyl (N terminus); delta-Glycosyloxy- (of Lysine) or beta-Glycosyloxy- (of Phenylalanine or Tyrosine); 4-Glycosyloxy-(hexosyl,C6) (of Proline); Benzyl Seryl; N-methyl Tyrosinyl; p-Nitrobenzyloxycarbonyl (4Nz); 2,4,5-Trichlorophenyl; 2,4,6-trimethyloxybenzyl (Tmob); Xanthyl (Xan); Phospho Threonyl; Tyrosine (Y, Tyr); Chlorophenylalanyl; Mesitylene-2-sulfonyl (Mts); Carboxymethyl Lysyl; Tryptophanyl (—W—, -Trp-); N-Lipoyl- (on Lysine); Matrix alpha cyano MH+; Benzyl Threonyl; Benzyl Cystenyl; Napthyl Alanyl; Succinyl Aspartamyl; Succinimidophenyl carb.; HMP (hydroxymethylphenyl)/TFA adduct; N-acetylhexosamines (GalNAc, GlcNAc); Tryptophan (W, Trp); Cystine ((Cys)2); Farnesylation; S-Farnesyl-; Myristoleylation (myristoyl with one double bond); Pyridylethyl Cystenyl; Myristoylation; 4-Methoxy-2,3,6-trimethylbenzenesulfonyl (Mtr); 2-Bromobenzyloxycarbonyl (BrZ); Formyl Tryptophanyl; Benzyl Glutamyl; Anisole Adducted Glutamyl; S-cystenyl Cystenyl; 9-Flourenylmethyloxycarbonyl (Fmoc); Lipoic acid (amide bond to lysine); Biotinylation (amide bond to lysine); Dimethoxybenzhydryl (Mbh); N-Pyridoxyl (on Lysine); Pyridoxal phosphate (Schiff Base formed to lysine); Nicotinyl Lysyl; Dansyl (Dns); 2-(p-biphenyl)isopropyl-oxycarbonyl (Bpoc); Palmitoylation; "Triphenylmethyl (Trityl, Trt)"; Tyrosinyl Sulphate; Phospho Tyrosinyl; Pbf (pentamethyldihydrobenzofuransulfonyl); 3,5-Diiodination (of Tyrosine); 3,5-di-I"; N alpha -(gamma-Glutamyl)-Glu2; O-GlcNAc-1-phosphorylation (of Serine); "2,2,5,7,8-Pentamethylchroman-6-sulphonyl (Pmc)"; Stearoylation; Geranylgeranylation; S-Geranylgeranyl; 5'phos dCytidinyl; iodo Tyrosinyl; Aldohexosyl Lysyl; Sialyl; N-acetylneuraminic acid (Sialic acid, NeuAc, NANA, SA); 5'phos dThymidinyl; 5'phos Cytidinyl; Glutathionation; O-Uridinylylation (of Tyrosine); 5'phos Uridinyl; S-farnesyl Cystenyl; N-glycolneuraminic acid (NeuGc); 5'phos dAdenosyl; O-panteheine-phosphorylation (of Serine); SucPhencarb Lysyl; 5'phos dGuanosyl; 5'phos Adenosinyl; O-5'-Adenosylation (of Tyrosine); 4'-Phosphopanteheine; GL2; S-palmityl Cystenyl; 5'phos Guanosyl; Biotinyl Lysyl; Hex-HexNAc; N alpha-(gamma-Glutamyl)-Glu3; Dioctyl Phthalate; PMC Lysyl; Aedans Cystenyl; Dioctyl Phthalate Sodium Adduct; di-iodo Tyrosinyl; PMC Arginyl; S-Coenzyme A; AMP Lysyl; 3,5,3'-Triiodothyronine (from Tyrosine); S-(sn-1-Dipalmitoyl-glyceryl)- (on Cysteine); S-(ADP-ribosyl)- (on Cysteine); N-(ADP-ribosyl)-(on Arginine); O-ADP-ribosylation (on Glutamate or C terminus); ADP-rybosylation (from NAD); S-Phycocyanobilin (on Cysteine); S-Heme (on Cysteine); N theta-(ADP-ribosyl) diphthamide (of Histidine); NeuAc-Hex-HexNAc; MGDG; O-8 alpha-Flavin [FAD])- (of Tyrosine); S-(6-Flavin [FAD])-(on Cysteine); N theta and N pi-(8alpha-Flavin) (on Histidine); (Hex)3-HexNAc-HexNAc; (Hex)3-HexNAc-(dHex)HexNAc.

A nonexclusive listing of possible nucleic acid modifications, such as base-specific, sugar-specific, or phospho-specific is as follows: halogenation (F, Cl, Br, I); Abasic sites; Alkylation; Crosslinkable adducts such as thiols or azides; Thiolation; Deamidation; Fluorescent-group labeling, and glycosylation.

A nonexclusive listing of possible heavy atom derivatizing agents is as follows: potassium hexachloroiridate (III); Potassium hexachloroiridate (IV); Sodium hexachloroiridate (IV); Sodium hexachloroiridate (III); Potassium hexanitritoiridate (III); Ammnoium hexachloroiridate (III); Iridium (III) chloride; Potassium hexanitratoiridate (III); Iridium (III) bromide; Barium (II) chloride; Barium (II) acetate; Cadmium (II) nitrate; Cadmium (II) iodide; Lead (II) nitrate; Lead (II) acetate; Trimethyl lead (IV) chloride; Trimethyl lead (IV) acetate; Ammonium hexachloro plumbate (IV); Lead (II) chloride; Sodium hexachlororhodiate (III); Strontium (II) acetate; Disodium thiomalonato aurate (I); Potassium dicyano aurate (I); Sodium dicyano aurate (I); Sodium thiosulphato aurate (III); Potassium tetracyano aurate (III); Potassium tetrachloro aurate (III); Hydrogen tetrachloro aurate (III); Sodium tetrachloro aurate (III); Potassium tetraiodo aurate (III); Potassium tetrabromo aurate (III); (acetato-o) methylmercury; Methyl (nitrato-o) mercury; Chloromethylmercury; Iodomethylmercury; Chloroethylmercury; Methyl mercury cation; Triethyl (m3-phosphato(3-)-0,0',0") tri mercury eth; [3-[(aminocarbonyl)amino]-2-methoxypropyl]chlorome; 1,4 diacetoxymercury 2-3 dimethoxy butane; Meroxyl mercuhydrin; Tetrakis (acetoxy mercuri)-methane; 1,4-bis(chloromercuri)-2,3-butanediol; Ethyl diacetoxymercurichloro acetate (dame); Mercuric (II) oxide; Methyl mercuri-2-mercaptoethanol; 3,6 bis (mercurimethyl dioxane acetate); Ethyl mercury cation; Billman's dimercurial; Para chloromercury phenyl acetate (pcma); Mercury phenyl glyoxal (mpg); Thiomersal, ethyl mercury thiosalicylate [emts]; 4-chloromercuribenesulphonic acid; 2,6 dichloromercuri-4-nitrophenol (dcmnp); [3-[[2(carboxymethoxy)benzoyl] mino-2 methoxy prop; Parachloromercury benzoate (pcmb), 4-chloromercury; (acetato-o)phenyl mercury; Phenyl mercuri benzoate (pmb); Para hydroxy mercuri benzoate (phmb); Mercuric imidosuccinate/mercury succinimide; 3-hydroxymercurybenzaldehyde; 2-acetoxy mercuri sulhpanilamide; 3-acetoxymercuri-4-aminobenzenesulphonamide; Methyl mercuri thioclycolic acid (mmtga); 2-hydroxymercuri-tolulen-4-sulphonic acid (hmts); Acetamino phenyl mercury acetate (apma); [3-[(aminocarbonyl)amino]-3-methoxypropyl 2-chloro; Para-hydroxymercuri benzene sulphonate (phmbs); Ortho-chloromercuri phenol (ocmp); Diacetoxymercury dipopylene dioxide (dmdx); Para-acetoxymercuri aniline (pama); (4-aminophenyl) chloromercury; Aniline mercury cation; 3-hydroxy-mercuri-s sulphosalicylic acid (msss); 3 or 5 hydroxymercuri salicylic acid (hmsa); Diphenyl mercury; 2,6 diacetoxymercurimethyl 1-4 thioxane (dmmt); 2,5-bls (chloromercury) furan; Ortho-chloromercuri nitrophenol (ocmnp); 5-mercurydeoxyuridine monosulphate; Mercury salicylate; [3-[[2-(carboxymethoxy)benzoyl] amino-2-methoxypro; 3,3 bis (hydroximercuri)-3-nitratomercuri pyruvic; 3-chloro mercuri pyridine; 3,5 bis acetoxymercuri methyl morpholine; Ortho-mercury phenol cation; Para-carboxymethyl mercaptomercuri benzensulphonyl; Para-mercuribenzoyl glucosamine; 3-acetetoxymercuri-5-nitrosalicyladehyde (msa); Ammonium tetrachloro mercurate (II); Potassium tetrathiocyanato mercurate (II); Sodium tetrathiocyanato mercurate (II); Potassium tetraisothiocyanto mercurate (II); Potassium tetraido mercurate (II); Ammonium tetrathiocyananato mercurate (II); Potassium tetrabromo mercurate (II); Potassium tetracyano mercurate (II); Mercury (II) bromide; Mercury (II) thiocyanate; Mercury (II) cyanide; Mercury (II) iodide; Mercuric (II) chloride; Mercury (II) acetate; Mercury (I) acetate; Dichlorodiamino mercurate (II); Beta mercury-mercapto-ethylamine hydrochloride; Mercury (II) sulphate; Mercury (II) chloroanilate; Dimercuriacetate; Chloro(2-oxoethyl) mercury; Phenol mercury nitrate; Mercury mercaptoethanol; Mercury mercaptoethylamine chloride; Mercury thioglycollic acid (sodium salt); O-hydroxymercuri-p-nitrophenol/2-hydroxymercuri-4-; Para chloromercuri phenol (pcmp); Acetylmercurithiosalicylate (amts); Iodine; Potassium iodide (iodine); 4-iodopyrazole; O-iodobenzoylglucasamine; P-iodobenzoylglucasamine; Potassium iodide/chloramine t; Ammonium iodide; 3-isothio-cyanato-4-iodobenzene sulphonate; Potassium iodide; 3'-iodo phenyltrazine; 4'-iodo phenyltrazine; Sodium iodide/iodine; Silver nitrate; Silver ( )trinitridosulphoxylate; Tobenamed; Samarium (III) chloride; Thulium (III) chloride; Lutetium (III) chloride; Europium (III) chloride; Terbium (III) chloride; Gadolinium (III) chloride; Erbium (III) chloride; Lanthanum (III) chloride; Samarium (III) nitrate; Samarium (III) acetate; Samarium (III) cation; Praseodymium (III) chloride; Neodymium (III) chloride; Ytterbium (III) chloride; Thulium (III) sulphate; Ytterbium (III) sulphate; Gadolinium (III) sulphate; Gadolinium (III) acetate; Dysprosium (III) chloride; Erbium (III) nitrate; Holmium (III) chloride; Penta amino ruthenium (III) chloride; Cesium nitridotiroxo osmium (viii); Potassium tetraoxo osmiate; Hexa amino osmium (III) iodide; Ammonium hexachloroosmiate (IV); Osmium (III) chloride; Potassium hexachloro osmiate (IV); Cesium trichloro triscarbonyl osmiate (?); Dinitritodiamine platinum (II); Cis dichlorodimethylammido platinum (II); Dichlorodiammine platinum (II); Dibromodiammine platinum (II); Dichloroethylene diamine platinum (II); Potassium dicholodinitrito platinate (II); Diethylenediamene platinum (II); Potassium dioxylato platinate (II); Dichlorobis (pyridine) platinum (II); Potassium (thimethyl dibenzyloamine) platinum (?); Potassium tetrabromoplatinate (II); Potassium tetrachloro platinate (II); Potassium tetranitrito platinum (II); Potassium tetracyano platinate (II); Sodium tetracyano platinate (II); Potassium tetrathiocyanato platinate (II); Ammonium tetranitrito platinate (II); Potassium tetraisocyanato platinate (II); Ammonium tetracyano platinum (II); Ammonium tetrachloro platinate (II); Potassium dinitritodioxalato platinate (IV); Dichlorotetraammino platinium (IV); Dibromodinitrito diammine platinium (IV); Potassium hexanitrito platinate (IV); Potassium hexachloro platinate (IV); Potassium hexabromo platinate (IV); Sodium hexachloroplatinate (IV); Potassium hexaiodo platinate (IV); Potassium hexathiocyanato platinate (IV); Tetrachloro bis(pyridine) platinum (IV); Ammonium hexachloro platinate (IV); Di-mu-iodo bis(ethylenediamine) di platinum (II) n; Potassium hexaisothiocyanato platinate (IV); Potassium tetraiodo platinate (II); 2,2',2" terpyridyl platinium (II); 2 hydroxyethanethiolate (2,2',2" terpyeidine) pla; Potassium tetranitro platinate (II); Trimethyl platinum (II) nitrate; Sodium tetraoxo rhenate (VII); Potassium tetraoxo rhenate (VI); Potassium tetraoxo rhenate (VII); Potassium hexachloro rhenium (IV); Rhenium (III) chloride; Ammonium hexachloro rhenate (IV); Dimethyltin (II) dichloride; Thorium (IV) nitrate; Uranium (VI) oxychloride; Uranium (VI) oxynitrate; Uranium (VI) oxyacetate; Uranium (VI) oxypyrophosphate; Potassium pentafluoro oxyuranate (VI); Sodium pentafluoro oxyuranate (VI); Potassium nanofluoro dioxyuranate (VI); Sodium triacetate oxyuranate (VI); Uranium (VI) oxyoxalate; Selenocyanate anion; Sodium tungstate; Sodium 12-tungstophosphate; Thallium (I) acetate; Thallium (I) fluoride; Thallium (I) nitrate; Potassium tetrachloro palladate (II); Potassium tetrabromo palladate (II); Potassium tetracyano palladate (II); Potassium tetraiodo palladate (II); Cobalt (II) chloride.

The PDMS material from which the chip can be formed is well suited for many of these targets, particularly biological samples. PDMS is a non-reactive and biologically inert compound that allows such molecules to maintain their appropriate shape, fold, and activity in a solublized state. The matrix and system can accommodate a range of target sizes and molecular weights, from a few hundred Daltons to the mega-Dalton regime. Biological targets, from small proteins and peptides to viruses and macromolecular complexes, fall within this range, and are generally anywhere from 3-10 kDa to >1-2 MDa in size.

6. Solute/Reagent Types

During crystallization screening, a large number of chemical compounds may be employed. These compounds include salts, small and large molecular weight organic compounds, buffers, ligands, small-molecule agents, detergents, peptides, crosslinking agents, and derivatizing agents. Together, these chemicals can be used to vary the ionic strength, pH, solute concentration, and target concentration in the drop, and can even be used to modify the target. The desired concentration of these chemicals to achieve crystallization is variable, and can range from nanomolar to molar concentrations. A typical crystallization mix contains set of fixed, but empirically-determined, types and concentrations, of 'precipitants', buffers, salts, and other chemical additives (e.g., metal ions, salts, small molecular chemical additives, cryo protectants, etc.). Water is a key solvent in many crystallization trials of biological targets, as many of these molecules may require hydration to stay active and folded.

As described above in connection with the pressurized out-gas priming (POP) technique, the permeability of PDMS to gases, and the compatibility of solvents with PDMS may be a significant factor in deciding upon precipitating agents to be used.

'Precipitating' agents act to push targets from a soluble to insoluble state, and may work by volume exclusion, changing the dielectric constant of the solvent, charge shielding, and molecular crowding. Precipitating agents compatible with the PDMS material of certain embodiments of the chip include, but are not limited to, non-volatile salts, high molecular weight polymers, polar solvents, aqueous solutions, high molecular weight alcohols, divalent metals.

Precipitating compounds, which include large and small molecular weight organics, as well as certain salts are used from under 1% to upwards of 40% concentration, or from <0.5M to greater than 4M concentration. Water itself can act in a precipitating manner for samples that require a certain level of ionic strength to stay soluble. Many precipitants may also be mixed with one another to increase the chemical diversity of the crystallization screen. The microfluidics devices described in this document are readily compatible with a broad range of such compounds. Moreover, many precipitating agents (such as long- and short-chain organics) are quite viscous at high concentrations, presenting a problem for most fluid handling devices, such as pipettes or robotic systems. The pump and valve action of microfluidics devices in accordance with embodiments of the present invention enable handling of viscous agents.

An investigation of solvent/precipitating agent compatibility with particular elastomer materials may be conducted to identify optimum crystallizing agents, which may be employed develop crystallization screening reactions tailored for the chip that are more effective than standard screens.

A nonexclusive list of salts which may be used as precipitants is as follows: Tartrate (Li, Na, K, Na/K, NH4); Phosphate (Li, Na, K, Na/K, NH4); Acetate (Li, Na, K, Na/K, Mg, Ca, Zn, NH4); Formate (Li, Na, K, Na/K, Mg, NH4); Citrate (Li, Na, K, Na/K, NH4); Chloride (Li, Na, K, Na/K, Mg, Ca, Zn, Mn, Cs, Rb, NH4); Sulfate (Li, Na, K, Na/K, NH4); Malate (Li, Na, K, Na/K, NH4); Glutamate (Li, Na, K, Na/K, NH4.

A nonexclusive list of organic materials which may be used as precipitants is as follows: PEG 400; PEG 1000; PEG 1500; PEG 2k; PEG 3350; PEG 4k; PEG 6k; PEG 8k; PEG 10k; PEG 20k; PEG-MME 550; PEG-MME 750; PEG-MME 2k; PEG-MME 5k; PEG-DME 2k; Dioxane; Methanol; Ethanol; 2-Butanol; n-Butanol; t-Butanol; Jeffamine M-600; Isopropanol; 2-methyl-2,4-pentanediol; 1,6 hexanediol.

Solution pH can be varied by the inclusion of buffering agents; typical pH ranges for biological materials lie anywhere between values of 3.5-10.5 and the concentration of buffer, generally lies between 0.01 and 0.25 M. The microfluidics devices described in this document are readily compatible with a broad range of pH values, particularly those suited to biological targets.

A nonexclusive list of possible buffers is as follows: Na-Acetate; HEPES; Na-Cacodylate; Na-Citrate; Na-Succinate; Na-K-Phosphate; TRIS; TRIS-Maleate; Imidazole-Maleate; BisTris Propane; CAPSO, CHAPS, MES, and imidizole.

Additives are small molecules that affect the solubility and/or activity behavior of the target. Such compounds can speed crystallization screening or produce alternate crystal forms of the target. Additives can take nearly any conceivable form of chemical, but are typically mono and polyvalent salts (inorganic or organic), enzyme ligands (substrates, products, allosteric effectors), chemical crosslinking agents, detergents and/or lipids, heavy metals, organo-metallic compounds, trace amounts of precipitating agents, and small molecular weight organics.

The following is a nonexclusive list of possible additives: 2-Butanol; DMSO; Hexanediol; Ethanol; Methanol; Isopropanol; sodium fluoride; potassium fluoride; ammonium fluoride; lithium chloride anhydrous; magnesium chloride hexahydrate; sodium chloride; Calcium chloride dihydrate; potassium chloride; ammonium chloride; sodium iodide; potassium iodide; ammonium iodide; sodium thiocyanate; potassium thiocyanate; lithium nitrate; magnesium nitrate hexahydrate; sodium nitrate; potassium nitrate; ammonium nitrate; magnesium formate; sodium formate; potassium formate; ammonium formate; lithium acetate dihydrate; magnesium acetate tetrahydrate; zinc acetate dihydrate; sodium acetate trihydrate; calcium acetate hydrate; potassium acetate; ammonium acetate; lithium sulfate monohydrate; magnesium sulfate heptahydrate; sodium sulfate decahydrate; potassium sulfate; ammonium sulfate; di-sodium tartate dihydrate; potassium sodium tartrate tetrahydrate; di-ammonium tartrate; sodium dihydrogen phosphate monohydrate; di-sodium hydrogen phosphate dihydrate; potassium dihydrogen phosphate; di-potassium hydrogen phosphate; ammonium dihydrogen phosphate; di-ammonium hydrogen phosphate; tri-lithium citrate tetrahydrate; tri-sodium citrate dihydrate; tri-potassium citrate monohydrate; di-ammonium hydrogen citrate; barium chloride; cadmium chloride dihydrate; cobaltous chloride dihydrate; cupric chloride dihydrate; strontium chloride hexahydrate; yttrium chloride hexahydrate; ethylene glycol; Glycerol anhydrous; 1,6 hexanediol; MPD; polyethylene glycol 400; trimethylamine HCl; guanidine HCl; urea; 1,2,3-heptanetriol; benzamidine HCl; dioxane; ethanol; iso-propanol; methanol; sodium iodide; L-cysteine; EDTA sodium salt; NAD; ATP disodium salt; D(+)-glucose monohydrate; D(+)-sucrose; xylitol; spermidine; spermine tetra-HCl; 6-aminocaproic acid; 1,5-diaminopentane di-HCl; 1,6-diaminohexane; 1,8-diaminooctane; glycine; glycyl-glycyl-glycine; hexaminecobalt trichloride; taurine; betaine monohydrate; polyvinylpyrrolidone K15; non-detergent sulfo-betaine 195; non-detergent sulfo-betaine 201; phenol; DMSO; dextran sulfate sodium salt; jeffamine M-600; 2,5 Hexanediol; (+/−)-1,3 butanediol; polypropylene glycol P400; 1,4 butanediol; tert-butanol; 1,3 propanediol; acetonitrile; gamma butyrolactone; propanol; ethyl acetate; acetone; dichloromethane; n-butanol; 2,2,2 trifluoroethanol; DTT; TCEP; nonaethylene glycol monododecyl ether, nonaethylene glycol monolauryl ether,; polyoxyethylene (9) ether; octaethylene glycol monododecyl ether, octaethylene glycol monolauryl ether,; polyoxyethylene (8) lauryl ether; Dodecyl-β-D-maltopyranoside; Lauric acid sucrose ester; Cyclohexyl-pentyl-β-D-maltoside; Nonaethylene glycol octylphenol ether; Cetyltrimethylammonium bromide; N,N-bis(3-D-gluconamidopropyl)-deoxycholamine; Decyl-β-D-maltopyranoside; Lauryldimethylamine oxide; Cyclohexyl-pentyl-β-D-maltoside; n-Dodecylsulfobetaine, 3-(Dodecyldimethylammonio)propane-1-sulfonate; Nonyl-β-D-glucopyranoside; Octyl-β-D-thioglucopyranoside, OSG; N,N-Dimethyldecylamine-β-oxide; Methyl-6-O-(N-heptylcarbamoyl)-a-D-glucopyranoside; Sucrose monocaproylate; n-Octanoyl-β-D-fructofuranosyl-a-D-glucopyranoside; Heptyl-β-D-thioglucopyranoside; Octyl-β-D-glucopyranoside, OG; Cyclohexyl-propyl-β-D-maltoside; Cyclohexylbutanoyl-N-hydroxyethylglucamide; n-decylsulfobetaine, 3-(Decyldimethylammonio)propane-1-sulfonate; Octanoyl-N-methylglucamide, OMEGA; Hexyl-β-D-glucopyranoside; Brij 35; Brij 58; Triton X-114; Triton X-305; Triton X-405; Tween 20; Tween 80; polyoxyethylene(6)decyl ether; polyoxyethylene (9)decyl ether; polyoxyethylene(10)dodecyl ether; polyoxyethylene(8)tridecyl ether; Isopropyl-β-D-thiogalactoside; Decanoyl-N-hydroxyethylglucamide; Pentaethylene glycol monooctyl ether; 3-[(3-cholamidopropyl)-dimethylammonio]-1-propane sulfonate; 3-[(3-Cholamidopropyl)-dimethylammonio]-2-hydroxy-1-propane sulfonate; Cyclohexylpentanoyl-N-hydroxyethylglucamide; Nonanoyl-N-hydroxyethyglucamide; Cyclohexylpropanol-N-hydroxyethylglucamide; Octanoyl-N-hydroxyethylglucamide; Cyclohexylethanoyl-N-hydroxyethylglucamide; Benzyldimethyldodecyl ammonium bromide; n-Hexadecyl-β-D-maltopyranoside; n-Tetradecyl-β-D-maltopyranoside; n-Tridecyl-β-D-maltopyranoside; Dodecylpoly(ethyleneglycoether)n; n-Tetradecyl-N,N-dimethyl-3-ammonio-1-propanesulfonate; n-Undecyl-β-D-maltopyranoside; n-Decyl-β-D-thiomaltopyranoside; n-dodecylphosphocholine; a-D-glucopyranoside, β-D-fructofuranosyl monodecanoate, sucrose mono-caprate; 1-s-Nonyl-β-D-thioglucopyranoside; n-Nonyl-β-D-thiomaltoyranoside; N-Dodecyl-N,N-(dimethlammonio)butyrate; n-Nonyl-β-D-maltopyranoside; Cyclohexyl-butyl-β-D-maltoside; n-Octyl-β-D-thiomaltopyranoside; n-Decylphosphocholine; n-Nonylphosphocholine; Nonanoyl-N-methylglucamide; 1-s-Heptyl-β-D-thioglucopyranoside; n-Octylphosphocholine; Cyclohexyl-ethyl-β-D-maltoside; n-Octyl-N,N-dimethyl-3-ammonio-1-propane-sulfonate; Cyclohexyl-methyl-β-D-maltoside.

Cryosolvents are agents that stabilize a target crystal to flash-cooling in a cryogen such as liquid nitrogen, liquid propane, liquid ethane, or gaseous nitrogen or helium (all at approximately 100-120° K.) such that crystal becomes embedded in a vitreous glass rather than ice. Any number of salts or small molecular weight organic compounds can be used as a cryoprotectant, and typical ones include but are not limited to: MPD, PEG-400 (as well as both PEG derivatives and higher molecular-weight PEG compounds), glycerol, sugars (xylitol, sorbitol, erythritol, sucrose, glucose, etc.), ethylene glycol, alcohols (both short- and long chain, both volatile and nonvolatile), LiOAc, LiCl, $LiCHO_2$, $LiNO_3$, $Li2SO_4$, $Mg(OAc)_2$, NaCl, $NaCHO_2$, $NaNO_3$, etc. Again, materials from which microfluidics devices in accordance with the present invention are fabricated may be compatible with a range of such compounds.

Many of these chemicals can be obtained in predefined screening kits from a variety of vendors, including but not limited to Hampton Research of Laguna Niguel, Calif., Emerald Biostructures of Bainbridge Island, Wash., and Jena BioScience of Jena, Germany, that allow the researcher to perform both 'sparse matrix' and 'grid' screening experiments. Sparse matrix screens attempt to randomly sample as much of precipitant, buffer, and additive chemical space as possible with as few conditions as possible. Grid screens typically consist of systematic variations of two or three parameters against one another (e.g., precipitant concentration vs. pH). Both types of screens have been employed with success in crystallization trials, and the majority of chemicals and chemical combinations used in these screens are compatible with the chip design and matrices in accordance with embodiments of the present invention.

Moreover, current and future designs of microfluidic devices may enable flexibly combinatorial screening of an array of different chemicals against a particular target or set of targets, a process that is difficult with either robotic or hand screening. This latter aspect is particularly important for optimizing initial successes generated by first-pass screens.

7. Additional Screening Variables for Crystallization

In addition to chemical variability, a host of other parameters can be varied during crystallization screening. Such parameters include but are not limited to: 1) volume of crystallization trial, 2) ratio of target solution to crystallization solution, 3) target concentration, 4) co-crystallization of the target with a secondary small or macromolecule, 5) hydration, 6) incubation time, 7) temperature, 8) pressure, 9) contact surfaces, 10) modifications to target molecules, and 11) gravity.

Volumes of crystallization trials can be of any conceivable value, from the picoliter to milliliter range. Typical values may include but are not limited to: 0.1, 0.2, 0.25, 0.4, 0.5, 0.75, 1, 2, 4, 5, 10, 15, 20, 25, 30, 35, 40, 45, 50, 60, 70, 75, 80, 90, 100, 125, 150, 175, 200, 225, 250, 275, 300, 350, 400, 450, 500, 550, 600, 700, 750, 800, 900, 1000,1100,1200, 1250,1300,1400,1500, 1600,1700,1800, 1900, 2000, 2250, 2500, 3000, 4000, 5000, 6000, 7000, 7500, 8000, 9000, and 10000 nL. The microfluidics devices previously described can access these values.

In particular, access to the low volume range for crystallization trials (<100 nL) is a distinct advantage of embodiments of the microfluidics chips in accordance with embodiments of the present invention, as such small-volume crystallization chambers can be readily designed and fabricated, minimizing the need the need for large quantities of precious target molecules. The low consumption of target material of embodiments in accordance with the present invention is particularly useful in attempting to crystallize scarce biological samples such as membrane proteins, protein/protein and protein/nucleic acid complexes, and small-molecule drug screening of lead libraries for binding to targets of interest.

The ratios of a target solution to crystallization mix can also constitute an important variable in crystallization screening and optimization. These rations can be of any conceivable value, but are typically in the range of 1:100 to 100:1 target: crystallization-solution. Typical target: crystallization-solution or crystallization-solution: target ratios may include but are not limited to: 1:100, 1:90, 1:80, 1:70, 1:60, 1:50, 1:40, 1:30, 1:25, 1:20, 1:15, 1:10, 1:9, 1:8, 1:7.5, 1:7, 1:6, 1:5, 1:4, 1:3, 1:2.5, 1:2, 1:1, 2:3, 3:4, 3:5, 4:5, 5:6, 5:7, 5:9, 6:7, 7:8, 8:9, and 9:10. As previously described, microfluidics devices in accordance with embodiments of the present invention can be designed to access multiple ratios simultaneously on a single chip.

Target concentration, like crystallization chemical concentration, can lie in a range of values and is an important variable in crystallization screening. Typical ranges of concentrations can be anywhere from <0.5 mg/ml to >100 mg/ml, with most commonly used values between 5-30 mg/ml. The microfluidics devices in accordance with embodiments of the present invention are readily compatible with this range of values.

Co-crystallization generally describes the crystallization of a target with a secondary factor that is a natural or non-natural binding partner. Such secondary factors can be small, on the order of about 10-1000 Da, or may be large macromolecules. Co-crystallization molecules can include but are not limited to small-molecule enzyme ligands (substrates, products, allosteric effectors, etc.), small-molecule drug leads, single-stranded or double-stranded DNAs or RNAs, complement proteins (such as a partner or target protein or subunit), monoclonal antibodies, and fusion-proteins (e.g., maltose binding proteins, glutathione S-transferase, protein-G, or other tags that can aid expression, solubility, and target behavior). As many of these compounds are either biological or of a reasonable molecular weight, co-crystallization molecules can be routinely included with screens in the microfluidics chips. Indeed, because many of these reagents are expensive and/or of limited quantity, the small-volumes afforded by the microfluidics chips in accordance with embodiment of the present invention make them ideally suited for co-crystallization screening.

Hydration of targets can be an important consideration. In particular, water is by far the dominant solvent for biological targets and samples. The microfluidics devices described in this document are relatively hydrophobic, and are compatible with water-based solutions.

The length of time for crystallization experiments can range from minutes or hours to weeks or months. Most experiments on biological systems typically show results within 24 hours to 2 weeks. This regime of incubation time can be accommodated by the microfluidics devices in accordance with embodiments of the present invention.

The temperature of a crystallization experiment can have a great impact on success or failure rates. This is particularly true for biological samples, where temperatures of crystallization experiments can range from 0-42° C. Some of the most common crystallization temperatures are: 0, 1, 2, 4, 5, 8, 10, 12, 15, 18, 20, 22, 25, 30, 35, 37, and 42. Microfluidics devices in accordance with embodiments of the present invention can be stored at the temperatures listed, or alternatively may be placed into thermal contact with small temperature control structures such as resistive heaters or Peltier cooling structures.

In addition, the small footprint and rapid setup time of embodiments in accordance with the present invention allow faster equilibration to desired target temperatures and storage in smaller incubators at a range of temperatures. Moreover, as the microfluidics systems in accordance with embodiments of the present invention do not place the crystallization experiment in contact with the vapor phase, condensation of water from the vapor phase into the drop as temperatures change, a problem associated with conventional macroscopic vapor-diffusion techniques, is avoided. This feature represents an advance over many conventional manual or robotic systems, where either the system must be maintained at the desired temperature, or the experiment must remain at room temperature for a period before being transferred to a new temperature.

Variation in pressure is an as yet understudied crystallization parameter, in part because conventional vapor-diffusion and microbatch protocols do not readily allow for screening at anything typically other than atmospheric pressure. The rigidity of the PDMS matrix enables experiments to probe the effects of pressure on target crystallization on-chip.

The surface on which the crystallization 'drop' sits can affect experimental success and crystal quality. Examples of solid support contact surfaces used in vapor diffusion and microbatch protocols include either polystyrene or silanized glass. Both types of supports can show different propensities to promote or inhibit crystal growth, depending on the target. In addition, the crystallization 'drop' is in contact with either air or some type of poly-carbon oil, depending on whether the experiment is a vapor-diffusion or microbatch setup, respectively. Air contact has the disadvantage in that free oxygen reacts readily with biological targets, which can lead to protein denaturation and inhibit or degrade crystallization success. Oil allows trace hydrocarbons to leach into the crystallization experiment, and can similarly inhibit or degrade crystallization success.

Microfluidics device designs in accordance with embodiments of the present invention may overcome these limitations by providing a nonreactive, biocompatible environment that completely surrounds the crystallization reaction. Moreover, the composition of the crystallization chambers in the microfluidics chips can conceivably be varied to provide new surfaces for contacting the crystallization reaction; this would allow for routine screening of different surfaces and surface properties to promote crystallization.

Crystallization targets, particularly those of biological origin, may often be modified to enable crystallization. Such modifications include but are not limited to truncations, limited proteolytic digests, site-directed mutants, inhibited or activated states, chemical modification or derivatization, etc. Target modifications can be time consuming and costly; modified targets require the same thorough screening as do unmodified targets. Microfluidics devices of the present invention work with such modified targets as readily as with the original target, and provide the same benefits.

The effect of gravity as a parameter for crystallization is yet another understudied crystallization parameter, because of the difficulty of varying such a physical property. Nonetheless, crystallization experiments of biological samples in zero gravity environments have resulted in the growth of crystals of superior quality than those obtained on Earth under the influence of gravity.

The absence of gravity presents problems for traditional vapor-diffusion and microbatch setups, because all fluids must be held in place by surface tension. The need to often set up such experiments by hand also poses difficulties because of the expense of maintaining personnel in space. Microfluidics devices in accordance with embodiments of the present invention, however, would enable further exploration of microgravity as a crystallization condition. A compact, automated metering and crystal growth system would allow for: 1) launching of satellite factory containing target molecules in a cooled, but liquid state, 2) distribution of targets and growth of crystals, 3) harvesting and cryofreezing of resultant crystals, and 4) return of cryo-stored crystals to land-based stations for analysis.

8. In Situ Crystallization Screening

The ability to observe the growth of crystals with a microscope is a step in deciding upon success or failure of crystallization trials. Conventional crystallization protocols may use transparent materials such as polystyrene or silanized glass to allow for visualization. The transparency of the PDMS matrix of embodiments in accordance with the present invention is particularly suited to the two primary methods by which crystallization trials are traditionally scored: 1) direct observation in the visible light regime by optical microscopes and 2) birefringence of polarized light.

Birefringence may be difficult to judge in conventional experiments as many plastics are themselves birefringent, interfering with sample assessment. However, the microfluidics devices described herein can be made without such optical interference properties, allowing for the design of an automated scanning system that routinely allows direct visualization with both polarizing and non-polarizing features.

In addition, robotic and, in particular, manually-set crystallization experiments can vary the placement of a crystallization drop on a surface by tens to hundreds of microns. This variability presents a problem for automated scanning systems, as it is difficult to program in the need for such flexible positioning without stable fiducials. However, the fixed placement of crystallization chambers in the microfluidics chips of embodiments of the present invention overcomes such problems, as every well can be positioned in a particular location with submicron accuracy. Moreover, such a system is readily scalable for the design of differently sized and positioned crystallization chambers, as masks and other templates used to design microfluidics devices in accordance with embodiments of the present invention can be simply digitized and ported into scanning software for visualization.

Once crystals are obtained by visual inspection, it may be possible to screen for diffraction directly through the chip itself. For example, a crystallization chamber within a chip could be outfitted with transparent 'windows' comprising glass, quartz, or thinned portions of the elastomer material itself, on opposite walls of the chamber. Crystals could then be exposed directly to x-rays through the chip to assay for diffraction capabilities, eliminating the need to remove, and thereby possibly damage, the crystalline sample. Such an approach could be used to screen successes from initial crystallization trials to determine the best starting candidate conditions for follow-up study. Similarly, crystals grown under a particular set of conditions could be 're-equilibrated' with new solutions (e.g., cryo-stabilizing agents, small-molecule drug leads or ligands, etc.), and the stability of the crystals to such environment changes monitored directly by x-ray diffraction.

9. Utilizing Microfluidic Devices for Purification/Crystallization

Crystallization of target biological samples such as proteins is actually the culmination of a large number of prior complex and difficult steps, including but not limited to protein expression, purification, derivatization, and labeling. Such steps prior to crystallization comprise shuttling liquids from a chamber with one set of solution properties to another area with a different set of properties. Mircofluidics technology is suited to perform such tasks, allowing for the combination of all necessary steps within the confines of a single chip.

Examples of microfluidic handling structures enabling performance of pre-crystallization steps have been described under section I above. For example, a microfluidics chip could act as a regulated bioreactor, allowing nutrients to flow into growing cells contained in cell pen structure while removing wastes and inducing recombinantly-modified organisms to produce target molecules (e.g., proteins) at a desired stage of cell growth. Following induction, these cells could be shunted from the cell pen to a different region of the chip for lysis by enzymatic or mechanical means. Solubilized target molecules could then be separated from cellular debris by molecular filtration units incorporated directly onto a chip.

The crude mixture of target molecules and contaminating cellular proteins and nucleic acids could then be funneled through porous matrices of differing chemical properties (e.g., cation-exchange, anion-exchange, affinity, size-exclusion) to achieve separation. If a target molecule were tagged with a fusion protein of a particular type to promote solubility, it could be affinity purified, briefly treated with a similarly-tagged, site-specific protease to separate the fusion product, and then repassaged though the affinity matrix as a clean-up step.

Once pure, the target could be mixed with different stabilizing agents, assayed for activity, and then transported to crystallization staging areas. Localized heating (such as an electrode) and refrigeration (such as a Peltier cooler) units stationed at various points on a chip or a chip holder would allow for differential temperature regulation at all stages throughout the processing and crystallization. Thus, the production, purification, and crystallization of proteins may be accomplished on an embodiment of a single microfluidics device in accordance with the present invention.

IV. Micro-Free Interface Diffusion

A conventional approach to crystallization has been to effect a gradual change in target solution conditions by introducing a crystallizing agent through slow diffusion. One method that is particularly effective at sampling a wide range of conditions is macroscopic free-interface diffusion. This technique requires the creation of a well-defined fluidic interface between two or more solutions, typically the protein stock, and the precipitating agent, and the subsequent equilibration of the two solutions via a diffusive process. As the solutions diffuse into one another, a gradient is established along the diffusion path, and a continuum of conditions is simultaneously sampled. Since there is a variation in the conditions, both in space, and in time, information regarding the location and time of crystal formation may be used in further optimization. FIGS. 29A-29D are simplified schematic diagrams plotting concentration versus distance for a solution A and a solution B in contact along a free interface. FIGS. 29A-D show that over time, a continuous and broad range of concentration profiles of the two solutions is ultimately created.

Figure 30A:
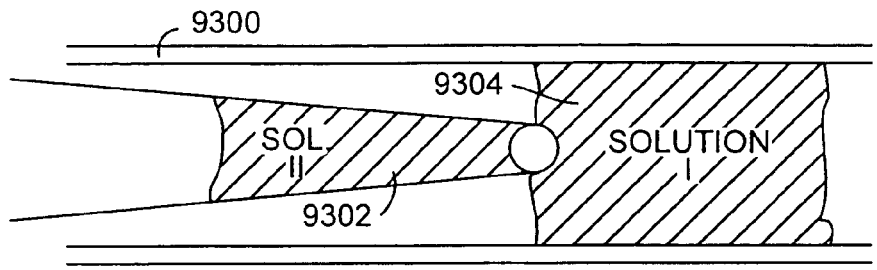
FIGS. 30A-B show simplified cross-sectional views of the attempted formation of a macroscopic free-interface in a capillary tube.
Figure 30B:
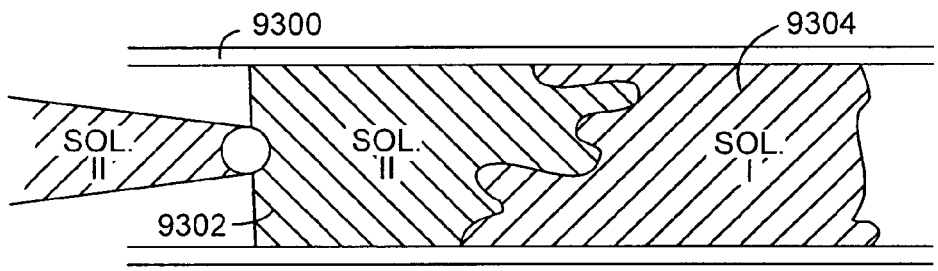

Despite the efficiency of macroscopic free-interface diffusion techniques, technical difficulties have rendered it unsuitable for high throughput screening applications, and it is not widely used in the crystallographic community for several reasons. First, the fluidic interfaces are typically established by dispensing the solutions into a narrow container; such as a capillary tube or a deep well in a culture plate. FIGS. 30A-B show simplified cross-sectional views of the attempted formation of a macroscopic free-interface in a capillary tube 9300. The act of dispensing a second solution 9302 into a first solution 9304 creates convective mixing and results in a poorly defined fluidic interface 9306.

Figure 31A:
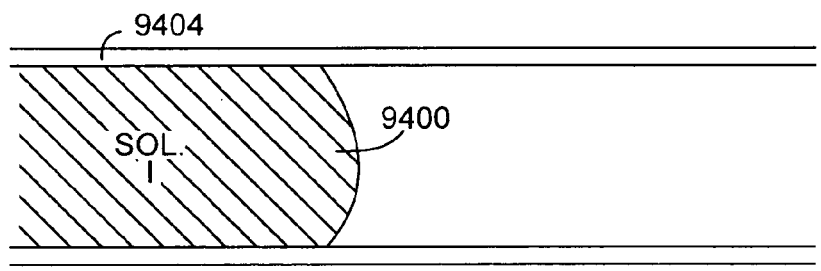
FIGS. 31A-B show simplified cross-sectional views of convective mixing between a first solution and a second solution in a capillary tube resulting from a parabolic velocity distribution of pressure driven Poiseuille flow
Figure 31B:
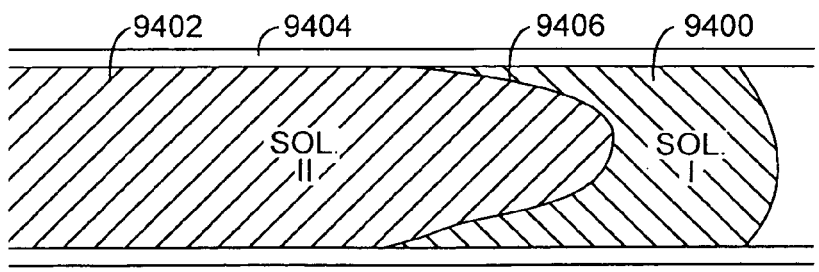

Moreover, the solutions may not be sucked into a capillary serially to eliminate this problem. FIGS. 31A-B show the mixing, between a first solution 9400 and a second solution 9402 in a capillary tube 9404 that would result due to the parabolic velocity distribution of pressure driven Poiseuille flow, resulting in a poorly defined fluidic interface 9406. Furthermore, the container for a macro free-interface crystallization regime must have dimensions making them accessible to a pipette tip or dispensing tool, and necessitating the use of large (10-100 µl) volumes of protein and precipitant solutions.

Figure 32A:
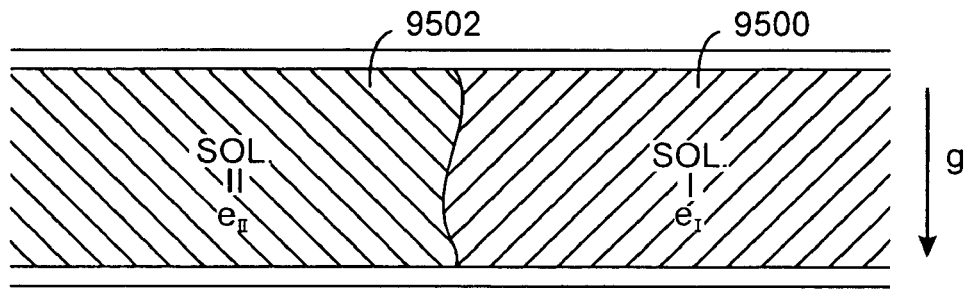
FIGS. 32A-C show simplified cross-sectional views of interaction in a capillary tube between a first solution having a density greater than the density of second solution.
Figure 32B:
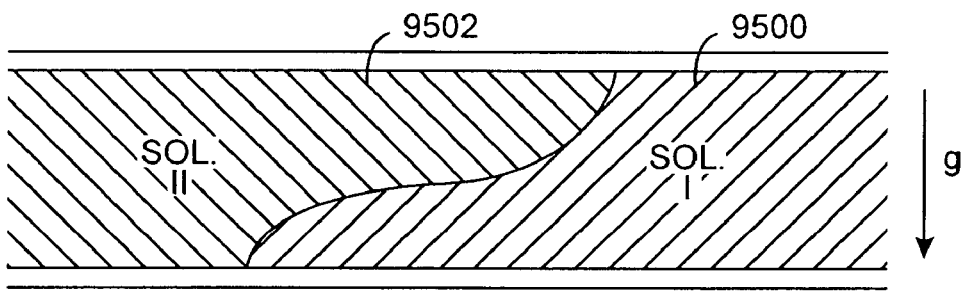
Figure 32C:
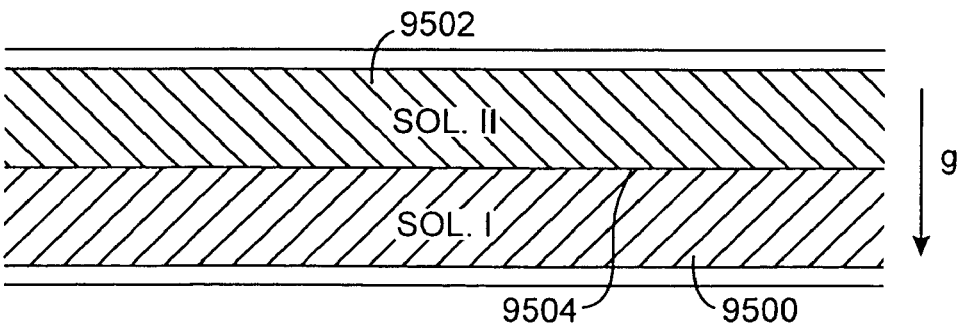

In order to avoid unwanted convective mixing, care must be taken both during dispensing and during crystal incubation. For this reason cumbersome protocols are often used to define a macro free-interface. For example, freezing one solution prior to the addition of the second. Moreover, two solutions of differing density will mix by gravity induced convection if they are not stored at the proper orientation, additionally complicating the storage of reactions. This is shown in FIGS. 32A-C, wherein over time first solution 9500 having a density greater than the density of second solution 9502 merely sinks to form a static bottom layer 9504 that is not conducive to formation of a diffusion gradient along the length of a capillary tube.

In accordance with embodiments of the present invention, a crystallization technique analogous to traditional macro-free interface diffusion, called gated micro free interface diffusion (Gated µ-FID), has been developed. Gated µ-FID retains the efficient sampling of phase space achieved by macroscopic free interface diffusion techniques.

A microfluidic free interface (µFI) in accordance with embodiments of the present invention is a localized interface between at least one static fluid and another fluid wherein mixing between them is dominated by diffusion rather than by convective flow. For the purposes of this application, the term "fluid" refers to a material having a viscosity below a particular maximum. Examples of such maximum viscosities include but are not limited to 1000 CPoise, 900 CPoise, 800 CPoise, 700 CPoise, 600 CPoise, 500 CPoise, 400 CPoise, 300 CPoise, 250 CPoise, and 100 CPoise, and therefore exclude gels or polymers containing materials trapped therein.

In a microfluidic free interface in accordance with an embodiment of the present invention, at least one dimension of the interface is restricted in magnitude such that viscous forces dominate other forces. For example, in a microfluidic free interface in accordance with an embodiment of the present invention, the dominant forces acting upon the fluids are viscous rather than buoyant, and hence the microfluidic free interface may be characterized by an extremely low Grashof number (see discussion below). The microfluidic free interface may also be characterized by its localized nature relative to the total volumes of the fluids, such that the volumes of fluid exposed to the steep transient concentration gradients present initially after formation of the interface between the pure fluids is limited.

Figure 33A:
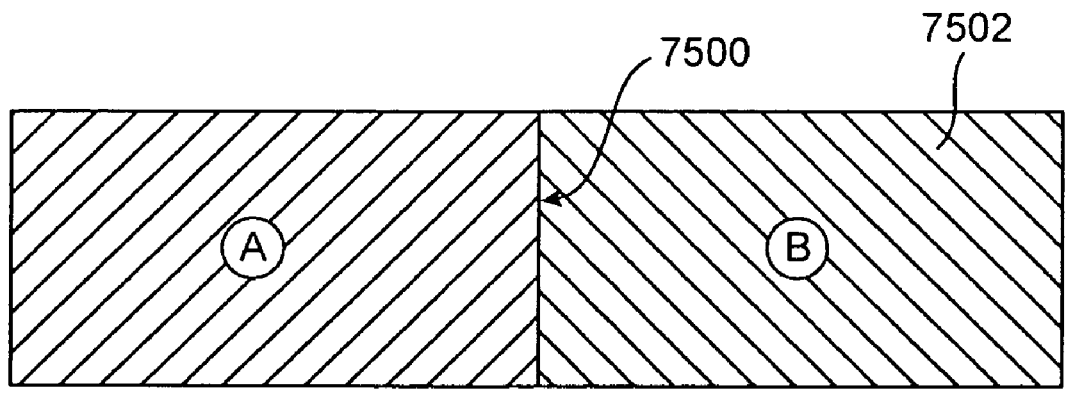
FIG. 33A shows a simplified cross-sectional view of a microfluidic free interface in accordance with an embodiment of the present invention.
Figure 33B:
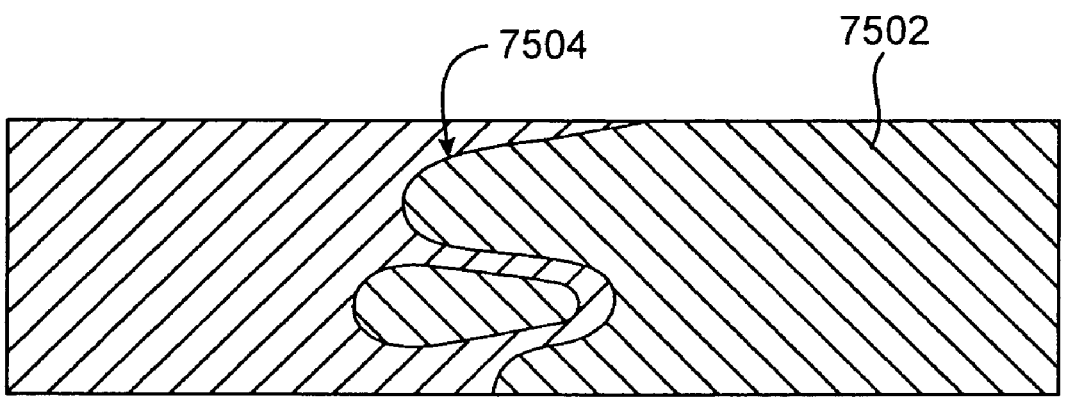
FIG. 33B shows a simplified cross-sectional view of a conventional non-microfluidic interface.

The properties of a microfluidic free interface created in accordance with embodiments of the present invention may be contrasted with a non-free microfluidic interface, as illustrated in FIGS. 33A and 33B. Specifically, FIG. 33A shows a simplified cross-sectional view of a microfluidic free interface in accordance with an embodiment of the present invention. Microfluidic free interface 7500 of FIG. 33A is formed between first fluid A and second fluid B present within channel 7502. The free microfluidic interface 7500 is substantially linear, with the result that the steep concentration gradient arising between fluids A and B is highly localized within the channel.

As described above, the dimensions of channel 7502 are extremely small, with the result that non-slip layers immediately adjacent to the walls of the channel in fact occupy most of the volume of the channel. As a result, viscosity forces are much greater than buoyant forces, and mixing between fluids A and B along interface 7500 occurs almost entirely as a result of diffusion, with little or no convective mixing.

Conditions associated with the microfluidic free interface of embodiments of the present invention can be expressed in terms of the Grashof number (Gr) per Equation (3) below, an expression of the relative magnitude of buoyant and viscous forces:

$$Gr = B/V = \frac{\alpha \Delta c g L^3}{\nu^2}, \text{ where:} \qquad (3)$$

Gr=Grashof number;
B=buoyancy force;
V=viscous force;
a=solutal expansivity;
c=concentration;
g=acceleration of gravity;
L=chamber critical dimension; and
ρ=kinematic viscosity.

According to Equation (3), a number of approaches may be taken to reduce the Grashof number and hence the presence of unwanted corrective flow. One such approach is to reduce g, and this is the tactic adopted by microgravity crystallization experiments conducted in space. Another approach is to increase ν, and this is the tactic adopted by investigators working with gel acupuncture techniques, as described generally by Garcia-Ruiz et al., "Agarose as Crystallization Media for Proteins I: Transport Processes", *J. Crystal Growth* 232, 165-172 (2001), hereby incorporated by reference for all purposes.

Embodiments in accordance with the present invention seek to reduce L and through the use of microfluid flow channels and vessels having extremely small dimensions. The effect of this approach is amplified by the cubed power of the variable (L) in Equation (3).

Microfluidic free interfaces in accordance with embodiments of the present invention would be expected to exhibit a Grashof number of 1 or less. The Grashof number expected with two fluids having the same density is zero, and thus Grashof, numbers very close to zero would be expected to be attained.

The embodiment of a microfluidic free interface illustrated above in FIG. 33A may be contrasted with the conventional non-microfluidic free interface shown in FIG. 33B. Specifically, first and second fluids A and B are separated by an interface 7504 that is not uniform or limited by the cross-sectional width of channel 7502. The steep concentration gradient occurring at the interface is not localized, but is instead present at various points along the length of the channel, exposing correspondingly large volumes of the fluids to the steep gradients. In addition, viscosity forces do not necessarily dominate over buoyancy forces, with the result that mixing of fluids A and B across interface 7504 can occur both as the result of diffusion and of convective flow. The Grashof number exhibited by a conventional non-microfluidic interface would be expected to exceed one.

1. Creation of Microfluidic Free Interface

A microfluidic free interface in accordance with embodiments of the present invention may be created in a variety of ways. One approach is to utilize the microfabricated elastomer structures previously described. Specifically, in certain embodiments the elastomeric material from which microfluidic structures are formed is relatively permeable to certain gases. This gas permeability property may be exploited utilizing the technique of pressurized out-gas priming (POP) to form well-defined, reproducible fluidic interfaces.

Figure 34A:
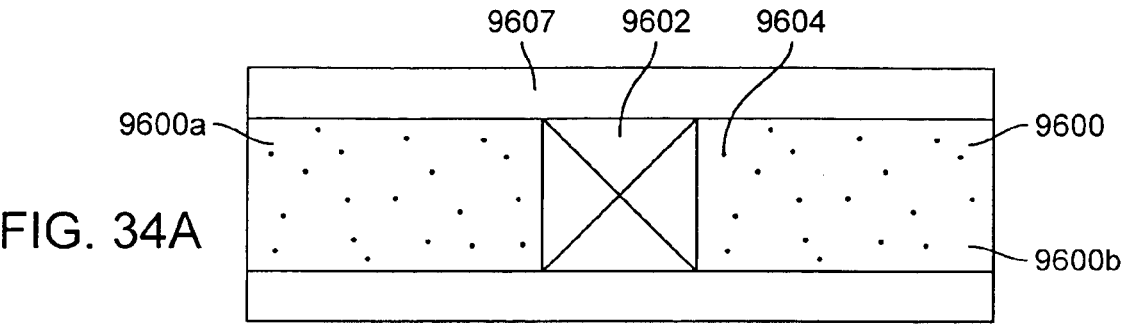
FIGS. 34A-D show plan views of the priming of a flow channel and formation of a microfluidic free interface in accordance with an embodiment of the present invention.

FIG. 34A shows a plan view of a flow channel 9600 of a microfluidic device in accordance with an embodiment of the present invention. Flow channel 9600 is separated into two halves by actuated valve 9602. Prior to the introduction of material, flow channel 9600 contains a gas 9604.

Figure 34B:
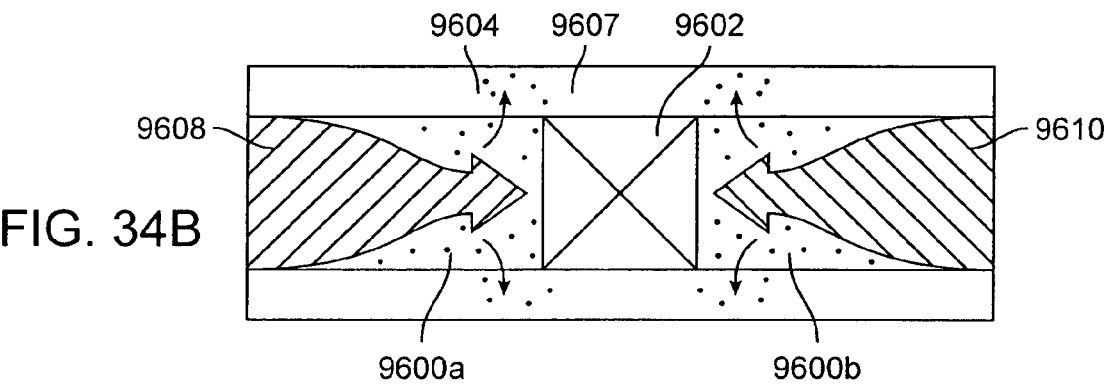

FIG. 34B shows the introduction of a first solution 9606 to first flow channel portion 9600a under pressure, and the introduction of a second solution 9608 to second flow channel portion 9600b under pressure. Because of the gas permeability of the surrounding elastomer material 9607, gas 9604 is displaced by the incoming solutions 9608 and 9610 and outgasses through elastomer 9607.

Figure 34C:
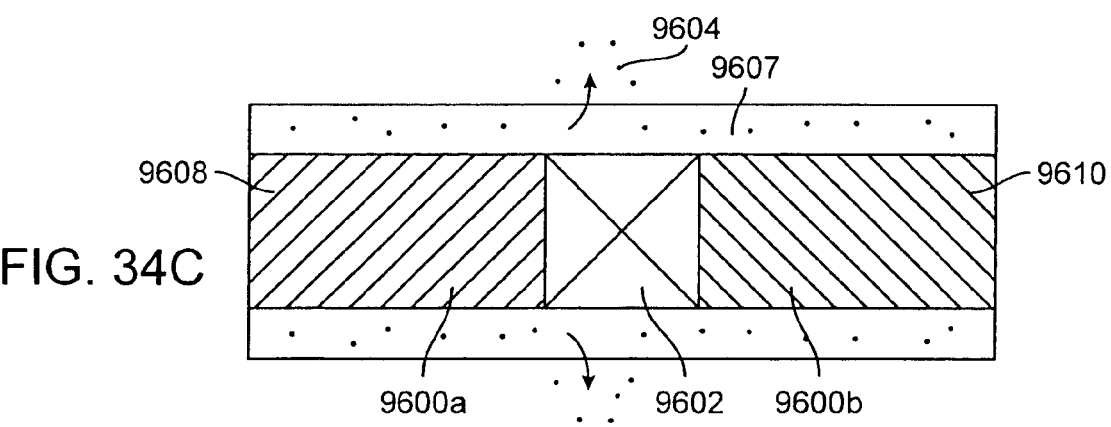
Figure 34D:
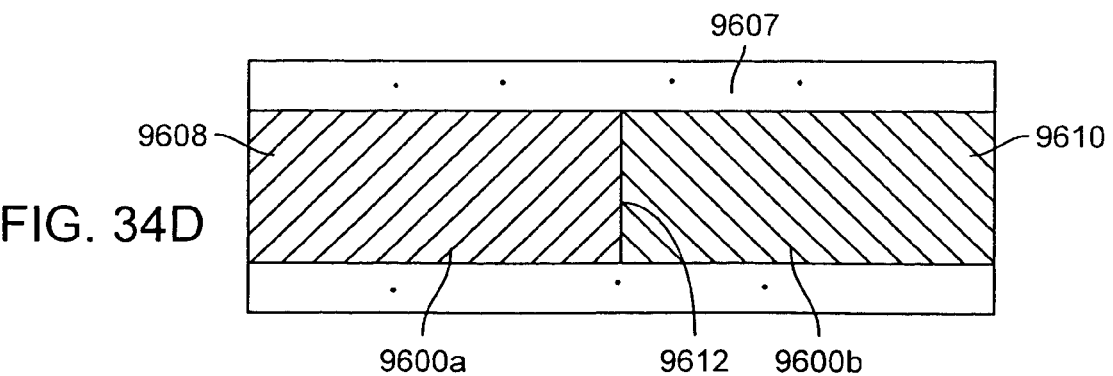

As shown in FIG. 34C, the pressurized out-gas priming of flow channel portions 9600a and 9600b allows uniform filling of these dead-ended flow channel portions without air bubbles. Upon deactuation of valve 9602 as shown in FIG. 34D, microfluidic free interface 9612 is defined, allowing for formation of a diffusion gradient between the fluids.

The formation of protein crystals utilizing gated μ-FID retains the efficient sampling of phase space achieved by macroscopic free interface diffusion techniques, with a number of added advantages, including the parsimonious use of sample solutions, ease of set-up, creation of well defined fluidic interfaces, control over equilibration dynamics, and the ability to conduct high-throughput parallel experimentation.

Figure 36A:
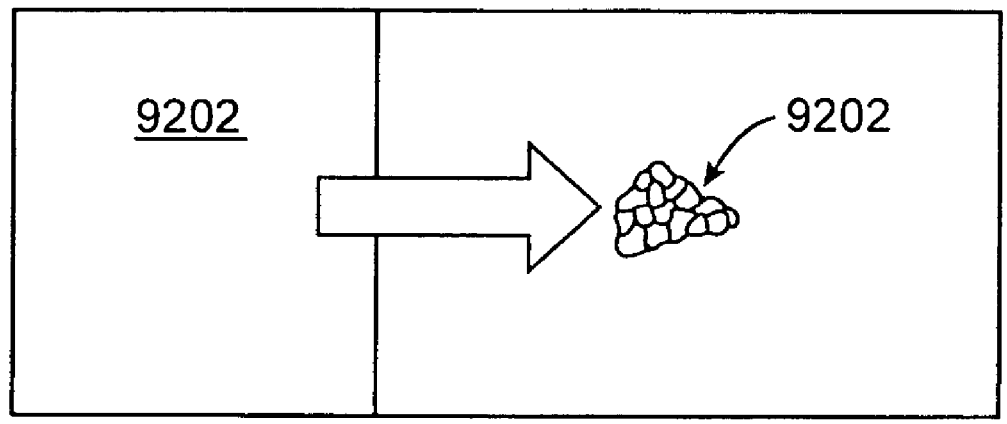
FIG. 36A shows a simplified schematic view of a protein crystal being formed utilizing a conventional macroscopic free interface diffusion technique.

Another possible advantage of the formation of protein crystals utilizing gated μ-FID is the formation of high quality crystals, as illustrated in connection with FIGS. 36A and 36B. FIG. 36A shows a simplified schematic view of a protein crystal being formed utilizing a conventional macroscopic free interface diffusion technique. Specifically, nascent protein crystal 9200 is exposed to sample from solution 9202 that is experiencing a net conductive flow of sample as a result of the action of buoyant forces. As a result of the directionality of this conductive flow, the growth of protein crystal 9200 is also directional. However, as described in Nerad et al., "Ground-Based Experiments on the Minimization of Convection During the Growth of Crystals from Solution", Journal of Crystal Growth 75, 591-608 (1986), assymetrical growth of a protein crystal can give rise to unwanted strain in the lattice of the growing crystal, promoting dislocations and/or the incorporation of impurities within the lattice, and otherwise adversely affecting the crystal quality.

Figure 36B:
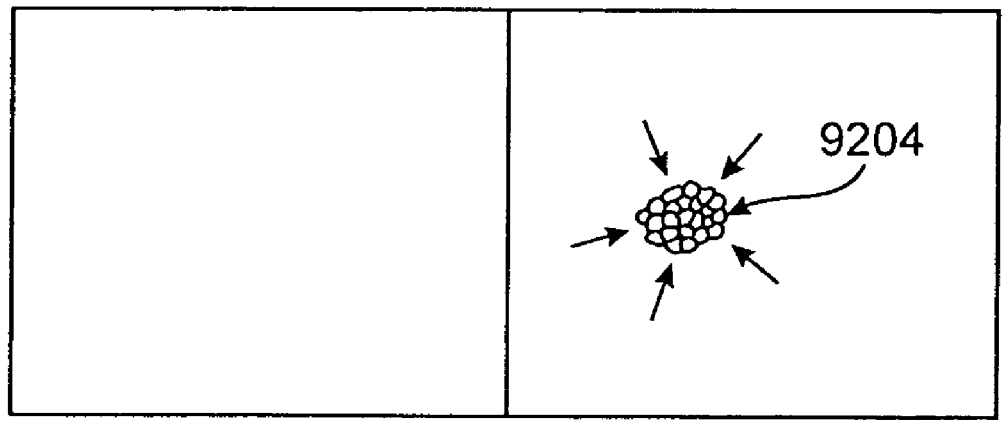
FIG. 36B shows a simplified schematic view of a protein crystal being formed utilizing diffusion across a microfluidic free interface in accordance with an embodiment of the present invention.

By contrast, FIG. 36B shows a simplified schematic view of a protein crystal being formed utilizing diffusion across a microfluidic free interface in accordance with an embodiment of the present invention. Nascent protein crystal 9204 is exposed to sample solution 9206 that is diffusing within the crystallizing agent. This diffusion is nondirectional, and the growth of protein crystal 9204 is also correspondingly nondirectional. Accordingly, the growing crystal avoids strain on the lattice and the attendant incorporation of impurities and dislocations experienced by the growing crystal shown in FIG. 36A. Accordingly, the quality of the crystal in FIG. 36B is of high quality.

While the specific embodiment just described exploits the permeability of the bulk material to dead end fill two or more chambers or channels separated by a closed valve, and creates a microfluidic free interface between the static fluids by the subsequent opening of this valve, other mechanisms for realizing a microfluidic free interface are possible.

Figure 46:
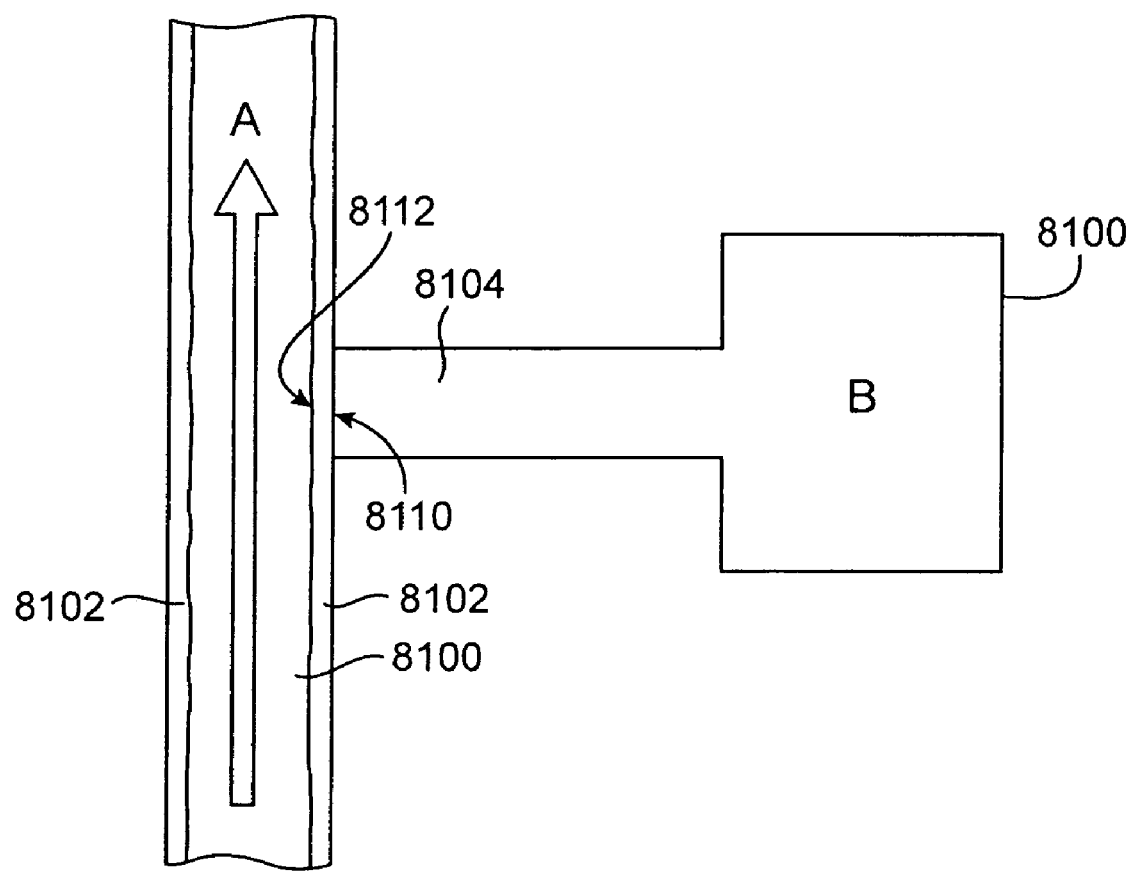
FIG. 46 shows a plan view of the creation of a microfluidic free interface between a flowing fluid and a dead-ended branch channel.

For example, FIG. 46 shows one potential alternative method for establishing a microfluidic free interface diffusion in accordance with the present invention. Microfluidic channel 8100 carries fluid A experiencing a convective flow in the direction indicated by the arrow, such that static non-slip layers 8102 are created along the walls of flow channel 8100. Branch channel 8104 and dead-ended chamber 8106 contain static fluid B. Because material surrounding the dead-ended channel and chamber provide a back pressure, fluid B remains static and microfluidic free interface 8110 is created at mouth 8112 of branch channel 8108 between flowing fluid A and static fluid B. As described below, diffusion of fluid A or components thereof across the microfluidic free interface can be exploited to obtain useful results. While the embodiment shown in FIG. 46 includes a dead-ended branch channel and chamber, this is not required by the present invention, and the branch channel could connect with another portion of the device, as long as a sufficient counter pressure was maintained to prevent any net flow of fluid through the channel.

Another potential alternative method for establishing a microfluidic free interface diffusion assay is the use of break-through valves and chambers. A break-through valve is not a true closing valve, but rather a structure that uses the surface tension of the working fluid to stop the advance of the fluid. Since these valves depend on the surface tension of the fluid they can only work while a free surface exists at the valve; not when the fluid continuously fills both sides and the interior of the valve structure.

A non-exclusive list of ways to achieve such a valve include but are not limited to patches of hydrophobic material, hydrophobic treatment of certain areas, geometric constrictions (both in height and width) of a channel, geometric expansions (both in height and in width of a channel), changes in surface roughness on walls of a channel, and applied electric potentials on the walls.

These "break-through" valves may be designed to withstand a fixed and well defined pressure before they "break through" and allow fluid to pass nearly unimpeded. The pressure in the channel can be controlled and hence the fluid can be caused to advance when desired. Different methods of controlling this pressure include but are not limited to externally applied pressure at an input or output port, pressure derived from centrifugal force (i.e. by spinning the device), pressure derived from linear acceleration (i.e. applying an acceleration to the device with a component parallel to the channel), elecrokinetic pressure, internally generated pressure from bubble formation (by chemical reaction or by hydrolysis), pressure derived from mechanical pumping, or osmotic pressure.

Figure 35A:
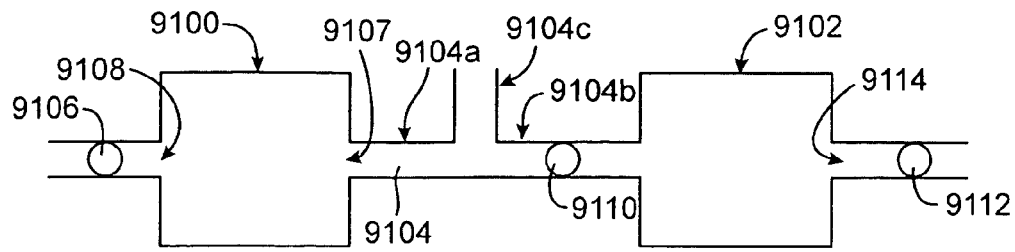
FIGS. 35A-E show simplified schematic views of the use of "break-through" valves to create a microfluidic free interface.

"Break-through" valves may be used to create a microfluidic free interface as shown and described in connection with FIGS. 35A-E. FIG. 35A shows a simplified plan view of a device for creating a microfluidic free interface utilizing break through valves. First chamber 9100 is in fluid communication with second chamber 9102 through branches 9104a and 9104b respectively, of T-shaped channel 9104.

First break through valve 9106 is located at outlet 9108 of first chamber 9100. Second break through valve 9110 is located in branch 9104b upstream of inlet 9105 of second chamber 9102. Third break through valve 9112 is located at outlet 9114 of second chamber 9102. Breakthrough valves 9106, 9110, and 9112 may be formed from hydrophobic patches, a constriction in the width of the flow channel, or some other way as described generally above. In FIGS. 35A-E, an open break through valve is depicted as an unshaded circle, and a closed break through valve is depicted as a shaded circle.

Figure 35B:
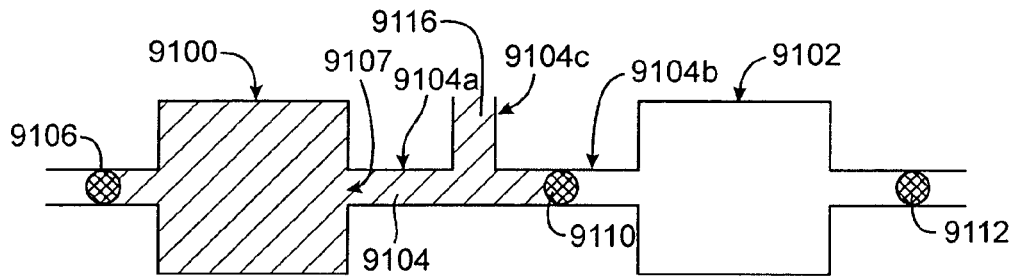
Figure 35C:
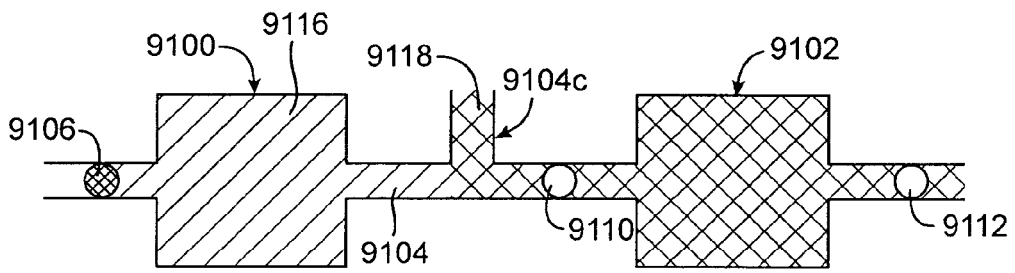

In the initial stage shown in FIG. 35B, first chamber 9100 is charged with first fluid 9116 introduced through stem 9104c and branch 9104a of T-shaped channel 9104 and chamber inlet 9107 at a pressure below the break through pressure of any of the valves 9106, 9110, and 9112. In the second stage shown in FIG. 35C, second chamber 9102 is charged with a buffer or other intermediate fluid 9118 introduced through stem 9104c of T-shaped channel 9104 and inlet 9105 at a pressure below the break through pressure of valve 9106 but greater than the break through pressures of valves 9110 and 9112.

Figure 35D:
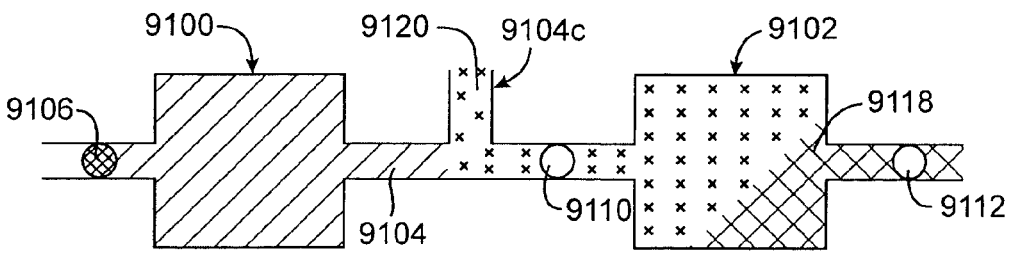
Figure 35E:
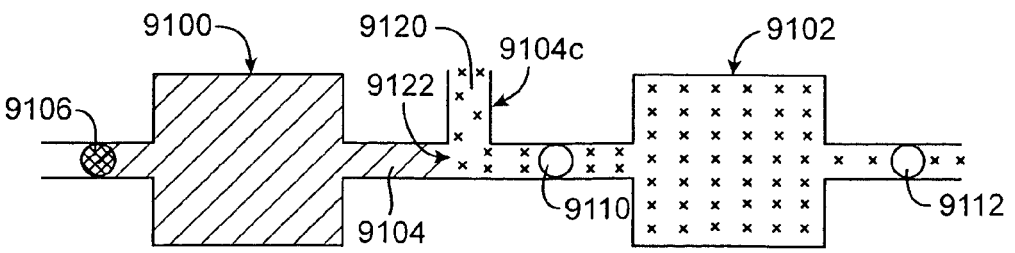

In the third stage shown in FIG. 35D, intermediate fluid 9118 is replaced in second chamber 9102 with second fluid 9120 introduced through stem 9104c of T-shaped channel 9104 and inlet 9105 at a pressure below the break through pressure of valve 9106 but greater than the break through pressures of valves 9110 and 9112. In the final stage depicted in FIG. 35E, second fluid 9120 has replaced the intermediate fluid, leaving the first and second fluids 9116 and 9120 in separate chambers but fluidically connected through T-junction 9104, creating a microfluidic free interface 9122.

The use of break through valves to create a microfluidic free interface in accordance with embodiments of the present invention is not limited to the specific example given above. For example, in alternative embodiments the step of flushing with a buffer or intermediate solution is not required, and the first solution could be removed by flushing directly with the second solution, with potential unwanted by-products of mixing removed by the initial flow of the second solution through the channels and chambers.

While the embodiments just described create the microfluidic free interface in a closed microfluidic device, this is not required by embodiments in accordance with the present invention. For example, an alternative embodiment in accordance with the present invention may utilize capillary forces to connect two reservoirs of fluid. In one approach, the open wells of a micro-titer plate could be connected by a segment of a glass capillary. The first solution would be dispensed into one well such that it fills the well and is in contact with the glass capillary. Capillary forces cause the first solution to enter and flow to the end of the capillary. Once at the end, the fluid motion ceases. Next, the second solution is added to the second well. This solution is in contact with the first solution at the capillary inlet and creates a microfluidic interface between the two wells at the end of the capillary.

The connecting path between the two wells need not be a glass capillary, and in alternative embodiments could instead comprise a strip of hydrophilic material, for example a strip of glass or a line of silica deposited by conventional CVD or PVD techniques. Alternatively, the connecting paths could be established by paths of less hydrophobic material between patterned regions of highly hydrophobic material. Moreover, there could be a plurality of such connections between the wells, or a plurality of interconnected chambers in various configurations. Such interconnections could be established by the user prior to use of the device, allowing for rapid and efficient variation in fluidic conditions.

Where as in the previous example the two reservoirs are not enclosed by a microfluidic device but are connected instead through a microfluidic path, an alternative embodiment could have reservoirs both enclosed and not enclosed. For example, sample could be loaded into a microfluidic device and pushed to the end of an exit capillary or orifice (by any of the pressure methods described above). Once at the end of the exit capillary, the capillary could be immersed in a reservoir of reagent. In this way, the microfluidic free interface is created between the external reservoir and the reservoir of reagent in the chip. This method could be used in parallel with many different output capillaries or orifices to screen a single sample against a plurality of different reagents using microfluidic free interface diffusion.

In the example just described, the reagent is delivered from one or many inlets to one or many different outlets "through" a microfluidic device. Alternatively, this reagent can be introduced through the same orifice that is to be used to create the microfluidic interface. The sample-containing solution could be aspirated into a capillary (either by applying suction, or by capillary forces, or by applying pressure to the solution) and then the capillary may be immersed in a reservoir of counter-reagent, creating a microfluidic interface between the end of the capillary and the reservoir. This could be done in a large array of capillaries for the parallel screening of many different reagents. Very small volumes of sample could be used since the capillaries can have a fixed length beyond which the sample will not advance. For crystallization applications (see below), the capillaries could be removed and mounted in an x-ray beam for diffraction studies, without requiring handling of the crystals.

2. Reproducible Control Over Equilibration Parameters

One advantage of the use of microfluidic free interface diffusion in accordance with embodiments of the present invention is the ability to create uniform and continuous concentration gradients that reproducibly sample a wide range of conditions. As the fluids on either side of the interface diffuse into one another, a gradient is established along the diffusion path, and a continuum of conditions is simultaneously sampled. Since there is a variation in the conditions, both in space and time, information regarding the location and time of positive results (i.e. crystal formation) may be used in further optimization.

In many applications it is desirable to create a gradient of a condition such as pH, concentration, or temperature. Such gradients may be used for screening applications, optimization of reaction conditions, kinetics studies, determination of binding affinities, dissociation constants, enzyme-rate profiling, separation of macromolecules, and many other applications. Due principally to the suppression of convective flow, diffusion across a microfluidic free interface in accordance with an embodiment of the present invention may be used to establish reliable and well-defined gradient.

The dimensional Einstein equation (4) may be employed to obtain a rough estimate of diffusion times across a microfluidic free interface.

$$t = \frac{x^2}{4D}; \text{ where:} \quad (4)$$

t=diffusion time;
x=longest diffusion length; and
D=diffusion coefficient

Generally, as shown in Equation (5) below, the diffusion coefficient varies inversely with the radius of gyration, and therefore as one over the cube root of molecular weight.

$$D \propto \frac{1}{r} \propto \frac{1}{m^{1/3}}; \text{ where:} \quad (5)$$

D=diffusion coefficient;
r=radius of gyration; and
m=molecular weight

In reviewing equation (5), it is important to recognize that correlation between the radius of gyration (r) and the molecular weight (m) is only an approximation. Because of the dominance of viscous forces over inertial forces, the diffusion coefficient is in fact independent of molecular weight and is instead dependent upon the size and hence drag experienced by the diffusing particle.

As compared with the rough 1.5 hr equilibration time for a dye, an approximate equilibration time for a protein of 20 KDa over the same distance is estimated to be approximately 45 hours. The equilibration time for a small salt of a molecular weight of 100 Da over the same distance is about 45 minutes.

The relative concentrations resulting from diffusion across a fluidic interface is determined not only by thermodynamic conditions explored during the equilibration, but also by the rate at which equilibration takes place. It is therefore potentially valuable to control the dynamics of equilibration.

In conventional macroscopic diffusion methods, only coarse control over the dynamics of equilibration may be available through manipulation of initial conditions. For macroscopic free interface diffusion, once diffusion begins, the experimenter has no control over the subsequent equilibration rate. For hanging drop experiments, the equilibration rate may be changed by modifying the size of the initial drop, the total size of the reservoir, or the temperature of incubation. In microbatch experiments, the rate at which the sample is concentrated may be varied by manipulating the size of the drop, and the identity and amount of the surrounding oil. Since the equilibration rates depend in a complicated manner on these parameters, the dynamics of equilibration may only be changed in a coarse manner. Moreover, once the experiment has begun, no further control over the equilibration dynamics is available.

By contrast, in a fluidic free interface experiment in accordance with an embodiment of the present invention, the parameters of diffusive equilibration rate may also be controlled by manipulating dimensions of chambers and connecting channels of a microfluidic structure. For example, in a microfluidic structure comprising reservoirs in fluid communication through a constricted channel, where no appreciable gradient exists in the reservoirs due to high concentrations or replenishment of material, to good approximation the time required for equilibration varies linearly with the required diffusion length. The equilibration rate also depends on the cross-sectional area of the connecting channels. The required time for equilibration may therefore be controlled by changing both the length, and the cross-sectional area of the connecting channels.

For example, FIG. 40A shows a plan view of a simple embodiment of a microfluidic structure in accordance with the present invention. Microfluidic structure 9701 comprises reservoirs 9700 and 9702 containing first fluid A and second fluid B, respectively. Reservoirs 9700 and 9702 are connected by channel 9704. Valve 9706 is positioned on the connecting channel between reservoirs 9700 and 9702.

Connecting channel 9704 has a much smaller cross-sectional area than either of the reservoirs. For example, in particular embodiments of microfluidic structures in accordance with the present invention, the ratio of reservoir/channel cross-sectional area and thus the ratio of maximum ratio of cross-sectional area separating the two fluids, may fall between 500 and 25,000. The minimum of this range describes a 50×50×50 µm chamber connected to a 50×10 µm channel, and the maximum of this range describes a 500× 500×500 µm chamber connected to a 10×1 µm channel.

Initially, reservoirs 9700 and 9702 are filled with respective fluids, and valve 9706 is closed. Upon opening valve 9706, a microfluidic free interface in accordance with an embodiment of the present invention is created, and fluids A and B diffuse across this interface through the channel into the respective reservoirs. Moreover, where the amount of diffusing material present in one reservoir is large and the capacity of the other reservoir to receive material without undergoing a significant concentration change is also large, the concentrations of material in the reservoirs will not change appreciably over time, and a steady state of diffusion will be established.

Diffusion of fluids in the simple microfluidic structure shown in FIG. 40 may be described by relatively simple equations. For example, the net flux of a chemical species from one chamber to the other may be simply described by equation (6):

$$J = D * A * \frac{\Delta C}{L}; \text{where:} \quad (6)$$

J=net flux of chemical species
D=diffusion constant of the chemical species;
A=cross-sectional area of the connecting channel;
ΔC=concentration difference between the two channels; and
L=length of the connection channel.

Following integration and extensive manipulation of the terms of equation (6), the characteristic time τ for the equilibration of the two chambers, where one volume $V_1$ is originally at concentration C and the other volume $V_2$ is originally at concentration 0, can therefore be taken to be as shown in Equation (7) below:

$$\tau = \frac{1}{V_1/V_2 + 1} * \frac{1}{D} * \frac{L}{A/V_1}; \text{where:} \quad (7)$$

τ=equilibration time;
$V_1$=volume of chamber initially containing the chemical species;
$V_2$=volume of chamber into which the chemical species is diffusing;
D=diffusion constant of the chemical species;
A=cross-sectional area of the connecting channel; and
L=length of the connection channel.

Therefore, for a given initial concentration of a chemical species in a chamber of a defined volume, the characteristic equilibration time depends in a linear manner from the diffusive length L and the ratio of the cross-sectional area to the volume (hereafter referred to simply as the "area"), with the understanding that the term "area" refers to the area normalized by the volume of the relevant chamber. Where two chambers are connected by a constricted channel, as in the structure of FIG. 40A, the concentration drop from one channel to the other occurs primarily along the connecting channel and there is no appreciable gradient present in the chamber. This is shown in FIG. 40B, which is a simplified plot of concentration versus distance for the structure of FIG. 40A.

The behavior of diffusion between the chambers of the microfluidic structure of FIG. 40A can be modeled, for example, utilizing the PDE toolbox of the MATLAB® software program sold by The MathWorks Inc. of Natick, Mass. FIGS. 41 and 42 accordingly show the results of simulating diffusion of sodium chloride from a 300 um×300 um×100 um chamber to another chamber of equal dimensions, through a 300 um long channel with a cross-sectional area of 1000 um. The initial concentrations of the chambers are 1 M and 0 M, respectively.

FIG. 41 plots the time required for the concentration in one of the reservoirs to reach 0.6 of the final equilibration concentration, versus channel length. FIG. 41 shows the linear relationship between diffusion time and channel length for this simple microfluidic system.

FIG. 42 plots the inverse of the time required for the concentration in one of the reservoirs to reach 0.6 of the final equilibration concentration ($T_{0.6}$), versus the area of the fluidic interface created upon opening of the valve. FIG. 42 shows the linear relationship between these parameters. The simple relationship between the equilibration time constant and the parameters of channel length and 1/channel area allows for a reliable and intuitive method for controlling the rate of diffusive mixing across a microfluidic free interface in accordance with an embodiment of the present invention.

This relationship further allows for one reagent to be diffusively mixed with a plurality of others at different rates that may be controlled by the connecting channel geometry. For example, FIG. 38A shows three sets of pairs of compound chambers 9800, 9802, and 9804, each pair connected by microchannels 9806 of a different length Δx. FIG. 38B plots equilibration time versus equilibration distance. FIG. 38B shows that the required time for equilibration of the chambers of FIG. 38A varies as the length of the connecting channels.

FIG. 39 shows four compound chambers 9900, 9902, 9904, and 9906, each having different arrangements of connecting microchannel(s) 9908. Microchannels 9908 have the same length, but differ in cross-sectional area and/or number of connecting channels. The rate of equilibration may thus be increased/decreased by decreasing/increasing the cross-sectional area, for example by decreasing/increasing the number of connecting channels or the dimensions of those channels.

Another desirable aspect of microfluidic free interface diffusion studies in accordance with embodiments of the present invention is the ability to reproducibly explore a wide range of phase space. For example, it may be difficult to determine, a priori, which thermodynamic conditions will be favorable for a particular application (i.e. nucleation/growth of protein crystals), and therefore it is desirable that a screening method sample as much of phase-space (as many conditions) as possible. This can be accomplished by conducting a plurality of assays, and also through the phase space sampled during the evolution of each assay in time.

FIG. 43 shows the results of simulating the counter-diffusion of lysozyme and sodium chloride utilizing the microfluidic structure shown in FIG. 40, with different relative volumes of the two reservoirs, and with initial concentrations normalized to 1. FIG. 43 presents a phase diagram depicting the phase space between fluids A and B, and the path in phase space traversed in the reservoirs as the fluids diffuse across the microfluidic free interface created by the opening of the valve in FIG. 40. FIG. 43 shows that the phase space sampled depends upon the initial relative volumes of the fluids contained in the two reservoirs. By utilizing arrays of chamber with different sample volumes, and then identifying instances where diffusion across the channel yielded desirable results (i.e. crystal formation), promising starting points for additional experimentation can be determined.

As described above, varying the length or cross-sectional area of a channel connecting two reservoirs changes the rate at which the species are mixed. However, so long as the channel volume remains small compared as compared with the total reaction volume, there is little or no effect on the evolution of concentration in the chambers through phase space. The kinetics of the mixing are therefore decoupled from the phase-space evolution of the reaction, allowing the exercise independent control over the kinetic and thermodynamic behavior of the diffusion.

For example, it is often desirable in crystallography to slow down the equilibration so as to allow for the growth of fewer and higher quality crystals. In conventional techniques this is often attempted by adding new chemical constituents such as glycerol, or by using microbatch methods. However, this addition of constituents is not well characterized, is not always effective, and may inhibit the formation of crystals. Microbatch methods also may pose the disadvantage of lacking a driving force to promote continued crystal growth as protein in the solution surrounding the crystal is depleted. Through the use of diffusion across a microfluidic free interface in accordance with an embodiment of the present invention, crystal formation may be slowed by a well-defined amount without altering the phase-space evolution, simply by varying the width or cross-sectional area of the connecting channel.

The ability to control the rate at which equilibration proceeds has further consequences in cases were one wishes to increase the total volume of a reaction while conserving both the thermodynamics and the microfluidic free interface diffusion mixing. One such case arises again in the context of protein crystallography, in which an initial, small volume crystallization assay results in crystals of insufficient size for diffraction studies. In such a case, it is desirable to increase the reaction volume and thereby provide more protein available for crystal growth, while at the same time maintaining the same diffusive mixing and path through phase space. By increasing the chamber volumes proportionally and decreasing the area of the channel, the area of the interface relative to the total assay volume is reduced, and a larger volume would pass through the same phase space as in the original small volume conditions.

Figure 47:
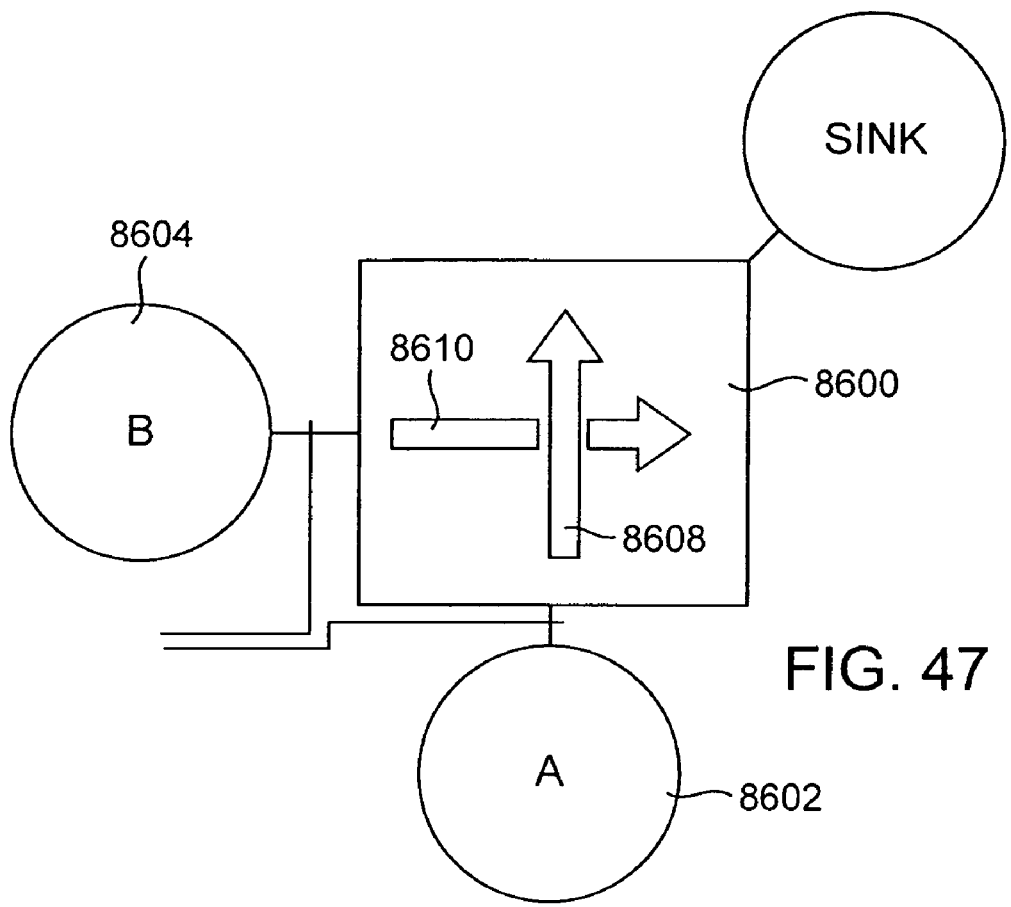
FIG. 47 shows a simplified plan view of one embodiment of a microfluidic structure in accordance with the present invention for creating diffusion gradients of two different species in different dimensions.

While the above description has focused upon diffusion of a single species, gradients of two or more of species which do not interact with each other may be created simultaneously and superimposed to create an array of concentration conditions. FIG. 47 shows a plan view of one example of a microfluidic structure for creating such superimposed gradients. Flat, shallow chamber 8600 constricted in the vertical direction is connected at its periphery to reservoirs 8602 and 8604 having fixed concentrations of chemical species A and B, respectively. Sink 8606 in the form of a reservoir is maintained at a substantially lower concentration of species A and B. After the initial transient equilibration, stable and well-defined gradients 8608 and 8610 of species A and B respectively, are established in two dimensions.

As evident from inspection of FIG. 47, the precise shape and profile of the concentration gradient will vary according to a host of factors, including but not limited to the relative location and number of inlets to the chamber, which can also act as concentration sinks for the chemical species not contained therein (i.e. reservoir 8604 may act as a sink for chemical species A). However, the spatial concentration profiles of each chemical species within the chamber may readily be modeled using the MATLAB program previously described to describe a two-dimensional, well-defined, and continuous spatial gradient.

The specific embodiment illustrated in FIG. 47 offers the disadvantage of continuous diffusion of materials. Hence, where diffusion of products of reaction between the diffusing species is sought to be discerned, these products will themselves diffuse in the continuous gradient, thereby complicating analysis.

Figure 48:
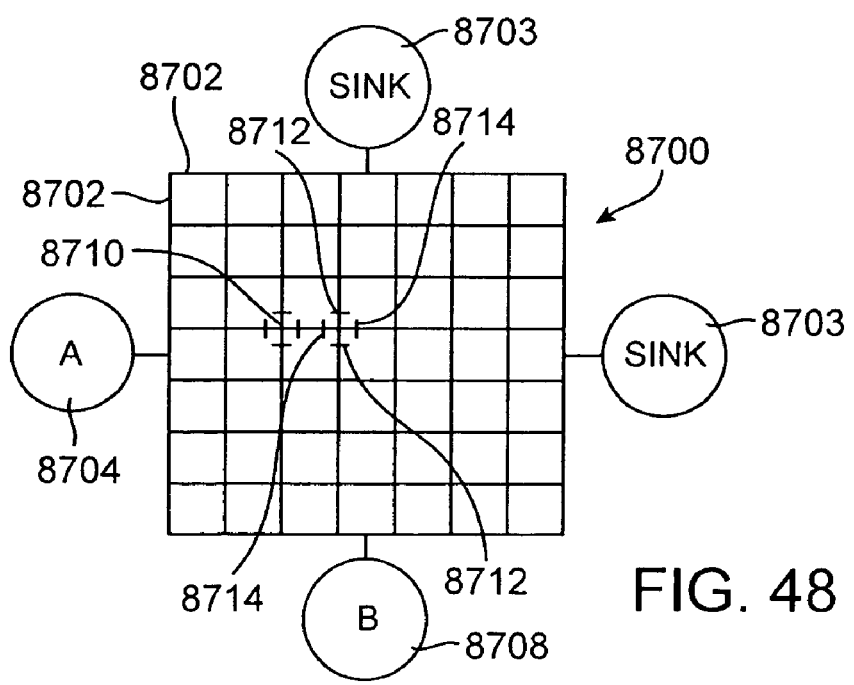
FIG. 48 shows a simplified plan view of an alternative embodiment of a microfluidic structure in accordance with the present invention for creating diffusion gradients of two different species in different dimensions.

Accordingly, FIG. 48 shows a simplified plan view of an alternative embodiment of a microfluidic structure for accomplishing diffusion in two dimensions. Grid 8700 of intersecting orthogonal channels 8702 establishes a spatial concentration gradient. Reservoirs 8704 and 8708 of fixed concentrations of chemical species A and B are positioned on adjacent edges of grid 8700. Opposite to these reservoirs on the grid are two sinks 8703 of lower concentration of the chemical present in the opposing reservoirs.

Surrounding each channel junction 8710 are two pairs of valves 8712 and 8714 which control diffusion through the grid in the vertical and horizontal directions, respectively. Initially, only valve pairs 8714 are opened to create a well-defined diffusion gradient of the first chemical in the horizontal direction. Next, valve pairs 8714 are closed and valve pairs 8712 opened to create a well-defined diffusion gradient of the second chemical in the vertical direction. Isolated by adjacent horizontal valves, the gradient of the first chemical species remains present in regions between the junctions.

Once the second (vertical) gradient is established, the two gradients can be combined and by opening all the valve pairs for a short time to allow partial diffusive equilibration. After the period of diffusion has passed, all the valve pairs are closed to contain the superimposed gradient. Alternatively, valve pairs 8712 and 8714 can be closed to halt diffusion in the vertical direction, with every second horizontal valve opened to create separate isolated chambers.

To summarize, conventional macro free-interface techniques employ capillary tubes or other containers having dimensions on the order of mm. By contrast, the fluidic interface in accordance with embodiments of the present invention is created in a microchannel having dimensions on the order of μm. At such small dimensions, unwanted convection is suppressed due to viscosity effects, and mixing is dominated by diffusion. A well-defined fluidic interface may thus be established without significant undesirable convective mixing.

V. Exploration of Phase Space

Closely related to the problem of protein crystallography is determining the solubility of a protein as a function of several chemical variables. Since it may be difficult to determine, a priori, which thermodynamic conditions will induce crystallization, a screening method should sample as much of phase-space (as many conditions) as possible. This can be accomplished by conducting a plurality of assays, and also through the phase space sampled during the evolution of each assay in time.

The mixing and metering functionality of microfluidic devices and methods in accordance with the present invention is suited to this task, whereby a protein sample may be mixed with a plurality of related solutions whose chemistry is systematically varied. It is possible to use the universal phase properties of the precipitant protein interaction to systematically design experiments that increase the chances of achieving crystal growth. In this way a solubility "phase-space" may be generated. The knowledge of this phase space may be used predict successful crystallization conditions or to refine identified conditions.

Figure 55:
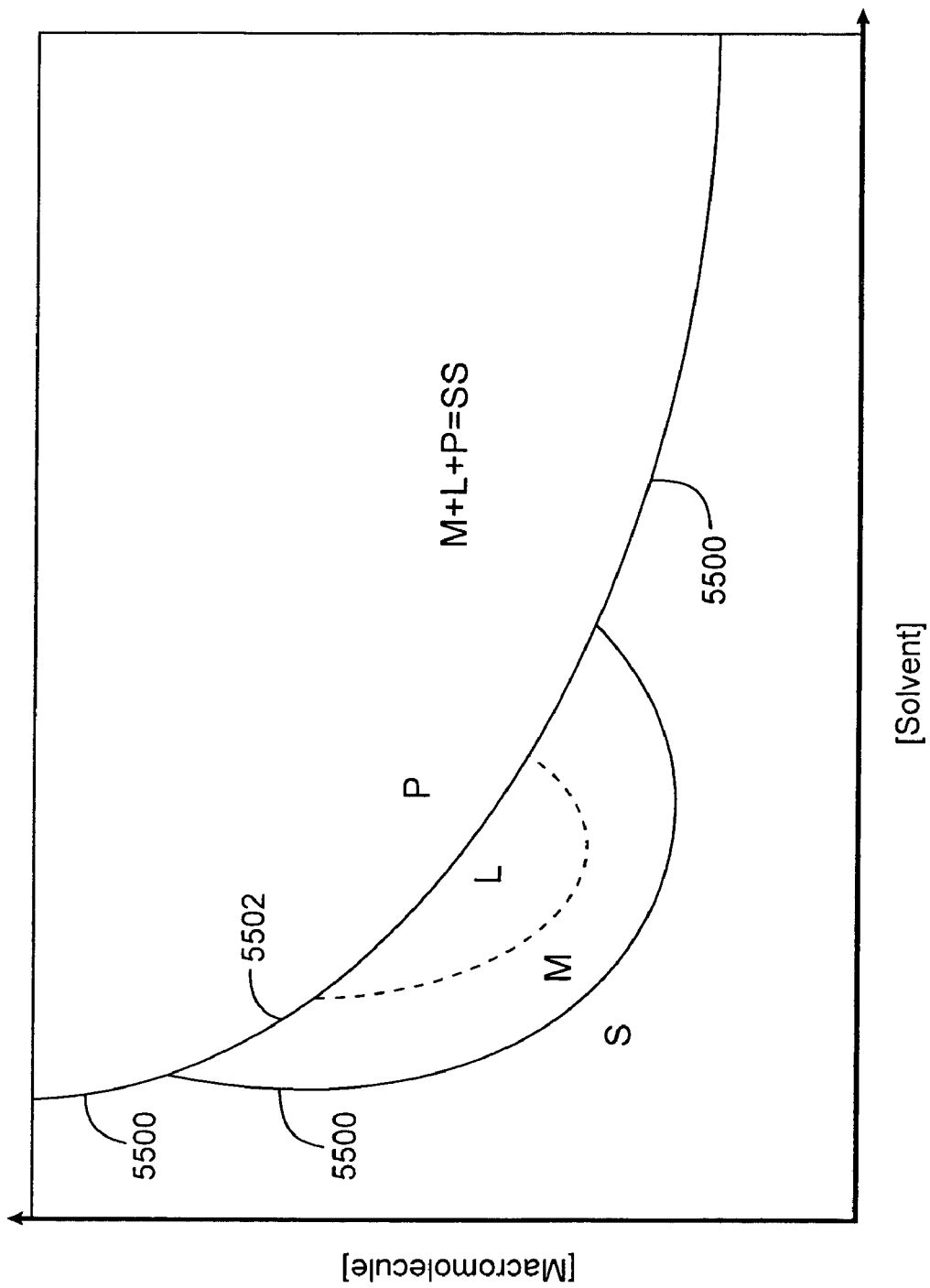
FIG. 55 plots macromolecule concentration versus solvent concentration to define a portion of phase space of one macromolecule solvent combination.

FIG. 55 is a simplified schematic diagram showing a phase space of a mixture comprising a macromolecule and a precipitating agent. This phase space is divided by solubility curve 5500 into soluble (S) and supersaturation (SS) regions determined by macromolecule solubility.

Figure 56A:
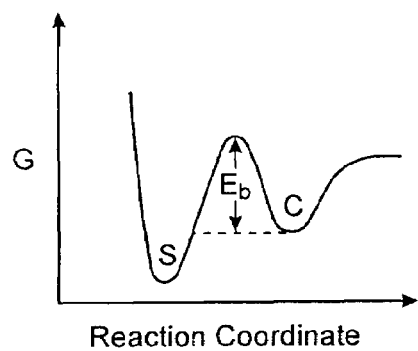
FIGS. 56A-F are Gibbs free energy diagrams of various regions of the phase space shown in FIG. 55.
Figure 56D:
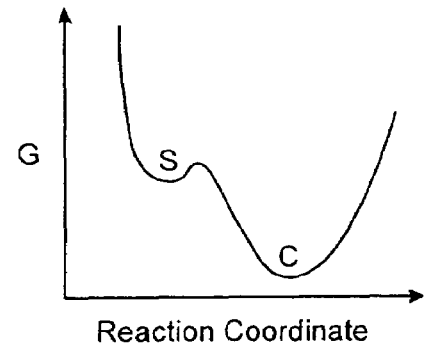
Figure 56B:
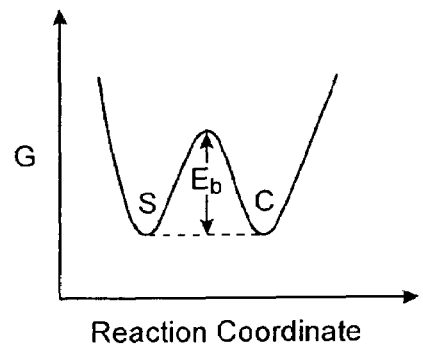
Figure 56E:
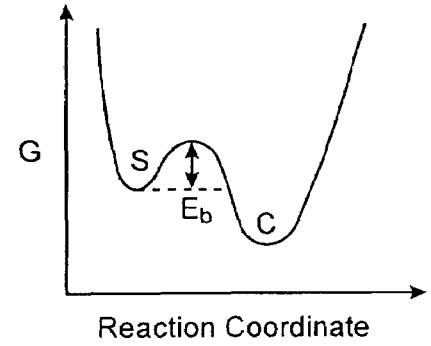
Figure 56C:
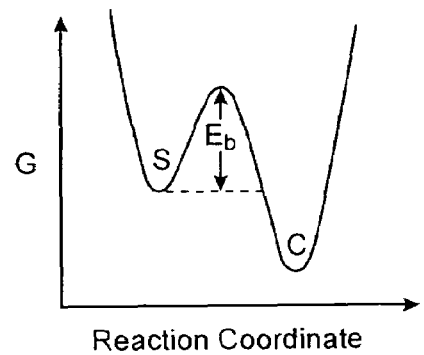

A Gibbs free energy diagram graphically represents the relative energies of soluble and precipitation phases, separated by a barrier energy (Eb) required to move from the energetically disfavored to the energetically favored state. FIG. 56A is a free energy diagram of soluble region (S) of FIG. 55. FIG. 56B is a free energy diagram along solubility curve 5500. FIG. 56C is a free energy diagram of supersaturated region (SS) of FIG. 55. Comparison of FIGS. 56A-C show energies of the soluble and precipitate phases to be evenly balanced along the solubility curve, with the soluble form energetically favored in the soluble region and the solid phase energetically favored in the supersaturated region.

Figure 56F:
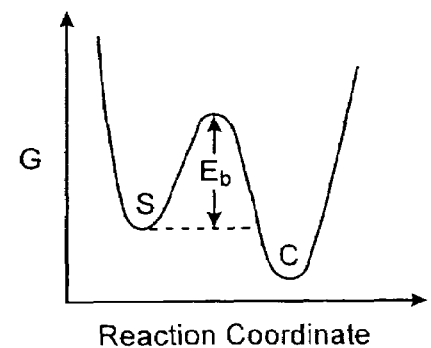

FIG. 55 also shows that supersaturation region (SS) may further be divided into a precipitation region (P) where amorphous precipitate lacking long range order (i.e. noncrystalline) forms rapidly, a labile region (L) near the precipitation curve 5502, and a metastable region (M) near the solubility curve 5500. FIGS. 56D, 56E and 56F show free energy diagrams for the precipitation, labile, and metastable regions, respectively.

In the precipitation region (P), amorphous aggregate is favored over crystalline solid, and the activation energy (Eb) is low, so that the transition between soluble and solid states occurs rapidly. In the labile region (L) the crystalline form is favored, but Eb is low, resulting in rapid nucleation and the corresponding formation of many small crystals. By contrast, in the metastable region (M) the relatively high activation energy suppresses nucleation but supports growth of existing crystals.

Since the three dimensional nucleation required for critical nucleus aggregation generally has a larger activation energy than that of subsequent one or two dimensional nucleation needed for crystal facet growth, an optimal crystal growth scheme should provide independent control over the these two phases of crystal growth. The BIM metering scheme provides exactly this property by implementing "free interface diffusion" between the precipitant and the protein solutions.

FIG. 57 is a simplified schematic diagram contrasting the evolution through a two-dimensional phase space having macromolecule concentration and precipitating agent concentration as variables, of conventional hanging drop and microbatch experiments, and μFID experiments in accordance with embodiments of the present invention. The phase-space trajectory taken by the chip during equilibration depends on the diffusion constants of the species involved. A short time after the chip interface valves are opened, the protein concentration on the protein side changes very little while that of the counter solvent, which typically has a much larger diffusion constant, increases to one of three final values determined by the lithographically defined mixing ratios. Subsequently, over a time of approximately 8-24 hours the protein concentration equilibrates, increasing on the solvent side and decreasing on the protein side. The final protein concentration is once again determined by the mixing ratios. The chip therefore takes a curved path through phase space, which in principle allows the protein solution to have efficient crystal nucleation in the labile region followed by high quality growth in the metastable region.

Accordingly, FIG. 57 shows evolution of a μFID reaction site having three different mixing ratios. Curves represent the average state of both the sample side and precipitating agent side of each compound well. The final states (I, II, III) are determined by the mixing ratio, and one can see that these curves have a greater chance of passing from regions with a high probability of nucleation to a region that supports high quality crystal growth. The break points of the curves are determined by the mixing ratios.

By contrast, the conventional micro batch and hanging drop approaches start at point IV where the target molecule is combined 1:1 with the precipitating agent. Microbatch experiments are incubated under immiscible oil, preventing subsequent concentration of reagents and therefore sampling only a single point in phase space.

In hanging drop experiments, the mixture is allowed to equilibrate through vapor diffusion with a large reservoir of precipitating agent, slowly concentrating the reagents and driving the sample into the super saturation region. This is undesirable because the resulting phase space trajectory moves into the precipitating region.

While the use of free interface diffusion techniques offers a promising way of sampling phase space, the sheer number and concentrations of potential crystallizing agents for any given macromolecule makes more systematic and rapid phase space mapping techniques desirable.

For example, before designing an experiment or a set of experiments to investigate crystal growth, it may first prove more efficient to identify the location of a curve for a particular combination of macromolecules and crystallizing agents. Once such a solubility curve is mapped in phase space, the investigator can then proceed to efficiently design a set of screening experiments in which the trajectory would be expected traverse regions promising phase space regions adjacent to this solubility curve.

The level of supersaturation of a macromolecule is generally defined by Equation (8) below:

$$SS = \frac{PC - MC}{MC} * 100, \text{ where:} \quad (8)$$

SS=level of supersaturation of a macromolecule;
PC=macromolecule concentration; and
MC=Maximum soluble macromolecule concentration in equilibrium.

For purposes of the instant invention, an alternative measure of the supersaturation of a macromolecule, hereto referred to as the immediate super saturation (ISS), is obtained if MC is replaced by the immediate maximum macromolecule concentration of protein (IMC). For the purposes of this invention, the IMC is defined as the maximum concentration of macromolecule that fails to produce a solid phase (either crystalline or amorphous), within 1 minute or less. The immediate supersaturation (ISS) is defined by Equation (9) below:

$$ISS = \frac{PC - IMC}{IMC}, \text{ where:} \quad (9)$$

ISS=immediate supersaturation;
PC=macromolecule concentration; and
IMC=Immediate maximum macromolecule concentration.

Crystallization of a macromolecule generally requires high supersaturation values typically in the range of 50% to 500%. Furthermore, it is generally undesirable to begin at positive ISS values in a crystallization experiment, as since this will result in immediate formation of a solid phase.

In a given phase space, the area bounded above by the IMC curve, and bounded below by the MC curve, defines a region in which protein crystal growth may be supported. Therefore if the IMC curve is known, for example by observation of rapid solid formation during high throughput screening utilizing combinatoric mixing, a crystallization experiment should be set to evolve near the IMC and with negative ISS values. For the purpose of this patent application, conditions having ISS values between about ±50% are considered near the IMC curve.

The combinatoric mixing device previously discussed in connection with FIGS. 17A-B, and variants thereof, offer a rapid and effective way to map the solubility curve of a crystallizing agent and a macromolecule. Specifically, the crystallizing agent sample could rapidly be prepared by injecting buffer and reagent into the rotary mixer flow channel to achieve a specific and precise concentration. Next, the sample injection port line, and pump could be used to introduce the macromolecule sample into the rotary mixer, followed by detection of formation of precipitate in the rotary mixer.

Detection of precipitate/crystal aggregation may be done in several ways. One method of detection aggregation is to image the mixing ring onto a camera. Simple image processing may then be done to distinguish a clear channel from one having particulates. Additionally, since some crystals show a degree of birefringence, a polarizing lens may be used to distinguish crystalline from amorphous solid. It should also be possible to use methods such as light scattering to detect the protein aggregates on smaller length scales.

Figure 24:
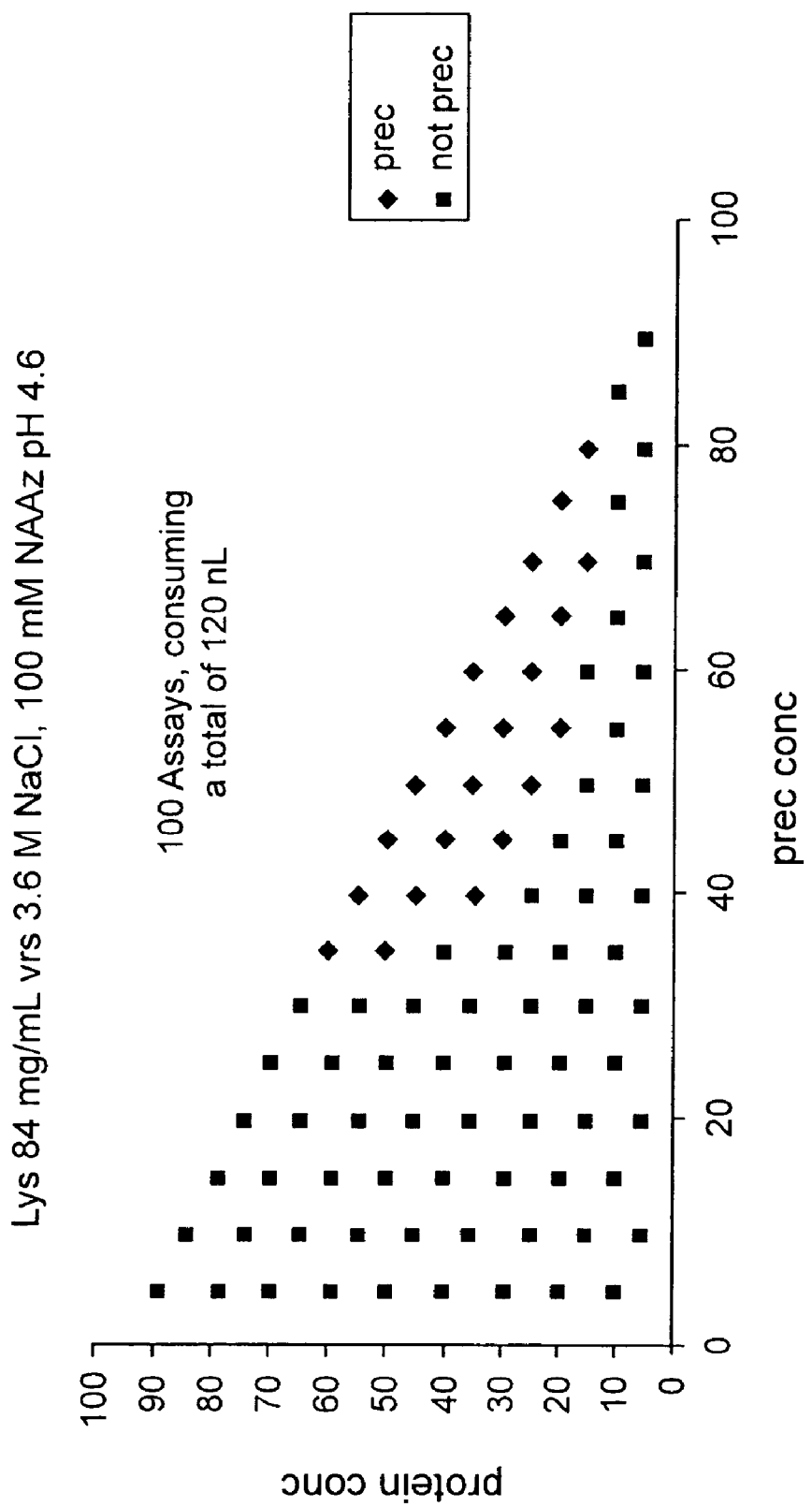
FIG. 24 shows a phase space of a mixture of protein and precipitating agent.

FIG. 24 shows a solubility "phase space" for a protein sample (Lysosyme 84 mg/ml) being titrated against a salt solution (3.6 M NaCl, and 100 mM sodium acetate (NaAc) @ pH 4.6). FIG. 24 shows the results of 100 assays, consuming a total volume of 120 mL. FIG. 24 represents only one of thousands of such graphs comprising a solubility phase-space.

The graph shown in FIG. 24 illustrates only the distinction between soluble and precipitating conditions. However, it may be possible to obtain more information by shifting the direction of change in relative concentration of macromolecule and crystallizing agent, to pass through the solubility curve in both directions. For example, if enough salt is added to a protein sample, it will form a solid that may be either amorphous (precipitate) or crystalline (micro-crystals). If this solution is slowly diluted, the solid will eventually dissolve back into solution. The concentration at which it dissolves occurs will, however, not typically be at the same concentration at which solidification originally occurred, and will generally be dependant upon whether the solid is crystalline or amorphous.

Specifically, while precipitation occurs nearly instantaneously, crystals take longer to form, suggesting a higher activation energy for the crystallization process. The higher activation energy for crystal nucleation/formation implies that observation of nucleation on a laboratory timescale requires substantial supersaturation. In contrast, the crystal form, once it appears, is favored over the soluble form for all supersaturation values greater than zero. Thus the magnitude of the hysteresis under conditions where the soluble phase is converted to solid, contrasted with conditions under which the solid phase is reconverted back to soluble phase, could reveal the presence of crystals versus precipitate, and thus conditions favorable to crystallization.

Figure 25:
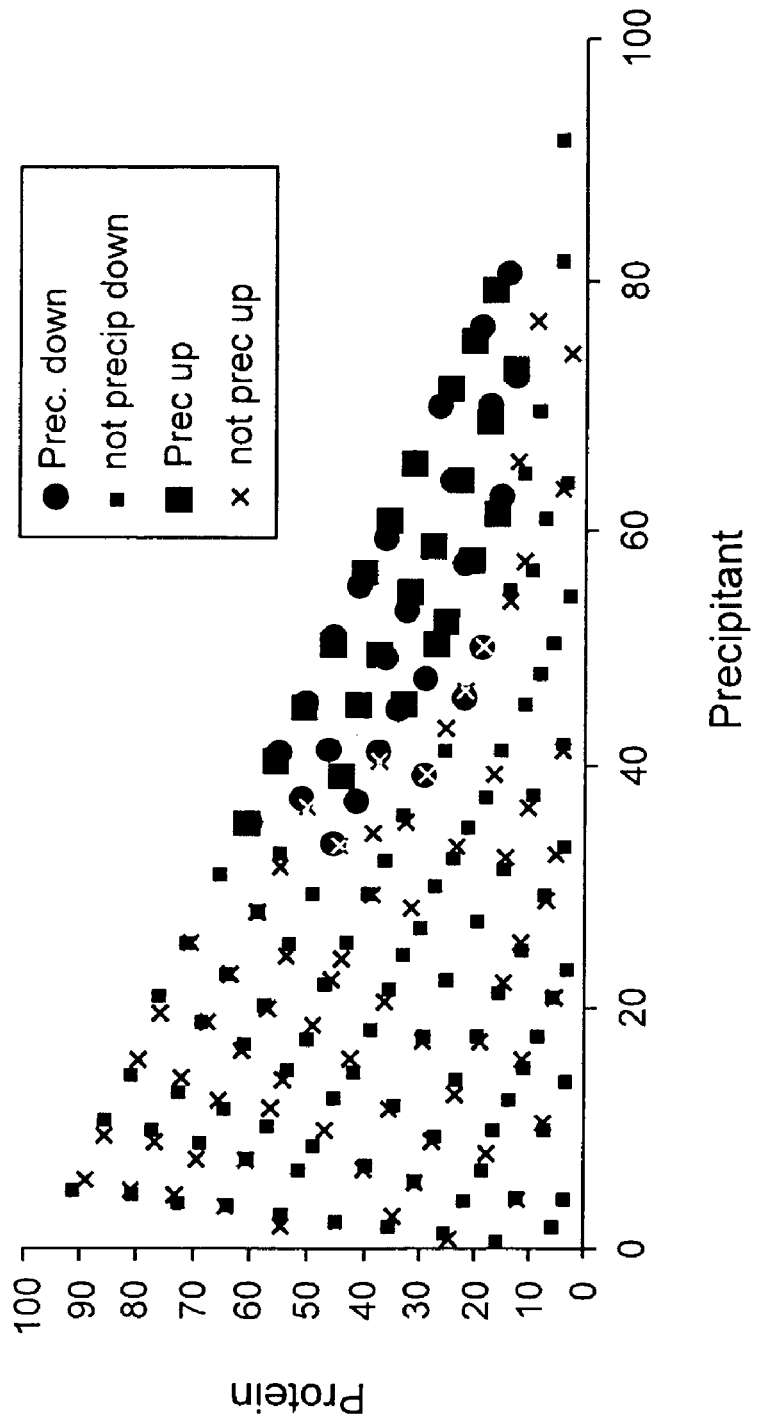
FIG. 25 shows a hysteresis effect in a phase space of a mixture of protein and precipitating agent.

FIG. 25 shows the precipitation of a sample of Lysozyme (84 mg/ml) precipitated by mixing with a crystallizing agent of (3.6M NaCl, and 0.11 M sodium citrate @ pH 4.6). Lack of coincidence between square (■) and circle (●) symbols indicates a hysteresis and a point for further promising exploration of phase space to identify crystal growth.

Detection of a hysteresis in precipitation formation as just described may also serve to prove extremely valuable for identifying whether or not a particular macromolecule/crystallizing agent combination holds promise of forming crystals at all. For example, inspection of FIG. 55 indicates that the labile and metastable supersaturation regions favorable to crystal formation do not occur uniformly along the solubility curve. Instead, such labile/metastable regions may be localized and surrounded by adjacent precipitation regions wherein formation of a solid material is amorphous and formation of ordered crystalline material is not possible. Detection of a hysteresis in accordance with an embodiment of the present invention may reveal the formation of some type of crystal, and thus provide a preliminary screening mechanism to minimize the time and effort required to map potentially favorable regions of the phase space It may further be possible to utilize light scattering techniques to directly measure the size of aggregated solids in a crystallization sample. Specifically, the virtual transparency of the PDMS of the chip to forms of incident electromagnetic radiation would enable optical interrogation of the flow channel of the rotary or other type of mixing device. Detection of radiation scattered from the sample utilizing techniques such as quasi-elastic light scattering (QELS) or dynamic light scattering (DLS) would enable the determination of the size of solid present in the sample, thereby allowing for determination of sample conditions at the onset of solid formation, when crystal nucleation may be favored.

Moreover, in "Predicting Protein Crystallization From a Dilute Solution Property", Acta Crystallogr. D. 50:361-365 (1994), George and Wilson demonstrated a relationship between protein crystallization behavior and the protein osmotic second virial coefficient ($B_{22}$), a basic parameter representing the integral of the intermolecular potential over distance. The George and Wilson article is incorporated in its entirety herein for all purposes.

The second virial coefficient of a macromolecule solution may be detected from the scattering behavior of a macromolecule solution. Moreover, the value of the second virial coefficient of protein solutions giving rise to crystallization has been found to lie in a universally narrow range. Thus on-chip evaluation of the second virial coefficient by light scattering techniques coupled with the ability to perform rapid combinatoric mixing with small volume samples would enable the rapid screening of different mixtures for potential crystallizability.

Systematic Investigation of Protein Phase Behavior with a Microfluidic Formulator The application of x-ray crystallography to the determination of protein structure with atomic resolution was a triumph of structural biology in the $20^{th}$ century. Since the first solution of the structure of myoglobin in 1958 by Kendrew et al., Nature 181, 662-666 (1958), incorporated by reference herein for all purposes, over 23,000 different structures have been deposited in the protein data bank, and their role in relating structure to function in biology has been profound.

Structure determination efforts continue to move past the most tractable crystallization targets (typically small soluble proteins), and focus instead on more challenging macromolecules such as large protein complexes and membrane proteins. See Loll, *Journal of Structural Biology* 142, 144-153 (2003), incorporated by reference herein for all purposes. Therefore, the need to better understand and explore the crystallization process has become urgent. That is because once high quality crystals are in hand, advances in x-ray sources, computer codes, and related technology have made it relatively straightforward to obtain the structure. However, these innovations have not been matched by techniques for rapidly expressing, purifying, and crystallizing proteins. As described by Chayen et al., *Acta Crystallographica Section D Biological Crystallography* 58, 921-927 (2002), incorporated by reference herein for all purposes, determining the appropriate crystallization conditions has become one of the most significant remaining bottlenecks to structure determination.

Understanding the phase behavior of proteins is a part of the crystallization process. The growth of crystals from a protein solution requires the existence of a nontrivial phase diagram which allows the protein state to be manipulated between at least two thermodynamic phases: soluble and precipitated. The processes of crystal nucleation and growth arise on the boundary between these two phases, and are governed by subtle effects in physical chemistry.

There are a variety of schemes that manipulate the kinetics of the crystallization process, and all take advantage of generic features of these phase diagrams. See Luft et al., *Macromolecular Crystallography, Pt A*, Vol. 276, pp. 110-131 (1997), incorporated by reference herein for all purposes. However, in practice the phase behavior of very few proteins has been studied in detail. See, e.g., Rosenbaum et al., *Journal of Crystal Growth* 169, 752-758 (1996); Ataka, *Phase Transitions* 45, 205-219 (1993); Carbonnaux et al., *Protein Science* 4, 2123-2128 (1995); Mikol et al., *Journal of Crystal Growth* 97, 324-332 (1989); Howard et al., *Journal of Crystal Growth* 90, 94-104 (1988); Kam et al., *Journal of Molecular Biology* 123, 539-555 (1978); Muschol et al., *Journal of Chemical Physics* 107, 1953-1962 (1997); Forsythe et al., *Journal of Chemical and Engineering Data* 44, 637-640 (1999), each of which is incorporated by reference herein for all purposes. In addition, solubility information for a specific protein is rarely available for crystallization and optimization experiments. See, e.g., Saridakis et al., *Acta Crystallographica Section D-Biological Crystallography* 50, 293-297 (1994); and Saridakis et al., *N. E. Biophysical Journal* 84, 1218-1222 (2003), incorporated by reference herein for all purposes.

Furthermore, it is often an arduous process to find the right combination of chemicals that yields appropriate phase behavior for a given protein. Every protein is different, and even a modest subset of stock precipitating solutions comprise a vast chemical phase space that must be explored. The large amounts of sample required make systematic exploration by conventional techniques infeasible, and screening is typically directed towards an incomplete factorial or sparse-matrix approach, which is a brute-force process requiring large numbers of experiments. See Carter et al., *J. Cryst. Growth* 90, 60-73 (1988); and Jancarik et al., *J. Appl. Crystallogr.* 24, 409-411 (1991), incorporated by reference herein for all purposes.

There have been numerous attempts to rationalize this procedure. One approach is to use computational approaches to predict phase behavior. See Carter et al., and Jancarik et al. Another approach is to try to correlate measurements of osmotic $2^{nd}$ virial coefficients with crystallization conditions. See George et al., *Acta Crystallographica Section D-Biological Crystallography* 50, 361-365 (1994); Guo et al., *Journal of Crystal Growth* 196, 424-433 (1999), incorporated by reference herein for all purposes. Practical limitations have thus far prevented these techniques from being generally applicable to the determination of crystallization conditions.

Here we describe a microfluidic formulation device that allows for the combinatorial mixing of 16 buffers and 16 precipitation agents with a purified protein sample. The ability of the formulation chip to access a vast number of chemical conditions, and to accurately dispense and mix fluids on the picoliter scale makes detailed characterization of macromolecule phase behavior both possible and practical. We used this device to screen 5,000 different solubility conditions of the model protein Endo-1,4-β-xylanase from *Trichoderma reesei*. Xylanase is a 21 KDa member of the gluconase enzyme family.

For those conditions that exhibited non-trivial phase behavior (ie precipitation), a full phase diagram was generated. From this thorough characterization of the phase behavior, we designed a rational crystallization screen for xylanase. Comparison of this screen to 4 commercially available sparse matrix screens showed nearly two orders of magnitude increase in crystallization success, and allowed new insight into the physics of crystallization.

Samples were prepared and crystallization protocols followed, as set forth below. Endo-1,4-β-xylanase (xylanase) from *Trichoderma reesei* (Hampton Research) was prepared in deionized water from stock (36 mg/mL protein, 43% wt/vol glycerol, 0.18 M sodium/potassium phosphate pH 7.0) by repeated buffer exchange at 4° C. using a centrifugal filter with a molecular weight cut-off of 10,000 Da (Micon Bio-separations). Protein concentration was measured by absorption at 280-nm and adjusted to 120 mg/mL. 10 μL aliquots were flash frozen in liquid nitrogen and stored at −80° C. To avoid sample-sample variations, a single sample preparation was used for all solubility screening, phase space mapping and corresponding crystallization experiments.

Batch crystallization trials were actively mixed by repeated aspiration and incubated under paraffin oil. Crystallization trials were inspected daily for a period of two weeks. Observed crystals were confirmed to be protein crystals by staining (IZIT dye; Hampton Research) and were recorded as crystallization hits.

All photo-masks for the master model were designed using AutoCAD (Autodesk) and printed at a resolution of 20,000 dpi on a transparency film (CAD/Art Services). The flow-layer master was fabricated from a combination of positive and negative photoresists using a three-step lithography process. 9 μm high channel sections defining the top and bottom of the mixing ring structure were fabricated from SU8-2010 resist. These features provide a channel section with well-defined rectangular cross-section that does not reflow during subsequent processing, thereby facilitating absorption and precipitation measurements.

SU8 2010 (MicroChem) was spun onto a silicon wafer (3,000 rpm for 45 seconds), pre-exposure baked (1 minute 65° C./3 minutes 95° C.), exposed through a negative transparency mask (40 seconds 7 mW/cm$^2$), post-exposure baked (1 minute 65° C./3 minutes 95° C.), and developed in SU8 nano developer (MicroChem).

Channel sections compatible with integrated valves were fabricated using SJR 5740 positive photoresist (Shipley). To promote photoresist adhesion the wafer was first treated with hexamethyldisilazane (Microprime HP-Primer; ShinEtsu MicroSi) (1 minute at 1 atmosphere). Photoresist was spun onto the patterned wafer (2,000 rpm for 60 seconds), soft baked (1 minute 45 seconds 95° C.), aligned to the existing features, exposed (45 seconds/seconds 7 mW/cm$^2$), and developed (20% Microposit 2401 developer; Shipley). The mold was then annealed (20 minutes/120° C.), resulting in a smooth rounded cross-section necessary for valve closure, and hard baked (2 hours/170° C.).

Low impedance input and output channels were fabricated to allow for the rapid flushing of viscous reagents. A 60 μm layer of SU8 2075 (MicroChem) was spun onto a silicon wafer (3,000 rpm for 60 seconds), pre-exposure baked (7 minute 65° C./20 minutes 95° C.), aligned to the primary flow structure, and exposed through a negative transparency mask (40 seconds 7 mW/cm$^2$), post-exposure baked (1 minute 65° C./15 minutes 95° C.), and developed in SU8 nano developer (MicroChem). 25 μm high control features were fabricated on a separate wafer using a single lithographic step. SU8 2025 (MicroChem) was spun onto a silicon wafer (3,000 rpm for 45 seconds), pre-exposure baked (1 minute 65° C./3 minutes 95° C.), aligned to the primary flow structure, and exposed through a negative transparency mask (40 seconds 7 mW/cm2), post-exposure baked (1 minute 65° C./3 minutes 95° C.), and developed in SU8 nano developer (MicroChem).

Microfluidic devices were fabricated as follows. The microfluidic formulator was fabricated from silicone elastomer (General Electric RTV 615) using the technique of multilayer soft lithography of Unger et al., *Science* 288, 113-116 (2000), incorporated by reference herein for all purposes. To facilitate the release of the elastomer from the mold all molds were treated with chlorotrimethylsilane (Aldrich). Consecutive replica molding from microfabricated masters and chemical bonding steps were used to create a three-layer elastomer device consisting of a 7 mm thick layer with patterned flow structure (top), a 35 μm control layer (middle), and a featureless sealing layer (bottom).

Liquid silicone elastomer (20 part A:1 part B) was spun onto the control master (2400 rpm for 60 seconds) and baked in a convection oven at 80° C. for 60 minutes. Liquid silicone elastomer (5 part A:1 part B) was poured on the flow master to a thickness of 7 mm, degassed, and baked at 80° C. for 75 minutes.

The partially cured flow layer was peeled from the master and aligned to the control mold. The two-layer structure was then baked for 75 minutes, chemically cross-linking the two layers into a single structure. The bonded elastomer was then peeled from the control mold and access ports were punched at the flow and control inlets using a 0.055 inch punch (Technical Innovations).

The structure was then placed on a featureless elastomer membrane (20 part A:1 part B) created by spinning elastomer on a plain silicon wafer at 2500 rpm for 1 minute and baking for 1 hour at 80° C. The assembled structure was then baked overnight, causing the three layers to bond into a monolithic multilayer device. Finally the device was peeled from the silicon wafer, cut to size, and sealed to a glass substrate for mechanical rigidity.

Experimental setup and data collection were performed as follows. Automation of metering, mixing and data acquisition allows for thousands of solubility experiments to be executed without the need for user intervention. In each solubility experiment a unique mixture of the 32 reagents and the protein sample is produced.

All device control and data acquisition was implemented using a custom software driver developed in LabView (National Instruments). Mixing recipes were generated using a spread-sheet program and translated into valve actuation sequences by the software driver. Off-chip solenoid valves (Lee Products Ltd.), controlled using a digital input output card (DIO-32HS; National Instruments), were used to generate square-wave pressure signals at the device control ports. A frame-grabber card (Imagenation PXC200A; CyberOptics) was used to automate image acquisition from a charge coupled device camera.

The on-chip peristaltic pumps were pneumatically actuated at 100 Hz, resulting in a maximum flow velocity of approximately 2 cm/s. At these flow rates complete mixing of aqueous reagents was achieved in less then 3 seconds, and solutions with viscosities of approximately 100 cP were mixed in 6 seconds.

Absorption and precipitation measurements were taken as follows. Absorption measurements were taken to determine the concentration of bromophenol blue sodium salt (absorption peak at 590-nm) in the mixing ring. A 9 μm high segment of the mixing ring (approximately 300 μm by 80 μm) having rectangular cross-section was illuminated with a 590-nm diode (AND180HYP; Newark Electronics) and imaged through a stereoscope (SMZ 1500; Nikon) onto a charge coupled device camera. Pixel intensities were averaged and compared to an identical adjacent reference channel containing the undiluted dye (2 mM bromophenol blue sodium salt, 100 mM TRIS-HCl pH 8.0). In some experiments glycerol was added to the injected dye to vary the viscosity. Dye concentrations were determined using the Beer-Lambert relation and used to calculate the injected volume.

Precipitation of the protein was automatically detected by imaging a portion of the mixing ring, calculating the standard deviation of the pixel intensities and comparing this value to the background (no protein added). To ensure even illumination, images were taken at 112 times magnification at a 9 μm high section of the mixing ring having rectangular cross-section.

The positive-displacement cross-injection metering scheme allows for sequential injection of precise sample aliquots from a single microfluidic channel into an array of reaction chambers through a positive displacement cross-injection (PCI) junction. FIGS. 62A-D show simplified schematic views of positive displacement cross-injection (PCI) for robust and programmable high precision dispensing on chip.

Figure 62A:
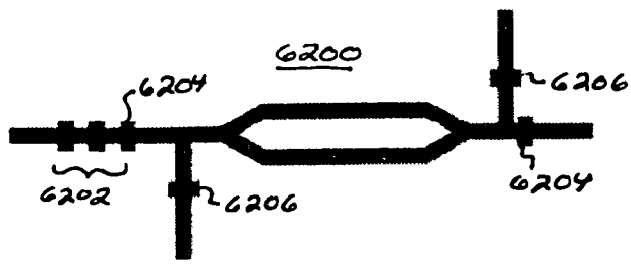
FIGS. 62A-D are simplified schematic diagrams illustrating positive displacement cross-injection (PCI) dispensing.

FIG. 62A shows a schematic view of a four port PCI junction. As shown in FIG. 62A, the PCI junction 6200 is formed by the combination of a three-valve peristaltic pump 6202 and a novel four-port cross-injection junction with integrated valves on each port. At each junction, two sets of valves 6204 and 6206 are actuated to direct the flow either horizontally or vertically. The split channel architecture creates a larger volume injector region, thereby allowing for an increased number of injections before recharging.

Figure 62B:
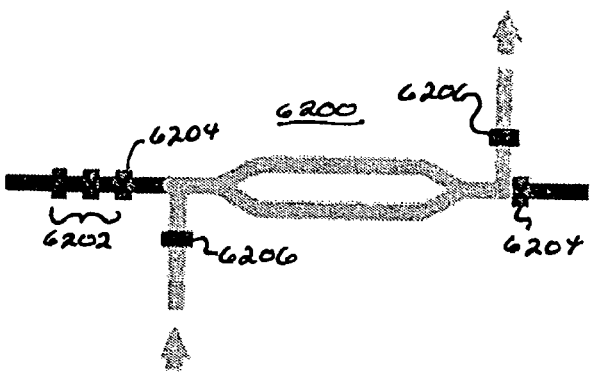

FIG. 62B shows charging the injector region of the PCI junction. To execute the metering task, the flow is switched vertically through the junction, charging the cross-injector with the sample fluid. Junction valves are actuated to direct the flow vertically through the junction, filling the injector region.

Figure 62C:
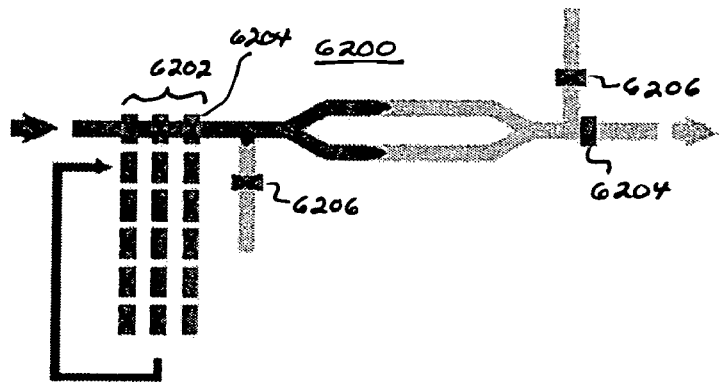

FIG. 62C shows precise positive displacement metering by actuation of peristaltic pump valves in pumping sequence. The flow is then directed horizontally through the junction and the three valves forming the peristaltic pump are actuated in a five state sequence to advance the fluid in the horizontal direction.

Figure 62D:
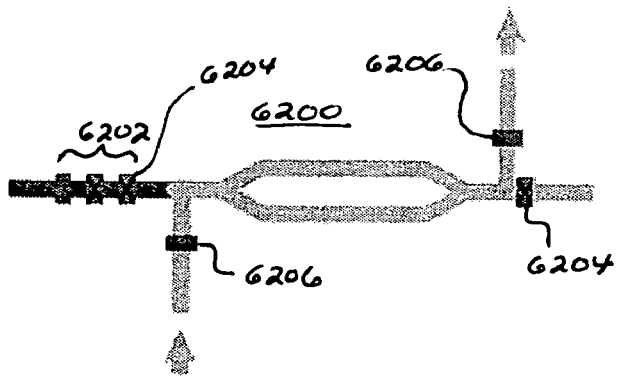

FIG. 62D shows the PCI junction sequentially charged with different solutions to create complex multi-component mixtures. Each cycle of the peristaltic pump injects a well-defined volume of sample (approximately 80 pL), determined by the dead volume under the middle valve of the peristaltic pump. The deflection of the valve membranes when not actuated is determined by the pressure difference across the membrane. The volume injected during each cycle therefore may be tuned continuously, allowing for variable positive displacement metering. By repeating the injection sequence, the volume of injected solution may be increased in 80 pL increments, allowing for the dynamic quantized control of the final downstream sample concentration.

The dearth of available information regarding protein solubility may be largely attributed to practical limitations of conventional fluid handling technology. Although small scale characterization of protein solubility by a pre-crystallization solubility assay has been reported by Stura et al., *Journal of Crystal Growth* 122, 273-285 (1992) and by Santesson et al., *Analytical Chemistry* 75, 1733-1740 (2003), both of which are incorporated by reference herein for all purposes, this technique has not been widely adopted since the large required sample volumes make it unsuitable for targets that cannot be expressed and purified in large quantities. Microfabricated dispensers have been used to reduce sample consumption in cases where the sequential addition of reagents to a levitated drop of microliter volume is sufficient to explore a restricted chemical space (Santesson et al). While micofluidic devices have been previously used to screen crystallization conditions using free interface diffusion by Hansen et al., *Proc. Nat'l. Academy of Sciences* 99, 16531-16536 (2002) and microbatch formats by Zheng et al., *Journal of the American Chemical Society* 125, 11170-11171 (2003), both of which are incorporated by reference herein for all purposes, they have not been applied to systematically measure phase behavior. Previous limitations in fluid handling functionality have limited the use of microfluidic devices in applications such as protein phase space mapping which may involve the complex on-chip mixing of reagents.

Thorough characterization of protein solubility behavior involves accessing chemical space through the combinatorial mixing of a limited number of stock reagents. The conventional reagents used in crystallization exhibit a large variation in physical properties such as viscosity, surface tension, ionic strength, and pH. This variation presents a formidable challenge for fluid handling systems that must allow for arbitrary fluid combinations and proportioning.

We developed a positive displacement cross-injection metering method that overcomes this obstacle, allowing for variable dispensing to be dynamically programmed by the user in 80 picoliter increments with less than 5% variation over a broad range of fluid properties. By combining this method with microfluidic mixing, Chu et al., *Biomedical Microdevices* 3, 323-330 (2001), incorporated by reference herein for all purposes, and multiplexing elements, Thorsen et al., *Science* 298, 580-584 (2002), incorporated by reference herein for all purposes, large scale combinatorial screening has been achieved on chip for the first time. The flexibility, precision and small volume requirements of this device make feasible the systematic mapping of crystallization phase space.

Figures 63A, 63B, 63C, 63D:
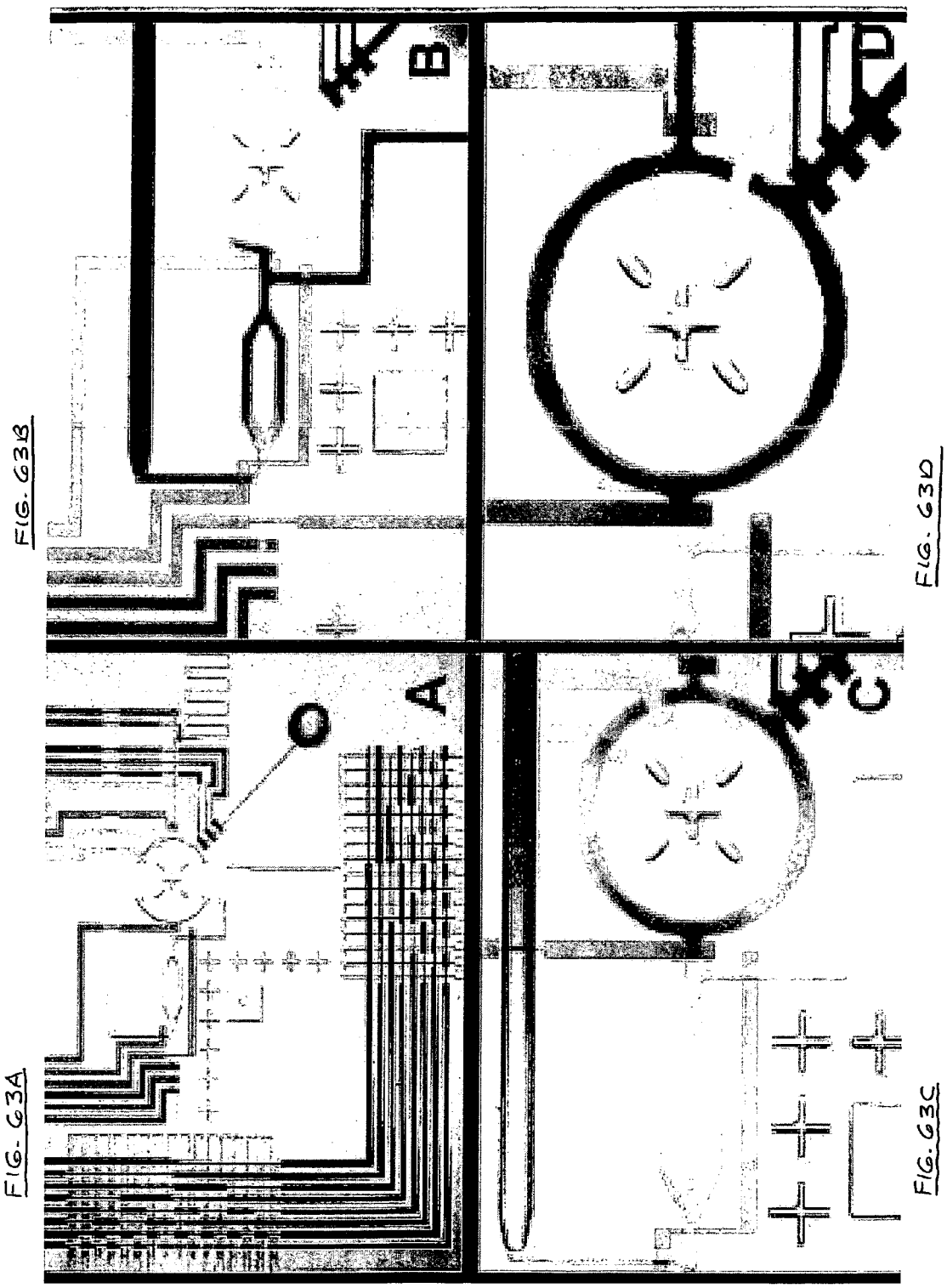
FIGS. 63A-D show photographs illustrating combinatoric mixing utilizing a microfluidic formulator.

FIGS. 63A-D show combinatorial mixing using a microfluidic formulator. FIG. 63A shows integration of the multiplexer, peristaltic pumps, rotary mixer, and PCI junction components for on-chip combinatorial formulation.

FIG. 63B shows injection of approximately 250 pL (4 injection cycles) of dye into rotary mixer. FIG. 63C shows the color gradient formed by consecutive injections into the mixing ring (8 injections blue, 8 injections green, 8 injections yellow, 8 injections red). FIG. 63D shows pumping around the ring for 3 seconds results in complete mixing of dye. Blue dye is added to mixture through sample injection inlet (bottom right).

The active region of microfluidic formulation chip that implements this scheme and allows for the arbitrary combinatorial mixing of 16 stock reagents into one of 16 buffer solutions is shown in FIGS. 63A-D. Two 16-solution multiplexer arrays, actuated by 8 control lines, allow for the selection of buffers (left) and reagents (bottom). A PCI junction, formed by a 3-valve peristaltic injection pump and cross-injection valves dispenses directly into a 5 nL ring reactor.

Once the reactor has been flushed, a reagent line is selected and the cross-injection sequence is executed. The extended split channel region increases the volume of the cross-injection junction, thereby allowing for up to 15 injections between flushing steps. The maximum number of consecutive injections that may be executed before the junction needs to be refreshed depends on the Taylor dispersion of the injected fluid as it is pumped down the channel, and is therefore a function of the viscosity. The Taylor dispersion is discussed by Taylor, *Proc. Royal Soc. London Series a-Mathematical and Physical Sciences* 219, 186-203 (1953), incorporated by reference herein for all purposes, FIG. 63B shows the injection of 4 slugs, each having a volume of 80 pL, into the ring reactor. Arbitrary combinations of 16 reagents may be produced in the reactor by sequential flushing and injection steps.

FIG. 63C shows a color gradient formed from injections of water, blue dye, green dye, yellow dye, and red dye. In screening applications that require the interrogation of a precious sample against many pre-mixed reagent formulations, the cross-injection flushing step is wasteful and is circumvented by the addition of a separate sample injection site, as shown in FIG. 63D.

After the ring is filled with the desired reagents, they are mixed by actuating a rotary peristaltic pump, as described by Chu et al.

The precision of metering was evaluated by injecting variable amounts of dye (bromophenol blue sodium salt; Sigma) into a reactor, mixing, and performing absorption measurements. FIG. 64A plots absorption measurements showing high precision and reproducibility of PCI injections. Each of the 9 clusters represents 100 identical injection sequences.

The set of 900 sequential titration experiments shown in FIG. 64A shows the metering to be both precise and reproducible, with a slope of 83.4 pL per injection cycle and a coefficient of correlation of 0.996. The standard deviation of the injected slug volume was determined to be approximately 0.6 pL.

Although positive displacement metering ensures that the injected volume is robust to changes in the fluid viscosity, the viscosity of the working fluid does reduce the bandwidth of the injector. It was found that for a solution having viscosity of 400 cP the frequency response of the injector began to roll off at 10 Hz. When operating at an injection frequency of 5 Hz all solutions having viscosities below 400 cP produced equal injection volumes. Since the metering mechanism is completely mechanical, there is no dependence on the pH or ionic strength of the injected fluid. Additionally, since the fluid is not dispensed from the chip, there is no phase interface, and therefore little dependence on surface tension, so that the metering technique is truly robust to the physical properties of the injected fluid.

Figure 64B:
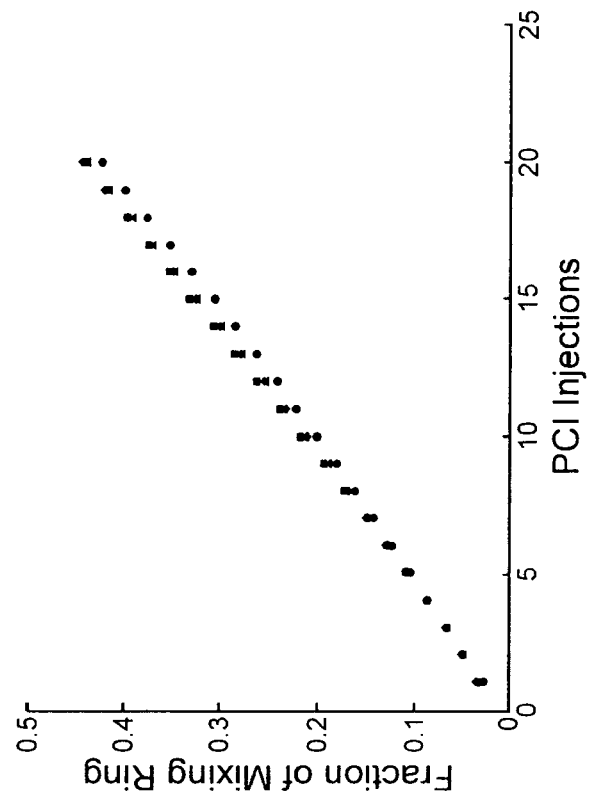
FIG. 64B plots the fraction of the ring of the combinatoric mixing structure occupied versus the number of PCI injections.
Figure 64A:
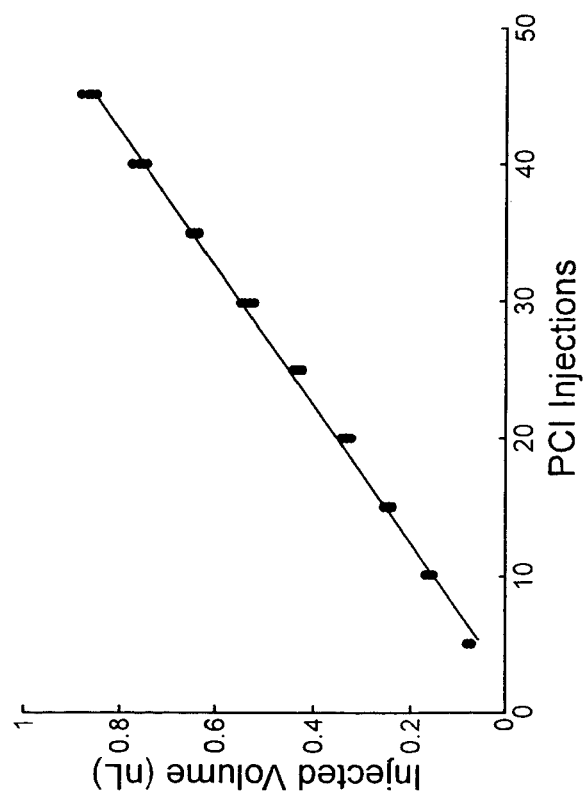
FIG. 64A plots injected volume versus the number of PCI injections.

FIG. 64B plots absorption measurements of 4 sets of 20 injection and mixing sequences showing metering to be robust to the viscosity of the injected fluid. Fluids contain varying amounts of glycerol and have viscosity ranging from 1 cP to 400 cP. FIG. 64B indicates that titration experiments with fluids of varying glycerol concentration show the injection volume to vary by less than 5% over a viscosity range of 1 cP to 400 cP without any modification to the injection sequence. Both FIGS. 64A-B show precise and robust microfluidic metering.

In order to demonstrate the utility of ab initio solubility characterization prior to crystallization trials, we explored the solubility behavior of a commercially available crystallization standard, Endo-1,4-β-xylanase (xylanase) from *Trichoderma reesei* (Hampton Research). See Torronen et al., *Embo Journal* 13, 2493-2501 (1994); and Torronen et al., *Biochemistry* 34, 847-856 (1995), both of which are incorporated by reference herein for all purposes. The standard deviation of imaged pixels was used as a metric of precipitation, allowing for distinction between precipitated and soluble conditions and a rough quantitative measure of the degree of precipitation. Specifically, precipitation of the protein was automatically detected by imaging a portion of the mixing ring, calculating the standard deviation of the pixel intensities and comparing this value to the background (no protein added). To ensure even illumination, images were taken at 112 times magnification at a 9 um high section of the mixing ring having rectangular cross-section.

FIGS. 65A-C show automated exploration of protein solubility using microfluidic formulator. FIG. 65A shows precipitation measurements at varying concentration of xylanase in 0.6 M Potassium Phosphate with 0.1 M TRIS/HCl pH 6.5. Standard deviation of pixels provides a quantitative metric of protein precipitation. Below the precipitation limit standard deviation shows constant background level with low variation. Above 12 mg/mL solution is in the precipitation regime where the pixel standard deviation exhibits an approximately linear dependence on protein concentration. All points represent the mean of 5 identical experiments with error bars indicating standard deviation of measurements. FIG. 65A shows that beyond the precipitation limit, the pixel standard deviation increases linearly with the protein concentration, and therefore is proportional to the concentration of precipitated protein present in the solution.

A two step protocol was used to map out the solubility space. An initial coarse search identified reagents that have strong precipitating effects on the target macromolecule. This generates a solubility fingerprint of the crystallization target. Each precipitation peak in this fingerprint represents a chemical condition that exerts a pronounced effect on solubility.

FIG. 65B shows solubility fingerprints of Xylanase over approximately 4200 chemical conditions. The solubility fingerprint of Xylanase of FIG. 65B was generated by 4 independent runs, each consisting of approximately 4000 titration experiments. Each data series represents a separate fingerprinting experiment using the same basis of chemical conditions. The crystallization conditions of FIG. 65B include the following groups: combinations of salts as major precipitants at pH values from 4 to 9; and PEGS with salts at various pH values.

The top solubility fingerprint of FIG. 65B generated using a sample having elevated protein concentration (90 mg/mL), exhibits both higher signal to noise and additional peaks not present in the other data series (70 mg/mL). The two center solubility fingerprints were generated sequentially on a single device (first the center top fingerprint, then the center bottom fingerprint) with the same loaded sample, demonstrating the stability of the protein over the time of the experiment (approximately 20 hours). The bottom solubility fingerprint was generated using the same sample as the top fingerprint but on a separate device, showing reproducibility of the results across different devices.

Each solubility fingerprint was generated over a period of approximately 35 hours and consumed approximately 8 µL of protein sample. Chemical formulations were created by flushing the ring with one of 16 buffers, injecting a precipitating agent (salt or polymer), diluting the ring with water, and then mixing. Protein sample was then introduced at a variety of concentrations and mixed prior to data acquisition. When a polymer was used as the major precipitating agent, a small amount of salt was also introduced as an additive (i.e. NaCl in FIGS. 65C22-23).

Experiments in FIG. 65B were grouped by the identity of the major precipitating agent so that each peak represents the effect of this reagent over a range of pH values and concentrations. The large width of these peaks indicates robustness and a high level of experimental redundancy, suggesting that a more efficient search could be conducted using less related chemical conditions. Specifically, a large peak width reveals that a large number of experiments with related conditions yielded precipitation (i.e. all pH values resulted in precipitation when the precipitant is a phosphate salt). The search is thus inefficient search (too exhaustive), and the experiments would be more powerful if more sparse in nature (i.e. sampling other multi-component and unrelated mixtures).

The solubility fingerprint is highly reproducible and is characteristic of the protein studied. For example, sodium chloride is a strong precipitating agent (and effective crystallization agent) for another well-studied crystallization standard (chicken egg white lysosyme) but does not produce a precipitation peak in the solubility fingerprint of Xylanase over the pH range studied. Thus with reference to the precipitation curves shown in FIGS. 65C22-23 and discussed below, sodium chloride is present as an additive only, with the major precipitant being PEG.

The solubility fingerprint of Xylanase revealed 5 salts (sodium citrate, di-potassium phosphate, ammonium sulfate, and sodium/potassium tartrate) as likely crystallizing agents. A high molecular weight polymer (polyethelyne glycol, M.W. 8,000) in combination with various salt additives was also identified to be a strong precipitating agent at high pH values. The high isoelectric point of xylanase suggests that the reduced effectiveness of this precipitant at low pH values is due two-body electrostatic repulsion. A smaller molecular weight polymer (polyethelyne glycol, M.W. 3,350) was found to be a much weaker precipitating agent and was not investigated further in phase-space mapping experiments.

Chemical combinations identified as effective to yield precipitation in FIG. 65B were then employed to map a two dimensional phase space of protein/precipitant concentrations. Specifically, the identified Xylanase precipitating conditions resulted in twenty-four expanded systematic grid searches over all accessible protein and precipitant concentrations. Each grid comprised seventy-two separate mixing experiments, creating a two-dimensional phase-space with protein concentration and precipitant concentration as variables. All twenty-four phase spaces were generated sequentially on a single device using less than 3 uL of protein sample (approximately 100 nL per phase space) and are shown as FIGS. 65C1-24. In FIGS. 65C1-24, the size of the diamonds reflect the magnitude of standard deviation of the pictures, and hence provide a quasi-quantitative measurement of the amount of precipitation observed.

FIG. 65D shows comparison of phase mapping done on chip and in conventional microbatch experiments utilizing Na/K Tartrate as the first precipitant stock. This comparison of a precipitation phase spaces measured for Xylanase in chip (5 nL reactions) and in microbatch format under paraffin oil (5 µL reactions) shows good agreement in detecting the precipitation boundary.

Since measurements of precipitation are made immediately after mixing (within 3 seconds), the locus of points that separate the precipitated and soluble regions of the graph generate a precipitation curve that is distinct from the thermodynamic solubility curve. Conditions that reside just below the precipitated region may be in a metastable state conducive to crystallization.

A detailed knowledge of protein solubility behavior provides an empirical basis for the design of maximum likelihood crystallization trials. For example, the 24 phase spaces generated for Xylanase shown in FIGS. 65C1-24 were used to design an optimal crystallization screen comprising the 48 reagent combinations shown in TABLE 2.

either too supersaturated and result only in protein aggregate, or are too undersaturated and result in the protein remaining in solution.

A single batch crystallization trial using the optimal screen was set by combining relative amounts of protein and precipitant stock so that the final condition was located on the boundary of the precipitation region. Specifically, protein was mixed with precipitant under oil at a ratio that places the final concentrations of protein and precipitant on the boundary of the empirically determined solubility curves.

The efficiency of this screen was evaluated by comparison with standard commercially available sparse matrix screens (Crystal Screen I and Crystal Screen II available from Hamp-

TABLE 2

| | | Buffer (100 mM) | | Precipitant | | Additive | | Xylanase | Crystals Observed? | |
|---|---|---|---|---|---|---|---|---|---|---|
| FIG. # | Cond. # | pH | Identity | Identity | Conc. (mM) | Identity | Conc. (mM) | Conc. (mg/mL) | Sample #1 | Sample #2 |
| 65C15 | 1 | 4.6 | NaCitrate | NaCitrate | 650 | — | 0 | 7 | N | N |
| 65C15 | 2 | 4.6 | NaCitrate | NaCitrate | 475 | — | 0 | 17 | Y | N |
| 65C14 | 3 | 6.5 | Tris/HCl | NaCitrate | 700 | — | 0 | 5 | Y | N |
| 65C14 | 4 | 6.5 | Tris/HCl | NaCitrate | 500 | — | 0 | 9 | Y | N |
| 65C13 | 5 | 8.45 | Tris/HCl | NaCitrate | 425 | — | 0 | 19 | N | N |
| 65C13 | 6 | 8.45 | Tris/HCl | NaCitrate | 475 | — | 0 | 9.5 | Y | N |
| 65C2 | 7 | 4.6 | NaCitrate | Na/K Tartrate | 1100 | — | 0 | 6.5 | N | N |
| 65C9 | 8 | 4.6 | NaCitrate | $K_2HPO_4$ | 800 | — | 0 | 9 | Y | N |
| 65C9 | 9 | 4.6 | NaCitrate | $K_2HPO_4$ | 1800 | — | 0 | 6.75 | N | N |
| 65C10 | 10 | 6.5 | Tris/HCl | $K_2HPO_4$ | 600 | — | 0 | 24.75 | N | N |
| 65C1 | 11 | 6.5 | Tris/HCl | Na/K Tartrate | 750 | — | 0 | 21 | N | N |
| 65C11 | 12 | 8.45 | Tris/HCl | $K_2HPO_4$ | 2800 | — | 0 | 6.75 | N | N |
| 65C4 | 13 | 4.6 | NaCitrate | $(NH_4)_2SO_4$ | 1080 | — | 0 | 9 | N | N |
| 65C5 | 14 | 6.5 | Tris/HCl | $(NH_4)_2SO_4$ | 1890 | — | 0 | 4.5 | N | N |
| 65C6 | 15 | 8.45 | Tris/HCl | $(NH_4)_2SO_4$ | 810 | — | 0 | 24.75 | Y | N |
| 65C9 | 16 | 4.6 | NaCitrate | $K_2HPO_4$ | 2800 | — | 0 | 3.5 | N | N |
| 65C2 | 17 | 4.6 | NaCitrate | Na/K Tartrate | 750 | — | 0 | 17 | Y | N |
| 65C11 | 18 | 8.45 | Tris/HCl | $K_2HPO_4$ | 400 | — | 0 | 31.5 | N | N |
| 65C4 | 19 | 4.6 | NaCitrate | $(NH_4)_2SO_4$ | 945 | — | 0 | 23.625 | N | N |
| 65C1 | 20 | 6.5 | Tris/HCl | Na/K Tartrate | 1400 | — | 0 | 4.5 | N | N |
| 65C5 | 21 | 6.5 | Tris/HCl | $(NH_4)_2SO_4$ | 1350 | — | 0 | 9 | Y | N |
| 65C3 | 22 | 8.45 | Tris/HCl | Na/K Tartrate | 900 | — | 0 | 6.75 | N | N |
| 65C3 | 23 | 8.45 | Tris/HCl | Na/K Tartrate | 700 | — | 0 | 13.5 | Y | Y |
| 65C6 | 24 | 8.45 | Tris/HCl | $(NH_4)_2SO_4$ | 1755 | — | 0 | 4.5 | N | N |
| 65C22 | 25 | 8.2 | Tris/HCl | P8000 | 16000 | NaCl | 100 | 42 | Y | Y |
| 65C22 | 26 | 8.2 | Tris/HCl | P8000 | 23000 | NaCl | 100 | 21 | Y | Y |
| 65C24 | 27 | 8.2 | Tris/HCl | P8000 | 15000 | — | 0 | 54 | Y | Y |
| 65C24 | 28 | 8.2 | Tris/HCl | P8000 | 24000 | — | 0 | 30 | Y | N |
| 65C20 | 29 | 8.2 | Tris/HCl | P8000 | 28000 | $NH_4CH_3CO_2$ | 100 | 18 | Y | N |
| 65C20 | 30 | 8.2 | Tris/HCl | P8000 | 19000 | $NH_4CH_3CO_2$ | 100 | 33 | Y | Y |
| 65C20 | 31 | 8.2 | Tris/HCl | P8000 | 14000 | $NH_4CH_3CO_2$ | 100 | 60 | Y | Y |
| — | 32 | 8.2 | Tris/HCl | P8000 | 20000 | K Citrate | 50 | 42 | Y | Y |
| — | 33 | 8.2 | Tris/HCl | P8000 | 14000 | K Citrate | 50 | 60 | Y | Y |
| — | 34 | 8.2 | Tris/HCl | P8000 | 16000 | K Citrate | 50 | 36 | Y | Y |
| 65C19 | 35 | 8.2 | Tris/HCl | P8000 | 24000 | $(NH_4)_2SO_4$ | 675 | 18 | N | Y |
| 65C7 | 36 | 8.2 | Tris/HCl | P8000 | 24000 | $(NH_4)_2SO_4$ | 675 | 6 | N | N |
| 65C17 | 37 | 8.2 | Tris/HCl | P8000 | 10000 | $MgSO_4$ | 50 | 66 | Y | Y |
| 65C17 | 38 | 8.2 | Tris/HCl | P8000 | 16000 | $MgSO_4$ | 50 | 30 | Y | Y |
| 65C17 | 39 | 8.2 | Tris/HCl | P8000 | 18000 | $MgSO_4$ | 50 | 36 | Y | Y |
| 65C23 | 40 | 7.6 | Tris/HCl | P8000 | 12000 | NaCl | 100 | 66 | Y | Y |
| 65C23 | 41 | 7.6 | Tris/HCl | P8000 | 28000 | NaCl | 100 | 18 | N | N |
| 65C12 | 42 | 7.6 | Tris/HCl | P8000 | 30000 | $K_2HPO_4$ | 100 | 12 | N | Y |
| 65C12 | 43 | 7.6 | Tris/HCl | P8000 | 22000 | $K_2HPO_4$ | 100 | 12 | N | N |
| 65C12 | 44 | 7.6 | Tris/HCl | P8000 | 16000 | $K_2HPO_4$ | 100 | 42 | Y | Y |
| 65C21 | 45 | 7.6 | Tris/HCl | P8000 | 18000 | $NH_4CH_3CO_2$ | 100 | 36 | Y | Y |
| 65C18 | 46 | 7.6 | Tris/HCl | P8000 | 28000 | K Citrate | 50 | 18 | N | Y |
| 65C8 | 47 | 7.6 | Tris/HCl | P8000 | 16000 | $(NH_4)_2SO_4$ | 675 | 54 | N | N |
| 65C16 | 48 | 7.6 | Tris/HCl | P8000 | 30000 | $MgSO_4$ | 50 | 12 | Y | N |

Specifically, the empirically determined solubility boundaries of FIGS. 65C1-24 were explored with crystallization trials, thereby eliminating 1) useless experiments on chemicals that do not alter solubility significantly (and hence will not produce crystals), and 2) useless experiments that are ton Research of Aliso Viejo, Calif., and Wizard I and Wizard II available from Emerald Biostructures of Bainbridge Island, Wash.)

Two batch crystallization trials of the 48 unique conditions listed in TABLE 2 were prepared for each of the 4 sparse matrix screens for a total of 384 individual assays. For each commercial screen final protein concentrations of 12.5 mg/mL and 25 mg/mL were used; the recommended concentration range for the crystallization of Xylanase is 10 mg/mL to 40 mg/mL.

FIGS. 67-68 compare microbatch crystallization experiments using commercially available sparse matrix screens to an optimal crystallization screen based on solubility phase spaces. FIG. 67 is a histogram showing number of successful crystallization conditions identified with sparse matrix screens (each at protein concentrations of 12 mg/mL and 23 mg/mL) and optimal screen.

Twenty-seven crystallization conditions were observed in the optimal screen compared to a total of 3 crystallization conditions in the 8 standard sparse matrix screens. The use of ab initio solubility information therefore resulted in a 72-fold enrichment in crystallization success.

A surprising result was that Xylanase crystals were observed in the optimal screen for all the precipitants identified in coarse screening. These results suggest that achieving optimal levels of supersaturation may be more important in the crystallization of Xylanase than the broad sampling of chemical space. In cases such as this, systematic screening for crystallization using a reduced chemical space may prove more effective than sparse matrix strategies.

FIG. 68 is a polarized micrograph of large single crystals grown directly from optimal screen (16% polyethelyne glycol 8000, 65 mM sodium chloride, 65 mM TRIS-HCl pH 8.2, 42 mg/mL Xylanase). FIG. 68 shows that certain crystallization conditions identified in the optimal screen gave large single three-dimensional crystals, whereas only flat plate clusters were observed in the standard screens.

In order to evaluate the influence of lot variability on these crystallization results, the crystallization trials based on the optimal screen of 48 reagent conditions, were repeated using new protein sample obtained from the same vendor, and prepared in the same way as the original sample. TABLE 2 also summarizes conditions under which Xylanase crystals were observed to form from at least one of the two batches of sample.

TABLE 2 indicates that certain crystallization conditions may be more robust to batch-dependent perturbations. Specifically, as indicated with underlining in TABLE 2, fourteen of seventeen polyethelyne glycol (PEG 8000) conditions yielding crystals in the original experiment were reproduced using the second Xylanase sample. By contrast, only one of ten of the salt based conditions yielding crystals in the original experiment were reproduced using the second sample.

To determine if the highly variable crystallization behavior observed in salt-based conditions was due to variations in phase-space behavior a complete phase-space of one chemical formulation (sodium/potassium tartrate, TRIS.HCl pH 8.5) was measured in microbatch format for both samples. The plots of FIGS. 69A-B compare phase space behavior and crystallization variability of the original and second samples respectively, in microbatch format. Conditions yielding no precipitate and no crystals are shown as circles. Conditions yielding crystal growth from clear solution are shown as diamonds. Conditions yielding crystal growth from immediate precipitate are shown as circles overlaid with diamonds. Conditions yielding immediate precipitate with no crystal growth are shown as squares.

FIGS. 69A-B indicate that although both samples exhibited very similar phase-space behavior, they produced different crystallization results. Eleven conditions produced crystals in the original sample compared to only one successful condition in the second sample. The reason for this difference in behavior is unclear but may be due to variable degrees of proteolysis, or trace amounts of chemical contaminants introduced during purification or concentration steps.

Another application of protein solubility phase space mapping is in transporting successful crystallization conditions from one experimental format to another. The successful crystallization of a protein is determined both by the established thermodynamic variables and the kinetic trajectory of an experiment. For this reason experiments conducted with different crystallization kinetics (eg. Hanging drop vapor diffusion, microbatch, free-interface diffusion) using the same precipitating agents will not necessarily produce similar results. For example, the hydroxylase domain of a cytochrome p450 alkane hydroxylase (Mutant 139-3 of BM-3) did not produce crystals in initial hanging drop trials, but was found to crystallize readily by microfluidic free interface diffusion (24) (1 part protein 20 mg/mL, 1 part 30% m/v polyethelyne glycol 8000, 0.2 M sodium acetate, 0.1 M TRIS-HCl pH 7.0). This condition was, however, unsuccessful when set in hanging drop vapor diffusion format, resulting only in amorphous precipitate. The microfluidic formulator was used to generate a phase space at constant buffer and salt concentration (100 mM TRIS-HCl pH 7.3; 200 mM sodium acetate) with polyethelene glycol concentration and protein concentration as variables.

Two hanging drop experiments were designed to equilibrate near the solubility limit determined from the phase space map. One condition (8 μL of 35 mg/mL protein sample mixed with 6.7 μL of 10% polyethelene glycol, 100 mM sodium acetate, 50 mM TRIS HCl pH 7.3, and equilibrated at 20° C. against 1 mM of 20% polyethelene glycol, 200 mm sodium acetate, 100 mM TRIS-HCl pH 7.3) produced crystals within 3 days. This success demonstrates the usefulness of solubility mapping in transporting conditions across crystallization formats.

Finally, we also used the formulator to make a direct observation of the supersaturation region of chicken egg white lysozyme. The concentrations of salt and lysozyme was manipulated while keeping the buffer concentration constant in order to evolve the chemical state of the mixing ring radially out from the origin and then back again. Measurements of precipitation were taken at approximately 1 minute intervals.

Figure 66:
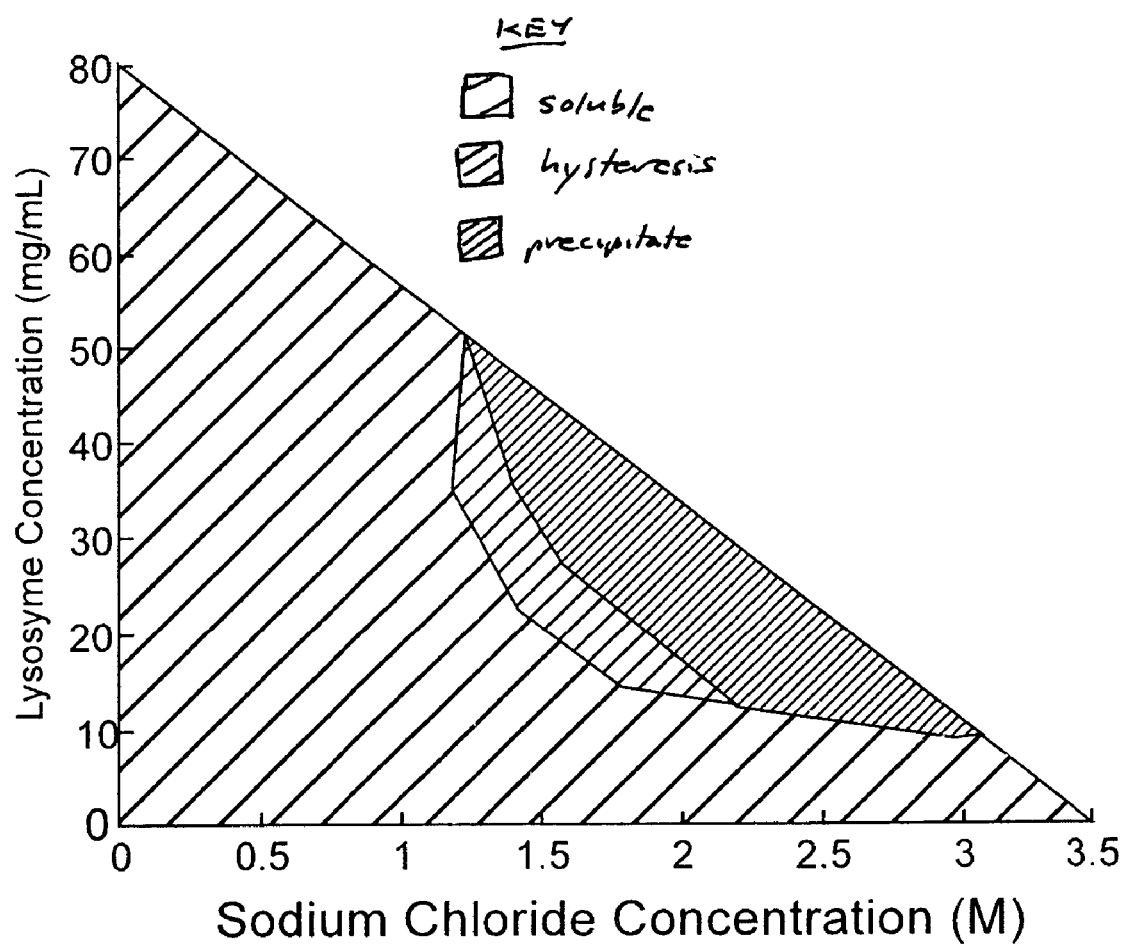
FIG. 66 is a simplified schematic plot of lysozymic phase space over different relative protein/salt concentrations.

The addition of a family of such radial titrations was used to generate two phase space diagrams for chicken egg white lysozyme; one for the outward titrations and one for the return titrations. FIG. 66 shows an overlay of two phase-space diagrams generated by outward and return titrations. Observed hysteresis in precipitation threshold identifies metastable region of phase space.

The first observation of protein precipitation appears at higher salt and protein concentration during the outward trajectory (increasing target material concentration) than on the return path (decreasing target material concentration), thereby exhibiting solubility hysteresis. The intersection of the soluble region of the outward phase space with the precipitated region of the return path phase space provides a direct observation of a metastable regime in which the aggregate phase is thermodynamically stable but not observed at short times. The observation of the reversible formation of a protein aggregate may be used to distinguish between denatured and well-folded protein aggregates. Additionally, the identified metastable regions in phase space provide likely candidate conditions for crystal seeding and growth experiments.

In conclusion, we have shown that complex sample processing at the nanoliter scale allows for a practical implementation of automated protein solubility characterization. Ab initio solubility information obtained through systematic protein phase space mapping provides a physical basis for the design of optimal crystallization screens, giving rise to dramatic enrichment in crystallization success.

It must be noted that chemical conditions and phase behavior are not the only variables that can be adjusted in the search for good crystals—it is often equally important to tune the properties of the protein by creating mutants with terminal amino acids removed. However, the path to crystallization always includes extensive chemical screening with precious protein sample, and for this step it appears that microfluidic formulations devices can play an important role. Beyond applications in protein crystallization the formulation capability of this device should find diverse applications in areas such as combinatorial chemistry, chemical synthesis, and cell culture studies.

While the present invention has been described herein with reference to particular embodiments thereof, a latitude of modification, various changes and substitutions are intended in the foregoing disclosure, and it will be appreciated that in some instances some features of the invention will be employed without a corresponding use of other features without departing from the scope of the invention as set forth. Therefore, many modifications may be made to adapt a particular situation or material to the teachings of the invention without departing from the essential scope and spirit of the present invention. It is intended that the invention not be limited to the particular embodiment disclosed as the best mode contemplated for carrying out this invention, but that the invention will include all embodiments and equivalents falling within the scope of the claims.

What is claimed is:

1. A method of crystallization comprising:
   utilizing a microfluidic formulator device to generate a solubility fingerprint of a crystallization target over a range of conditions;
   utilizing the microfluidic formulator to map phase space around precipitating conditions of the solubility fingerprint resulting in precipitation of the crystallization target and soluble conditions of the solubility fingerprint where the crystallization target precipitate dissolves; and
   determining a hysteresis between precipitating and soluble phase spaces.

2. The method of claim 1 wherein the solubility fingerprint is generated by combining the crystallization target with a buffer and a precipitant.

3. The method of claim 2 wherein the solubility fingerprint is generated by combining the crystallization target with the buffer, the precipitant, and an additive.

4. The method of claim 3 wherein the solubility fingerprint is generated by combining the crystallization target with the precipitant comprising polyethylene glycol, and with the additive comprising a salt.

5. The method of claim 3 wherein a mixed volume of the crystallization target and the precipitant is about 1 µL or less.

6. The method of claim 2 wherein solubility of the target is indicated by a change in transmission of incident light through a mixing chamber.

7. The method of claim 6 further comprising:
   imaging a portion of the mixing chamber;
   calculating a standard deviation of pixel intensities of light transmitted through the portion; and
   comparing the standard deviation to a background value recorded in an absence of the crystallization target.

8. The method of claim 7 wherein an approximate linear dependence of pixel standard deviation on crystallization target concentration indicates precipitation of the crystallization target.

9. The method of claim 2 wherein the conditions are generated by mixing the crystallization target with a precipitant in a rotary flow microfluidic device.

10. The method of claim 1 further comprising designing an optimal screen for the crystallization target based upon the phase space map.

11. The method of claim 1 wherein the phase space map indicates a boundary of a precipitation region for the crystallization target, the method further comprising designing an optimal screen for the crystallization target so that a final condition is located on the boundary of the precipitation region.

12. The method of claim 8 wherein the final condition is achieved by mixing the crystallization target with a precipitant in a microfluidic device.

13. The method of claim 8 wherein the final condition is achieved by performing at least one of a microbatch and a hanging drop crystallization experiment.

14. The method of claim 1 further comprising:
   mapping a first phase space by altering a concentration of at least one of the crystallization target and a precipitant in order to precipitate the crystallization target;
   observing a condition of initial precipitation as a first precipitation threshold;
   mapping a second phase space by altering the concentration of least one of the crystallization target and the precipitate to dissolve the precipitated crystallization target;
   observing a condition of last remaining precipitate as a second precipitation threshold;
   determining a hysteresis between the first and second precipitation thresholds.

15. The method of claim 1 wherein the hysteresis indicates a metastable region of phase space for the crystallization target, the method further comprising reproducing conditions in the metastable region.

16. The method of claim 15 further comprising reproducing a condition in the metastable region to create crystals of the crystallization target.

17. The method of claim 16 wherein the condition in the metastable region is reproduced by mixing the crystallization target with a precipitant in a microfluidic device.

18. The method of claim 16 wherein the condition in the metastable region is reproduced by performing at least one of a microbatch and a hanging drop crystallization experiment.

19. A crystallization method comprising:
   empirically determining a solubility curve for a crystallization target mixed with a precipitant utilizing a microfluidic device; and
   mixing the crystallization target with the precipitant at a ratio that places a final concentration of the crystallization target and the precipitant on a boundary of the solubility curve.

20. The method of claim 19 wherein the solubility curve is empirically determined by a change in transmission of light through the microfluidic device.

21. The method of claim 20 further comprising:
   transmitting light through the microfluidic device;
   detecting an intensity of the transmitted light received by a plurality of pixels;
   calculating a standard deviation of the pixels; and comparing the standard deviation to a background value recorded in an absence of the crystallization target.

22. The method of claim 21 wherein an approximate linear dependence of pixel standard deviation on crystallization target concentration indicates precipitation of the crystallization target.

23. The method of claim 19 wherein the solubility curve is empirically determined by mixing the crystallization target with a precipitant in a rotary flow microfluidic device.

24. The method of claim 19 further comprising designing an optimal screen for the crystallization target based upon the empirically determined solubility curve.

25. The method of claim 24 further comprising mixing the crystallization target with the precipitant so that a final condition of the optimal screen is located on a boundary of the solubility curve.

26. The method of claim 25 wherein the final condition is achieved by mixing the crystallization target with the precipitant in a microfluidic device.

27. The method of claim 26 wherein a combined volume of crystallization target and the precipitant of about 1 μL or less is mixed to achieve the final condition.

28. The method of claim 25 wherein the final condition is achieved by performing at least one of a microbatch and a hanging drop crystallization experiment.

29. The method of claim 19 wherein a combined volume of crystallization target and the precipitant of about 1 μL or less is mixed to achieve the final condition.

30. The method of claim 19 wherein a volume of crystallization target of between about 100 nL or less is mixed with the precipitant to achieve the final concentration.

* * * * *

UNITED STATES PATENT AND TRADEMARK OFFICE
CERTIFICATE OF CORRECTION

PATENT NO.       : 7,459,022 B2                                                   Page 1 of 1
APPLICATION NO.  : 11/006522
DATED            : December 2, 2008
INVENTOR(S)      : Carl L. Hansen et al.

It is certified that error appears in the above-identified patent and that said Letters Patent is hereby corrected as shown below:

Column 1, lines 33-43, delete "Work described herein has been supported, in part, by NSF (xyz in a chip program); National Institute of Health grant CA 77373; NSERC (Julie Payette Fellowship); David H. & Lucille M. Packard Foundation; and G. Harold and Leila Y. Mathers Charitable Foundation. Work described herein has also been supported in part by National Science Foundation Grant No. CTS 0088649, National Institutes of Health Grant Nos. CA 77373 and HG 1642-02, and Army Research Office Grant No. DAAD19-00-1-0392 awarded by DARPA. The United States Government may have certain rights in the invention." and insert --This invention was made with government support under the xyz in a chip program and Grant No. CTS 0088649 awarded by the National Science Foundation, under Grant Nos. CA 77373 and HG-01642-02 awarded by the National Institute of Health, under the Julie Payette Fellowship awarded by NSERC, under the David H. & Lucille M. Packard Foundation, under the G. Harold and Leila Y. Mathers Charitable Foundation, and under the Army Research Office (ARO) Grant No. DAAD19-00-1-0392 awarded by the Defense Advanced Research Projects Agency. The government has certain rights in the invention.--

Signed and Sealed this

Fourteenth Day of April, 2009

JOHN DOLL
*Acting Director of the United States Patent and Trademark Office*